(12) United States Patent
Stoessel et al.

US011611046B2

(10) Patent No.: US 11,611,046 B2
(45) Date of Patent: Mar. 21, 2023

(54) ORGANIC ELECTROLUMINESCENT DEVICE

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt (DE); Anja Jatsch, Frankfurt am Main (DE); Joachim Kaiser, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 625 days.

(21) Appl. No.: 15/125,209

(22) PCT Filed: Feb. 18, 2015

(86) PCT No.: PCT/EP2015/000360
§ 371 (c)(1),
(2) Date: Sep. 12, 2016

(87) PCT Pub. No.: WO2015/135624
PCT Pub. Date: Sep. 17, 2015

(65) Prior Publication Data
US 2017/0077418 A1 Mar. 16, 2017

(30) Foreign Application Priority Data
Mar. 13, 2014 (EP) .................................... 14000911

(51) Int. Cl.
| | | |
|---|---|---|
| *H01L 51/00* | (2006.01) | |
| *H01L 51/50* | (2006.01) | |
| *C07D 471/08* | (2006.01) | |
| *C09K 11/06* | (2006.01) | |
| *H01L 51/52* | (2006.01) | |
| *H01L 51/56* | (2006.01) | |

(52) U.S. Cl.
CPC ........ *H01L 51/0072* (2013.01); *C07D 471/08* (2013.01); *C09K 11/06* (2013.01); *H01L 51/006* (2013.01); *H01L 51/0054* (2013.01); *H01L 51/0067* (2013.01); *H01L 51/5012* (2013.01); *H01L 51/5028* (2013.01); *C09K 2211/1007* (2013.01); *C09K 2211/1029* (2013.01); *H01L 51/0003* (2013.01); *H01L 51/0004* (2013.01); *H01L 51/0008* (2013.01); *H01L 51/0013* (2013.01); *H01L 51/0056* (2013.01); *H01L 51/0058* (2013.01); *H01L 51/0059* (2013.01); *H01L 51/0077* (2013.01); *H01L 51/5004* (2013.01); *H01L 51/5016* (2013.01); *H01L 51/5206* (2013.01); *H01L 51/5221* (2013.01); *H01L 51/56* (2013.01); *H01L 2251/5376* (2013.01); *H01L 2251/55* (2013.01); *H01L 2251/552* (2013.01)

(58) Field of Classification Search
CPC ............ C09K 11/06; H01L 2251/5376; H01L 2251/55; H01L 2251/552; H01L 51/5004; H01L 51/5012
See application file for complete search history.

(56) References Cited

U.S. PATENT DOCUMENTS

| | | | |
|---|---|---|---|
| 8,643,268 B2 | 2/2014 | Ogiwara et al. | |
| 9,099,658 B2 | 8/2015 | Kawamura et al. | |
| 9,153,788 B2 | 10/2015 | Adachi et al. | |
| 9,219,242 B2 | 12/2015 | Ogiwara et al. | |
| 9,276,228 B2 | 3/2016 | Seo et al. | |
| 10,032,998 B2 | 7/2018 | Ogiwara et al. | |
| 2005/0095451 A1* | 5/2005 | Begley ............... | H01L 51/0054 428/690 |
| 2012/0248968 A1 | 10/2012 | Ogiwara et al. | |
| 2014/0034930 A1 | 2/2014 | Seo et al. | |
| 2015/0001502 A1* | 1/2015 | Seo ..................... | H01L 51/5012 257/40 |
| 2015/0105564 A1 | 4/2015 | Adachi et al. | |
| 2016/0329512 A1* | 11/2016 | Nishide ............... | H01L 51/5028 |
| 2017/0256720 A1* | 9/2017 | Adachi ................. | C09K 11/06 |

FOREIGN PATENT DOCUMENTS

| | | |
|---|---|---|
| CN | 103579530 A | 2/2014 |
| JP | 2002063988 A | 2/2002 |
| JP | 2014022666 A | 2/2014 |
| JP | 2014045179 A | 3/2014 |
| WO | WO-2012133188 A1 | 10/2012 |
| WO | WO-2013081088 A1 | 6/2013 |
| WO | WO-2013154064 A1 | 10/2013 |
| WO | WO-2013180241 A1 | 12/2013 |
| WO | WO-2014013947 A1 | 1/2014 |

OTHER PUBLICATIONS

Uoyama, H., Goushi, K., Shizu, K., Nomura, H., Adachi, C., Highly Efficient Organic Light-Emitting Diodes from Delayed Fluorescence, Nature, 2012, 492, 234-238. (Year: 2012).*
Endo, A., Sato, K., Yoshimura K., Kai, T., Kawada, A., Miyazaki, H., Adachi, C., Efficient up-conversion of triplet excitons into a singlet state and its application for organic light emitting diodes, Appl. Phys. Lett., 2011, 98, 088302. (Year: 2011).*
International Search Report for PCT/EP2015/000360 dated Jun. 12, 2015.
International Search Report for PCT/EP2015/000377 dated May 7, 2015.
Ishimatsu, R., et al., "Solvent Effect on Thermally Activated Delayed Fluorescence by 1,2,3,5-Tetrakis(carbazol-9-yl)-4,6-dicyanobenzene", Journal of Physical Chemistry A, vol. 117, No. 27, (2013), pp. 5607-5612.

(Continued)

*Primary Examiner* — Sean M DeGuire
(74) *Attorney, Agent, or Firm* — Faegre Drinker Biddle & Reath LLP

(57) ABSTRACT

The present invention relates to organic electroluminescent devices, the emitting layer thereof containing a blend of a luminescent material having a narrow singlet-triplet gap and a fluorescent emission material having high steric shielding.

14 Claims, No Drawings

(56) References Cited

OTHER PUBLICATIONS

Uoyama, H., et al., "Highly efficient organic light-emitting diodes from delayed fluorescence", Nature, vol. 492, No. 7428, (2012), pp. 234-238.
Ziegler, J., et al., "Silica-Coated inP/ZnS Nanocrystals as Converter Material in White LEDs", Advanced Materials, vol. 20, No. 21, (2008), pp. 4068-4073.
English Translation of Chinese Office Action for Chinese Application No. 201580013701.1, dated Oct. 31, 2017.

* cited by examiner

ORGANIC ELECTROLUMINESCENT DEVICE

CROSS-REFERENCE TO RELATED APPLICATIONS

This application is a national stage application (under 35 U.S.C. § 371) of PCT/EP2015/000360, filed Feb. 18, 2015, which claims benefit of European Application No. 14000911.9, filed Mar. 13, 2014, both of which are incorporated herein by reference in their entirety.

The present invention relates to organic electroluminescent devices comprising, in the emitting layer, a mixture of a luminescent material having a small singlet-triplet gap and a fluorescent emission material having high steric shielding.

The structure of organic electroluminescent devices (OLEDs) in which organic semiconductors are used as functional materials is described, for example, in U.S. Pat. Nos. 4,539,507, 5,151,629, EP 0676461 and WO 98/27136, Emitting materials used here are especially also organometallic iridium and platinum complexes which exhibit phosphorescence rather than fluorescence (M. A. Baldo et al., *Appl. Phys. Lett.* 1999, 75, 4-6). For quantum-mechanical reasons, up to four times the energy efficiency and power efficiency is possible using organometallic compounds as phosphorescent emitters.

In spite of the good results which are achieved with organometallic iridium and platinum complexes, however, they also have a number of disadvantages: for instance, iridium and platinum are scarce and costly metals. It would therefore be desirable for conservation of resources to be able to avoid the use of these metals. Furthermore, there is a need for improvement especially in the case of the lifetime of phosphorescent OLEDs containing Ir or Pt emitters when the operation of the OLED involves relatively high temperatures, as is the case in some applications.

An alternative development is the use of emitters which exhibit thermally activated delayed fluorescence (TADF) (e.g. H. Uoyama et al., Nature 2012, vol. 492, 234). These are organic materials in which the energy gap between the lowest triplet state $T_1$ and the first excited singlet state $S_1$ is sufficiently small that the $S_1$ state is thermally accessible from the $T_1$ state. For quantum-statistical reasons, on electronic excitation in the OLED, 75% of the excited states are in the triplet state and 25% in the singlet state. Since purely organic molecules cannot usually emit efficiently from the triplet state, 75% of the excited states cannot be utilized for emission, which means that it is possible in principle to convert only 25% of the excitation energy to light. If, however, the energy gap between the lowest triplet state and the lowest excited singlet state is sufficiently small, the first excited singlet state of the molecule is accessible from the triplet state by thermal excitation and can be populated thermally. Since this singlet state is an emissive state from which fluorescence is possible, this state can be used to generate light. Thus, in principle, the conversion of up to 100% of the electrical energy to light is possible when purely organic materials are used as emitter. Thus, the prior art describes an external quantum efficiency of more than 19%, which is within the same order of magnitude as for phosphorescent OLEDs. It is thus possible with purely organic materials of this kind to achieve very good efficiencies and at the same time to avoid the use of scarce metals such as iridium or platinum.

The prior art describes the use of various matrix materials in combination with emitters that exhibit thermally activated delayed fluorescence (called TADF compound hereinafter), for example carbazole derivatives (H. Uoyama et al., Nature 2012, 492, 234; Endo et al., Appl. Phys. Left. 2011, 98, 083302; Nakagawa et al., Chem. Commun. 2012, 48, 9580; Lee et al., Appl. Phys. Lett. 2012, 101, 093306/1), phosphine oxide-dibenzothiophene derivatives (H. Uoyama et al., Nature 2012, 492, 234) or silane derivatives (Mehes et al., Angew. Chem. Int. Ed. 2012, 51, 11311; Lee et al., Appl. Phys. Lett. 2012, 101, 093306/1).

What is common to the electroluminescent devices described in the prior art is that the TADF compound is used as emitting compound in the emitting layer. Since a prerequisite for the presence of a TADF compound is a small gap between the $T_1$ and $S_1$ levels, the choice of TADF compound is limited. Thus, it can be difficult to provide TADF compounds having every desired emission color. It would therefore be desirable to utilize the advantages of TADF but nevertheless to be able to use the base structures of fluorescent emitters that are typically used, in order to be able to exploit their positive properties. Fluorescent emitters are available in all emission colors, and so this would also lead to a greater selection of emitting compounds. Moreover, TADF compounds frequently have a broad emission spectrum, and so it would be desirable, for greater color purity, to have available emitting compounds having a relatively narrow emission spectrum, as is frequently the case for standard fluorescent emitters. Moreover, further improvements in lifetime are desirable.

It has been found that, surprisingly, this object is achieved by organic electroluminescent devices having a TADF compound and a fluorescent compound in the emitting layer, the fluorescent compound having high steric shielding with respect to its environment, as defined more specifically below. This device construction makes it possible to provide organic electroluminescent devices which emit in all emission colors, in that it is possible to use the base structures of known fluorescent emitters which nevertheless exhibit the high efficiency of electroluminescent devices with TADF. The present invention therefore provides organic electroluminescent devices of this kind.

US 2012/248968 describes an organic electroluminescent device comprising, in the emitting layer, a TADF compound and a fluorescent compound. It is not disclosed that the fluorescent compound is sterically shielded. Further improvements are desirable here, especially in relation to efficiency.

The present invention provides an organic electroluminescent device comprising cathode, anode and at least one emitting layer comprising a sterically shielded fluorescent compound, characterized in that the emitting layer or a layer adjoining the emitting layer contains a luminescent organic compound having a gap between the lowest triplet state $T_1$ and the first excited singlet state $S_1$ of ≤0.30 eV (TADF compound), where the peak emission wavelength of the sterically shielded fluorescent compound is greater than or equal to the peak emission wavelength of the TADF compound.

The sterically shielded fluorescent compound is also referred to in the description which follows merely as fluorescent compound. What is meant in the context of the present invention by a sterically shielded compound and how it is possible to determine whether a compound is a sterically shielded compound is elucidated in detail in the description which follows and in the examples section.

The way in which the peak emission wavelength is determined in the context of the present application is elucidated in general terms in the examples section.

In a preferred embodiment of the invention, the peak emission wavelength of the sterically shielded fluorescent compound is at least 10 nm greater than that of the TADF compound, more preferably at least 20 nm greater and most preferably at least 30 nm greater.

In one embodiment of the invention, the emitting layer comprises a mixture of the sterically shielded fluorescent compound and the TADF compound.

In a further embodiment of the invention, the electroluminescent device comprises, adjoining the emitting layer on the anode side, a layer comprising the TADF compound.

In yet a further embodiment of the invention, the electroluminescent device comprises, adjoining the emitting layer on the cathode side, a layer comprising the TADF compound.

In a preferred embodiment of the invention, the emitting layer further comprises, apart from the materials detailed above, at least one further compound. This further compound is referred to hereinafter as matrix compound or matrix material. This may be a further TADF compound in the context of the definition detailed above. In general, the matrix compound, however, is not a TADF compound.

There follows a detailed description of the luminescent compound having a gap between the lowest triplet state $T_1$ and the first excited singlet state $S_1$ of ≤0.30 eV. This is a compound which exhibits TADF (thermally activated delayed fluorescence). This compound is abbreviated in the description which follows to "TADF compound".

The TADF compound is preferably an organic compound. An organic compound in the context of the present invention is a carbonaceous compound that does not contain any metals. More particularly, the organic compound is formed from the elements C, H, D, B, Si, N, P, O, S, F, Cl, Br and I.

A luminescent compound in the context of the present invention is a compound capable of emitting light at room temperature under optical excitation in an environment as exists in the organic electroluminescent device. This compound preferably has a luminescence quantum efficiency of at least 40%, more preferably of at least 50%, even more preferably of at least 60% and especially preferably of at least 70%. The luminescence quantum efficiency is determined in a layer such as that which is to be used in the organic electroluminescent device, but one which does not contain the fluorescent compound. The way in which the determination of the luminescence quantum yield is conducted in the context of the present invention is described in a general and detailed manner in the examples section.

It is additionally preferable when the layer comprising the TADF compound has a short decay time. The decay time is preferably ≤50 μs, more preferably ≤20 μs, even more preferably ≤10 μs and especially preferably ≤5 μs. The way in which the determination of the decay time is conducted in the context of the present invention is described in a general and detailed manner in the examples section.

The energy of the lowest excited singlet state ($S_1$) and the lowest triplet state ($T_1$) are determined by quantum-chemical calculation. The way in which this determination is conducted in the context of the present invention is described in a general and detailed manner in the examples section.

As described above, the gap between $S_1$ and $T_1$ must be no more than 0.30 eV, in order that the compound is a TADF compound in the sense of the present invention; the smaller the gap, the better. Preferably, therefore, the gap between $S_1$ and $T_1$ is ≤0.25 eV, more preferably ≤0.15 eV, even more preferably ≤0.10 eV and especially preferably ≤0.08 eV.

The TADF compound is preferably an aromatic compound having both donor and acceptor substituents, with only slight spatial overlap between the LUMO and the HOMO of the compound. What is understood by donor and acceptor substituents is known in principle to those skilled in the art. Suitable donor substituents are especially diaryl- or -heteroarylamino groups and carbazole groups or carbazole derivatives, each preferably bonded to the aromatic compound via N. These groups may also have further substitution. Suitable acceptor substituents are especially cyano groups, but also, for example, electron-deficient heteroaryl groups which may also have further substitution, for example substituted or unsubstituted triazine groups.

When the emitting layer, apart from the TADF compound and the sterically shielded fluorescent compound, comprises a matrix compound, it is preferable to avoid exciplex formation in the emitting layer when the following applies to LUMO(TADF), i.e. the LUMO of the TADF compound, and the HOMO(matrix), i.e. the HOMO of the matrix compound:

LUMO(TADF)−HOMO(matrix)≥$S_1$(TADF)−0.4 eV,
more preferably:
LUMO(TADF)−HOMO(matrix)≥$S_1$(TADF)−0.3 eV,
and even more preferably:
LUMO(TADF)−HOMO(matrix)≥$S_1$(TADF)−0.2 eV.

$S_1$(TADF) here is the first excited singlet state $S_1$ of the TADF compound.

The preferred dopant concentrations of the TADF compound in the emitting layer are described hereinafter. Because of the difference in production of the organic electroluminescent device, the dopant concentration in the case of production of the emitting layer by vapor deposition is reported in % by volume, and in the case of production of the emitting layer from solution in % by weight. The dopant concentrations in % by volume and % by weight are generally very similar.

In a preferred embodiment of the invention, in the case of production of the emitting layer by vapor deposition, the TADF compound is present in a dopant concentration of 1% to 25% by volume in the emitting layer, more preferably of 2% to 20% by volume, even more preferably of 5% to 15% by volume and especially 7% to 12% by volume.

In a preferred embodiment of the invention, in the case of production of the emitting layer from solution, the TADF compound is present in a dopant concentration of 1% to 25% by weight in the emitting layer, more preferably of 2% to 20% by weight, even more preferably of 5% to 15% by weight and especially 7% to 12% by volume.

The general art knowledge of the person skilled in the art includes knowledge of which materials are generally suitable as TADF compounds. The following references disclose, by way of example, materials that are potentially suitable as TADF compounds:

Tanaka et al., Chemistry of Materials 25(18), 3766 (2013).
Lee et al., Journal of Materials Chemistry C 1(30), 4599 (2013).
Zhang et al., Nature Photonics advance online publication, 1 (2014), doi: 10.1038/nphoton.2014.12.
Serevicius et al., Physical Chemistry Chemical Physics 15(38), 15850 (2013).
Li et al., Advanced Materials 25(24), 3319 (2013).
Youn Lee et al., Applied Physics Letters 101(9), 093306 (2012).
Nishimoto et al., Materials Horizons 1, 264 (2014), doi: 10.1039/C3MH00079F.
Valchanov et al., Organic Electronics, 14(11), 2727 (2013).
Nasu et al., ChemComm, 49, 10385 (2013).

In addition, the following patent applications disclose potential TADF compounds: WO 2013/154064, WO 2013/133359, WO 2013/161437, WO 2013/081088, WO 2013/081088, WO 2013/011954, JP 2013/116975 and US 2012/0241732.

In addition, the person skilled in the art is able to infer design principles for TADF compounds from these publications. For example, Valchanov et al. show how the color of TADF compounds can be adjusted.

Examples of suitable molecules which exhibit TADF are the structures shown in the following table:
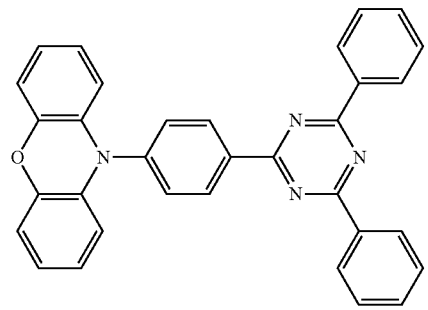 [SMILES: c1ccc(-c2nc(-c3ccccc3)nc(-c3ccc(N4c5ccccc5Oc5ccccc54)cc3)n2)cc1]
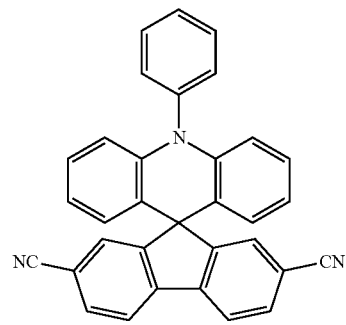 [SMILES: N#Cc1ccc2c(c1)C1(c3cc(C#N)ccc3-2)c2ccccc2N(c2ccccc2)c2ccccc21]
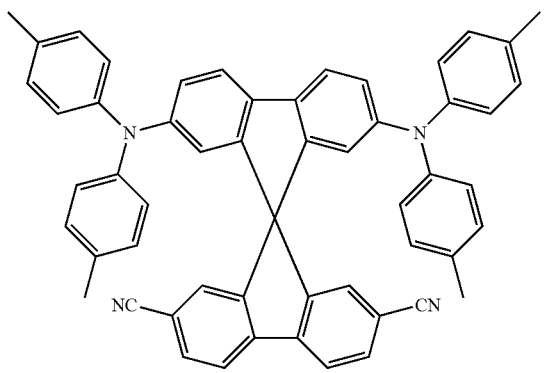
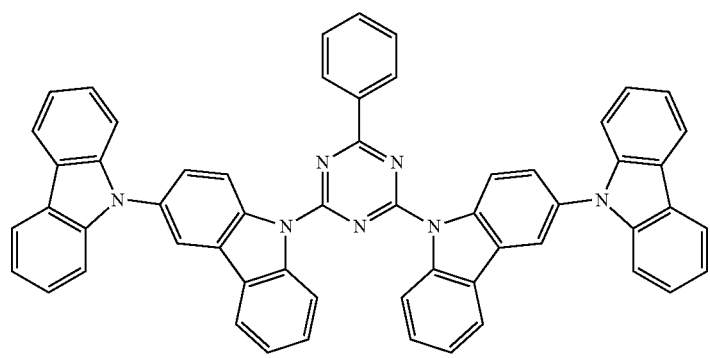 [SMILES: c1ccc(-c2nc(-n3c4ccccc4c4cc(-n5c6ccccc6c6ccccc65)ccc43)nc(-n3c4ccccc4c4cc(-n5c6ccccc6c6ccccc65)ccc43)n2)cc1]

-continued
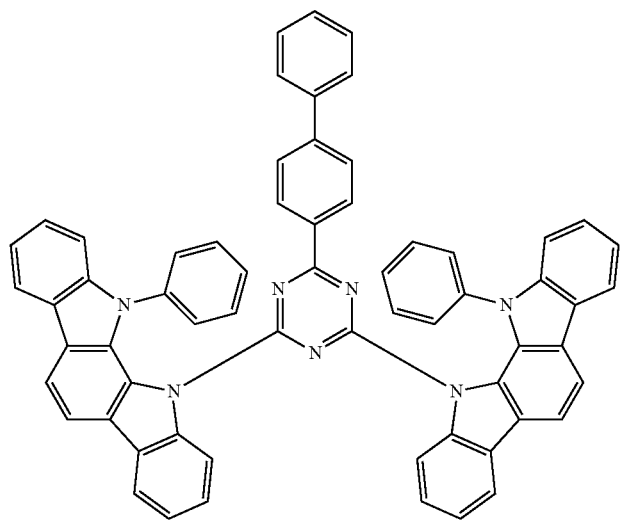 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]
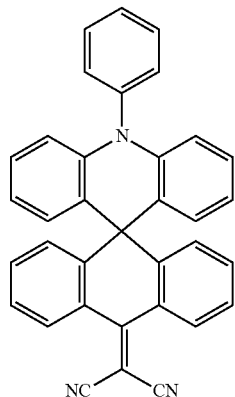 [SMILES: N#CC(C#N)=C1c2ccccc2C2(c3ccccc31)c1ccccc1N(c1ccccc1)c1ccccc12]
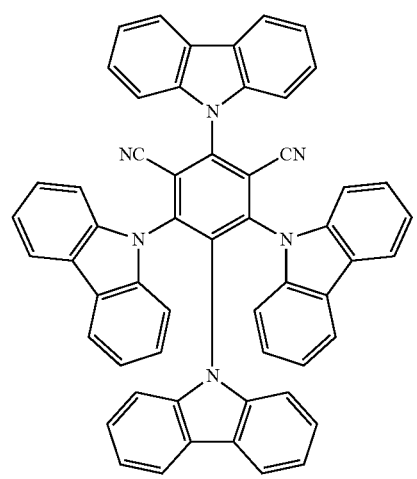 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

-continued
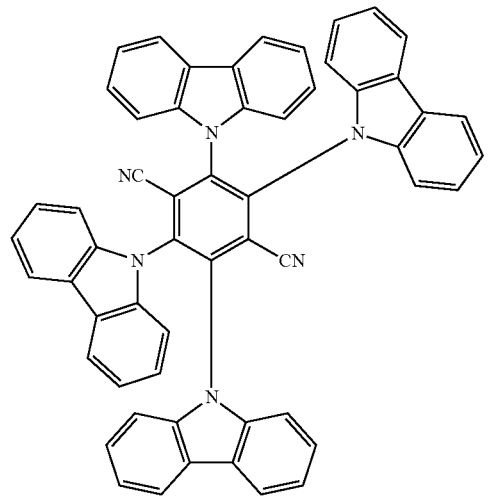 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]
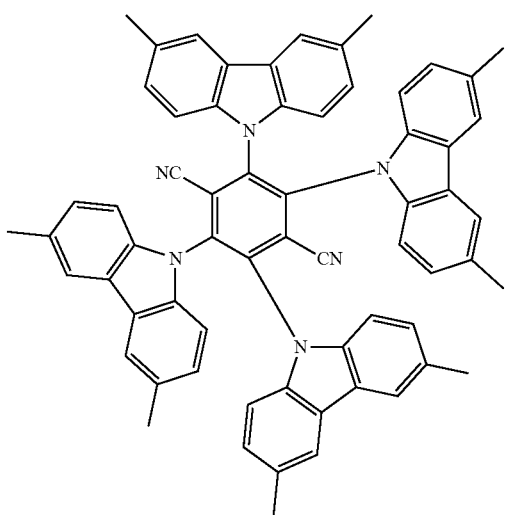
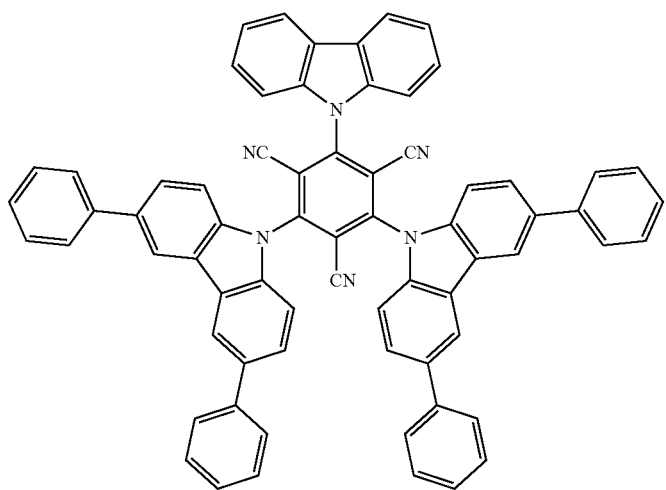 [SMILES: N#Cc1c(-n2c3ccccc3c3ccccc32)c(C#N)c(-n2c3ccc(-c4ccccc4)cc3c3cc(-c4ccccc4)ccc32)c(C#N)c1-n1c2ccc(-c3ccccc3)cc2c2cc(-c3ccccc3)ccc21]

-continued
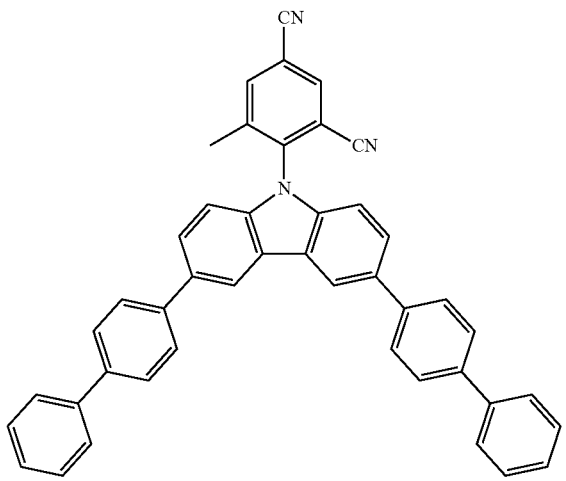 [SMILES: Cc1cc(C#N)cc(C#N)c1-n1c2ccc(-c3ccc(-c4ccccc4)cc3)cc2c2cc(-c3ccc(-c4ccccc4)cc3)ccc21]
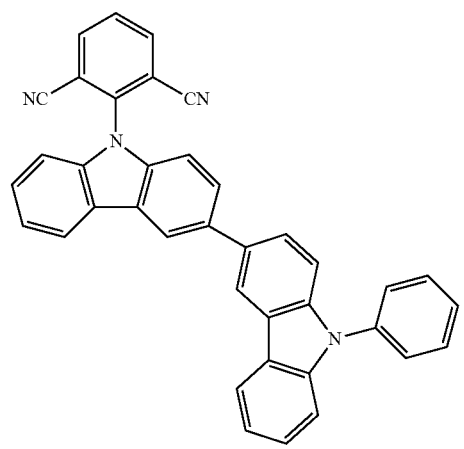 [SMILES: N#Cc1cccc(C#N)c1-n1c2ccccc2c2cc(-c3ccc4c(c3)c3ccccc3n4-c3ccccc3)ccc21]
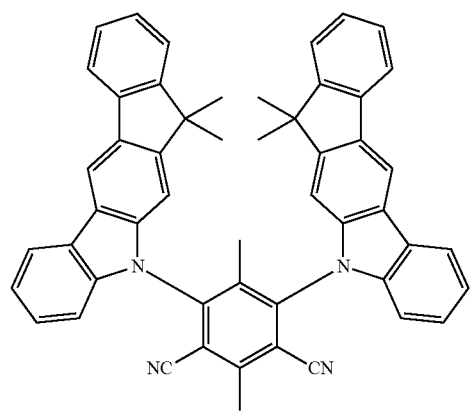 [SMILES: Cc1c(C#N)c(-n2c3ccccc3c3cc4c(cc32)C(C)(C)c2ccccc2-4)c(C)c(-n2c3ccccc3c3cc4c(cc32)C(C)(C)c2ccccc2-4)c1C#N]

-continued
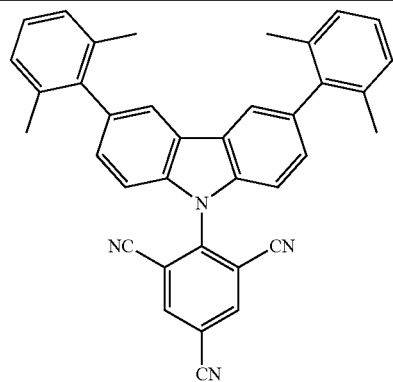
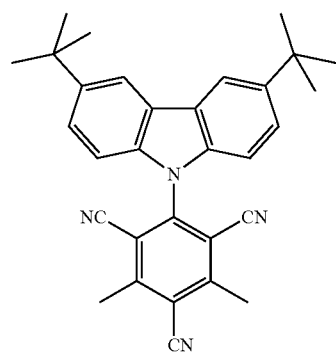 [SMILES: Cc1c(C#N)c(C)c(C#N)c(-n2c3ccc(C(C)(C)C)cc3c3cc(C(C)(C)C)ccc32)c1C#N]
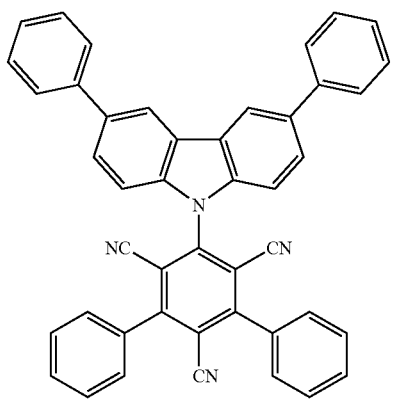 [SMILES: N#Cc1c(-c2ccccc2)c(C#N)c(-n2c3ccc(-c4ccccc4)cc3c3cc(-c4ccccc4)ccc32)c(C#N)c1-c1ccccc1]
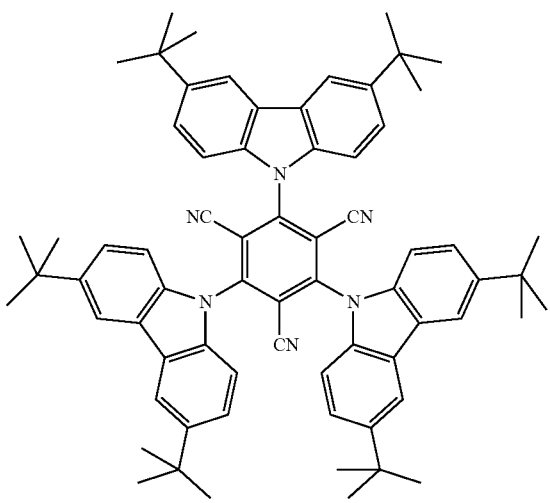 [SMILES: CC(C)(C)c1ccc2c(c1)c1cc(C(C)(C)C)ccc1n2-c1c(C#N)c(-n2c3ccc(C(C)(C)C)cc3c3cc(C(C)(C)C)ccc32)c(C#N)c(-n2c3ccc(C(C)(C)C)cc3c3cc(C(C)(C)C)ccc32)c1C#N]

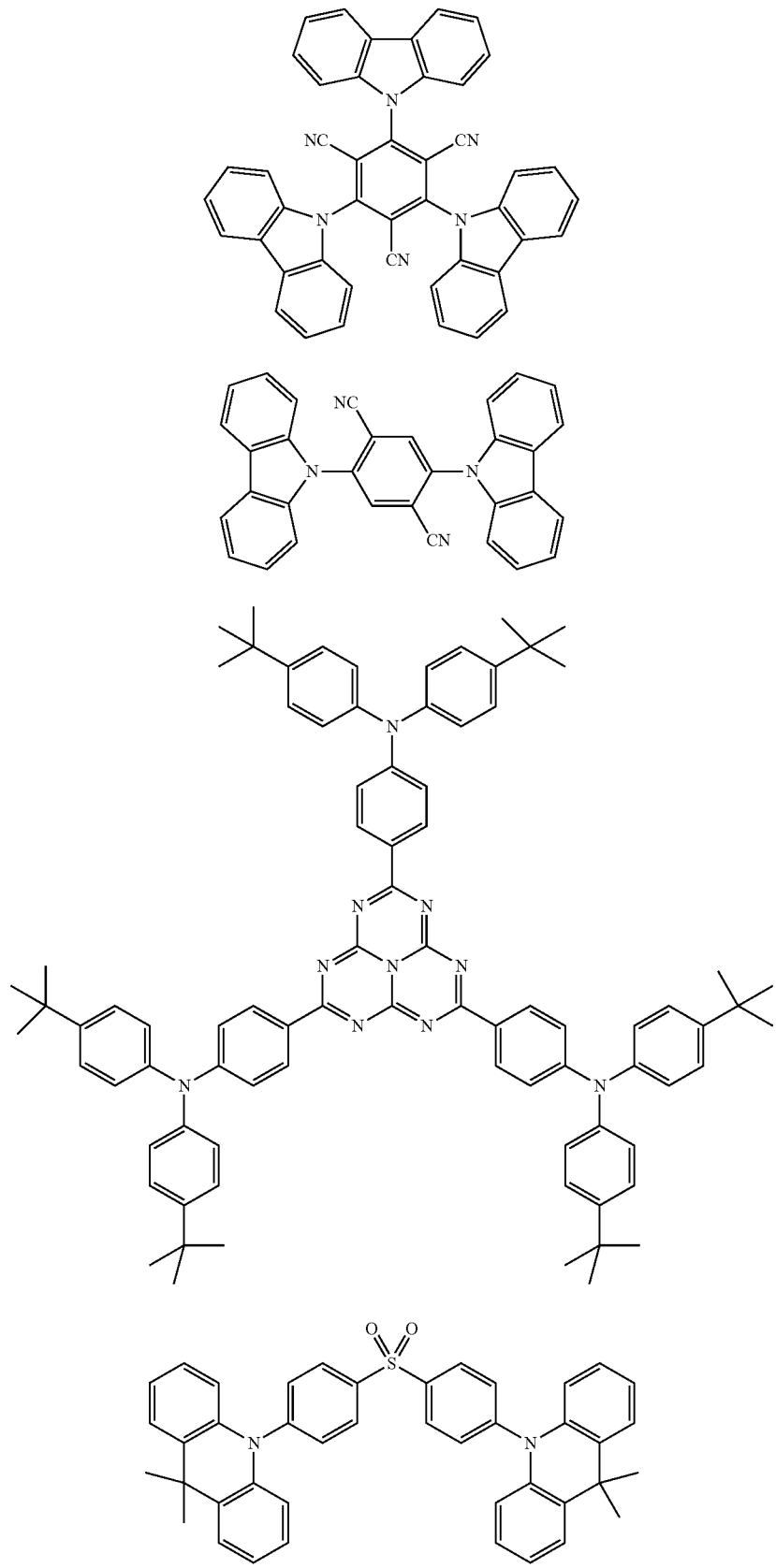

-continued
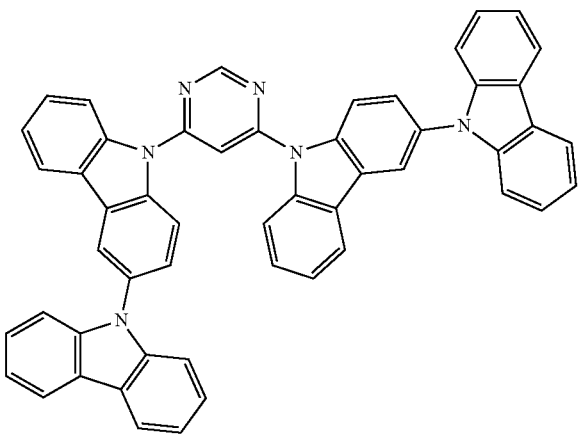 [SMILES: c1ccc2c(c1)c1ccccc1n2-c1ccc2c(c1)c1ccccc1n2-c1cc(-n2c3ccccc3c3cc(-n4c5ccccc5c5ccccc54)ccc32)ncn1]
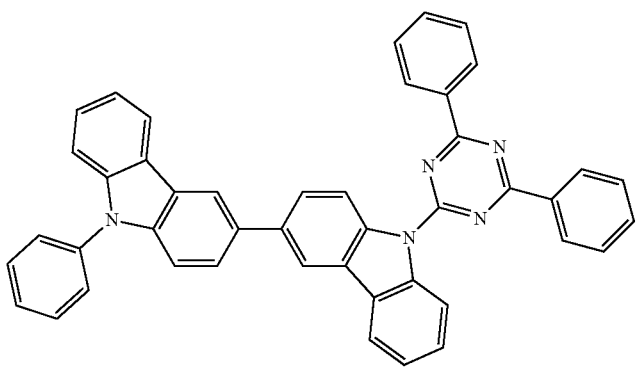 [SMILES: c1ccc(-c2nc(-c3ccccc3)nc(-n3c4ccccc4c4cc(-c5ccc6c(c5)c5ccccc5n6-c5ccccc5)ccc43)n2)cc1]
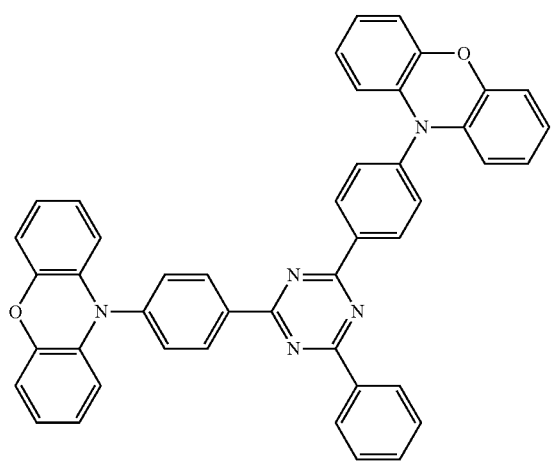 [SMILES: c1ccc(-c2nc(-c3ccc(N4c5ccccc5Oc5ccccc54)cc3)nc(-c3ccc(N4c5ccccc5Oc5ccccc54)cc3)n2)cc1]

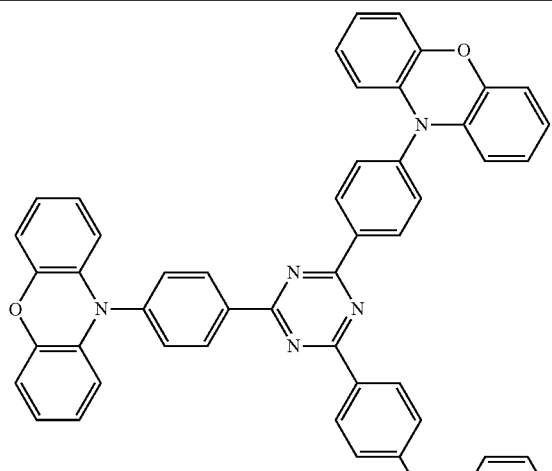
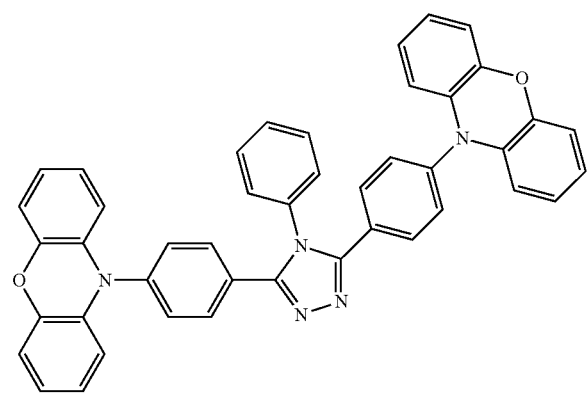 [SMILES: c1ccc(-n2c(-c3ccc(N4c5ccccc5Oc5ccccc54)cc3)nnc2-c2ccc(N3c4ccccc4Oc4ccccc43)cc2)cc1]
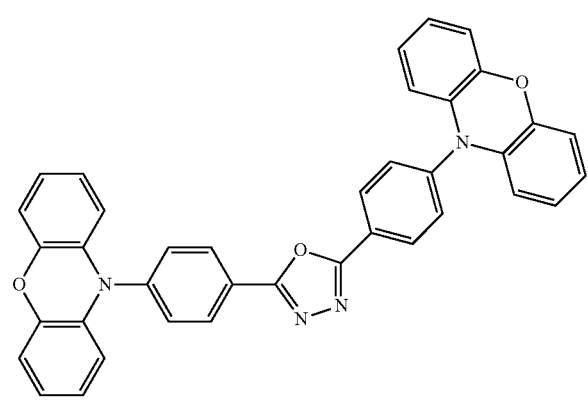 [SMILES: c1ccc2c(c1)Oc1ccccc1N2c1ccc(-c2nnc(-c3ccc(N4c5ccccc5Oc5ccccc54)cc3)o2)cc1]

-continued

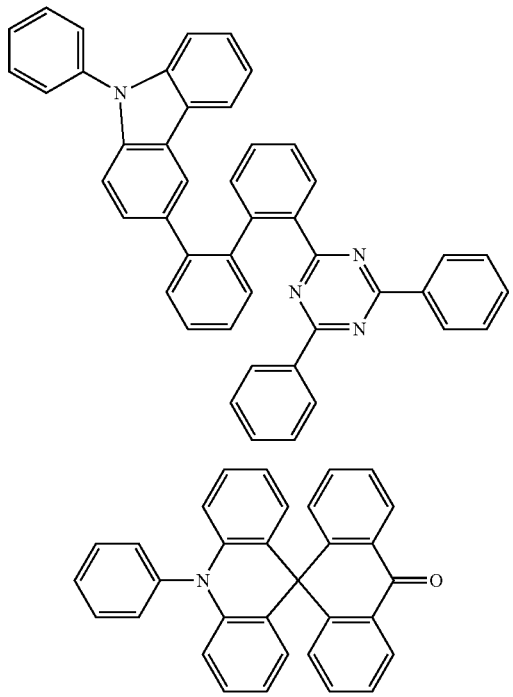

The sterically shielded fluorescent compound is described more specifically hereinafter.

The fluorescent compound is preferably an organic compound. An organic compound in the context of the present invention is a carbonaceous compound that does not contain any metals. More particularly, the organic compound is formed from the elements C, H, D, B, Si, N, P, O, S, F, Cl, Br and I. In a further embodiment of the invention, the fluorescent compound may also be a fluorescent metal complex, for example an aluminum complex.

A fluorescent compound in the context of the present invention is a compound capable of emitting light at room temperature under optical excitation in an environment as exists in the organic electroluminescent device, the emission being effected from an excited singlet state. This compound preferably has a luminescence quantum efficiency of at least 60%, more preferably of at least 80%, even more preferably of at least 90% and especially preferably of at least 95%. The luminescence quantum efficiency is determined in a solution in toluene. The way in which the determination of the luminescence quantum yield is conducted in the context of the present invention is described in a general and detailed manner in the examples section.

In a preferred embodiment, the peak emission wavelength of the fluorescent compound is between 430 and 650 nm. The way in which the determination of the peak emission wavelength is conducted in the context of the present invention is described in a general and detailed manner in the examples section.

Because of the difference in production of the organic electroluminescent device, the dopant concentration of the fluorescent compound in the case of production of the emitting layer by vapor deposition is reported in % by volume, and in the case of production of the emitting layer from solution in % by weight.

In a preferred embodiment of the invention, in the case of production of the emitting layer by vapor deposition, the fluorescent compound is present in a dopant concentration of 0.1% to 25% by volume in the emitting layer, preferably of 1% to 20% by volume, more preferably of 2% to 12% by volume, even more preferably 5% to 10% by volume and especially 7% to 10% by volume.

In a preferred embodiment of the invention, in the case of production of the emitting layer from solution, the fluorescent compound is present in a dopant concentration of 0.1% to 25% by weight in the emitting layer, preferably of 1% to 20% by weight, more preferably of 2% to 12% by weight, even more preferably 5% to 10% by weight and especially 7% to 10% by volume.

It is possible here that, especially in the case of a low dopant concentration of the fluorescent compound, the OLED exhibits mixed emission composed of the fluorescent compound and residual emission of the TADF compound. This can also be utilized in a controlled manner to generate mixed colors.

Base structures used for the fluorescent compound may be any compounds as used according to prior art for fluorescent OLEDs.

The steric shielding of these compounds is accomplished by electronically inert, sterically demanding substituents which surround the electronically active core of the fluorescent compound and thus shield it substantially from contact with adjacent molecules in the layer.

The degree of steric shielding can be determined by means of a shielding parameter S. The way in which this shielding parameter is determined via quantum-chemical calculation in the context of the present application is described in general terms in the examples section. This steric shielding parameter embraces different properties of the molecule. First of all, the fluorescent compound is divided into active portions and an insulating shell. This division is made according to the degree in which the atoms are involved in the HOMO or LUMO of the compound or in other electronically active molecular orbitals. When the involvement thereof in the relevant molecular orbitals is lower than a limit defined as below, these atoms are assigned by definition to the insulating shell. Then what is called the Connolly surface of the fluorescent compound is determined. This is accomplished by rolling a sphere of a particular size, in the present case 4 Å, on the surface of the fluorescent compound. This simulates how well another molecule, for example the TADF compound, can approach the fluorescent compound, which is important for the determination of whether or not Dexter energy transfer can take place between the compounds. Dexter energy transfer can take place only in the part of the surface of the fluorescent compound which is sufficiently close to the active core of the fluorescent compound, i.e. is not sufficiently shielded. Shielding in the context of the present invention is regarded as the ratio of the surface area where Dexter energy transfer can take place to the total surface area of the fluorescent compound, where this parameter depends not just on the fluorescent compound itself but also on the TADF compound used. When this proportion is lower than a particular limit, as defined below, the compound in the context of the present invention is regarded as being sterically shielded.

By definition, a compound is regarded as being sterically shielded in the context of the present invention when the shielding parameter S as defined below in the examples section is ≤0.6, preferably ≤55, more preferably ≤0.5, even more preferably ≤0.4, more preferably still ≤0.3 and especially preferably ≤0.2.

As described above, the fluorescent core used in the fluorescent compound may be any base structure as used customarily as a fluorescent emitter in organic electroluminescent devices. Preferred fluorescent compounds are rigid π systems substituted by large aliphatic or cycloaliphatic radicals. In addition, aromatic substituents which may be substituted by aliphatic or cycloaliphatic radicals are also an option when they are arranged in steric terms such that they are not active groups in the context of the present invention, i.e. the proportion thereof in the relevant molecular orbitals is below a limit as described below. By contrast, for example, arylamino substituents or heteroaryl groups are too highly involved in HOMO or LUMO and are therefore unsuitable as shielding groups.

Examples of suitable aromatic base skeletons of fluorescent compounds are the groups of the formulae (1) to (50) shown below:

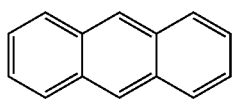

Formula (1)

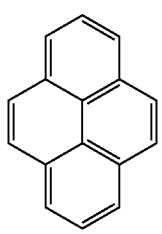

Formula (2)

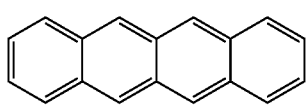

Formula (3)

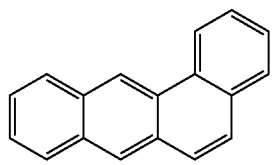

Formula (4)

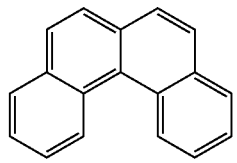

Formula (5)

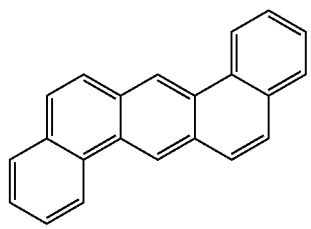

Formula (6)

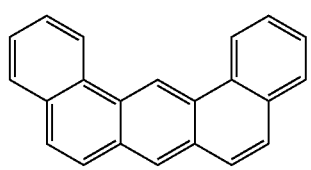

Formula (7)

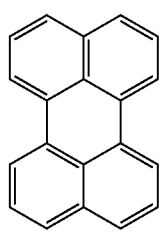

Formula (8)

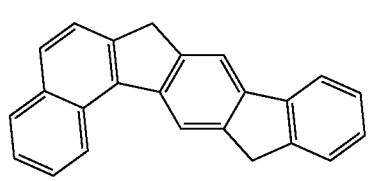

Formula (9)

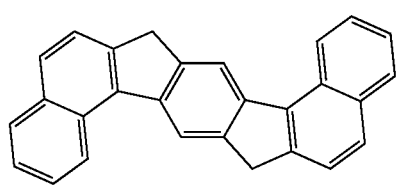

Formula (10)

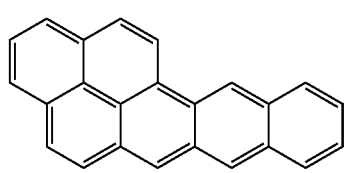

Formula (11)

-continued
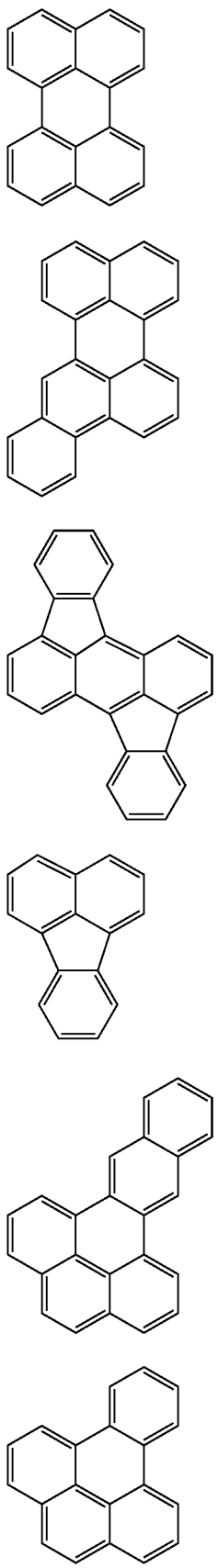
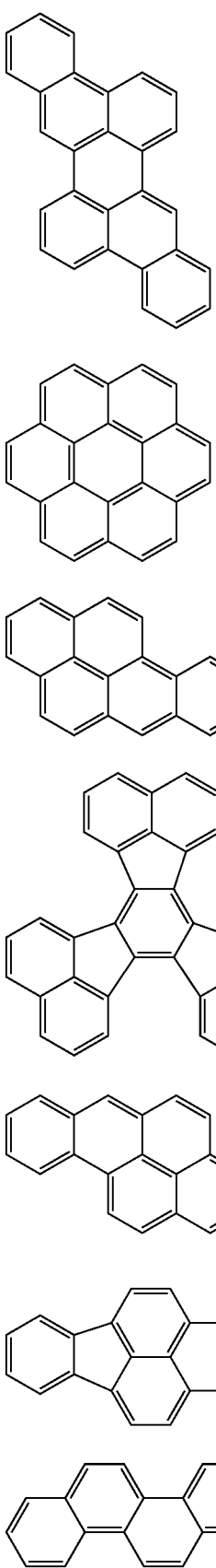
Formula (12)
Formula (13)
Formula (14)
Formula (15)
Formula (16)
Formula (17)
Formula (18)
Formula (19)
Formula (20)
Formula (21)
Formula (22)
Formula (23)
Formula (24)

Formula (25)
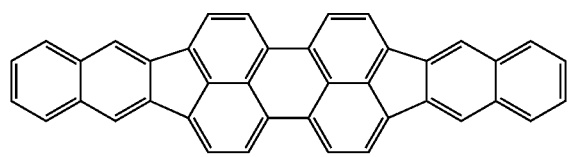
Formula (26)
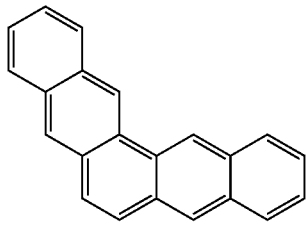
Formula (27)
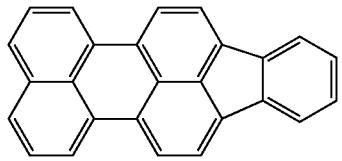
Formula (28)
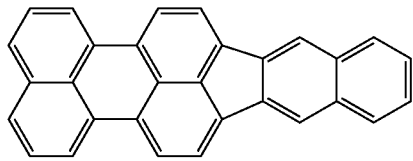
Formula (29)
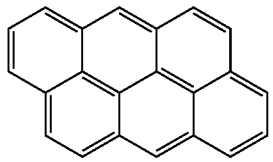
Formula (30)
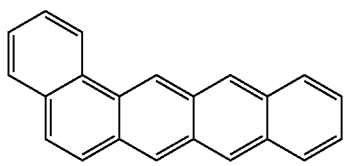
Formula (31)
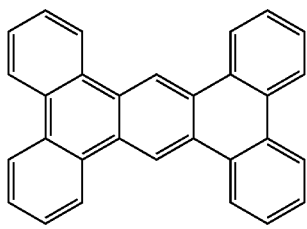
Formula (32)
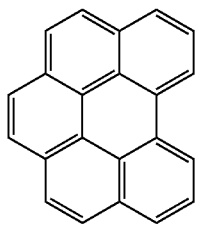
Formula (33)
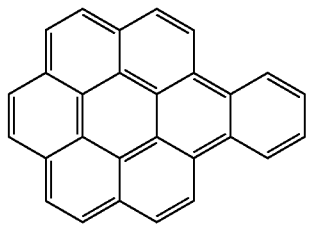
Formula (34)
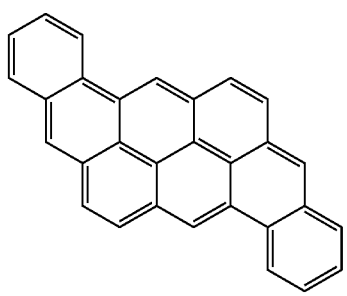
Formula (35)
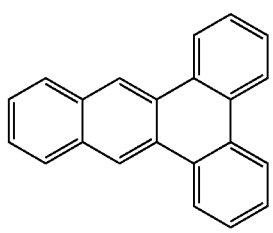
Formula (36)
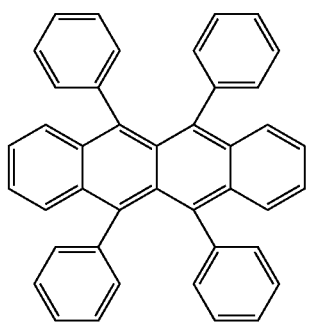
Formula (37)
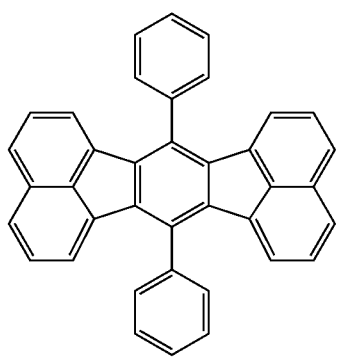

Formula (38)
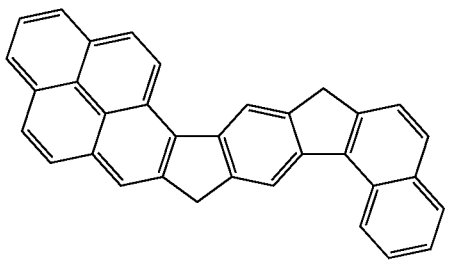
Formula (39)
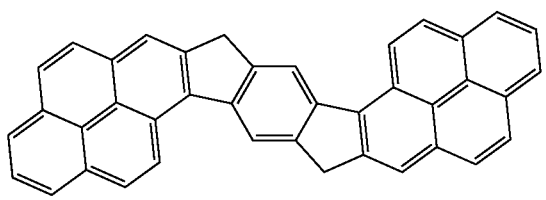
Formula (40)
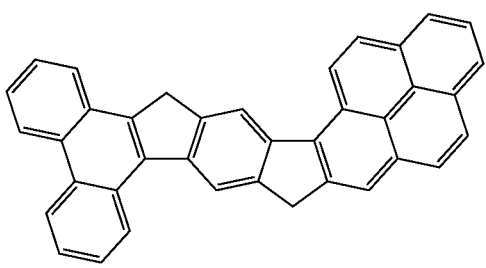
Formula (41)
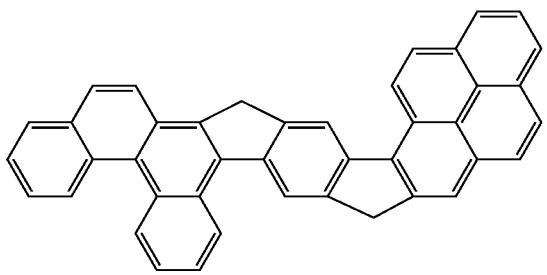
Formula (42)
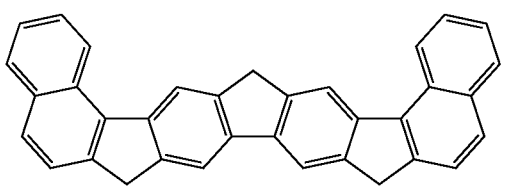
Formula (43)
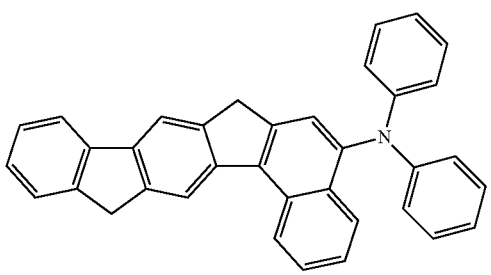
Formula (44)
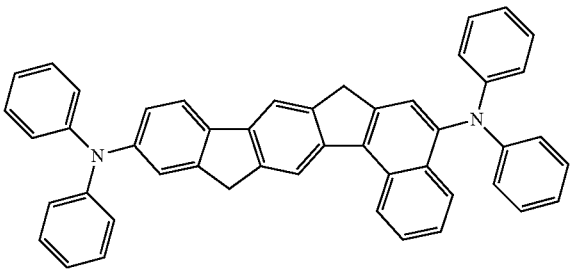
Formula (45)
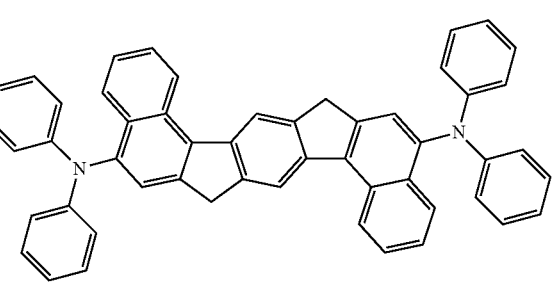
Formula (46)
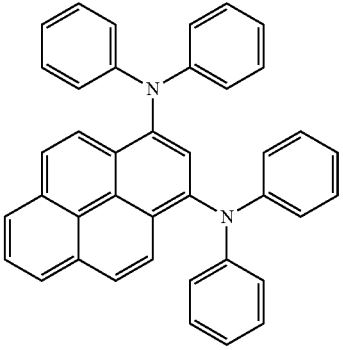
Formula (47)
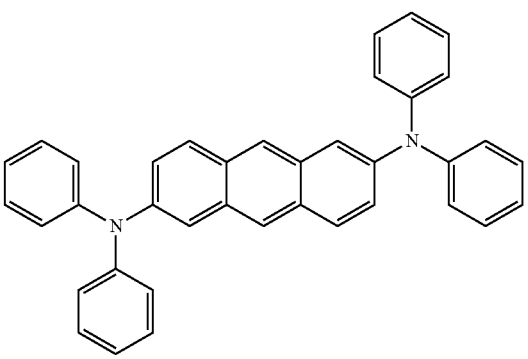
Formula (48)
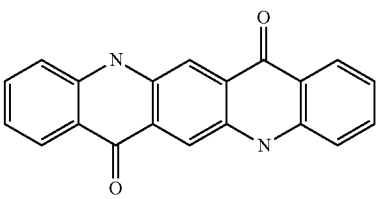

Formula (49)

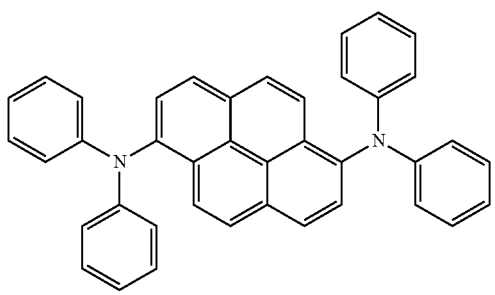

Formula (50)

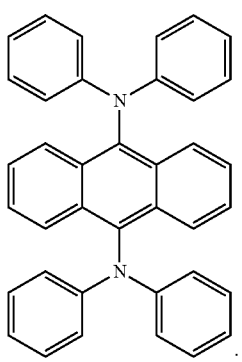

Examples of suitable heteroaromatic base skeletons of fluorescent compounds are the abovementioned groups of the formulae (1) to (50) in which one, two, three or four carbon atoms in the fused aromatic nucleus are replaced by nitrogen. Preferably, one, two or three carbon atoms are replaced by nitrogen, more preferably one or two carbon atoms and most preferably exactly one carbon atom.

Examples of suitable heteroaromatic base skeletons of fluorescent compounds are additionally the groups of the formulae (51) to (70) shown below:

Formula (51)

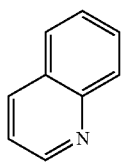

Formula (52)

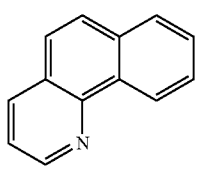

Formula (53)

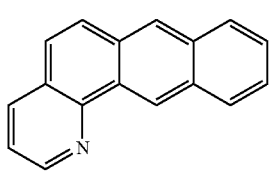

Formula (54)

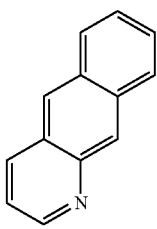

Formula (55)

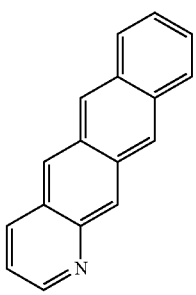

Formula (56)

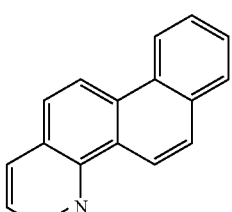

Formula (57)

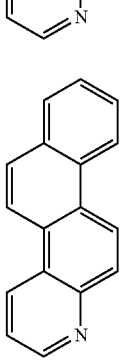

Formula (58)

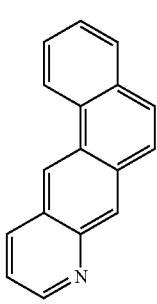

Formula (59)

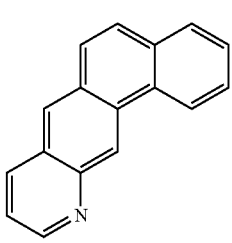

Formula (60)
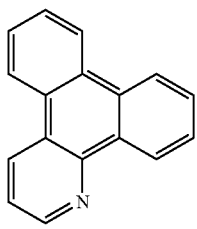

Formula (61)
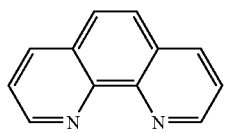

Formula (62)
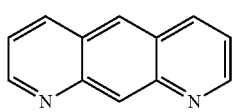

Formula (63)
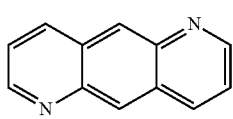

Formula (64)
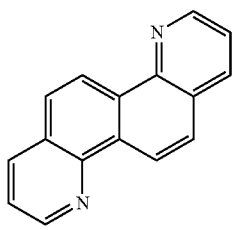

Formula (65)
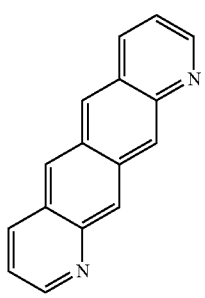

Formula (66)
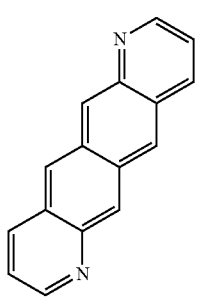

Formula (67)
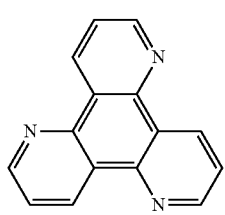

Formula (68)
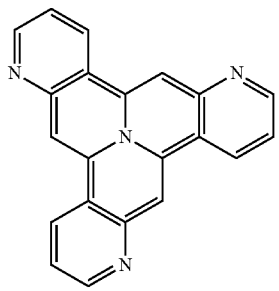

Formula (69)
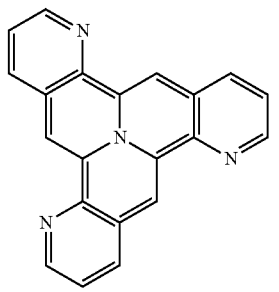

Formula (70)
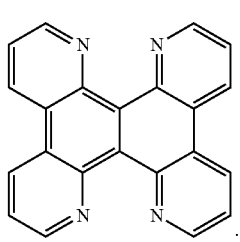

These structures, as described above, are substituted by sterically demanding substituents and may also be substituted by further substituents that can not be regarded as being sterically demanding, provided that these substituents are not electronically active or are substituted in turn by sterically shielding substituents.

There follows a description of suitable sterically demanding substituents which can be used in order to substitute the fluorescent cores, for example the abovementioned aromatics and heteroaromatics, and hence to arrive at sterically shielded fluorescent compounds.

Suitable sterically demanding substituents are, for example, alkyl groups, especially having 3 to 20 carbon atoms, preferably having 4 to 10 carbon atoms, in which hydrogen atoms may also be replaced by F, alkoxy groups, especially having 3 to 20 carbon atoms, preferably having 4 to 10 carbon atoms, aralkyl groups, especially having 7 to 30 carbon atoms, and aromatic ring systems, especially having 6 to 30 carbon atoms, where it is also possible for the aryl groups in the aralkyl groups and aromatic ring systems to be substituted by one or more alkyl groups having 1 to 10 carbon atoms. It is also possible here for a plurality of adjacent substituents to form a ring system with one another.

When the substituent is an aralkyl group or an aromatic ring system, it is preferable when these do not have any fused aryl groups having more than 10 carbon atoms in which aryl groups are fused directly to one another via a common edge. More preferably, it does not have any fused aryl groups at all in which aryl groups are fused directly to one another via a common edge. Thus, it is preferable when the aromatic ring system, for example, does not have any anthracene or pyrene groups, and particularly preferable when the aromatic ring system does not have any naphthalene groups either. By contrast, it may have, for example, biphenyl or terphenyl groups, since these do not have any fused aryl groups. In addition, it may also have, for example, fluorene or spirobifluorene groups, since no aryl groups are fused directly to one another via a common edge in these groups.

When the sterically demanding substituent is an alkyl group, this alkyl group preferably has 4 to 10 carbon atoms. Preference is given to a secondary, tertiary or cyclic alkyl group in which the secondary or tertiary carbon atom is either bonded to the fluorescent base skeleton directly or bonded to the fluorescent base skeleton via a CH$_2$ group. More preferably, this alkyl group is selected from the structures of the following formulae (R-1) to (R-33):

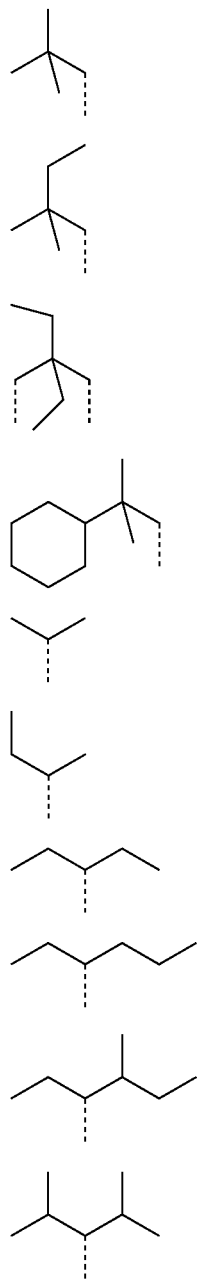

(R-1)

(R-2)

(R-3)

(R-4)

(R-5)

(R-6)

(R-7)

(R-8)

(R-9)

(R-10)

-continued

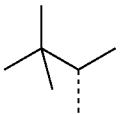
(R-11)

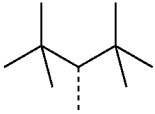
(R-12)

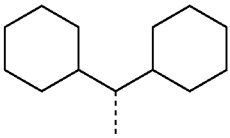
(R-13)

(R-14)

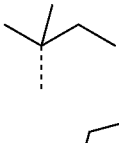
(R-15)

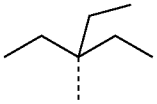
(R-16)

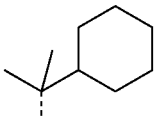
(R-17)

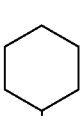
(R-18)

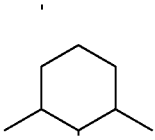
(R-19)

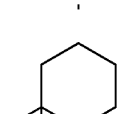
(R-20)

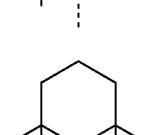
(R-21)

(R-22)

-continued

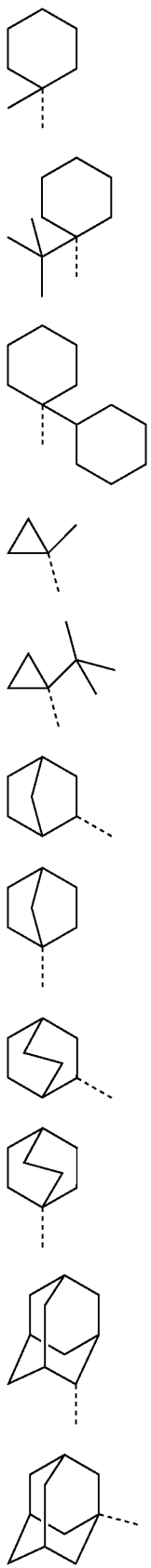

(R-23)
(R-24)
(R-25)
(R-26)
(R-27)
(R-28)
(R-29)
(R-30)
(R-31)
(R-32)
(R-33)

where the dotted bond indicates the linkage of these groups to the fluorescent base skeleton.

When the sterically demanding substituent is an alkoxy group, this alkoxy group preferably has 3 to 10 carbon atoms and is preferably branched or cyclic. Preferably, this alkoxy group is selected from the structures of the following formulae (R-34) to (R-47):

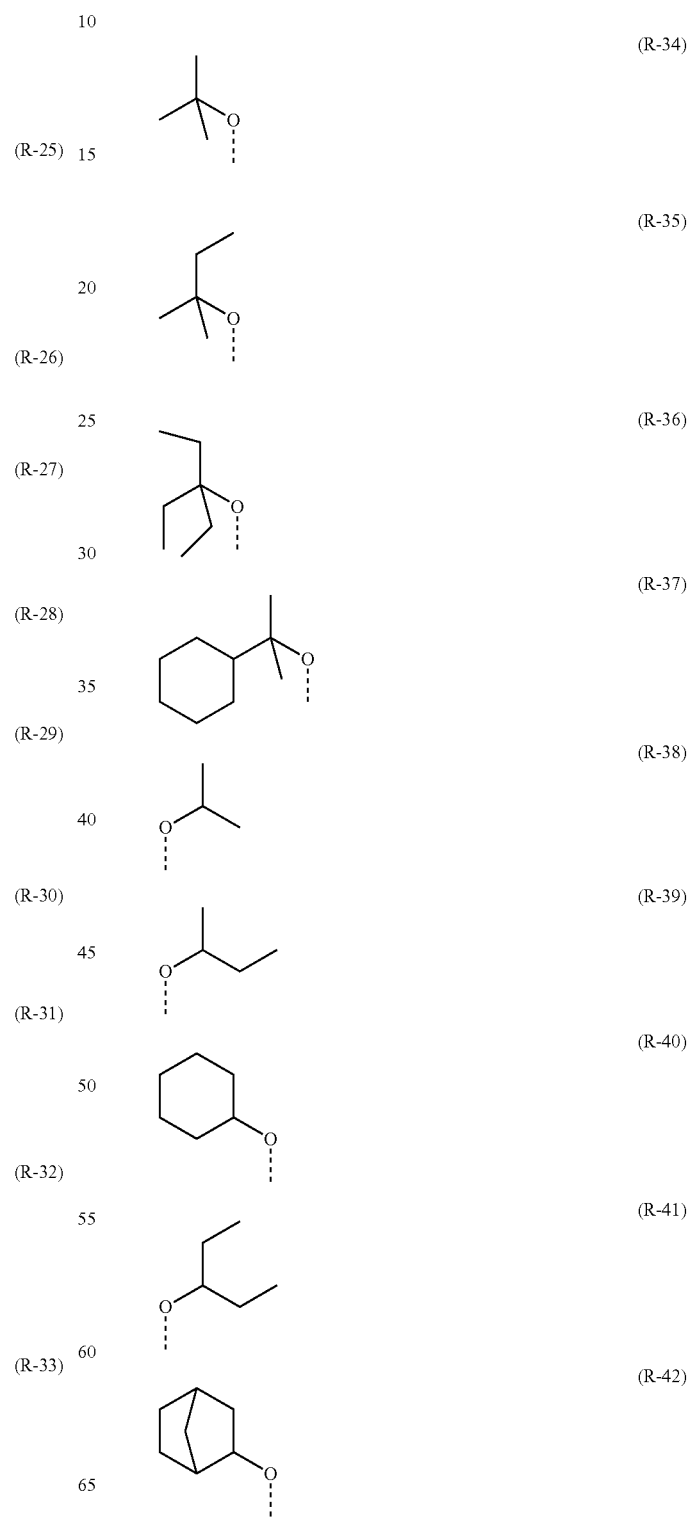

(R-43)
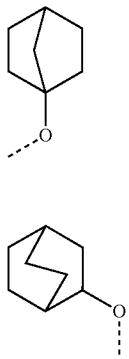
(R-44)
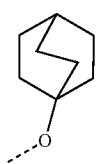
(R-45)
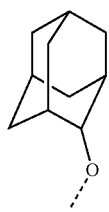
(R-46)
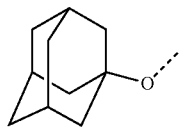
(R-47)
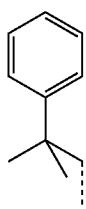
where the dotted bond indicates the linkage of these groups to the fluorescent base skeleton.
When the sterically demanding substituent is an aralkyl group, this aralkyl group is preferably selected from the structures of the following formulae (R-48) to (R-61):
(R-48)
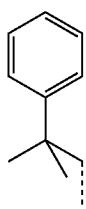
(R-49)
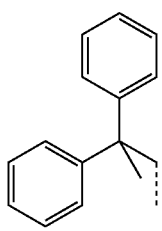
(R-50)
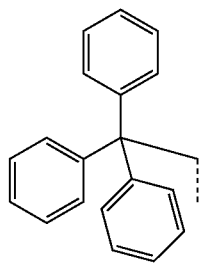
(R-51)
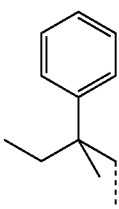
(R-52)
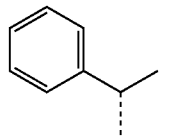
(R-53)
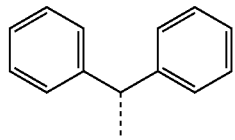
(R-54)
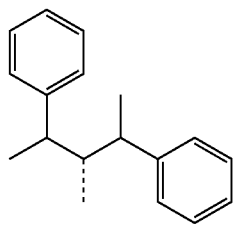
(R-55)
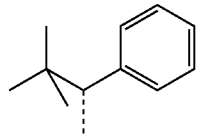
(R-56)
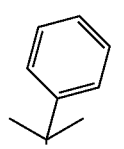
(R-57)
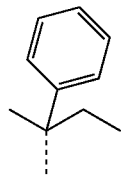

(R-58)

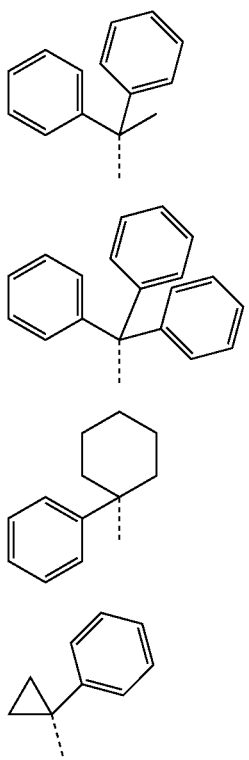

(R-59)

(R-60)

(R-61)

where the dotted bond indicates the linkage of these groups to the fluorescent base skeleton and the phenyl groups may each be substituted by one or more $R^a$ radicals, where $R^a$ is as defined below for ring (1) to ring (7).

When the sterically demanding substituent is an aromatic ring system, this aromatic ring system preferably has 6 to 30 aromatic ring atoms, more preferably 6 to 24 aromatic ring atoms. In addition, this aromatic ring system contains preferably only phenyl groups. In this case, the aromatic ring system is preferably selected from the structures of the following formulae (R-62) to (R-76):

(R-62)

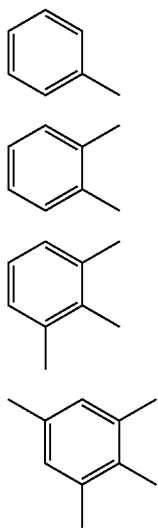

(R-63)

(R-64)

(R-65)

(R-66)

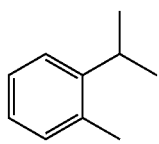

(R-67)

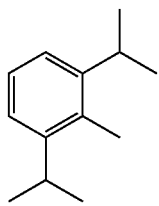

(R-68)

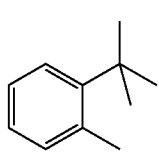

(R-69)

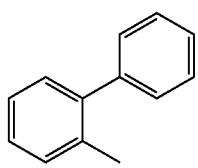

(R-70)

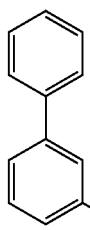
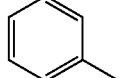

(R-71)

(R-72)

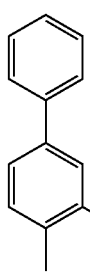
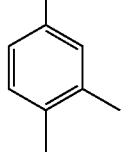

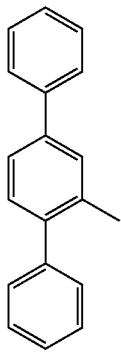
(R-73)

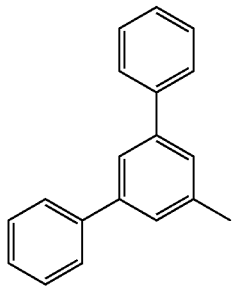
(R-74)

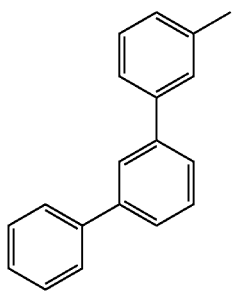
(R-75)

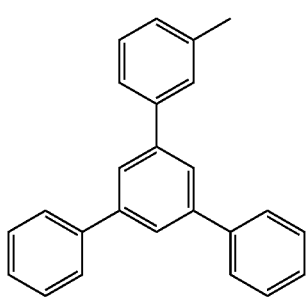
(R-76)

where the dotted bond indicates the linkage of these groups to the fluorescent base skeleton and the phenyl groups may each be substituted by one or more $R^a$ radicals, where $R^a$ is as defined below for ring (1) to ring (7).

Suitable sterically demanding groups are additionally fused-on aliphatic groups which preferably do not have any acidic protons in the benzylic position. Preference is given to the structures of the following formulae (Ring-1) to (Ring-7):

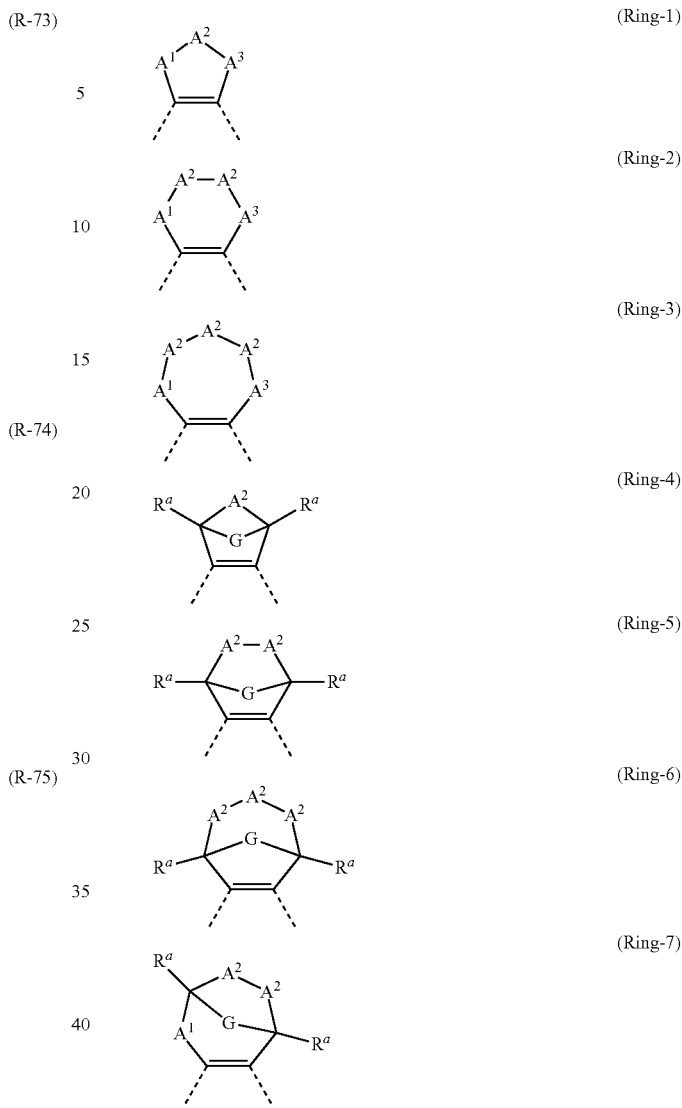

where the dotted bonds indicate the linkage of the two carbon atoms within the fluorescent base skeleton and in addition:

$A^1$, $A^2$, $A^3$ is the same or different at each instance and is $C(R^a)_2$, O or S;

G is an alkylene group which has 1, 2 or 3 carbon atoms and may be substituted by one or more $R^b$ radicals or an ortho-bonded arylene group which has 5 to 14 aromatic ring atoms and may be substituted by one or more $R^b$ radicals;

$R^a$ is the same or different at each instance and is selected from the group consisting of H, D, F, a straight-chain alkyl group having 1 to 40 carbon atoms or a branched or cyclic alkyl group having 3 to 40 carbon atoms, each of which may be substituted by one or more $R^b$ radicals, an aromatic ring system having 5 to 60 aromatic ring atoms, each of which may be substituted by one or more $R^b$ radicals, or an aralkyl group which has 5 to 60 aromatic ring atoms and may be substituted by one or more $R^b$ radicals, where it is optionally possible for two or more adjacent $R^a$ substituents to form a ring system which may be substituted by one or more $R^b$ radicals;

$R^b$ is selected from the group consisting of H, D, F, an aliphatic hydrocarbyl radical having 1 to 20 carbon atoms, an aromatic ring system having 5 to 30 aromatic ring atoms, where two or more adjacent $R^b$ substituents together may form a ring system;

with the proviso that no two heteroatoms in these groups are bonded directly to one another.

In the structures (Ring-1) to (Ring-7) and the further embodiments of these structures specified as preferred, a double bond is formed in a formal sense between the two carbon atoms. This is a simplification of the chemical structure since these two carbon atoms are incorporated into the aromatic or heteroaromatic system of the fluorescent core and hence the bond between these two carbon atoms is formally between the bonding level of a single bond and that of a double bond. The drawing of the formal double bond should thus not be interpreted so as to limit the structure; instead, it will be apparent to the person skilled in the art that this is an aromatic bond.

When $R^a$ or $R^b$ is an aralkyl group or an aromatic ring system, it is preferable when these do not have any fused aryl groups having more than 10 carbon atoms in which aryl groups are fused directly to one another via a common edge. More preferably, it does not have any fused aryl groups at all in which aryl groups are fused directly to one another via a common edge.

It is preferable in the case of the (Ring-1) to (Ring-7) groups when they do not have any acidic benzylic protons. Benzylic protons are understood to mean protons which bind to a carbon atom bonded directly to the ligand. The absence of acidic benzylic protons in (Ring-1) to (Ring-3) and (Ring-7) is achieved by virtue of $A^1$ and $A^3$, when they are $C(R^a)_2$, being defined such that $R^a$ is not H or D. This is therefore a preferred embodiment. The absence of acidic benzylic protons in (Ring-4) to (Ring-7) is achieved in that the structure is a bicyclic structure. Because of the rigid spatial arrangement, $R^a$, when it is H, is much less acidic than benzylic protons since the corresponding anion of the bicyclic structure is not mesomerically stabilized. Even when $R^a$ in (Ring-4) to (Ring-7) is H, this is therefore a non-acidic proton in the context of the present application.

In a preferred embodiment of the structure (Ring-1) to (Ring-7), not more than one of the $A^1$, $A^2$ and $A^3$ groups is a heteroatom, especially O, and the other groups are $C(R^a)_2$, or $A^1$ and $A^3$ are the same or different at each instance and are O, and $A^2$ is $C(R^a)_2$. In a particularly preferred embodiment of the invention, $A^1$, $A^2$ and $A^3$ are the same or different at each instance and are $C(R^a)_2$.

Preferred embodiments of (Ring-1) are thus the structures (Ring-1A), (Ring-1B), (Ring-1C) and (Ring-1D)

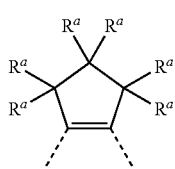

(Ring-1A)

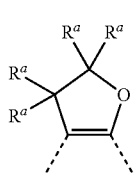

(Ring-1B)

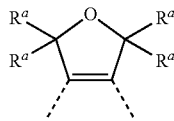

(Ring-1C)

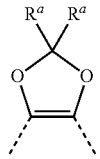

(Ring-1D)

where $R^a$ have the definitions given above. In this case, $R^a$ in the benzylic positions is preferably not H or D.

Preferred embodiments of (Ring-2) are the structures (Ring-2A) to (Ring-2F)

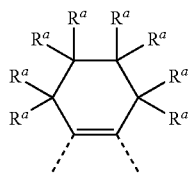

(Ring-2A)

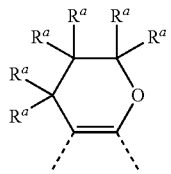

(Ring-2B)

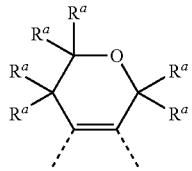

(Ring-2C)

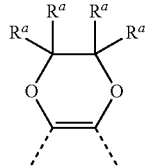

(Ring-2D)

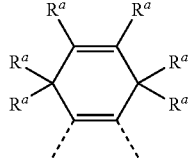

(Ring-2E)

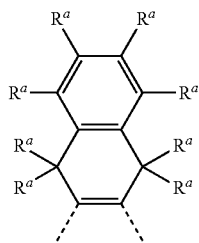
(Ring-2F)

where $R^a$ has the definitions given above. In this case, $R^a$ in the benzylic positions is preferably not H or D.

Preferred embodiments of (Ring-3) are the structures (Ring-3A) to (Ring-3E)

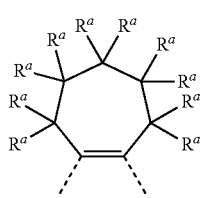
(Ring-3A)

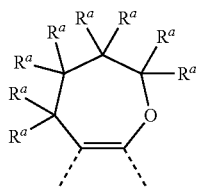
(Ring-3B)

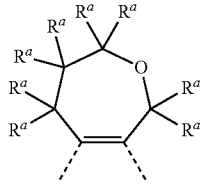
(Ring-3C)

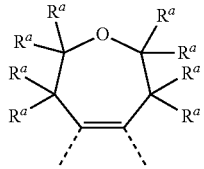
(Ring-3D)

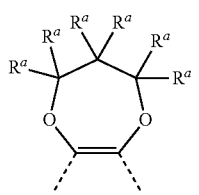
(Ring-3E)

where $R^a$ has the definitions given above. In this case, $R^a$ in the benzylic positions is preferably not H or D.

In a preferred embodiment of (Ring-4), the $R^a$ radicals bonded to the bridgehead are H, D, F or CH$_3$. Further preferably, $A^2$ is G($R^a$)$_2$ or O, and more preferably C($R^3$)$_2$. Preferred embodiments of (Ring-4) are thus the structures (Ring-4A) and (Ring-4B)

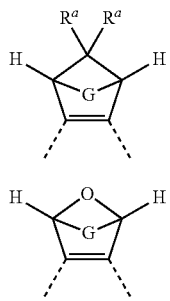
(Ring-4A)

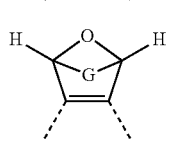
(Ring-4B)

where the symbols used have the definitions given above.

In a preferred embodiment of (Ring-5), (Ring-6) and (Ring-7), the $R^a$ radicals bonded to the bridgehead are H, D, F or CH$_3$. Further preferably, $A^2$ is C($R^a$)$_2$. Preferred embodiments of (Ring-5), (Ring-6) and (Ring-7) are thus the structures (Ring-5A), (Ring-6A) and (Ring-7A)

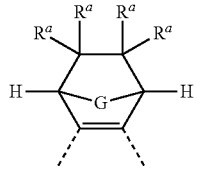
(Ring-5A)

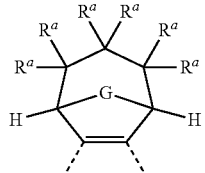
(Ring-6A)

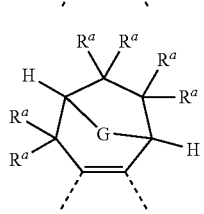
(Ring-7A)

where the symbols used have the definitions given above. In this case, $R^a$ in the benzylic positions in (Ring-7A) is preferably not H or D.

Further preferably, the G group in the abovementioned formulae is a 1,2-ethylene group which may be substituted by one or more $R^b$ radicals, where $R^b$ is preferably the same or different at each instance and is H or an alkyl group having 1 to 4 carbon atoms, or an ortho-arylene group which has 6 to 10 carbon atoms and may be substituted by one or more $R^b$ radicals, but is preferably unsubstituted, especially an ortho-phenylene group which may be substituted by one or more $R^b$ radicals, but is preferably unsubstituted.

In a further preferred embodiment of the invention, the $R^a$ substituent, especially when it is bonded in a benzylic position, in (Ring-1) to (Ring-7) and in the preferred embodiments, is the same or different at each instance and is F, a straight-chain alkyl group having 1 to 8 carbon atoms or a branched or cyclic alkyl group having 3 to 10 carbon atoms, where one or more hydrogen atoms in each case may be replaced by D or F, or an aromatic ring system which has 6 to 14 aromatic ring atoms and may be substituted in each case by one or more $R^b$ radicals; at the same time, two $R^a$ radicals bonded to the same carbon atom may together form a ring system and thus form a spiro system; in addition, $R^a$ may form an aliphatic ring system with a further $R^a$ radical. In this way, for example, a homoadamantane radical may be formed.

In a particularly preferred embodiment of the invention, $R^a$, especially when it is bonded in a benzylic position, in (Ring-1) to (Ring-7) and in the preferred embodiments, is the same or different at each instance and is F, a straight-chain alkyl group having 1 to 3 carbon atoms, especially methyl, or an aromatic ring system which has 6 to 12 aromatic ring atoms, especially phenyl, and may be substituted in each case by one or more $R^b$ radicals, but is preferably unsubstituted; at the same time, two $R^a$ radicals bonded to the same carbon atom may together form a ring system and thus form a spiro system; in addition, $R^a$ may form an aliphatic ring system with a further $R^a$ radical. In this way, for example, a homoadamantane radical may be formed.

Examples of particularly suitable (Ring-1) groups are the (Ring-1-1) to (Ring-1-49) groups listed hereinafter, particular preference being given to (Ring-1-1), (Ring-1-2) and (Ring-1-27):

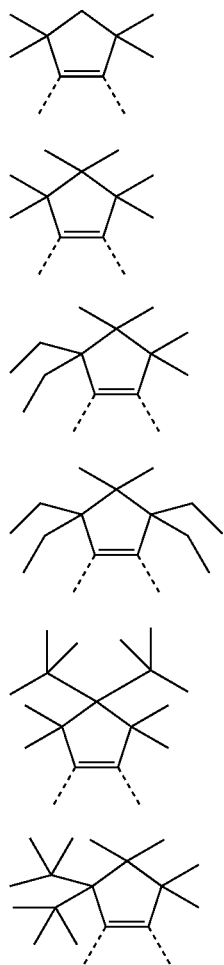

(Ring-1-1)

(Ring-1-2)

(Ring-1-3)

(Ring-1-4)

(Ring-1-5)

(Ring-1-6)

(Ring-1-7)

(Ring-1-8)

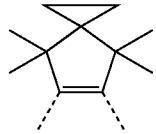

(Ring-1-9)

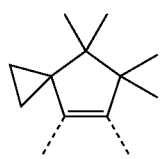

(Ring-1-10)

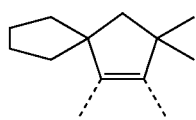

(Ring-1-11)

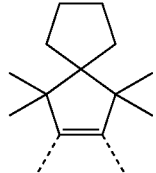

(Ring-1-12)

(Ring-1-13)

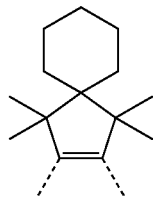

(Ring-1-14)

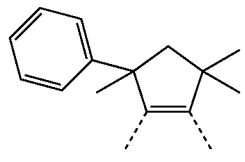

(Ring-1-15)

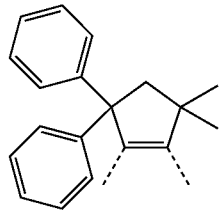

(Ring-1-16)

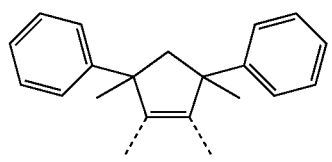

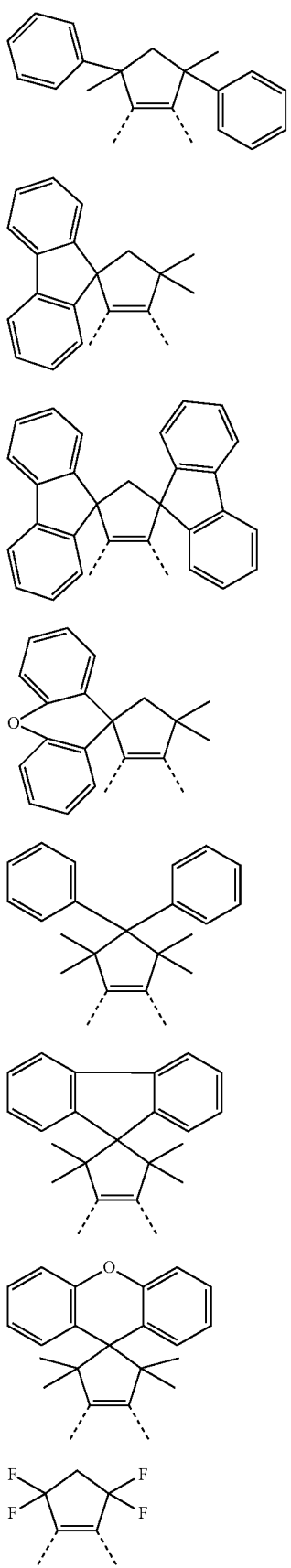
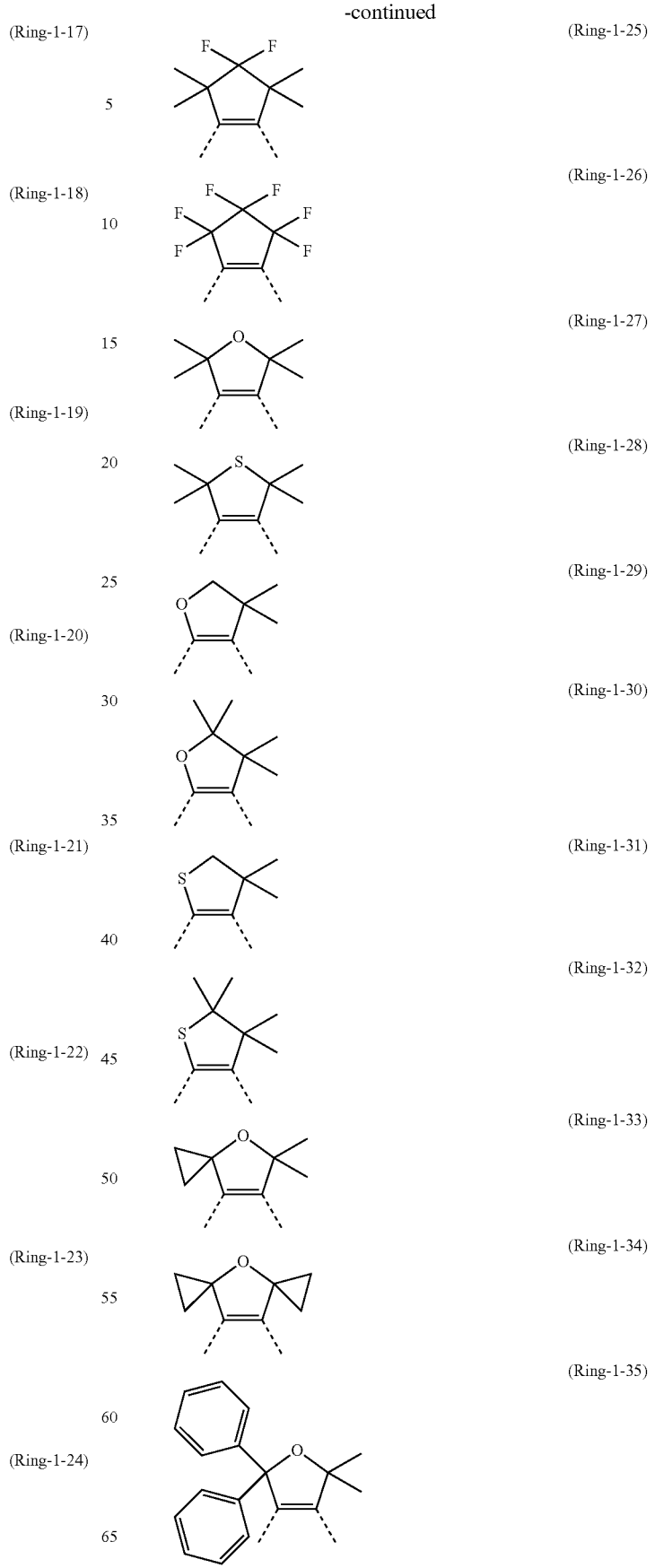

(Ring-1-36)
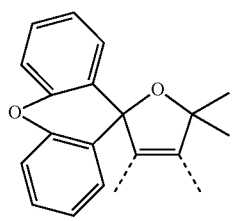
(Ring-1-37)
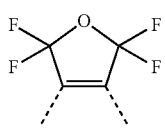
(Ring-1-38)
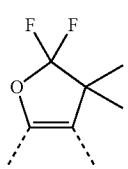
(Ring-1-39)
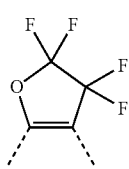
(Ring-1-40)
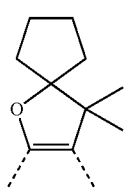
(Ring-1-41)
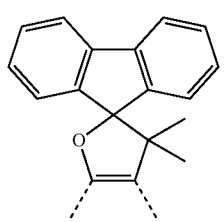
(Ring-1-42)
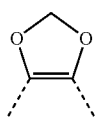
(Ring-1-43)
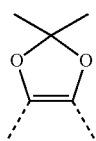
(Ring-1-44)
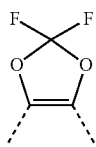
(Ring-1-45)
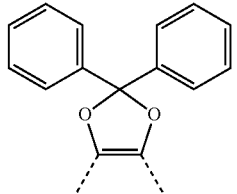
(Ring-1-46)
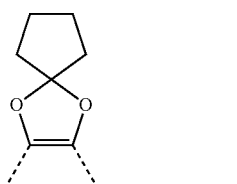
(Ring-1-47)
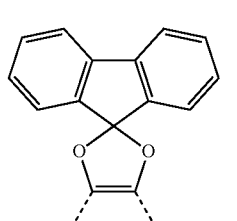
(Ring-1-48)
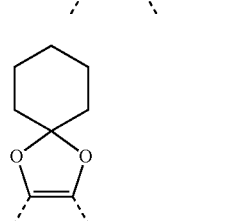
(Ring-1-49)
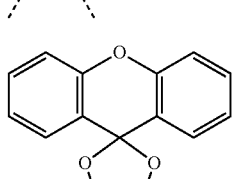
Examples of particularly suitable (Ring-2) groups are the (Ring-2-1) to (Ring-2-12) groups listed hereinafter, particular preference being given to (Ring-2-1):
(Ring-2-1)
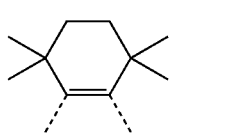
(Ring-2-2)
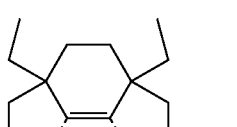
(Ring-2-3)
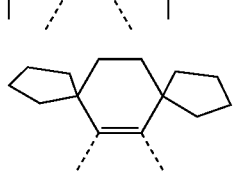

(Ring-2-4)
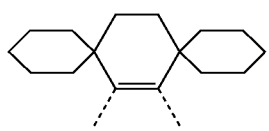

(Ring-2-5)
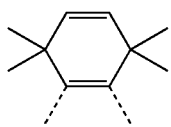

(Ring-2-6)
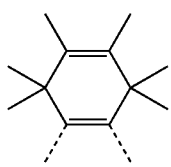

(Ring-2-7)
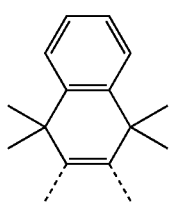

(Ring-2-8)
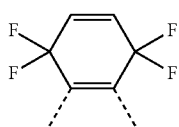

(Ring-2-9)
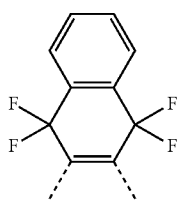

(Ring-2-10)

(Ring-2-11)
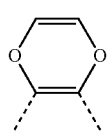

(Ring-2-12)
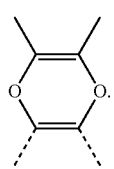

Examples of particularly suitable (Ring-3), (Ring-6) and (Ring-7) groups are the (Ring-3-1), (Ring-6-1), (Ring-7-1) and (Ring-7-2) groups listed hereinafter, particular preference being given to (Ring-7-1) and (Ring-7-2):

(Ring-3-1)
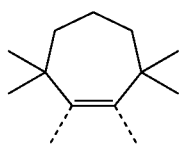

(Ring-6-1)
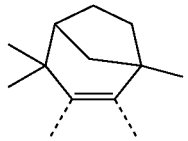

(Ring-7-1)
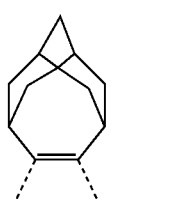

(Ring-7-2)
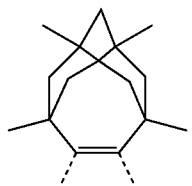

Examples of particularly suitable (Ring-4) groups are the (Ring-4-1) to (Ring-4-22) groups listed hereinafter, particular preference being given to (Ring-4-4), (Ring-4-5) and (Ring-4-7):

(Ring-4-1)

(Ring-4-2)
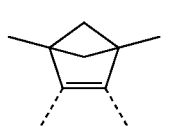

(Ring-4-3)
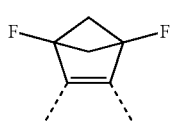

(Ring-4-4)
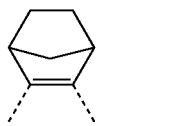

(Ring-4-5)
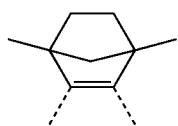

-continued
(Ring-4-6)
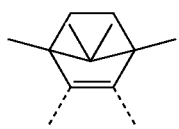
(Ring-4-7)
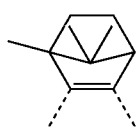
(Ring-4-8)
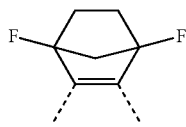
(Ring-4-9)
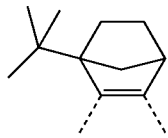
(Ring-4-10)
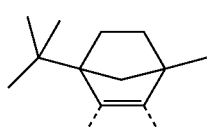
(Ring-4-11)
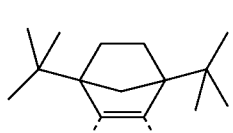
(Ring-4-12)
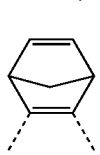
(Ring-4-13)
(Ring-4-14)
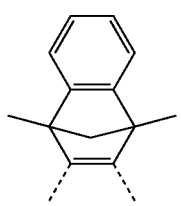
(Ring-4-15)
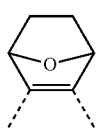
(Ring-4-16)
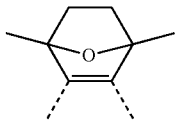
(Ring-4-17)
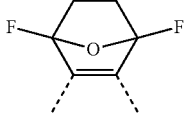
(Ring-4-18)
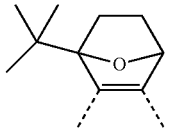
(Ring-4-19)
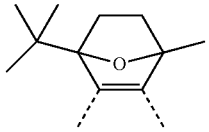
(Ring-4-20)
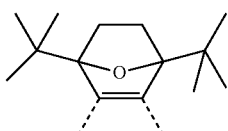
(Ring-4-21)
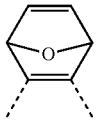
(Ring-4-22)
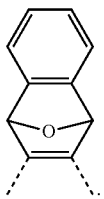
Examples of particularly suitable (Ring-5) groups are the (Ring-5-1) to (Ring-5-5) groups listed hereinafter, particular preference being given to (Ring-5-1) and (Ring-5-3):
(Ring-5-1)
(Ring-5-2)
(Ring-5-3)
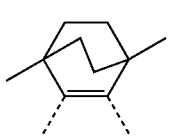

(Ring-5-4)

(Ring-5-5)

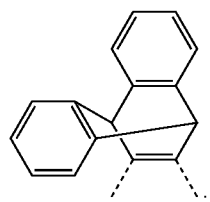

Schemes 1 to 8 which follow show the synthesis of structures of this kind. In these schemes, R in each case is a sterically demanding substituent as described above, and * indicates the positions where an aliphatic cycle as described above is fused on. Alternatively, in scheme 1 and scheme 5, a curved line indicates the fused-on aliphatic cycle. The synthesis can preferably be effected here by means of a Povarov cyclization reaction as shown in scheme 1. These reaction types are common knowledge to the person skilled in the art.

Scheme 1

1) Povarov reaction

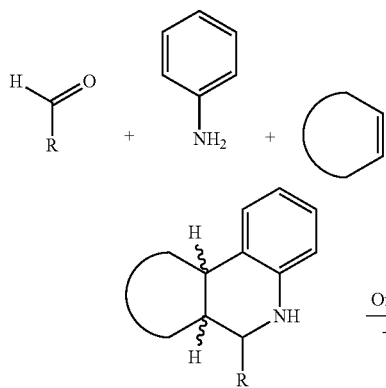

2)

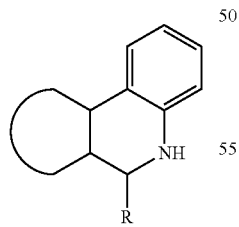

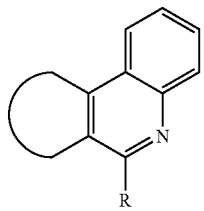

R: preferably aromatic/heteroaromatic

Scheme 2: Accessibility of various heteroaromatics by the synthesis shown in scheme 1 proceeding from monoamines 6 pi

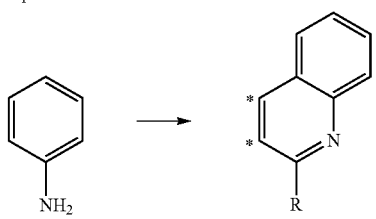

10 pi

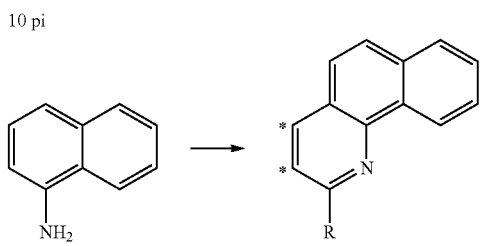

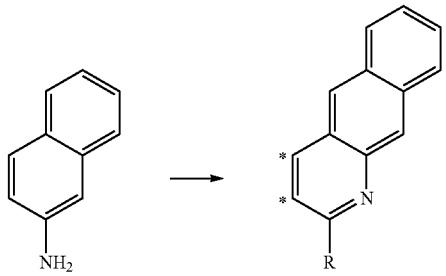

14 pi linear

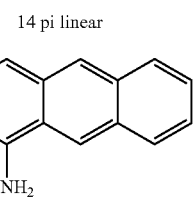

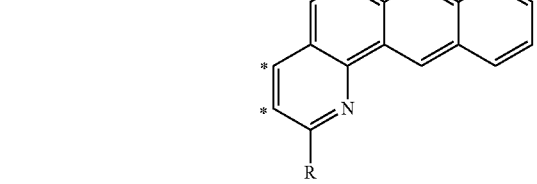

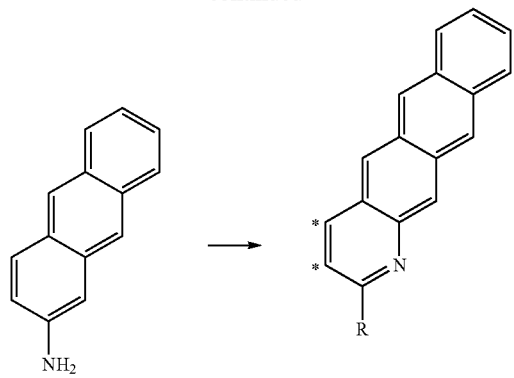
14 pi angled
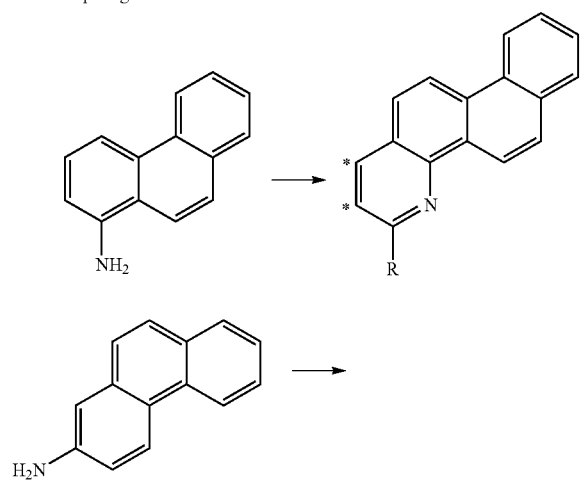
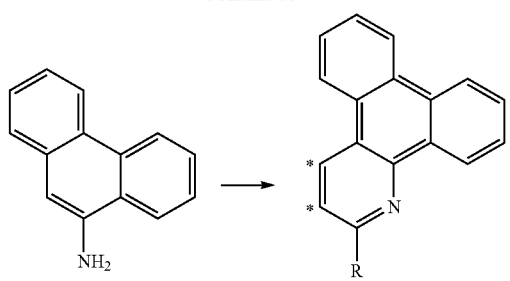
Scheme 3: Accessibility of various heteroaromatics by the synthesis shown in scheme 1 proceeding from diamines
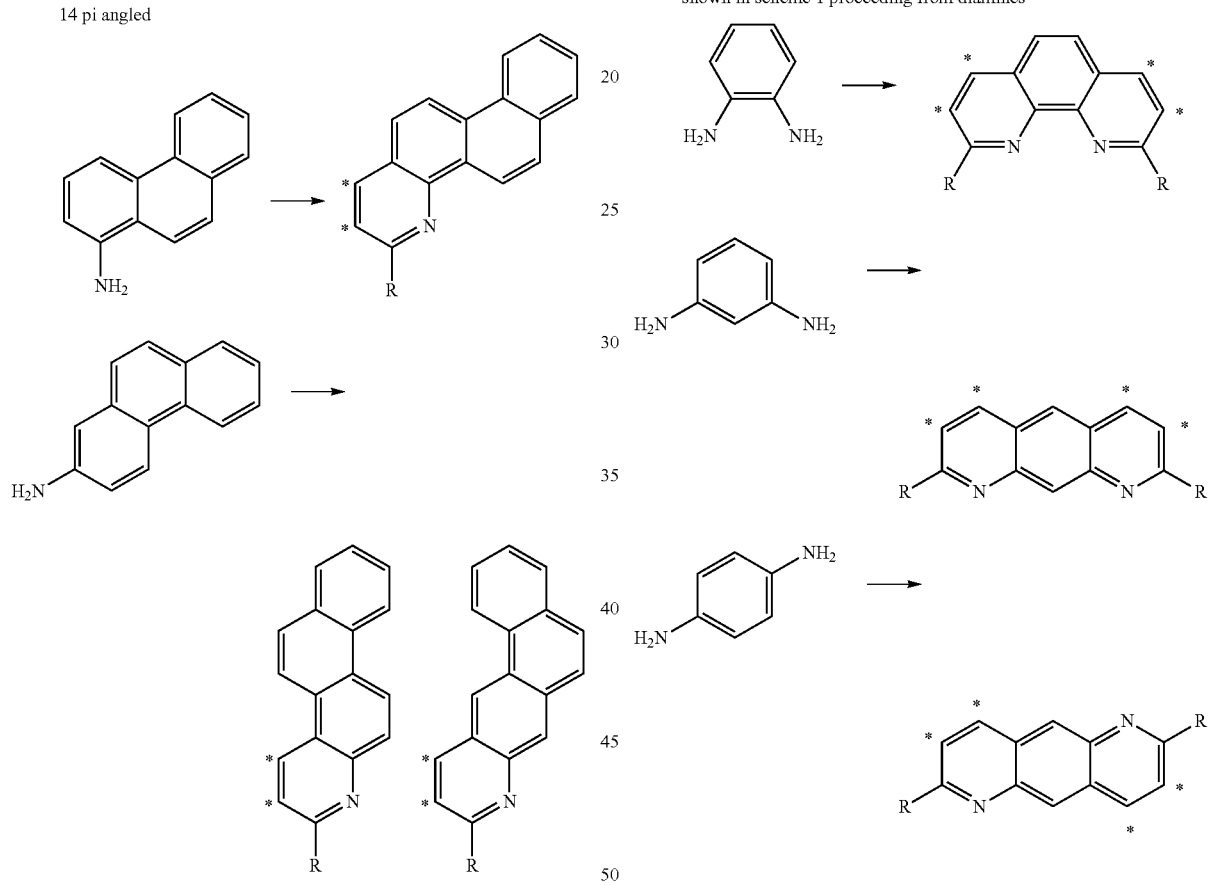
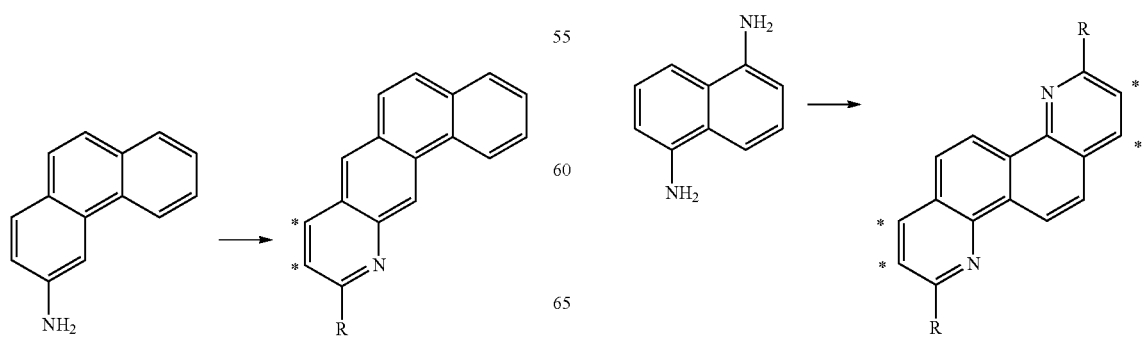

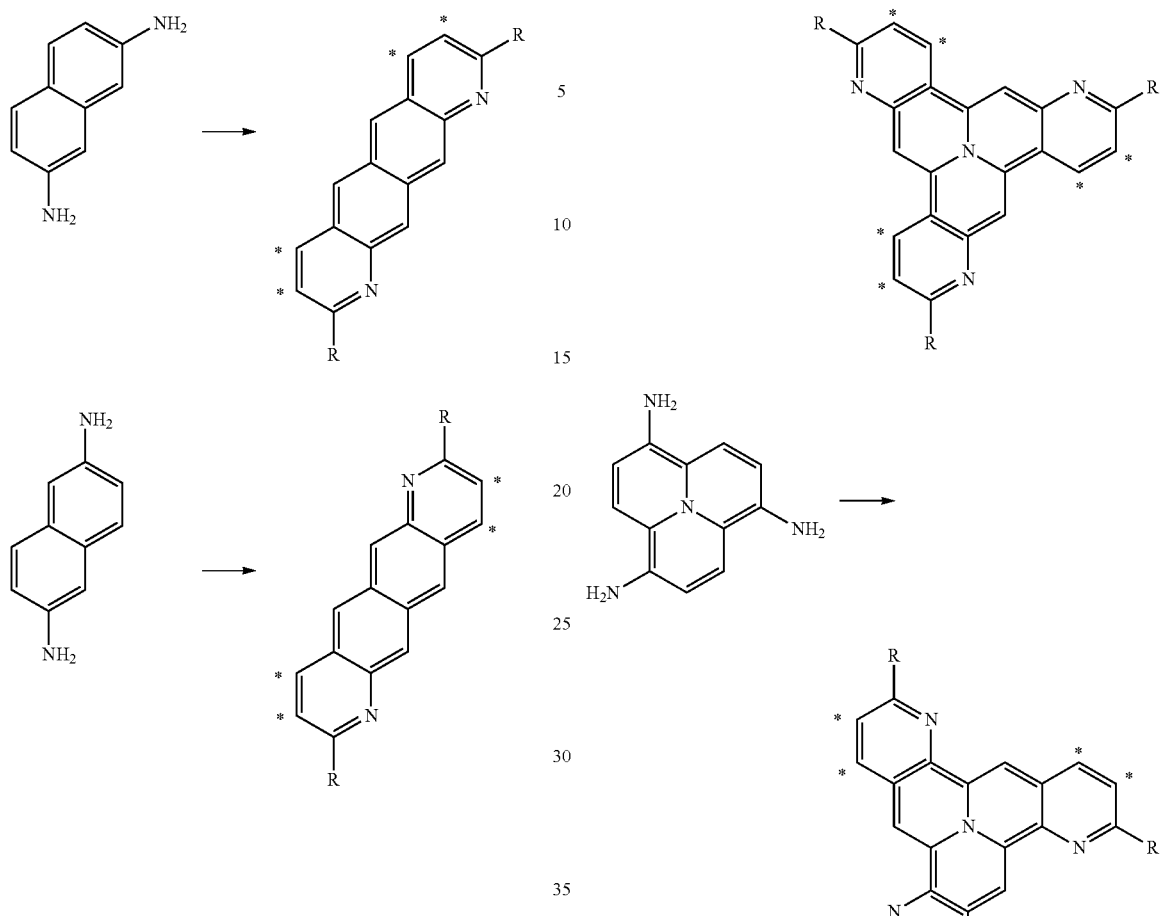
Scheme 4: Accessibility of various heteroaromatics by the synthesis shown in scheme 1 proceeding from tri- or tetramines
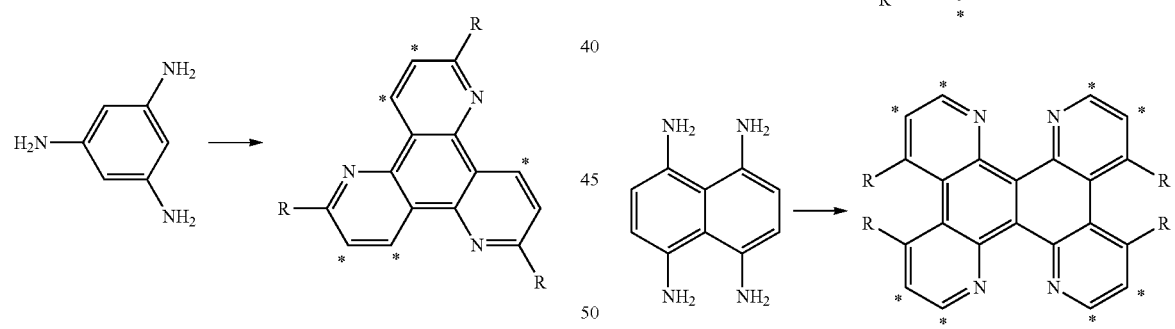
Alternatively, it is possible to synthesize other substitution patterns by the reaction shown in scheme 5.
Scheme 5: Accessibility of other substitution patterns
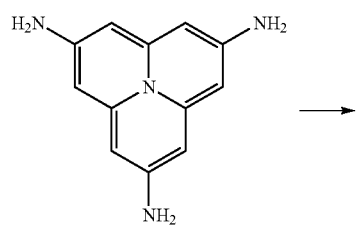
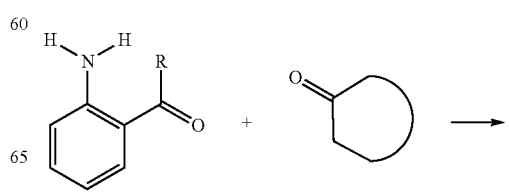

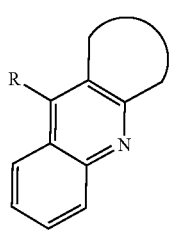
Scheme 6: Accessibility of various heteroaromatics by the synthesis shown in scheme 5 proceeding from monoamines
6 pi
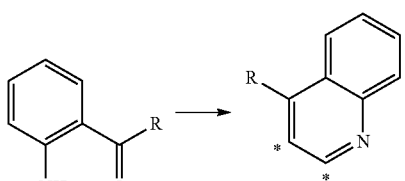
10 pi
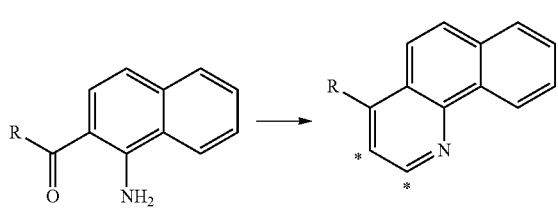
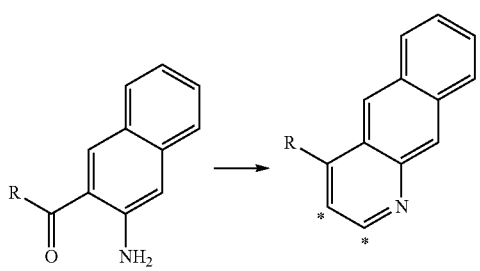
14 pi linear
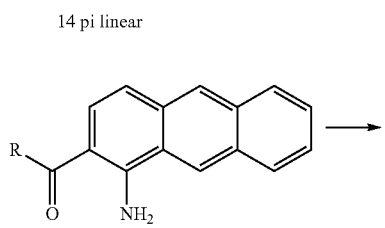
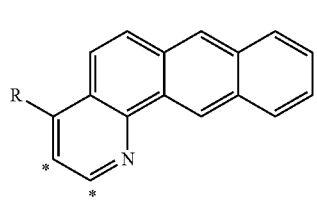
14 pi angled
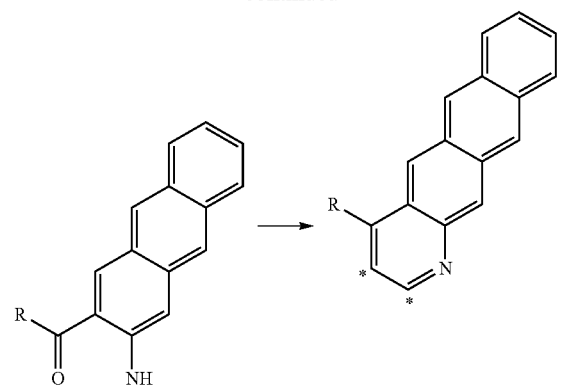
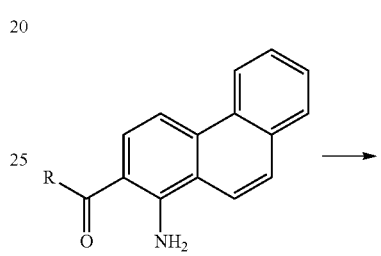
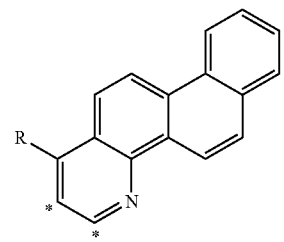
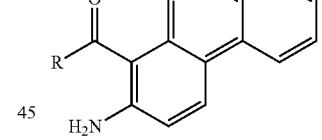
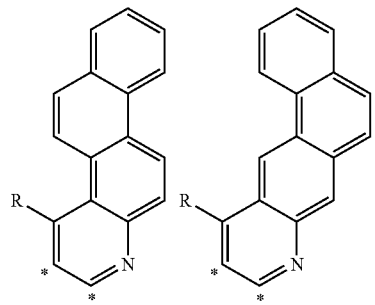
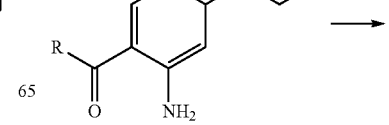

67
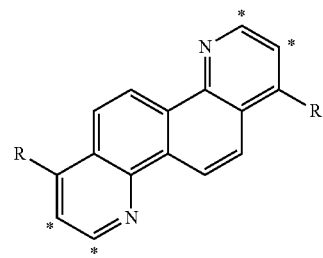
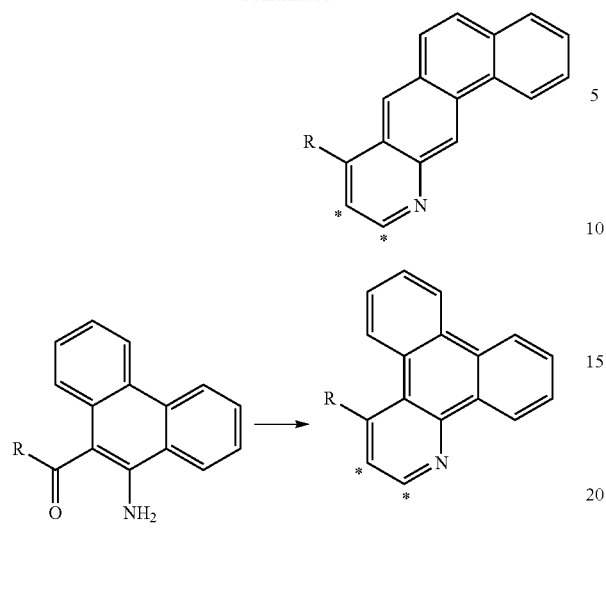
Scheme 7: Accessibility of various heteroaromatics by the synthesis shown in scheme 5 proceeding from diamines
68
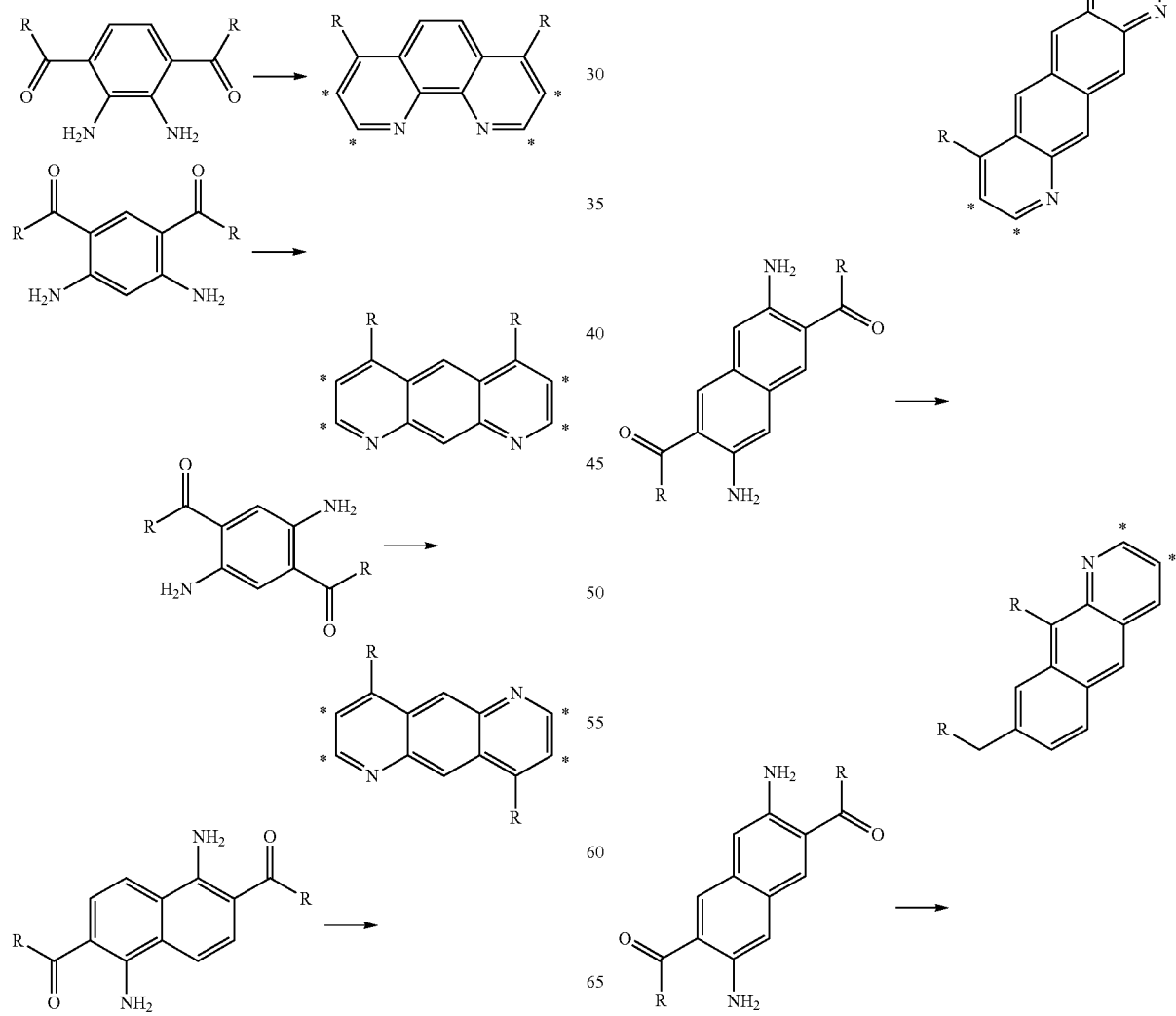

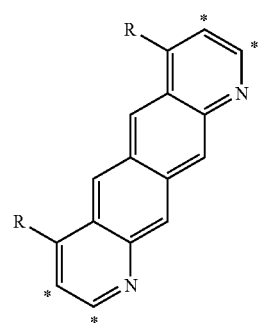
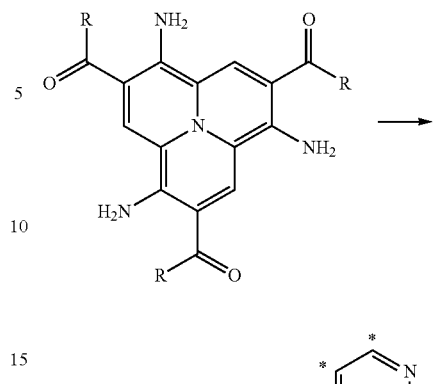
Scheme 8: Accessibility of various heteroaromatics by the synthesis shown in scheme 5 proceeding from triamines
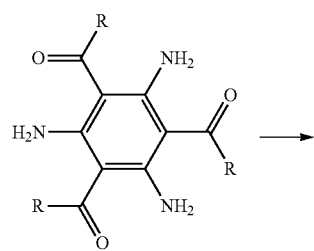
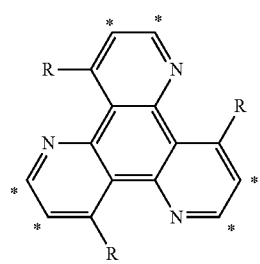
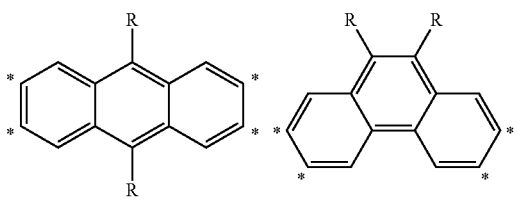
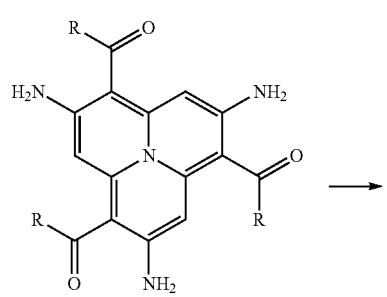
Suitable aromatic fluorescent base skeletons having fused-on aliphatic cycles are the structures depicted below, where * in each case indicates the positions by which the aliphatic cycles are fused on:
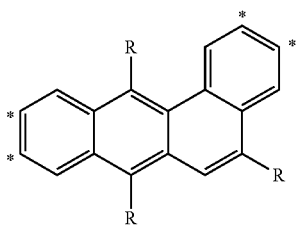
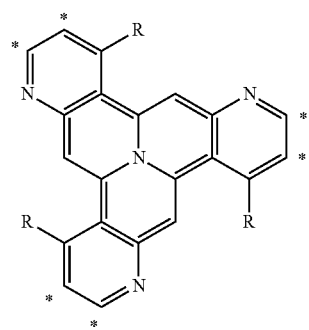
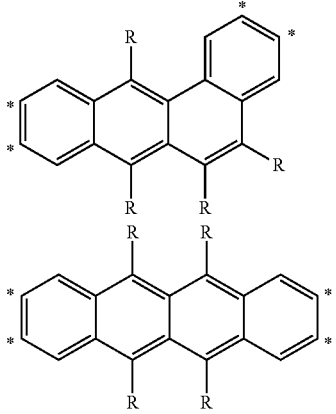

-continued

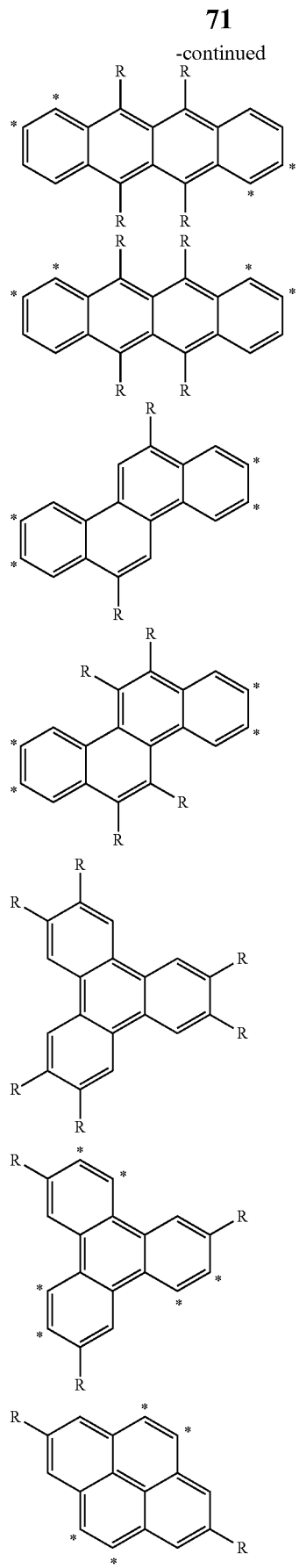

-continued

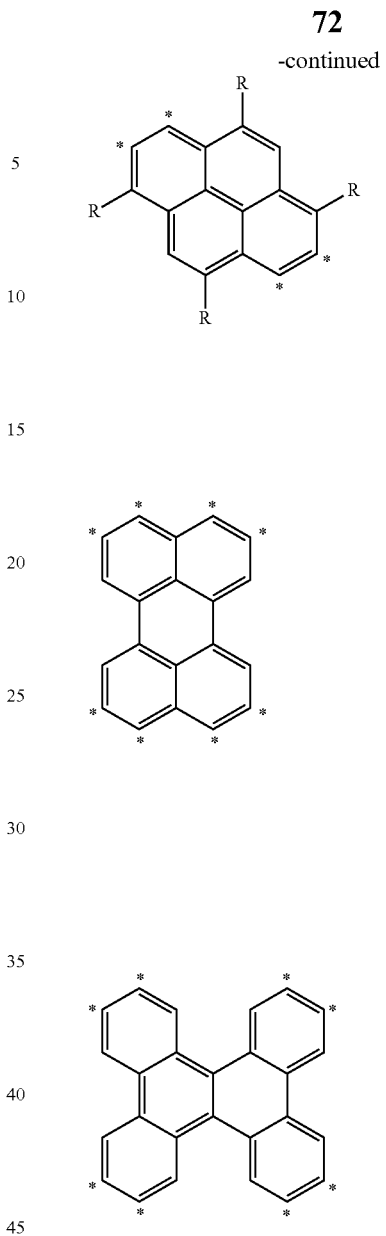

In these structures, R in each case is preferably a sterically demanding substituent as defined above.

It is preferable when, in the sterically shielded fluorescent compounds, not more than two unsubstituted carbon or nitrogen atoms are present between two substituents, more preferably not more than one unsubstituted carbon or nitrogen atom.

Examples of sterically shielded fluorescent compounds having high steric shielding are shown below. The shielding parameter S reported was determined assuming that the fluorescent compound is used in combination with the TADF compound D1 (see examples section). For combination with other TADF compounds, the shielding parameters may be different.

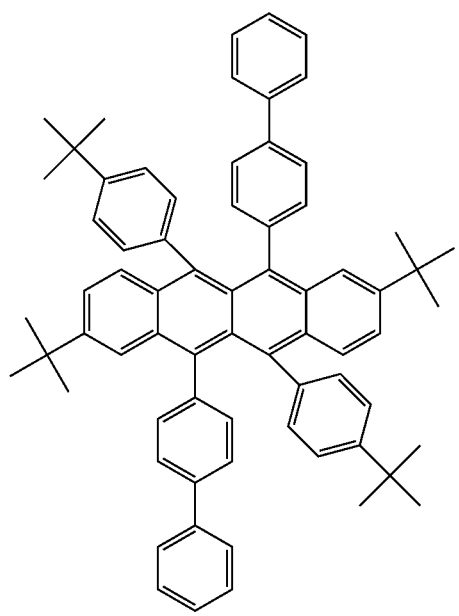
SE1, S = 0.518
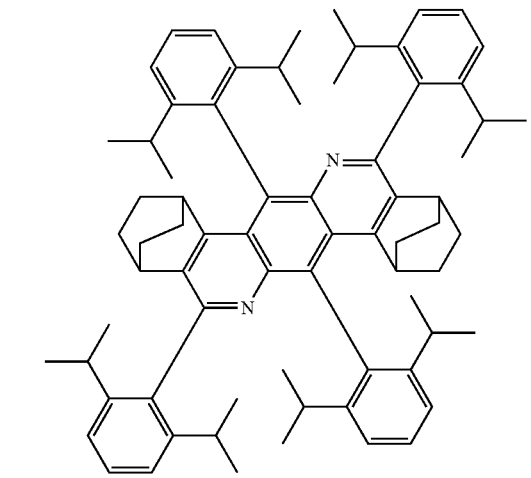
S = 0.489
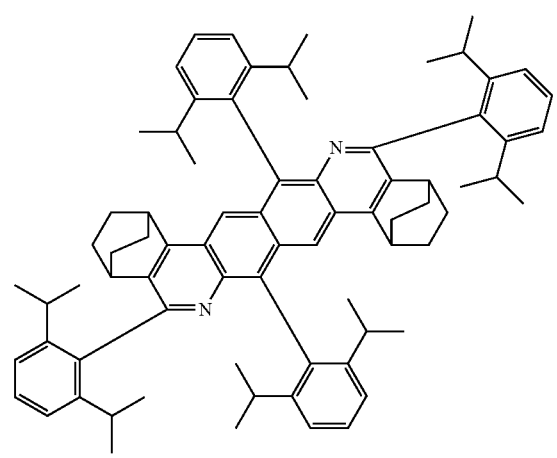
S = 0.510
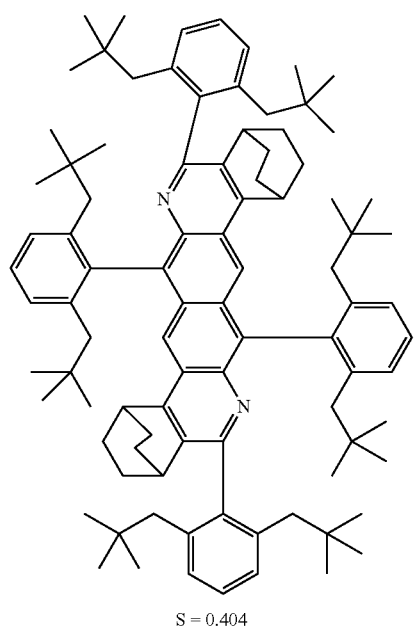
S = 0.404
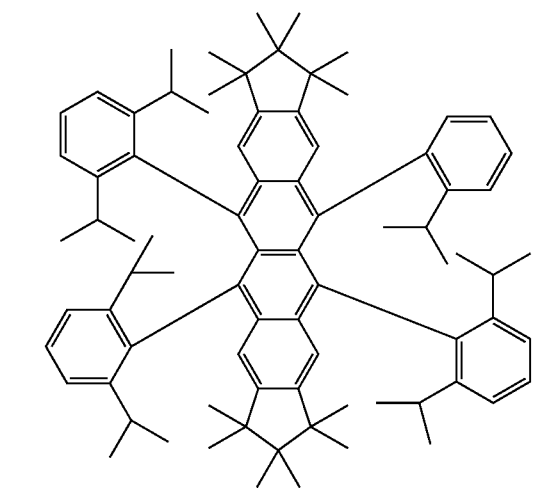
S = 0.521

-continued

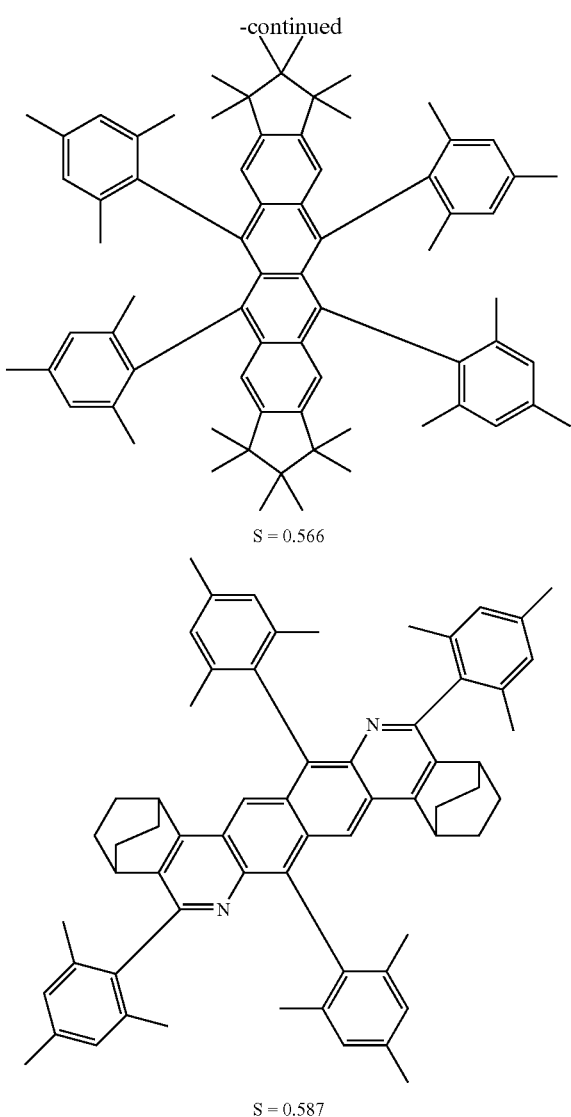

S = 0.566

S = 0.587

There follows a more particular description of the matrix compound, if the emitting layer comprises a matrix compound.

In a preferred embodiment of the invention, the matrix contribution makes no significant contribution, if any, to the emission of the mixture.

It is preferable that the lowest triplet energy of the matrix compound is not more than 0.1 eV lower than the triplet energy of the TADF compound.

Especially preferably, $T_1(\text{matrix}) \geq T_1(\text{TADF})$.
More preferably: $T_1(\text{matrix}) - T_1(\text{TADF}) \geq 0.1$ eV;
most preferably: $T_1(\text{matrix}) - T_1(\text{TADF}) \geq 0.2$ eV.

$T_1(\text{matrix})$ here is the lowest triplet energy of the matrix compound and $T_1(\text{TADF})$ is the lowest triplet energy of the TADF compound. The triplet energy of the matrix compound $T_1(\text{matrix})$ is determined here by quantum-chemical calculation, as described in general terms in the examples section at the back.

Examples of suitable matrix compounds which can be used in the emitting layer of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, dibenzofuran derivatives, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, pyrimidine derivatives, quinoxaline derivatives, Zn complexes, Al complexes or Be complexes, for example according to EP 652273 or WO 2009/062578, or bridged carbazole derivatives, for example according to US 2009/0136779, WO 2010/050778, WO 2011/042107 or WO 2011/088877. These are incorporated into the present invention by reference. It is also possible to use mixtures of two or more of these matrix materials.

Preferably, the matrix compound has a glass transition temperature TG of greater than 70° C., more preferably greater than 90° C., most preferably greater than 110° C.

The matrix compounds are preferably charge-transporting, i.e. electron-transporting or hole-transporting, or bipolar compounds. Matrix compounds used may additionally also be compounds which are neither hole- nor electron-transporting in the context of the present application.

An electron-transporting compound in the context of the present invention is a compound having a LUMO≤−2.50 eV. Preferably, the LUMO is ≤−2.60 eV, more preferably ≤−2.65 eV, most preferably ≤−2.70 eV. The LUMO is the lowest unoccupied molecular orbital. The value of the LUMO of the compound is determined by quantum-chemical calculation, as described in general terms in the examples section at the back.

A hole-transporting compound in the context of the present invention is a compound having a HOMO≥−5.5 eV. The HOMO is preferably ≥−5.4 eV, more preferably ≥−5.3 eV. The HOMO is the highest occupied molecular orbital. The value of the HOMO of the compound is determined by quantum-chemical calculation, as described in general terms in the examples section at the back.

A bipolar compound in the context of the present invention is a compound which is both hole- and electron-transporting.

There follows a description of classes of compounds that are preferentially suitable as electron-conducting matrix compound in the organic electroluminescent device of the invention.

Suitable electron-conducting matrix compounds are selected from the substance classes of the triazines, the pyrimidines, the lactams, the metal complexes, especially the Be, Zn and Al complexes, the aromatic ketones, the aromatic phosphine oxides, the azaphospholes, the azaboroles substituted by at least one electron-conducting substituent, and the quinoxalines.

In a preferred embodiment of the invention, the electron-conducting compound is a purely organic compound, i.e. a compound containing no metals.

When the electron-conducting matrix compound is a triazine or pyrimidine compound, this compound is preferably selected from the compounds of the following formulae (M1) and (M2):

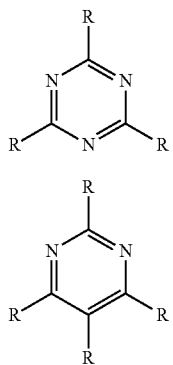

Formel (M1)

Formel (M2)

where the symbols used are as follows:

R is the same or different at each instance and is selected from the group consisting of H, D, F, Cl, Br, I, CN, NO$_2$, N(Ar)$_2$, N(R$^1$)$_2$, C(=O)Ar, C(=O)R$^1$, P(=O)(Ar)$_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more R$^1$ radicals, where one or more nonadjacent CH$_2$ groups may be replaced by R$^1$C=CR$^1$, C≡C, Si(R$^1$)$_2$, C=O, C=S, C=NR$^1$, P(=O)(R$^1$), SO, SO$_2$, NR$^1$, O, S or CONR$^1$ and where one or more hydrogen atoms may be replaced by D, F, Cl, Br, I, CN or NO$_2$, an aromatic or heteroaromatic ring system which has 5 to 80, preferably 5 to 60, aromatic ring atoms and may be substituted in each case by one or more R$^1$ radicals, an aryloxy or heteroaryloxy group which has 5 to 60 aromatic ring atoms and may be substituted by one or more R$^1$ radicals, or an aralkyl or heteroaralkyl group which has 5 to 60 aromatic ring atoms and may be substituted by one or more R$^1$ radicals, where it is optionally possible for two or more adjacent R substituents to form a monocyclic or polycyclic, aliphatic, aromatic or heteroaromatic ring system which may be substituted by one or more R$^1$ radicals;

R$^1$ is the same or different at each instance and is selected from the group consisting of H, D, F, Cl, Br, I, CN, NO$_2$, N(Ar)$_2$, N(R$^2$)$_2$, C(=O)Ar, C(=O)R$^2$, P(=O)(Ar)$_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more R$^2$ radicals, where one or more nonadjacent CH$_2$ groups may be replaced by R$^2$C=CR$^2$, C≡C, Si(R$^2$)$_2$, C=O, C=S, C=NR$^2$, P(=O)(R$^2$), SO, SO$_2$, NR$^2$, O, S or CONR$^2$ and where one or more hydrogen atoms may be replaced by D, F, Cl, Br, I, CN or NO$_2$, an aromatic or heteroaromatic ring system which has 5 to 60 aromatic ring atoms and may be substituted in each case by one or more R$^2$ radicals, an aryloxy or heteroaryloxy group which has 5 to 60 aromatic ring atoms and may be substituted by one or more R$^2$ radicals, or an aralkyl or heteroaralkyl group having 5 to 60 aromatic ring atoms, where it is optionally possible for two or more adjacent R$^1$ substituents to form a monocyclic or polycyclic, aliphatic, aromatic or heteroaromatic ring system which may be substituted by one or more R$^2$ radicals;

Ar is the same or different at each instance and is an aromatic or heteroaromatic ring system which has 5-60 aromatic ring atoms and may be substituted by one or more nonaromatic R$^2$ radicals; at the same time, two Ar radicals bonded to the same nitrogen atom or phosphorus atom may also be bridged to one another by a single bond or a bridge selected from N(R$^2$), C(R$^2$)$_2$, O and S;

R$^2$ is selected from the group consisting of H, D, F, CN, an aliphatic hydrocarbyl radical having 1 to 20 carbon atoms, an aromatic or heteroaromatic ring system having 5 to 30 aromatic ring atoms in which one or more hydrogen atoms may be replaced by D, F, Cl, Br, I or CN, where two or more adjacent R$^2$ substituents together may form a mono- or polycyclic, aliphatic, aromatic or heteroaromatic ring system.

Adjacent substituents in the context of the present application are substituents that are either bonded to the same carbon atom or that are bonded to carbon atoms that are in turn bonded directly to one another.

The definitions detailed hereinafter relate not just to the matrix compound but to the entire present invention, i.e. to the sterically shielded fluorescent compound.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatics joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or CH$_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethyihexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-30 or 5-60 aromatic ring atoms and may also be substituted in each case by the abovementioned R, $R^1$ or $R^2$ radicals is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the compounds of formula (M1) or formula (M2), at least one of the R substituents is an aromatic or heteroaromatic ring system. In formula (M1), more preferably all three R substituents are an aromatic or heteroaromatic ring system which may be substituted in each case by one or more $R^1$ radicals. In formula (M2), more preferably one, two or three R substituents are an aromatic or heteroaromatic ring system which may be substituted by one or more $R^1$ radicals, and the other R substituents are H. Preferred embodiments are thus the compounds of the following formulae (M1a) and (M2a) to (M2d):

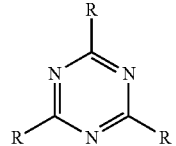

Formula (M1a)

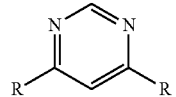

Formula (M2a)

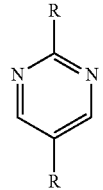

Formula (M2b)

Formula (M2c)

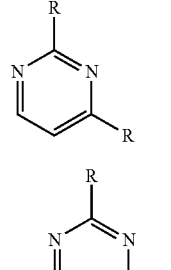

Formula (M2d)

where R is the same or different and is an aromatic or heteroaromatic ring system which has 5 to 60 aromatic ring atoms and may be substituted in each case by one or more $R^1$ radicals, and $R^1$ has the definition given above.

In the case of the pyrimidine compounds, preference is given to the compounds of the formulae (M2a) and (M2d), especially compounds of the formula (M2d).

Preferred aromatic or heteroaromatic ring systems contain 5 to 30 aromatic ring atoms, especially 6 to 24 aromatic ring atoms, and may be substituted by one or more $R^1$ radicals. At the same time, the aromatic or heteroaromatic ring systems preferably do not contain any fused aryl or heteroaryl groups in which more than two aromatic six-membered rings are fused directly to one another. More preferably, they do not contain any aryl or heteroaryl groups in which aromatic six-membered rings are fused directly to one another at all. The reason for this preference is the relatively high triplet energy of such substituents. Thus, it is particularly preferable when R does not, for example, have any naphthyl groups or higher fused aryl groups and likewise does not have any quinoline groups, acridine groups, etc. In contrast, it is possible that R includes, for example, carbazole groups, dibenzofuran groups, fluorene groups, etc., since there are no 6-membered aromatic or heteroaromatic rings fused directly to one another in these structures.

Preferred R substituents are the same or different at each instance and are selected from the group consisting of benzene, ortho-, meta- or para-biphenyl, ortho-terphenyl, meta-terphenyl, para-terphenyl or branched terphenyl, ortho-quaterphenyl, meta-quaterphenyl, para-quaterphenyl or branched quaterphenyl, 1-, 2-, 3- or 4-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, 2-, 3- or 4-pyridine, 2-, 4- or 5-pyrimidine, pyrazine, pyridazine, triazine, phenanthrene or combinations of two or three of these groups, each of which may be substituted by one or more $R^1$ radicals. It is also possible for one or more carbon atoms in the abovementioned aromatic ring systems to be replaced by N.

Preferred biphenyl, terphenyl and quaterphenyl groups are the groups of the following formulae (Bi-1) to (Bi-3), (Ter-1) to (Ter-3) and (Quater-1) to (Quater-4):

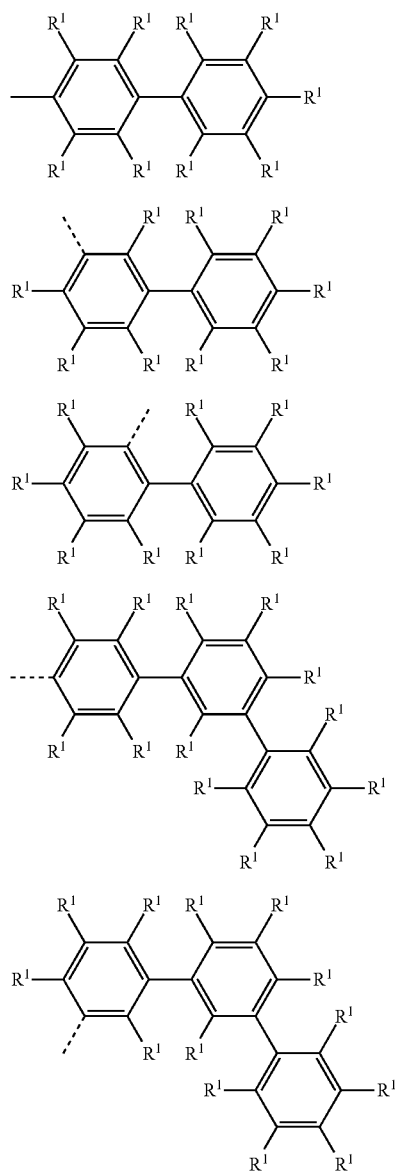

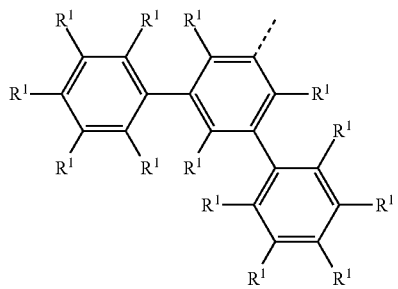

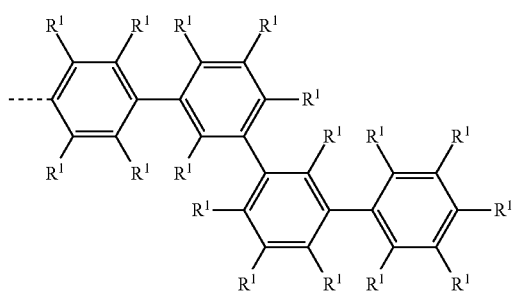

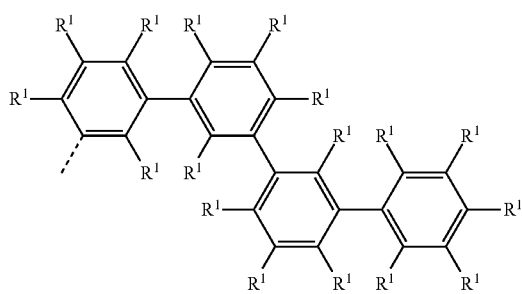

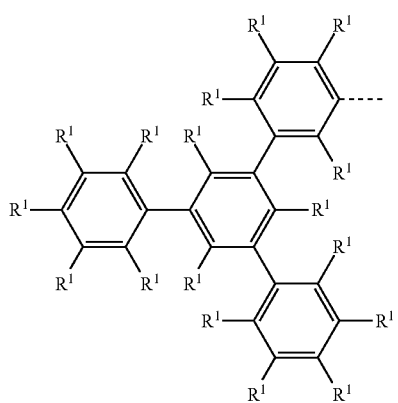

Quater-4

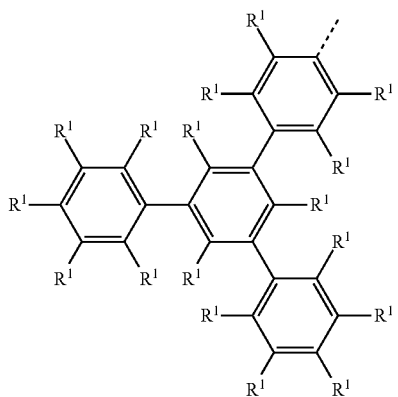

where R[1] has the definitions given above and the dotted bond indicates the bond to the triazine or pyrimidine.

It is especially preferable when at least one R group is selected from the structures of the following formulae (M3) to (M44):

Formula (M3)

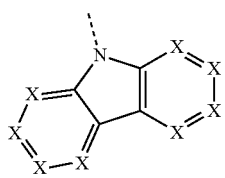

Formula (M4)

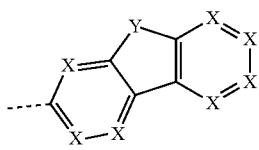

Formula (M5)

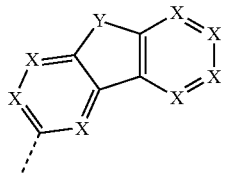

Formula (M6)

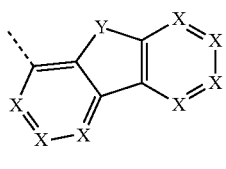

Formula (M7)

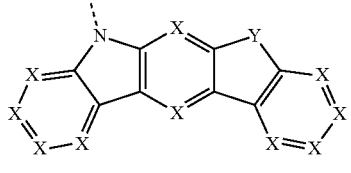

Formula (M8)

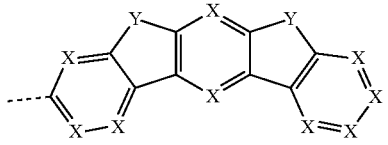

Formula (M9)

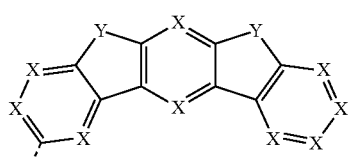

Formula (M10)

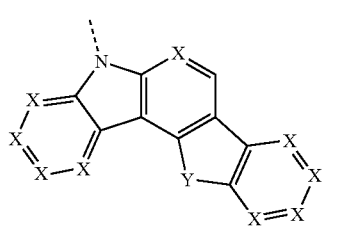

Formula (M11)

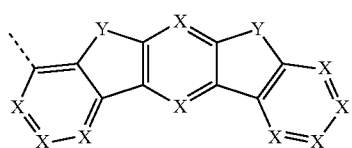

Formula (M12)

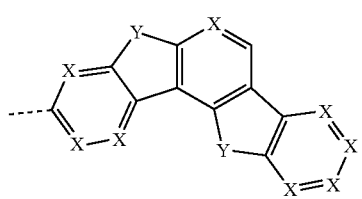

Formula (M13)

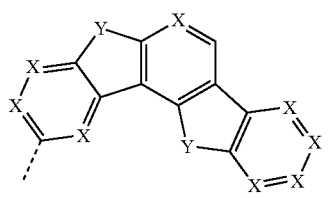

Formula (M14)

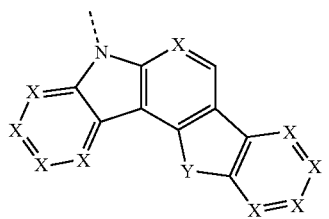

Formula (M15)

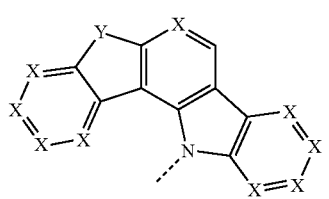

Formula (M16)

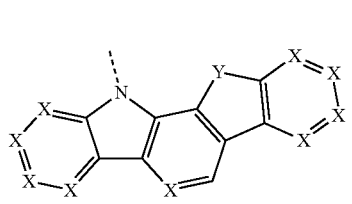

Formula (M17)
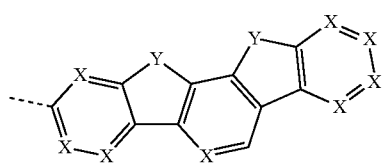
Formula (M18)
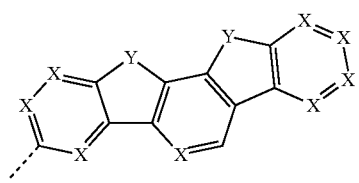
Formula (M19)
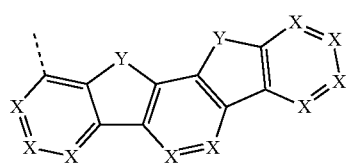
Formula (M20)
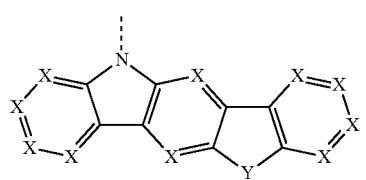
Formula (M21)
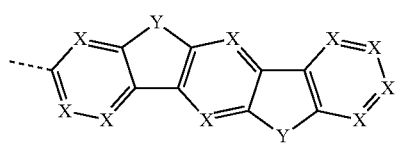
Formula (M22)
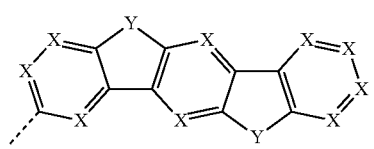
Formula (M23)
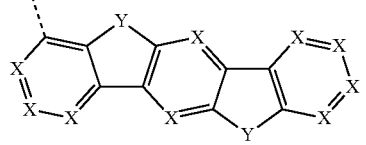
Formula (M24)
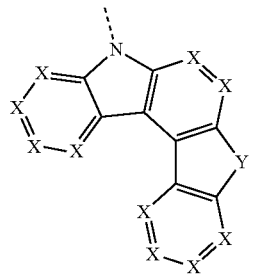
Formula (M25)
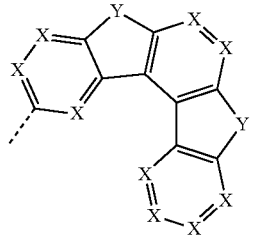
Formula (M26)
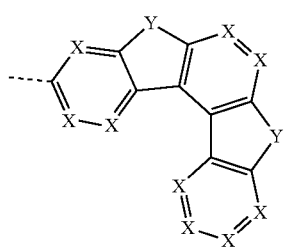
Formula (M27)
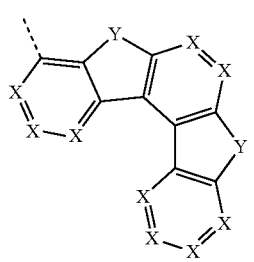
Formula (M28)
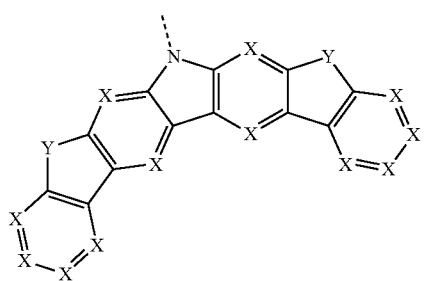
Formula (M29)
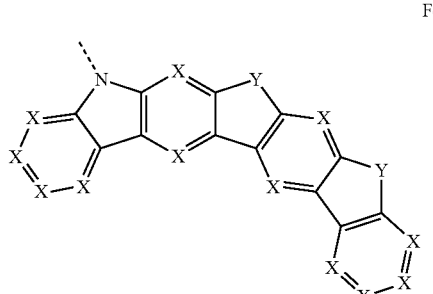
Formula (M30)
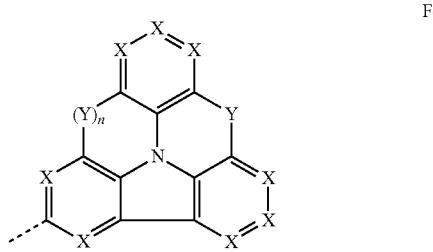

Formula (M31)
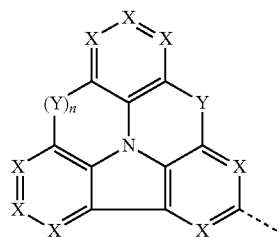
Formula (M32)
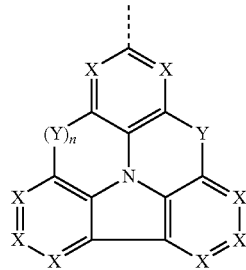
Formula (M33)
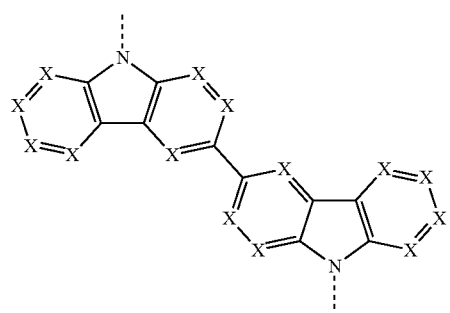
Formula (M34)
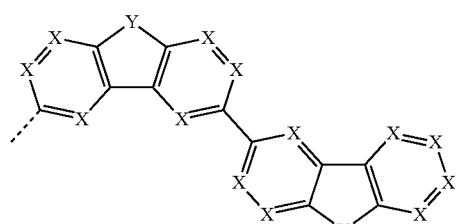
Formula (M35)
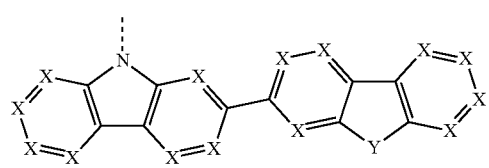
Formula (M36)
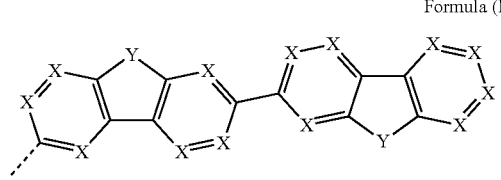
Formula (M37)
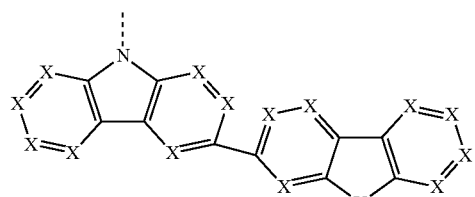
Formula (M38)
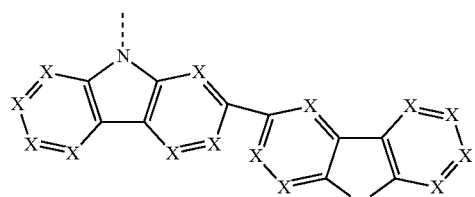
Formula (M39)
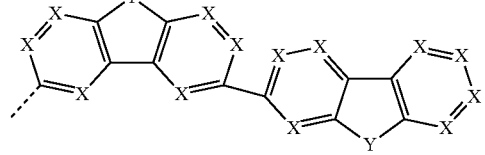
Formula (M40)
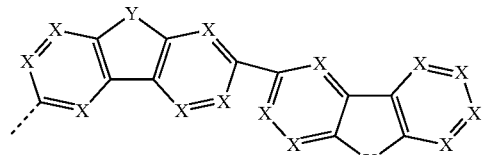
Formula (M41)
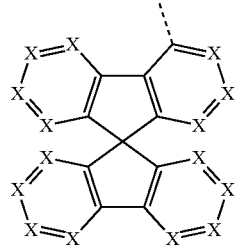
Formula (M42)
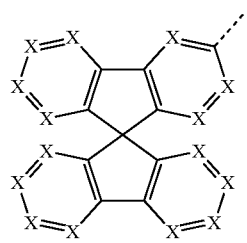
Formula (M43)
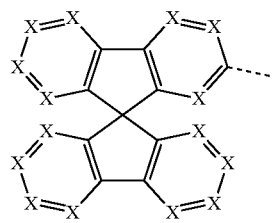

Formula (M44)

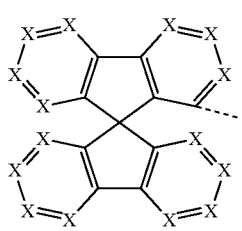

where R¹ and R² have the definitions given above, the dotted bond indicates the bond to the group of the formula (M1) or (M2) and in addition:

X is the same or different at each instance and is CR¹ or N, where preferably not more than 2 X symbols per cycle are N;

Y is the same or different at each instance and is C(R¹)₂, NR¹, O or S;

n is 0 or 1, where n=0 means that no Y group is bonded at this position and R¹ radicals are bonded to the corresponding carbon atoms instead.

The expression "per cycle" mentioned above and also used hereinafter relates in the context of the present application to each individual ring present in the compound, i.e. to each individual 5- or 6-membered ring.

In preferred groups of the abovementioned formulae (M3) to (M44), not more than one X symbol per cycle is N. More preferably, the X symbol is the same or different at each instance and is CR¹, especially CH.

When the groups of the formulae (M3) to (M44) have two or more Y groups, possible options for these include all combinations from the definition of Y. Preference is given to groups of the formulae (M3) to (M44) in which one Y group is NR¹ and the other Y group is C(R¹)₂ or in which both Y groups are NR¹ or in which both Y groups are O.

In a further preferred embodiment of the invention, at least one Y group in the formulae (M3) to (M44) is the same or different at each instance and is C(R¹)₂ or NR¹.

When Y is NR¹, the substituent R¹ bonded to the nitrogen atom is preferably an aromatic or heteroaromatic ring system which has 5 to 24 aromatic ring atoms and may also be substituted by one or more R² radicals. In a particularly preferred embodiment, this substituent R¹ is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more R² radicals. Particular preference is given to the structures Bi-1 to Bi-3, Ter-1 to Ter-3 and Quater-1 to Quater-4 listed above.

When Y is C(R¹)₂, R¹ is preferably the same or different at each instance and is a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more R² radicals. Most preferably, R¹ is a methyl group or a phenyl group. In this case, the R¹ radicals together may also form a ring system, which leads to a spiro system.

It may further be preferable when the group of the abovementioned formulae (M3) to (M44) does not bind directly to the triazine in formula (M1) or the pyrimidine in formula (M2), but binds via a bridging group. In that case, this bridging group is preferably selected from an aromatic or heteroaromatic ring system having 5 to 24 aromatic ring atoms, especially having 6 to 12 aromatic ring atoms, which may be substituted in each case by one or more R¹ radicals. Preferred aromatic ring systems are ortho-, meta- or para-phenylene or a biphenyl group, each of which may be substituted by one or more R¹ radicals, but are preferably unsubstituted.

Examples of preferred compounds of formula (M1) or (M2) are the following compounds:

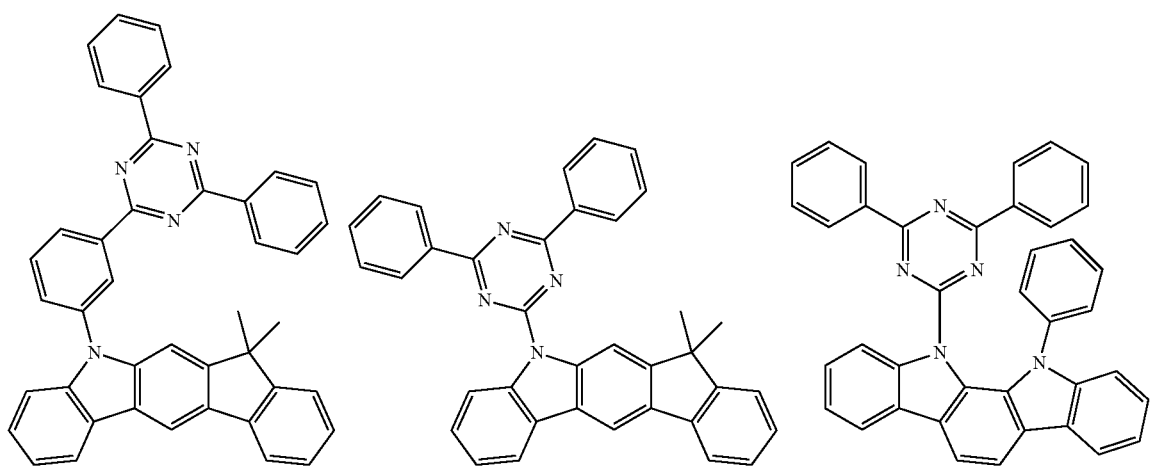

-continued
91 92
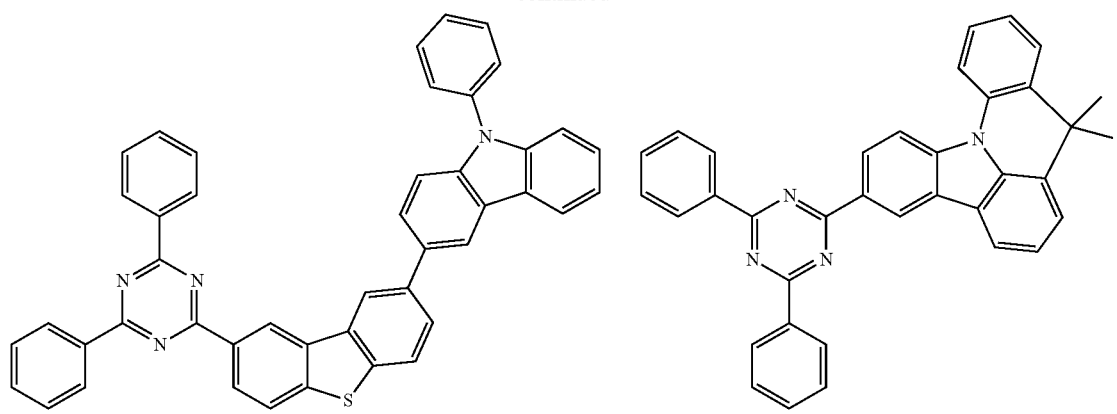
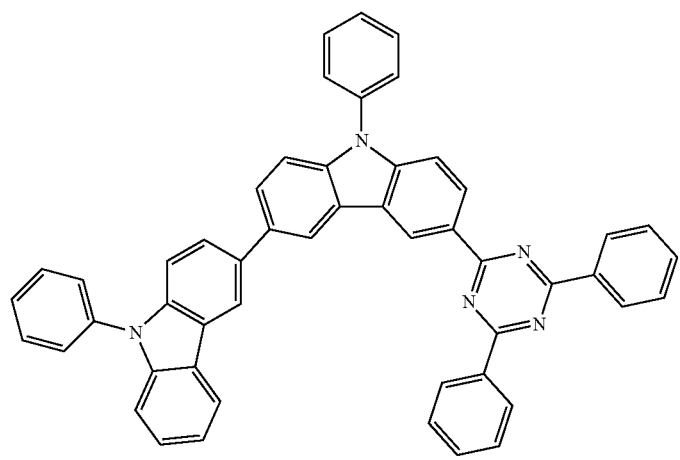
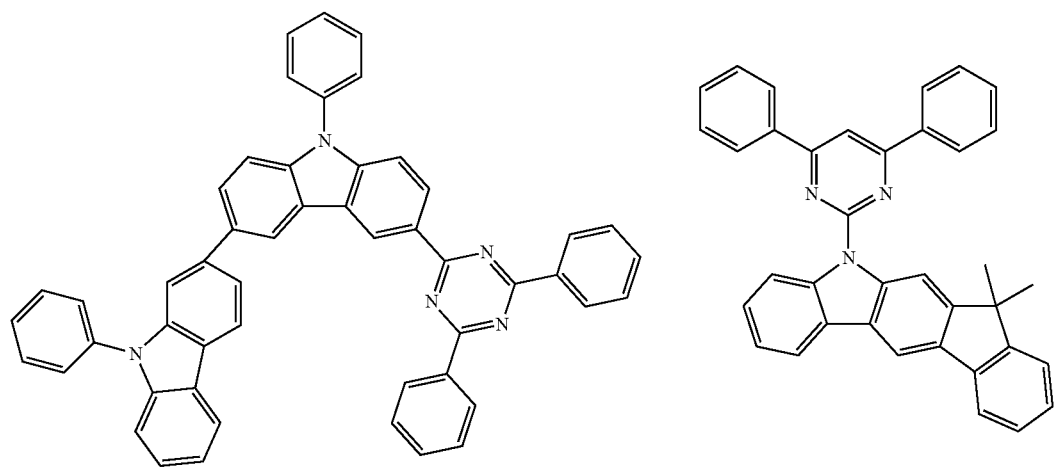

93
94
-continued
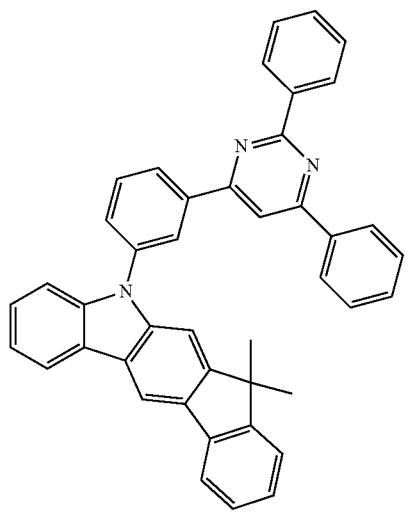
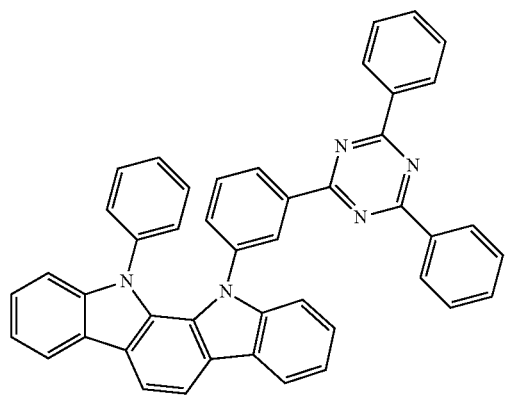
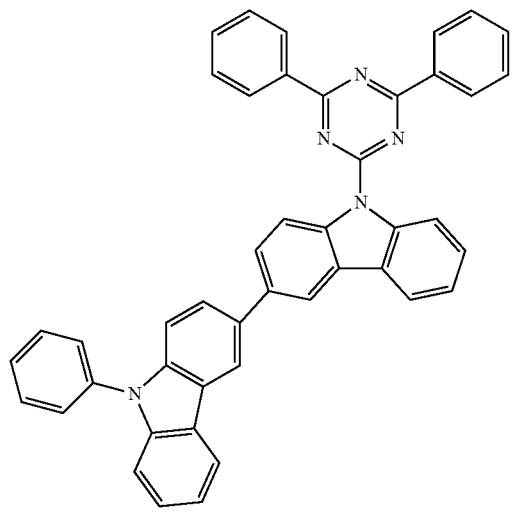
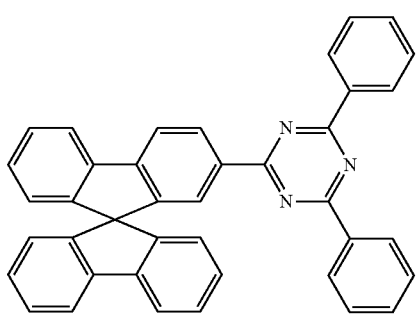
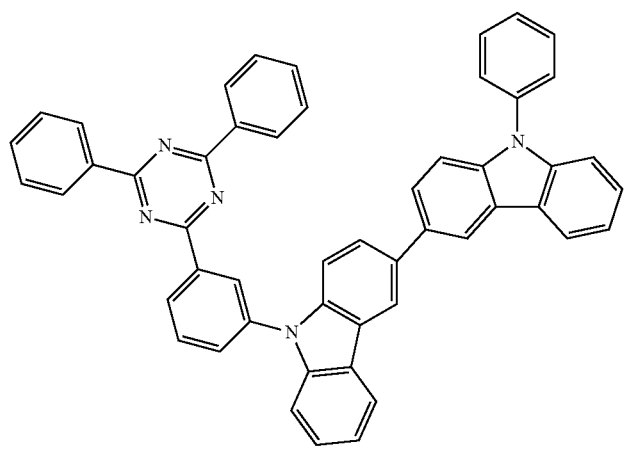
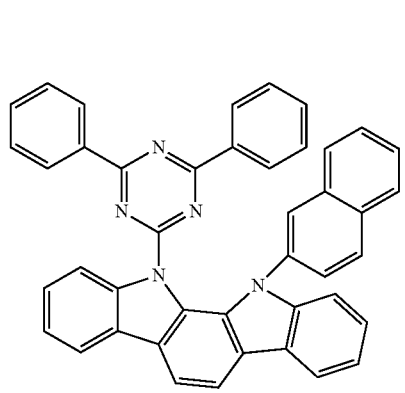

-continued
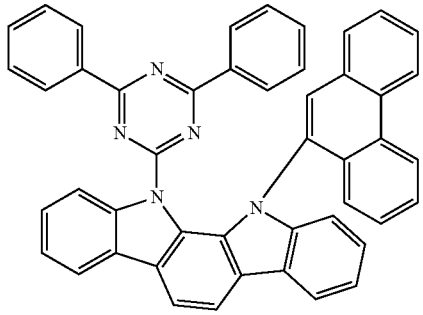
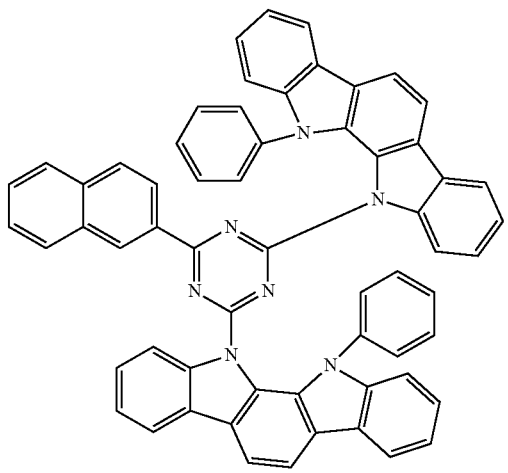
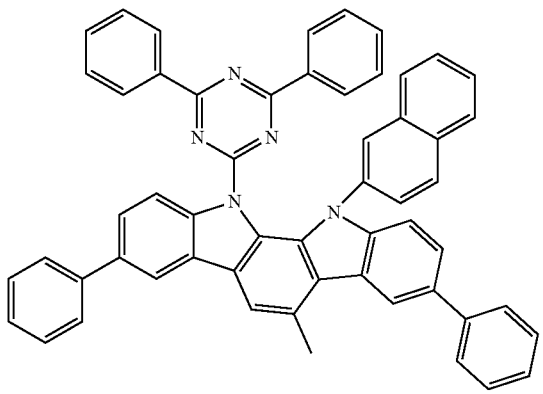
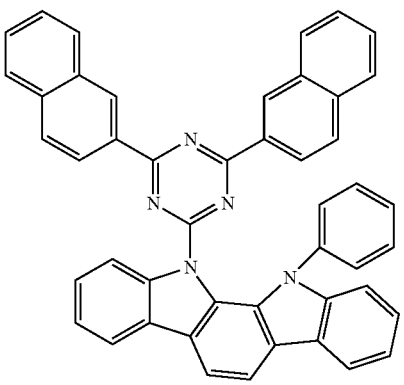
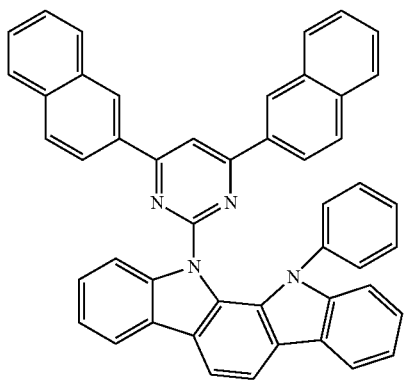
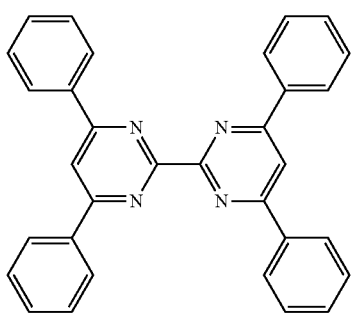
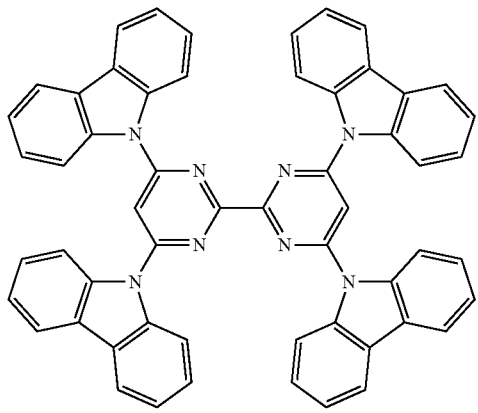
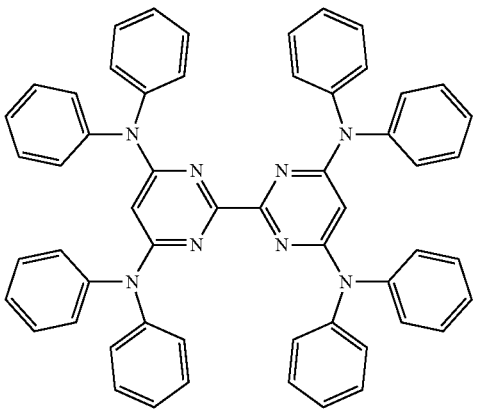

-continued
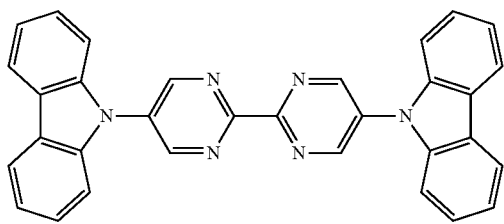
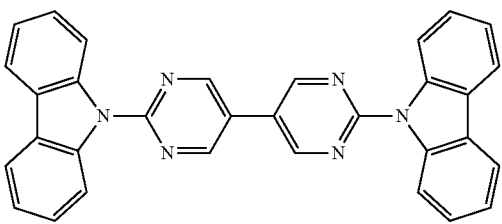
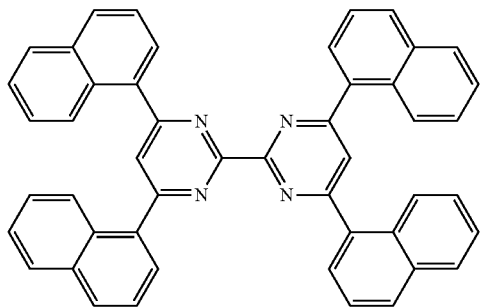
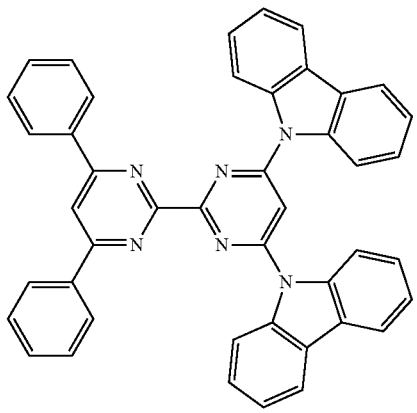
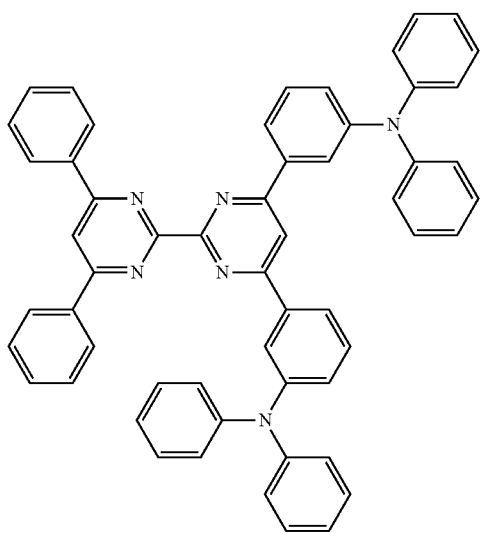
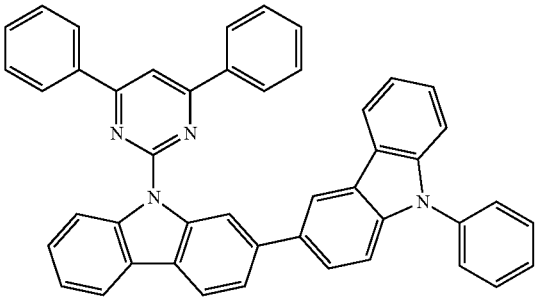
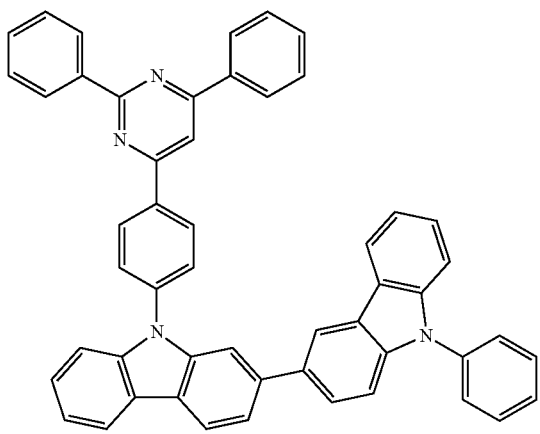
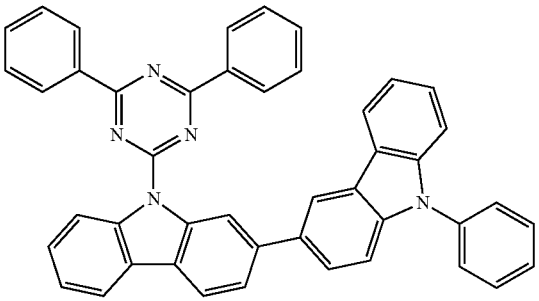

-continued
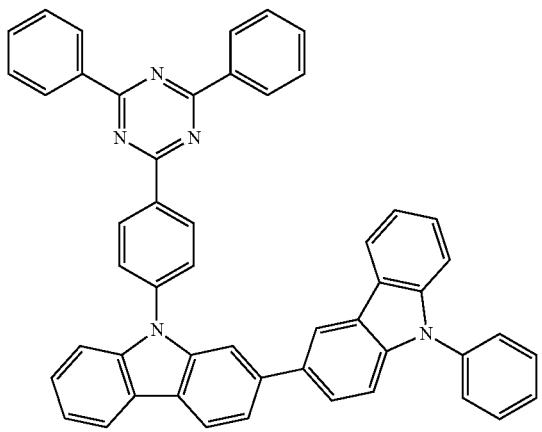
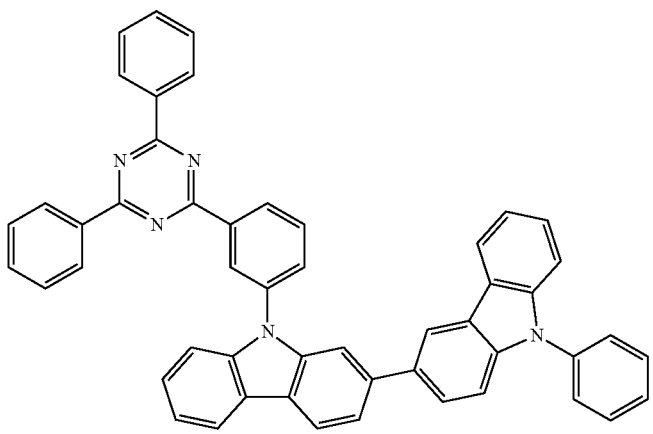
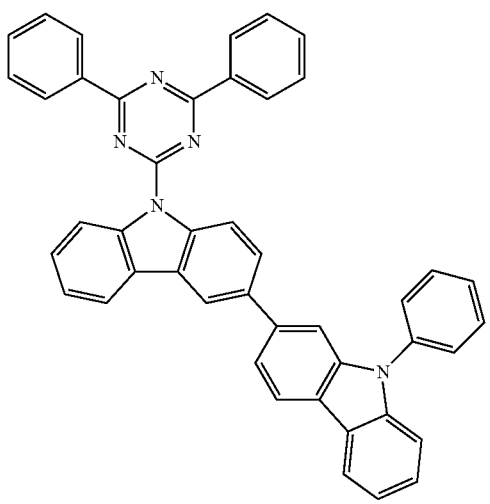
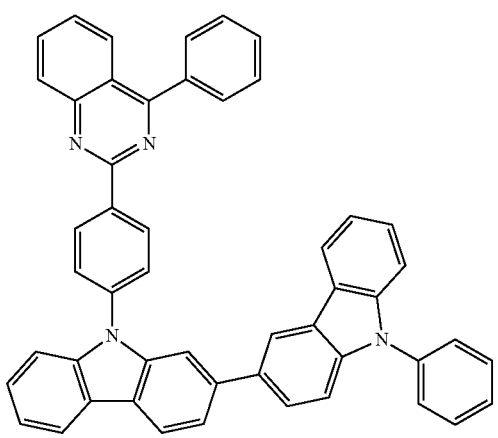

-continued
101
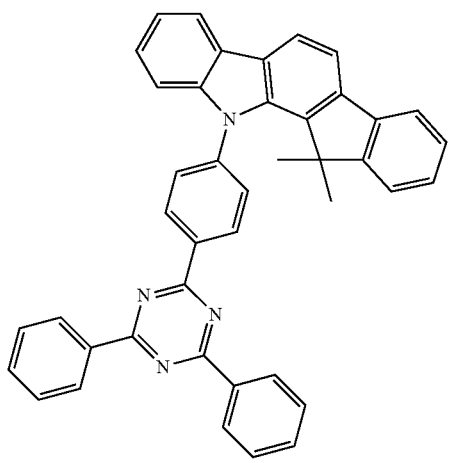
102
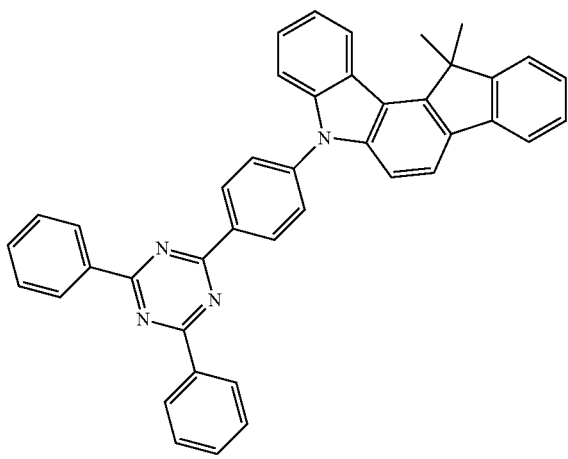
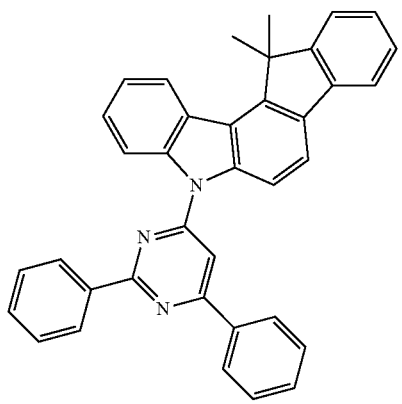
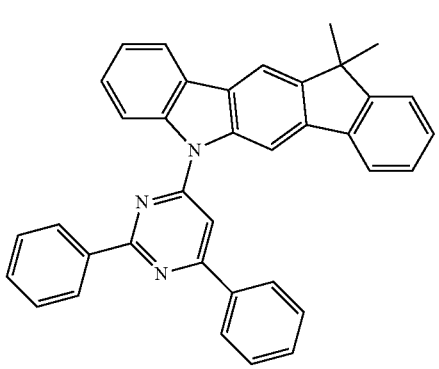
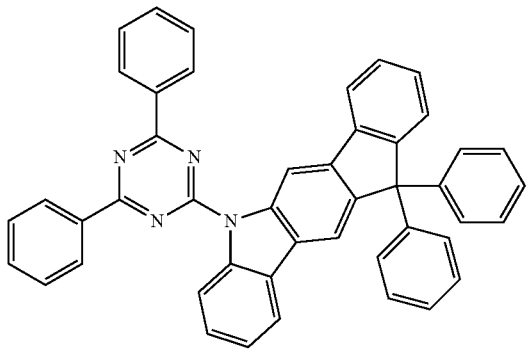
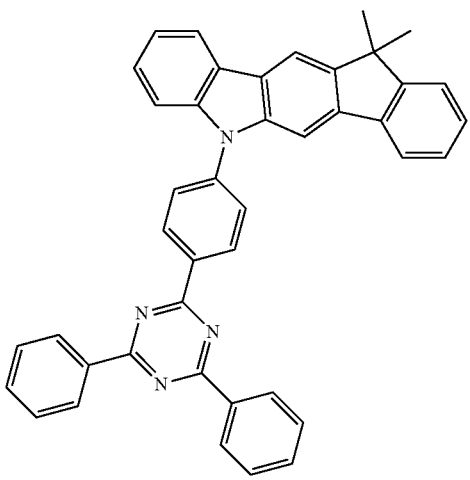
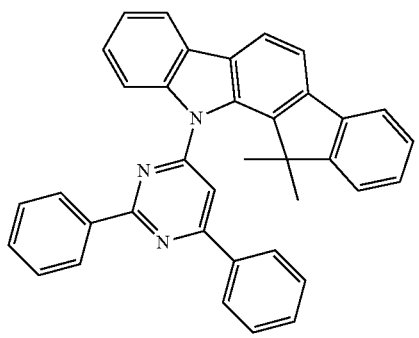
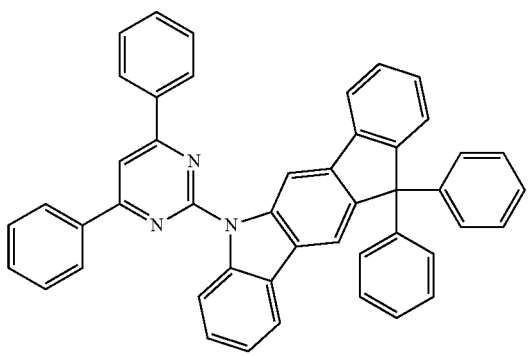

-continued
| 103 | 104 |
|---|---|
| 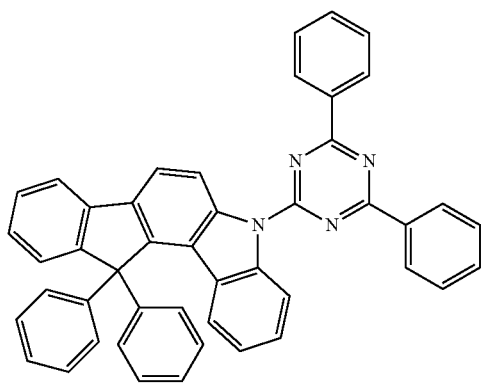 | 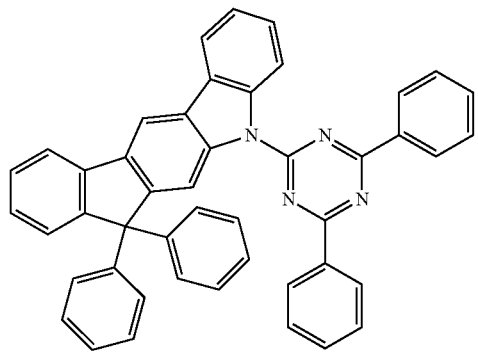 |
| 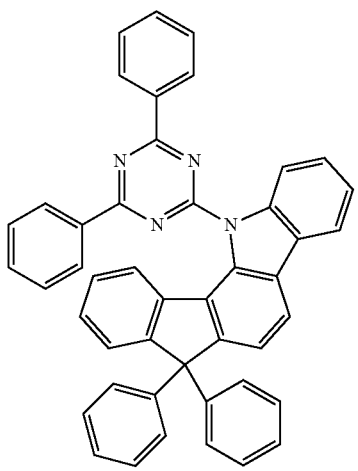 | 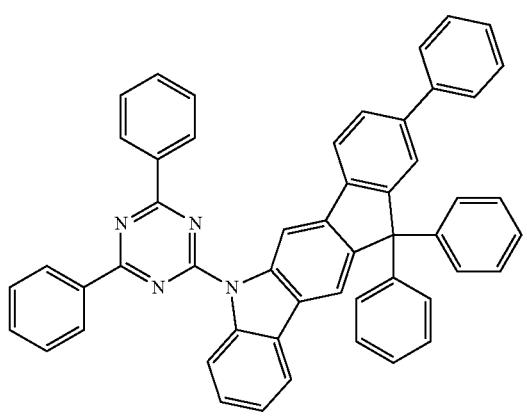 |
| 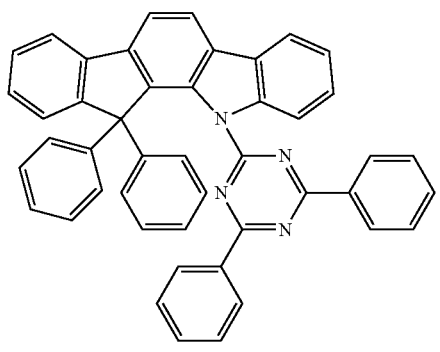 | 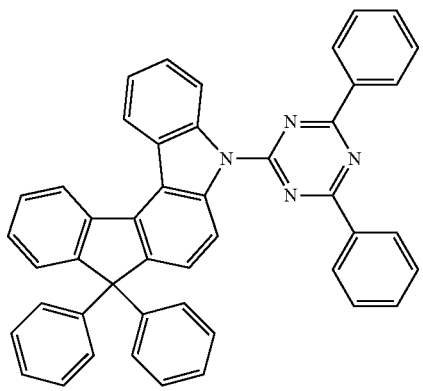 |

105 106
-continued
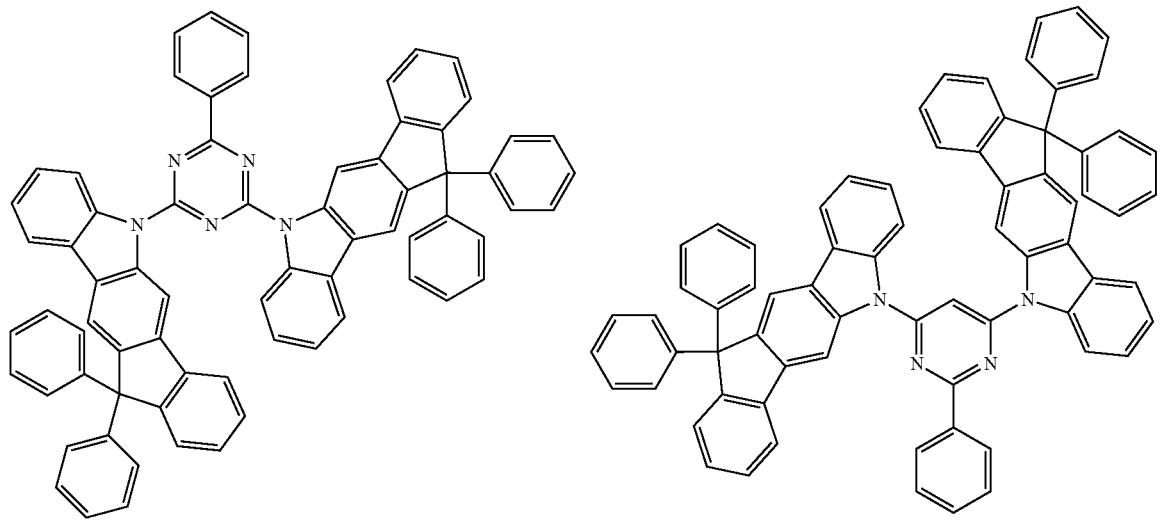
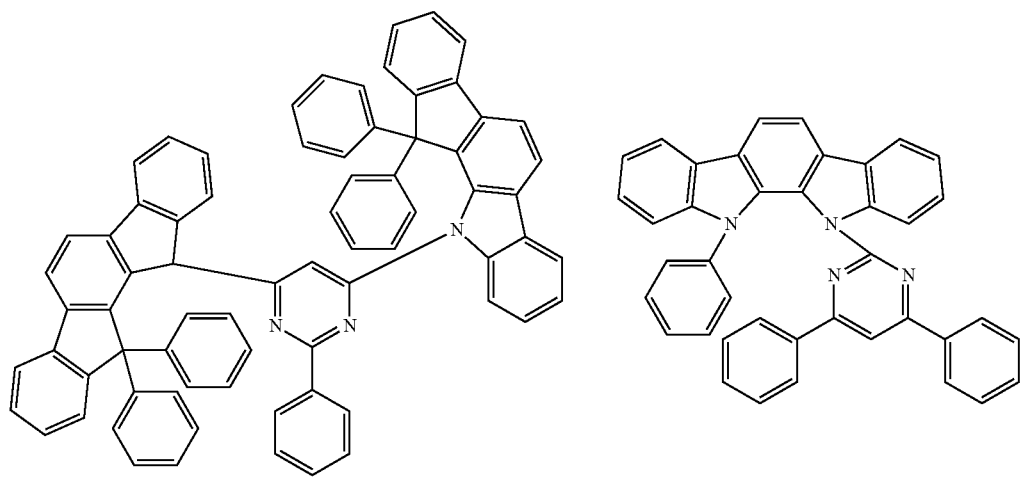
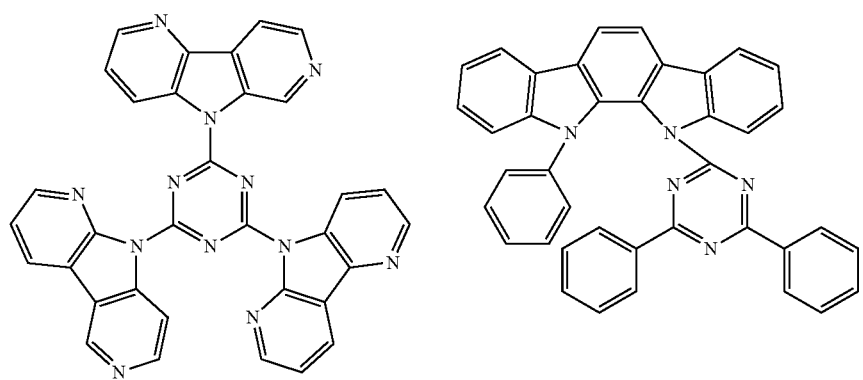

107
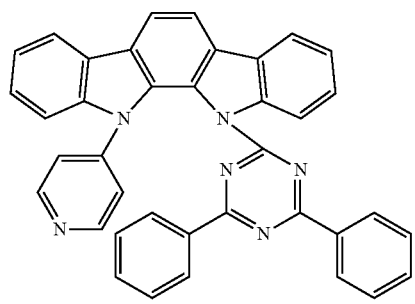
108
-continued
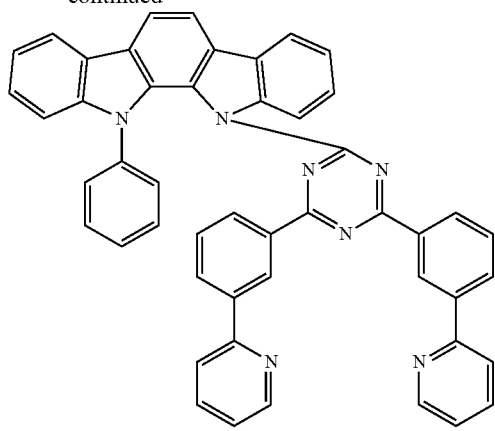
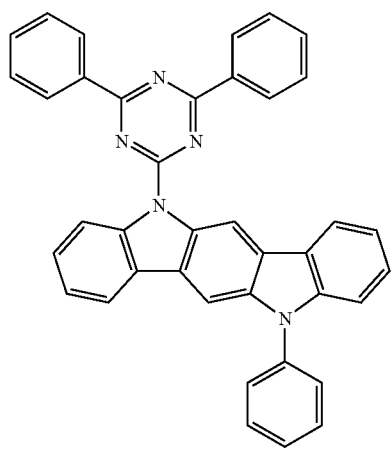
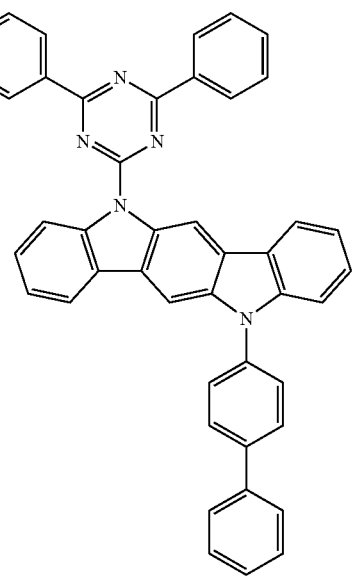
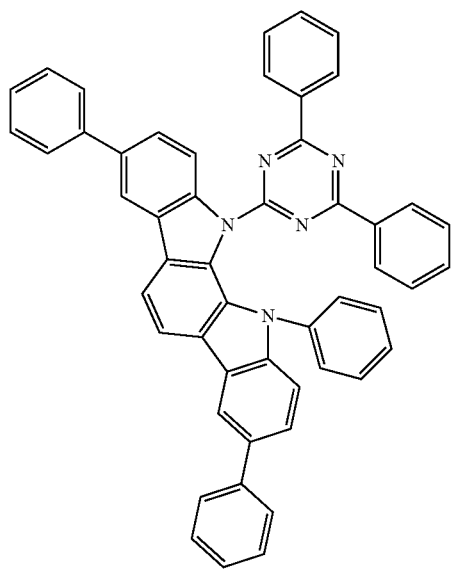
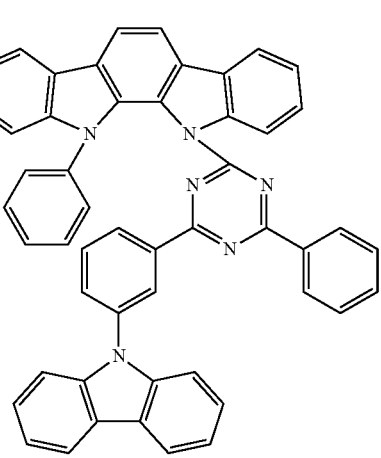

109
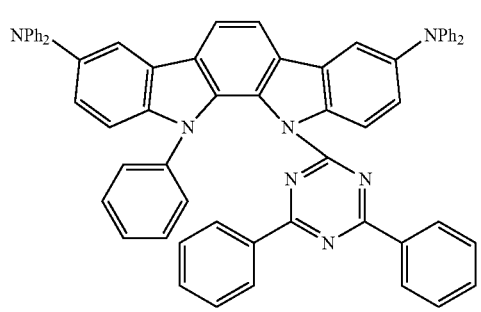
110
-continued
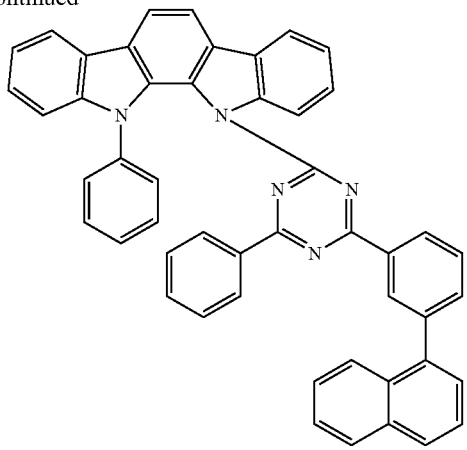
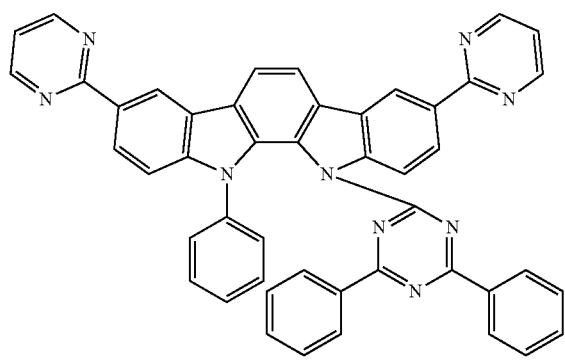
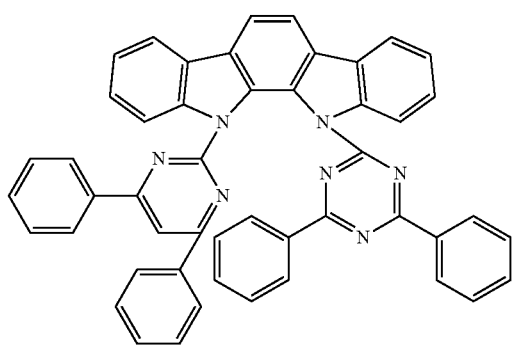
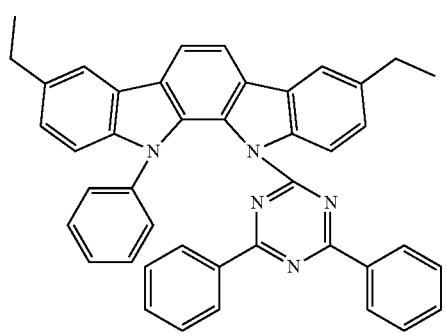
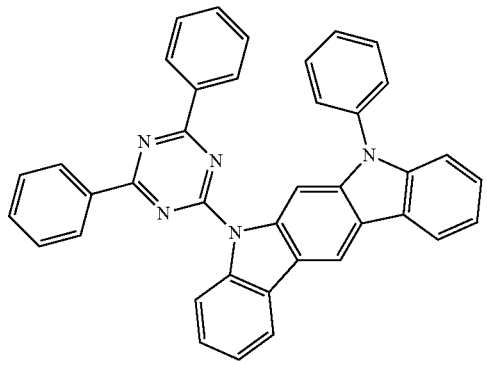
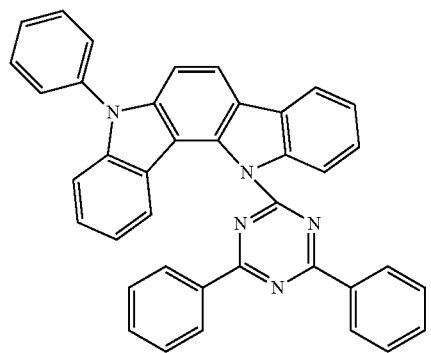
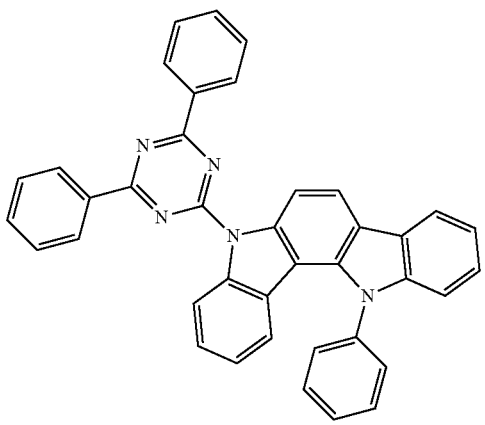

111
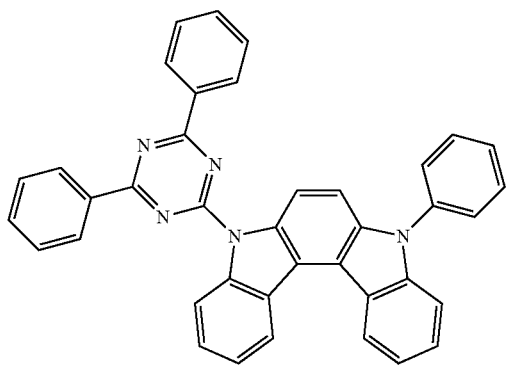
112
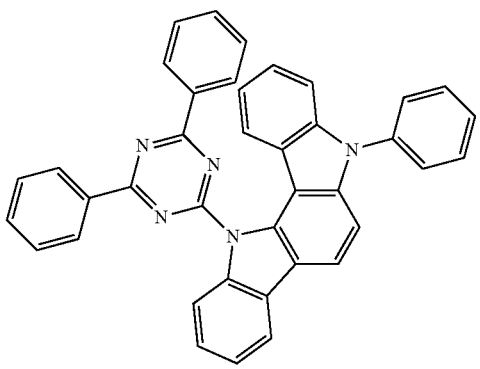
-continued
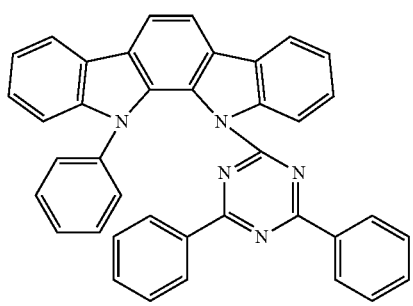
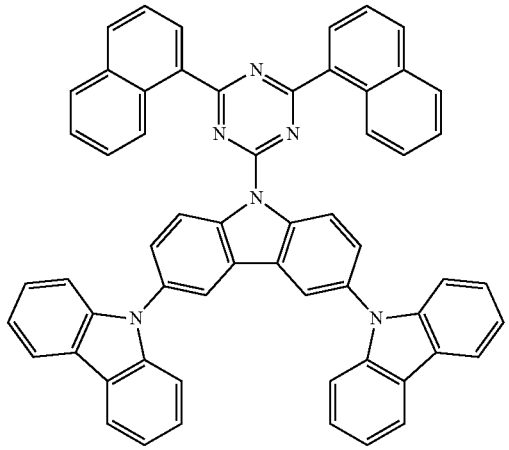
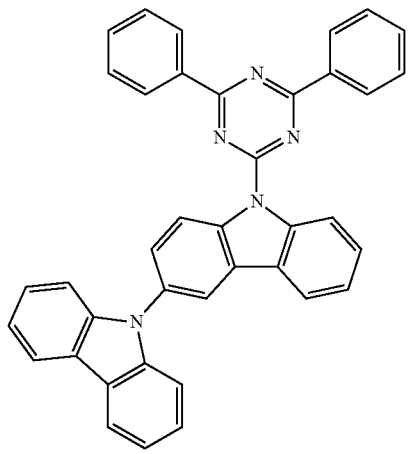
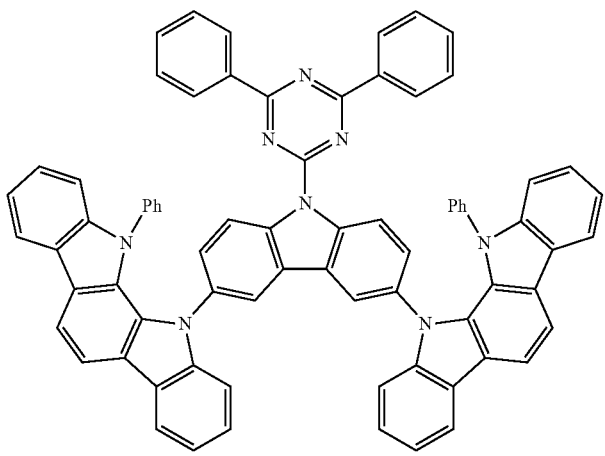

-continued
113
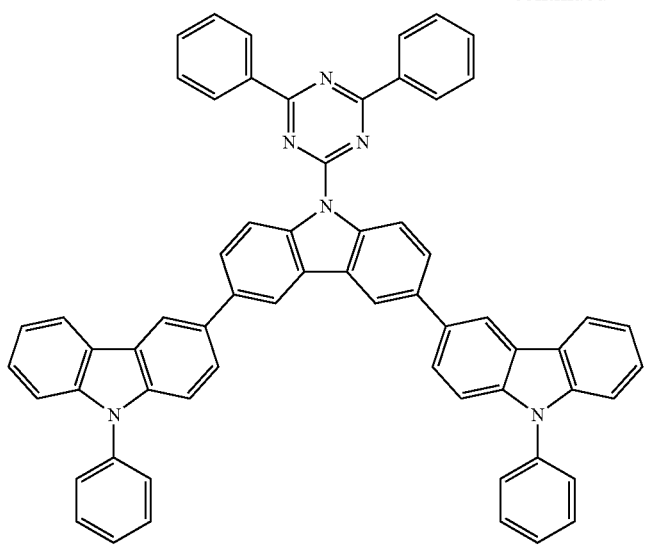
114
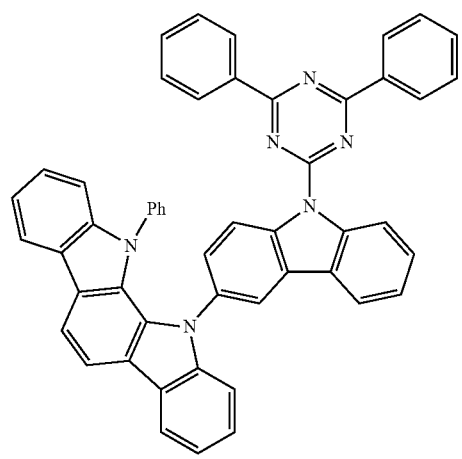
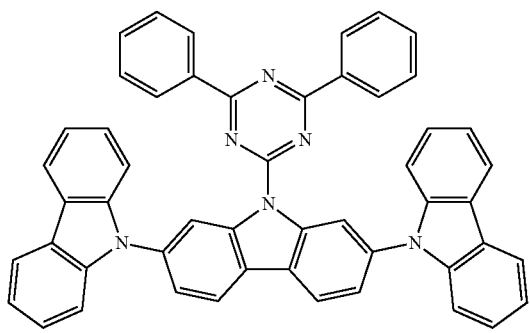
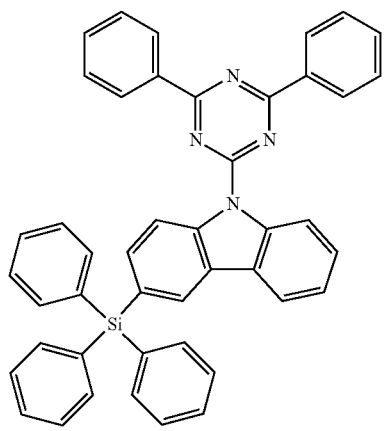
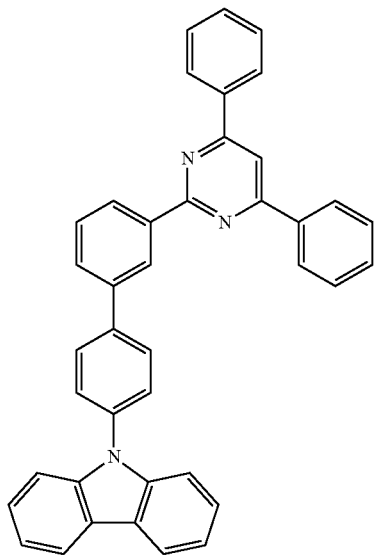
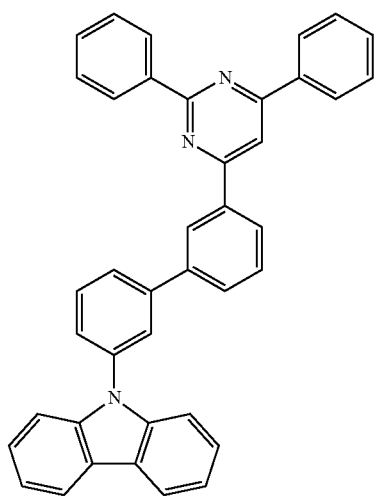

-continued
115
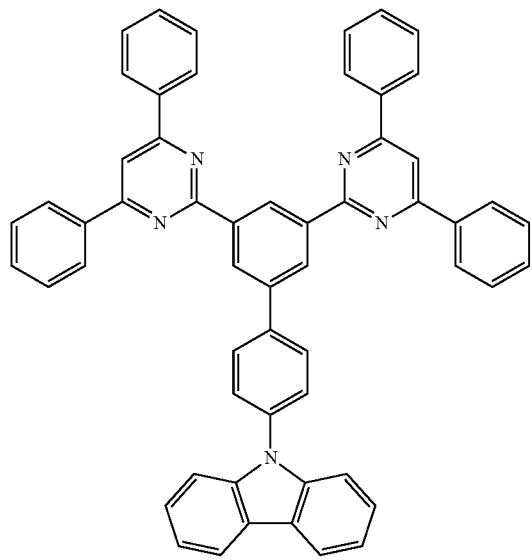
116
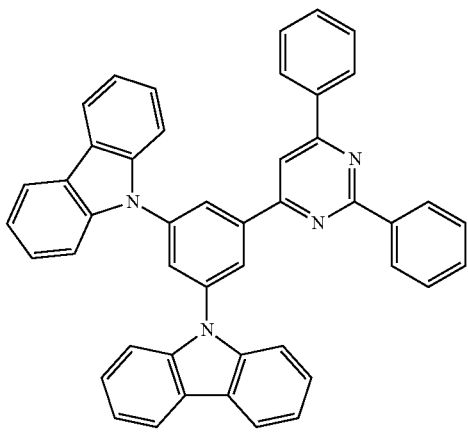
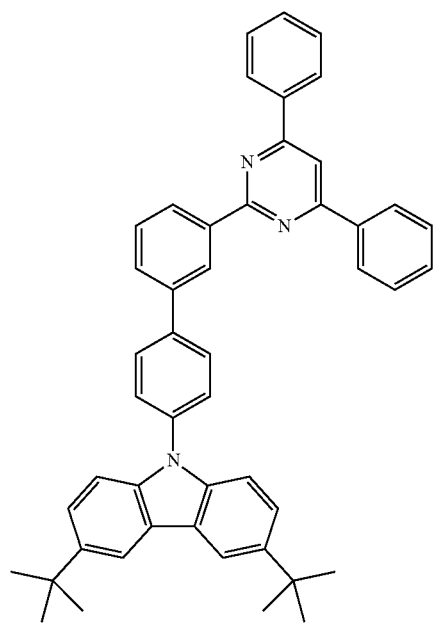
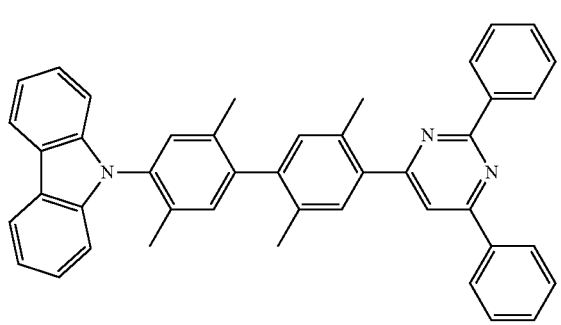
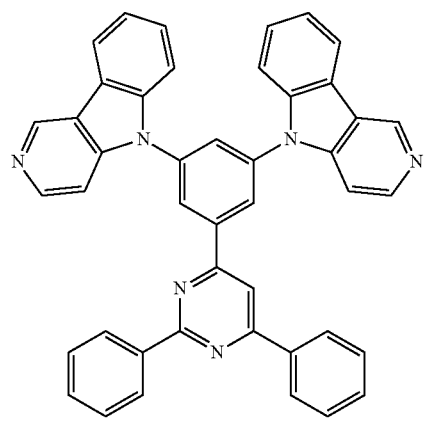
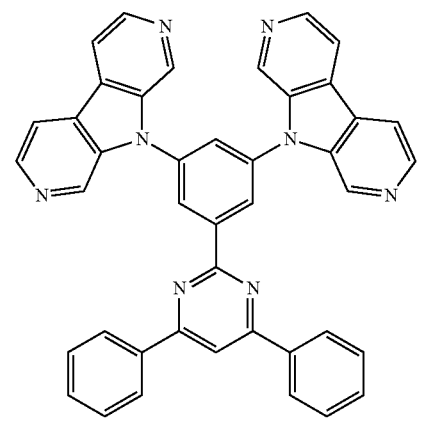

117
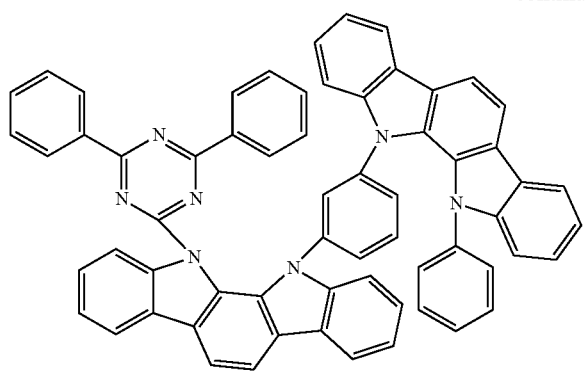
118
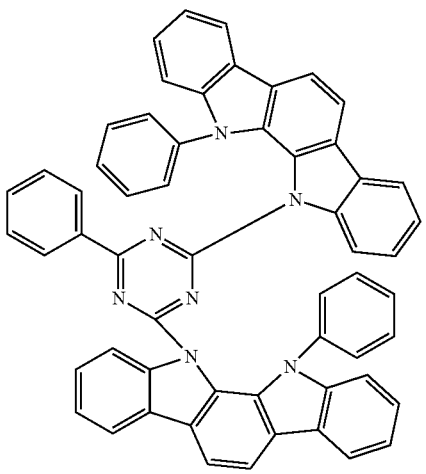
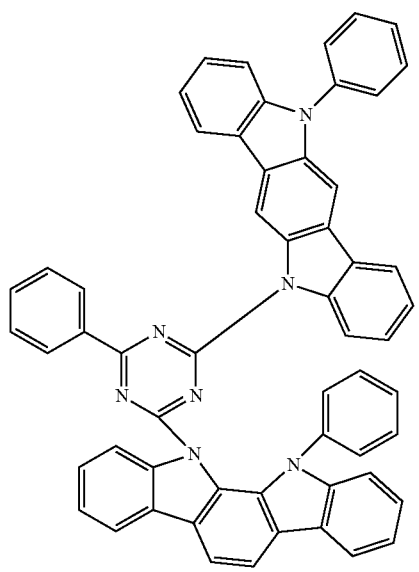
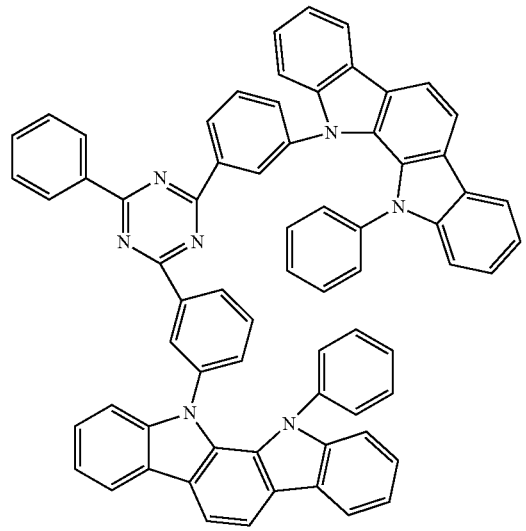
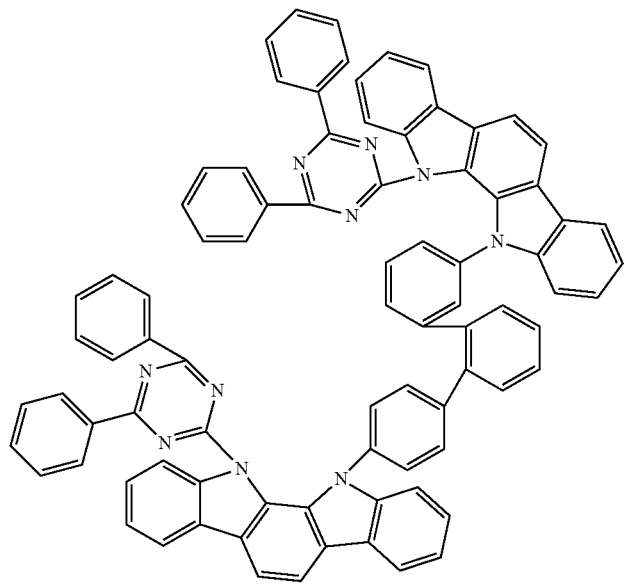
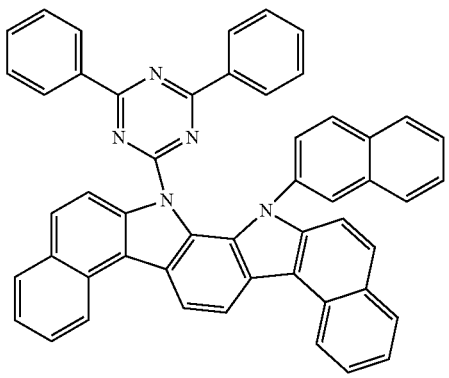

-continued
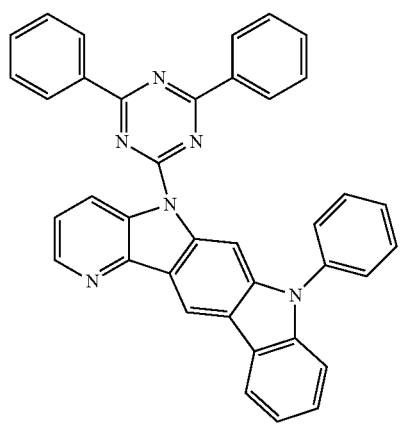
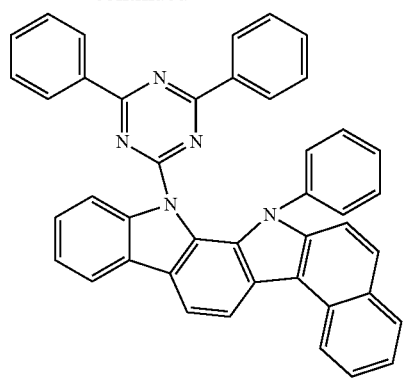
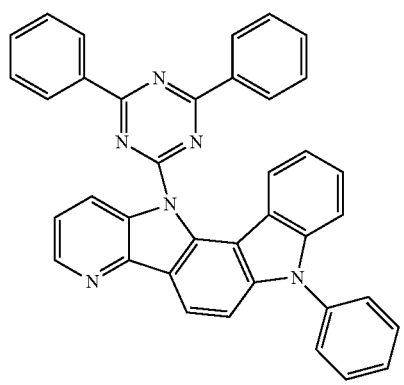
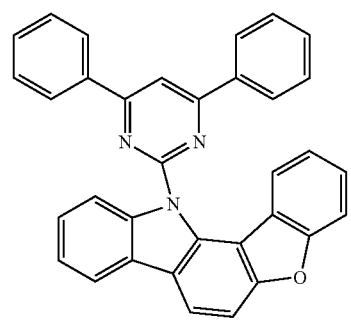
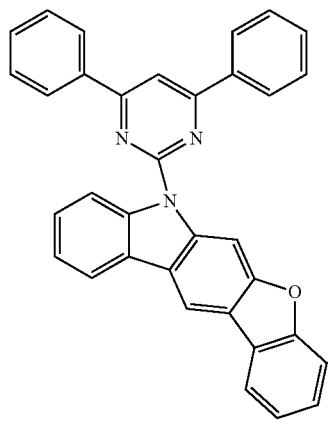
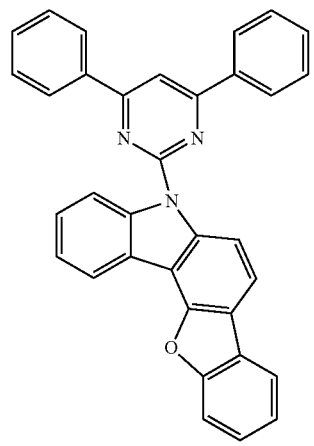

-continued
121
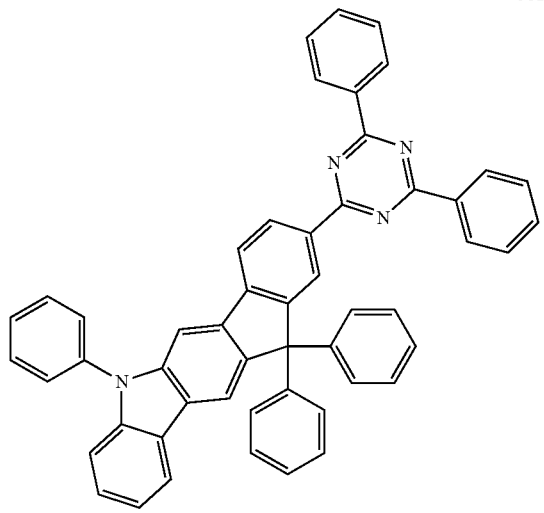
122
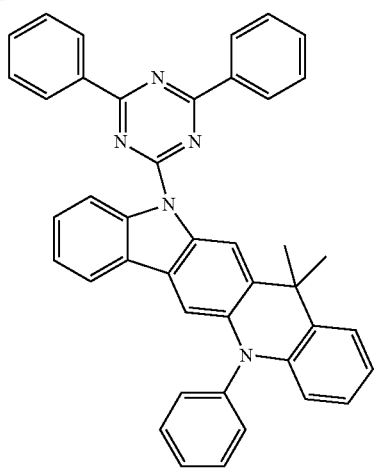
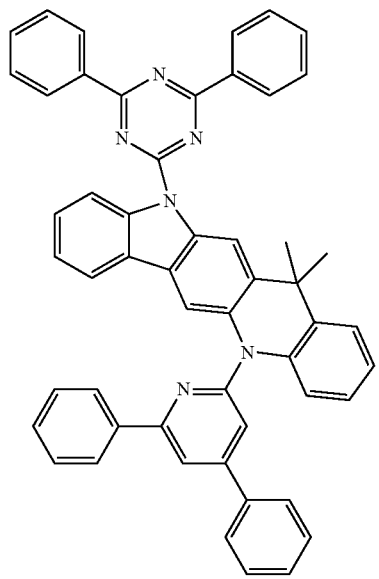
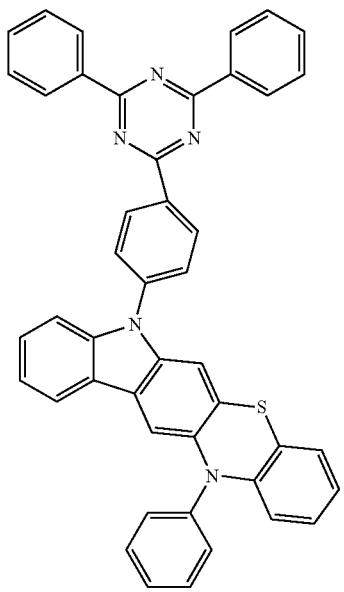
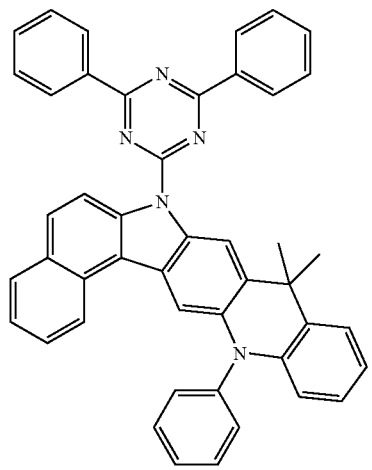
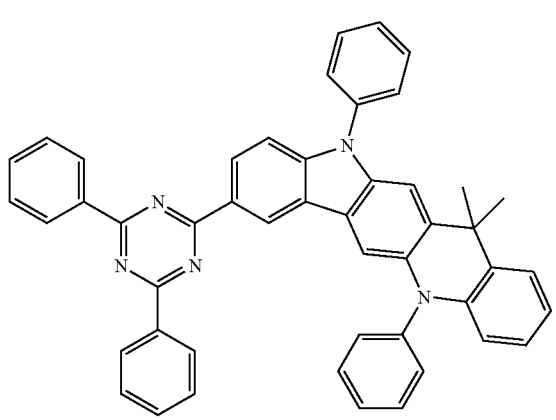

123
124
-continued
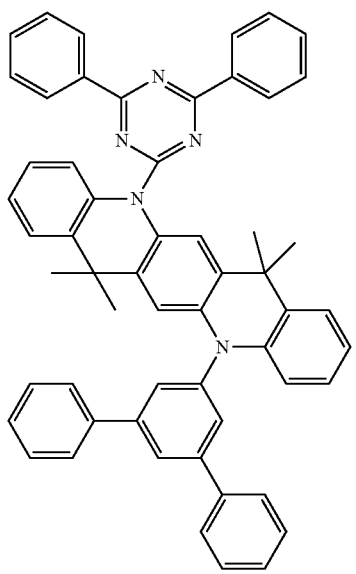
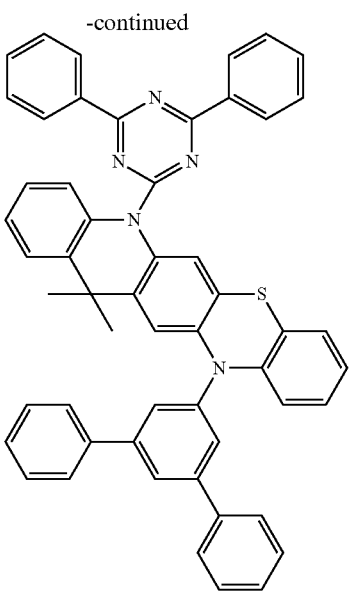
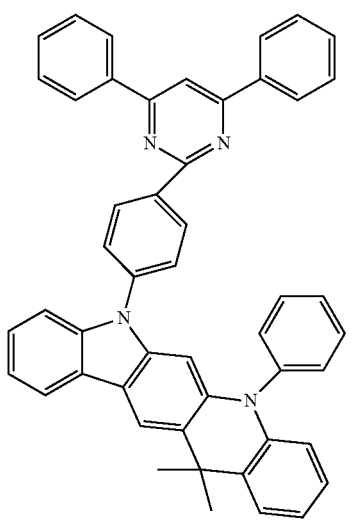
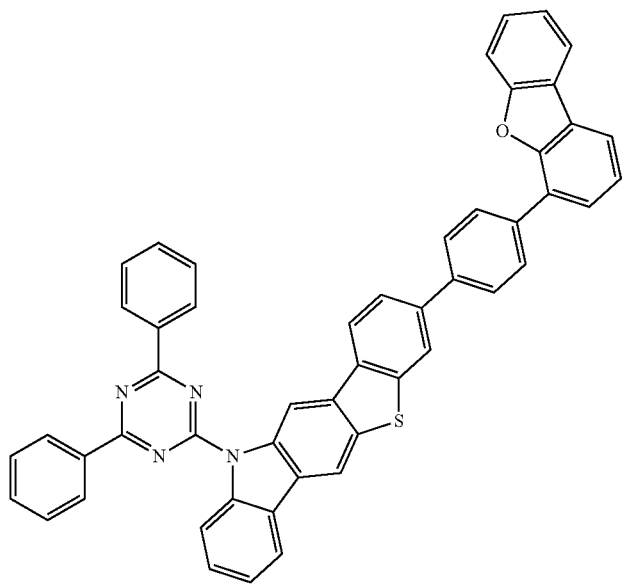
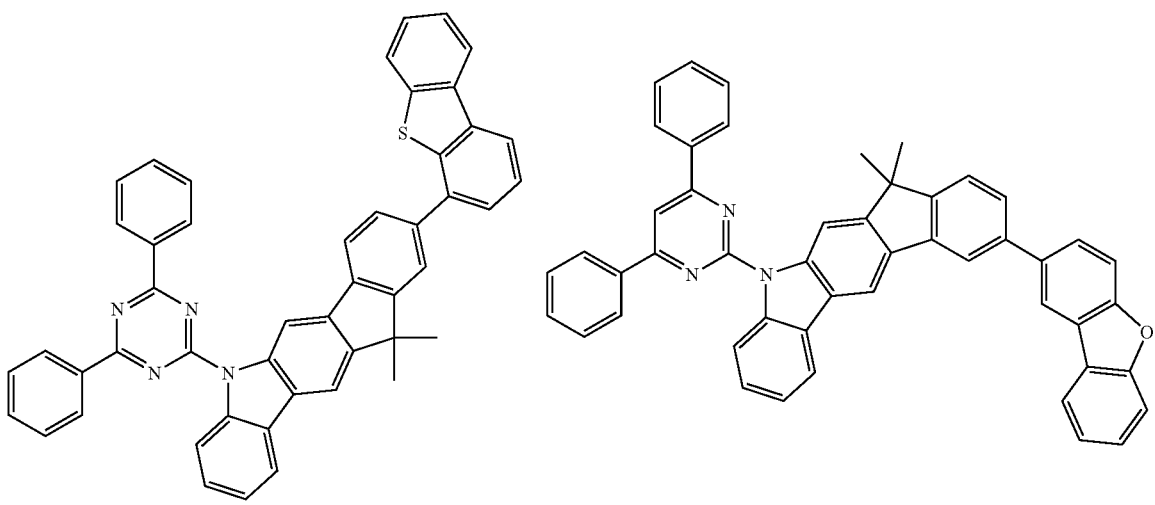

-continued
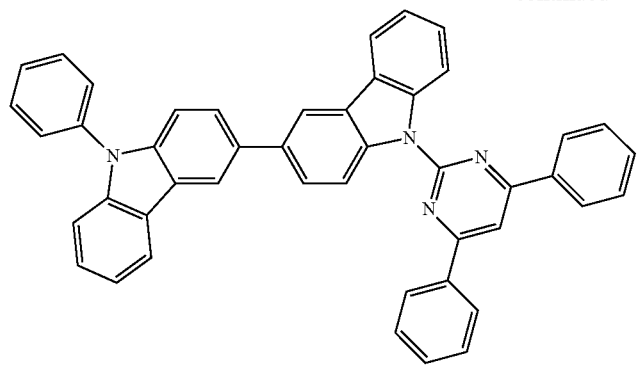
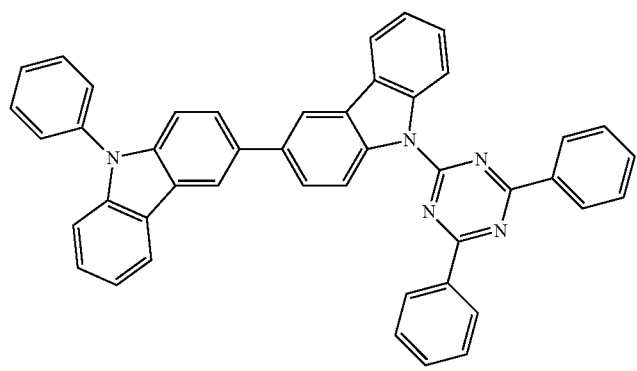
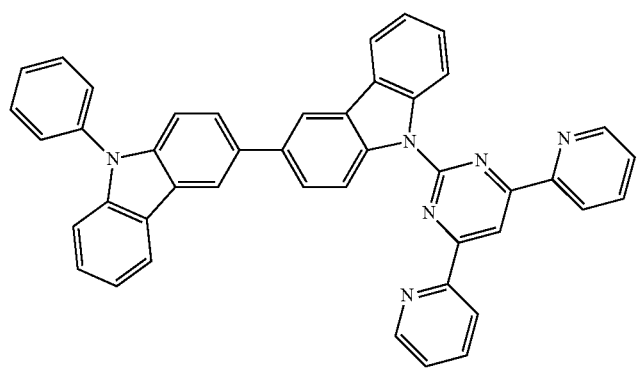
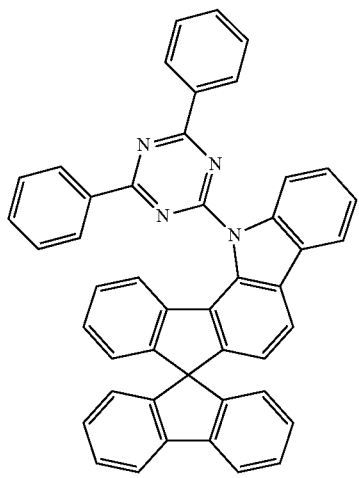

-continued
127
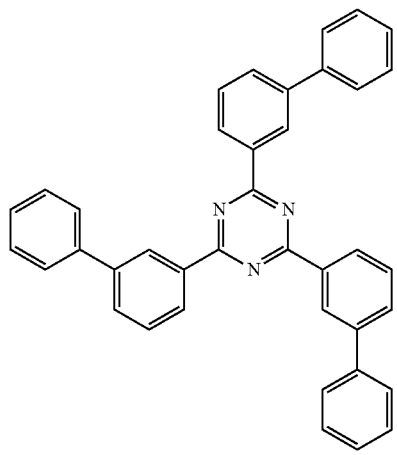
128
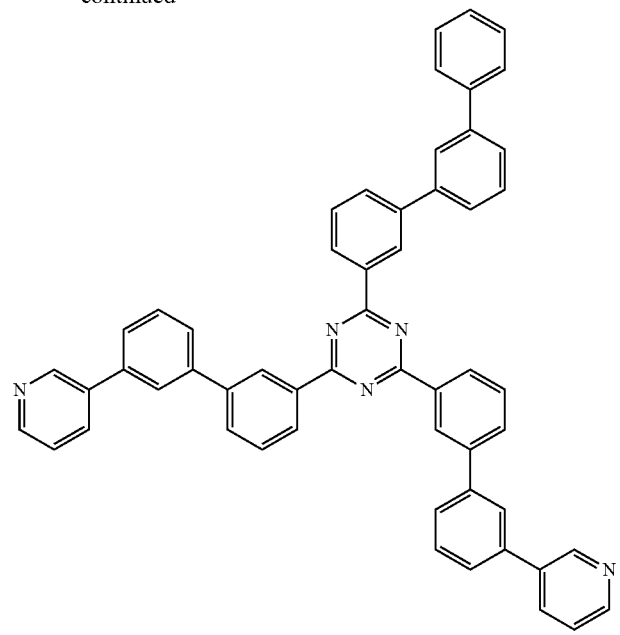
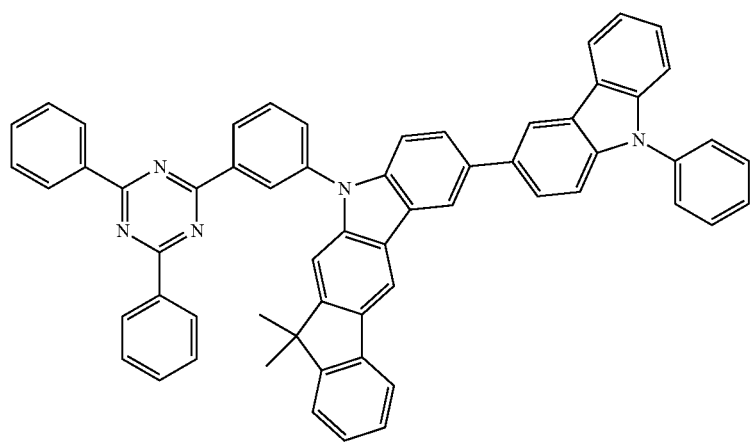
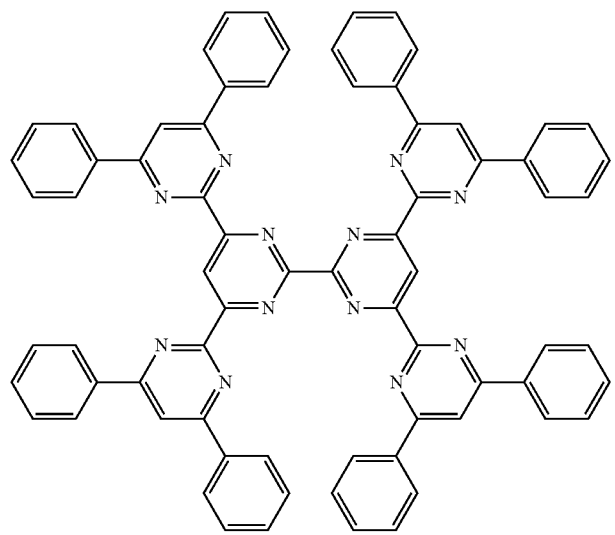

-continued
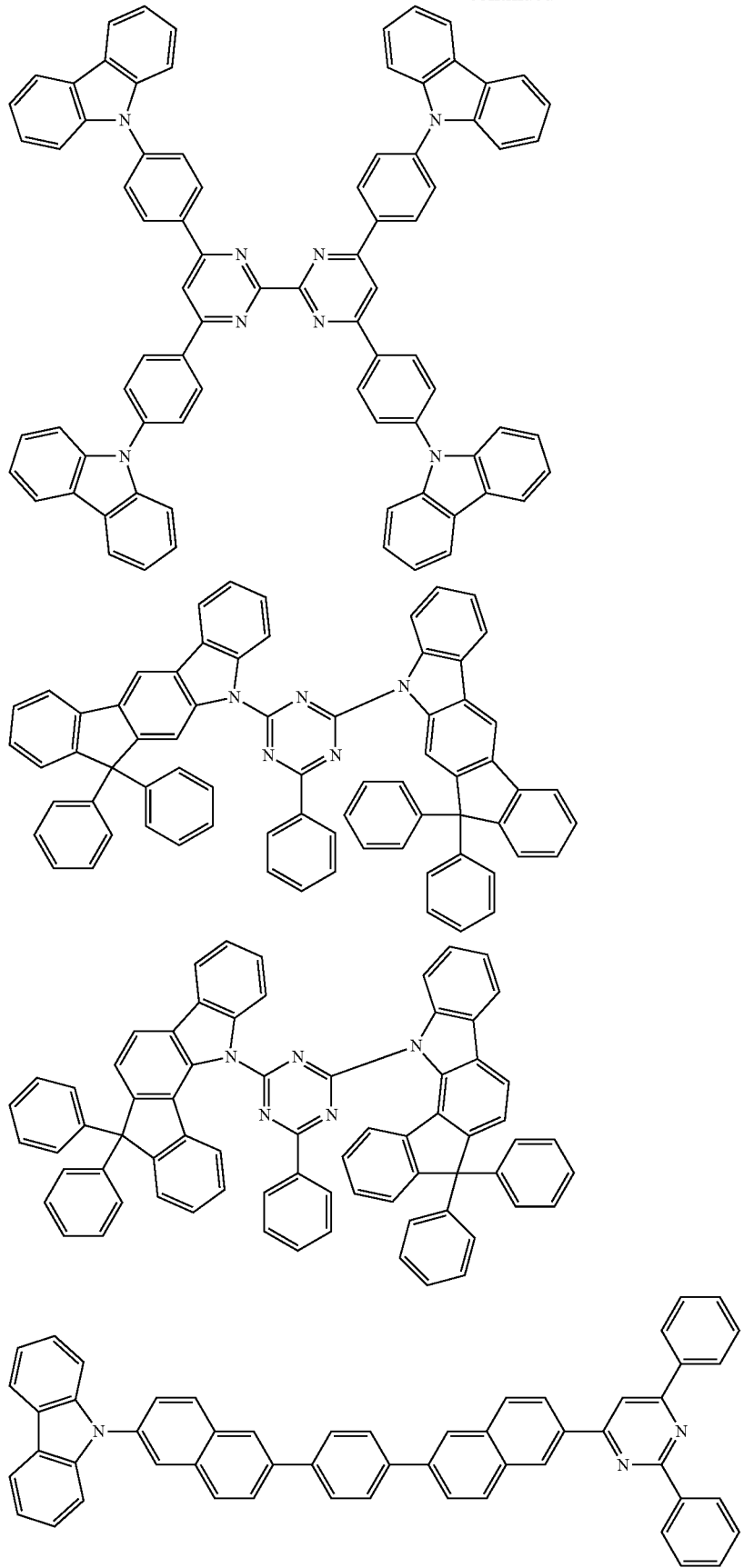

-continued
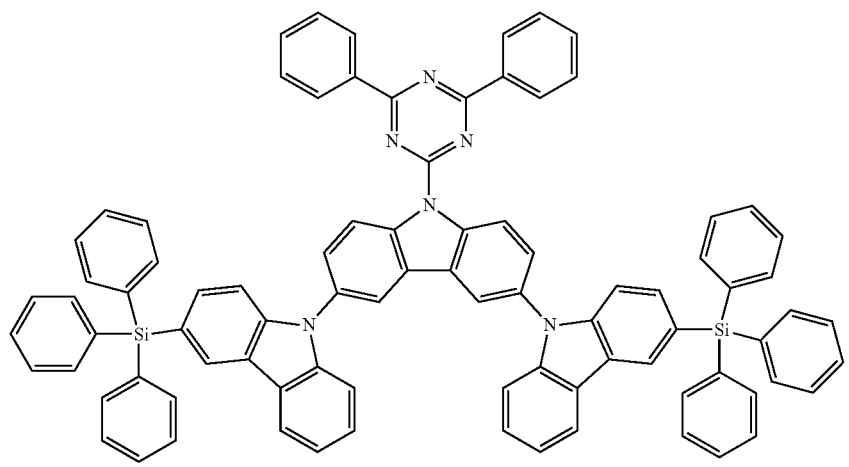
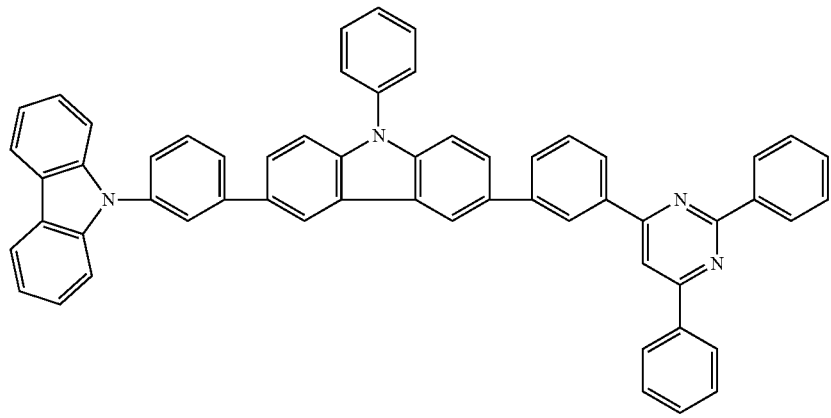
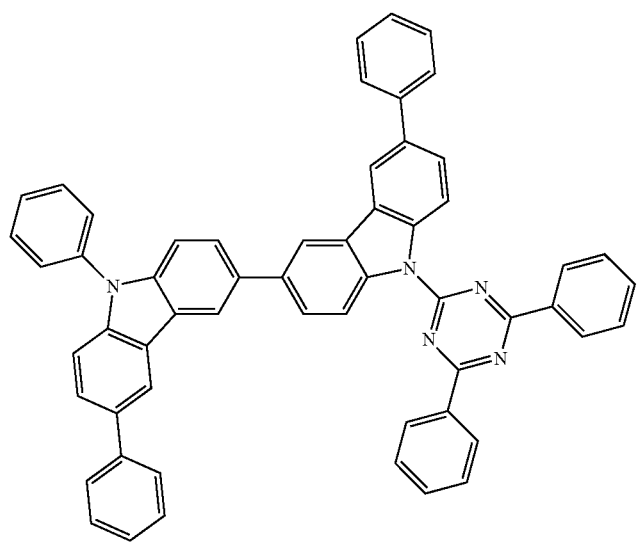

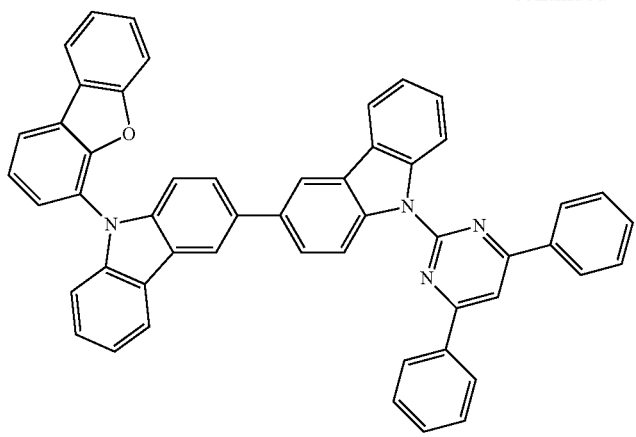
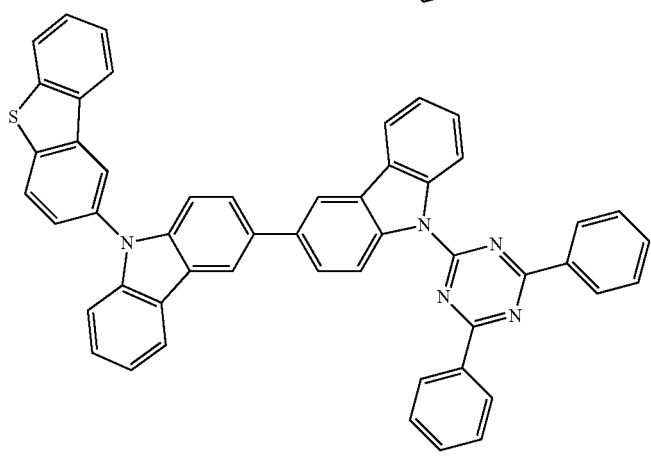
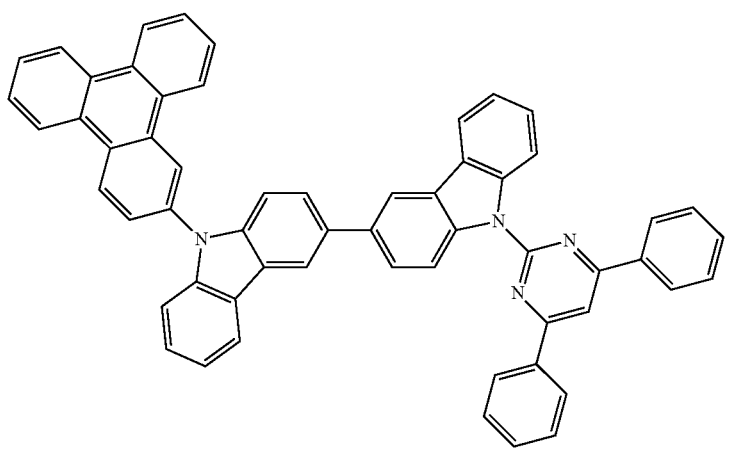
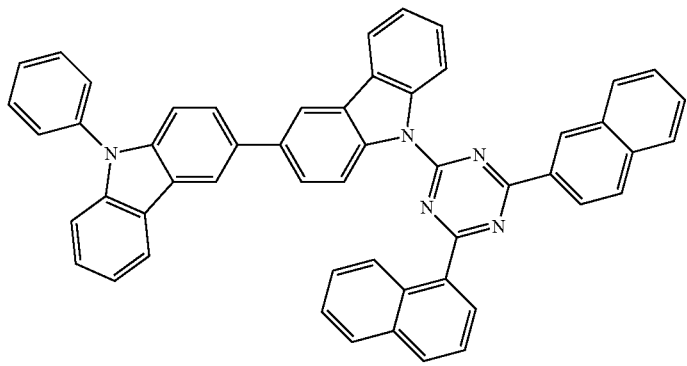

When the electron-conducting compound is a lactam, this compound is preferably selected from the compounds of the following formulae (M45) and (M46):

Formula (M45)

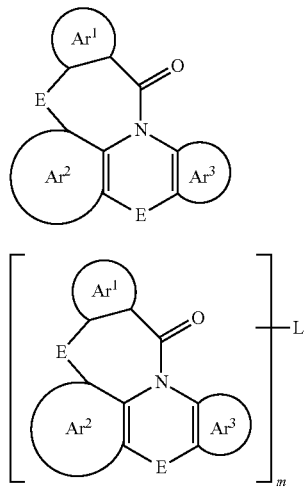

Formula (M46)

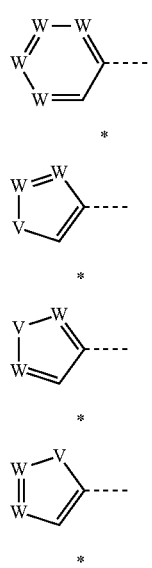

where R, $R^1$, $R^2$ and Ar have the definitions given above and the further symbols and indices used are as follows:

E is the same or different at each instance and is a single bond, NR, $CR_2$, O, S, $SiR_2$, BR, PR and P(=O)R;

$Ar^1$, $Ar^2$, $Ar^3$ is the same or different at each instance and, together with the carbon atoms shown explicitly, is an aromatic or heteroaromatic ring system which has 5 to 30 aromatic ring atoms and may be substituted by one or more R radicals;

L when m=2 is a single bond or a bivalent group, or when m=3 is a trivalent group, or when m=4 is a tetravalent group, each of which is bonded at any desired position to Ar', Ar² or $Ar^3$ or in place of an R radical to E;

m is 2, 3 or 4.

In a preferred embodiment of the compound of formula (M45) or (M46), the $Ar^1$ group is a group of the following formula (M47), (M48), (M49) or (M50)

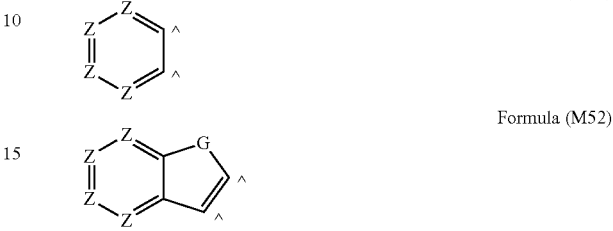

where the dotted bond indicates the linkage to the carbonyl group, * indicates the position of the linkage to E or Ar² and in addition:

W is the same or different at each instance and is CR or N, or two adjacent W groups are a group of the following formula (M51) or (M52)

Formula (M51)

Formula (M52)

where G is $CR_2$, NR, O or S, Z is the same or different at each instance and is CR or N and A indicate the corresponding adjacent W groups in the formula (M47) to (M50);

V is NR, O or S.

In a further preferred embodiment of the invention, the $Ar^2$ group is a group of one of the following formulae (M53), (M54) or (M55):

where the dotted bond indicates the linkage to N, # indicates the position of the linkage to E or $Ar^3$, * indicates the linkage to E or $Ar^1$ and W and V have the definitions given above.

In a further preferred embodiment of the invention, the $Ar^3$ group is a group of one of the following formulae (M56), (M57), (M58) or (M59):

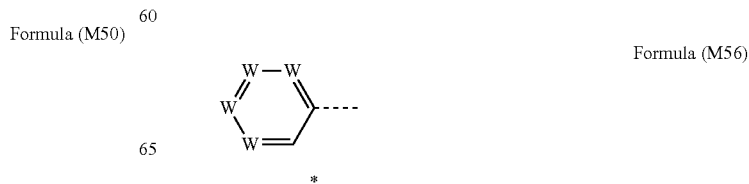

Formula (M57)

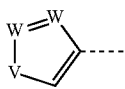

Formula (M58)

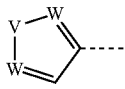

Formula (M59)

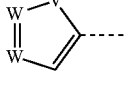

where the dotted bond indicates the linkage to N, * indicates the linkage to E or Ar² and W and V have the definitions given above.

At the same time, the abovementioned preferred Ar¹, Ar² and Ar³ groups may be combined with one another as desired.

In a further preferred embodiment of the invention, at least one E group is a single bond.

In a preferred embodiment of the invention, the abovementioned preferences occur simultaneously. Particular preference is therefore given to compounds of formula (M45) or (M46) where:

Ar¹ is selected from the groups of the abovementioned formulae (M47), (M48), (M49) and (M50);
Ar² is selected from the groups of the abovementioned formulae (M53), (M54) and (M55);
Ar³ is selected from the groups of the abovementioned formulae (M56), (M57), (M58) and (M59).

More preferably, at least two of the Ar¹, Ar² and Ar³ groups are a 6-membered aryl or a 6-membered heteroaryl group. Thus, more preferably, Ar¹ is a group of the formula (M47) and at the same time Ar² is a group of the formula (M53), or Ar¹ is a group of the formula (M47) and at the same time Ar³ is a group of the formula (M56), or Ar² is a group of the formula (M53) and at the same time Ar³ is a group of the formula (M59).

Particularly preferred embodiments of the formula (M45) are therefore the compounds of the following formulae (M60) to (M69):

Formula (M60)

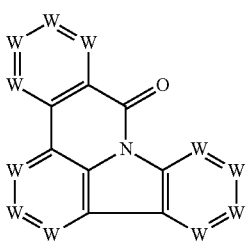

Formula (M61)

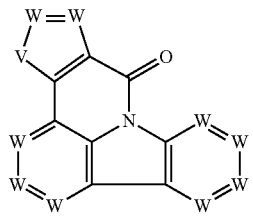

Formula (M62)

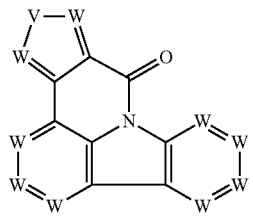

Formula (M63)

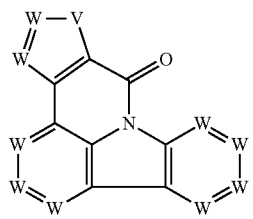

Formula (M64)

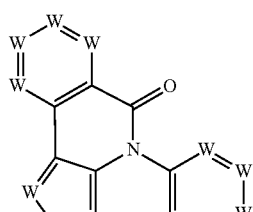

Formula (M65)

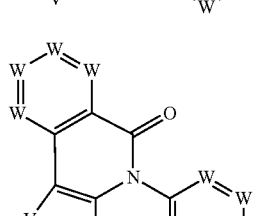

Formula (M66)

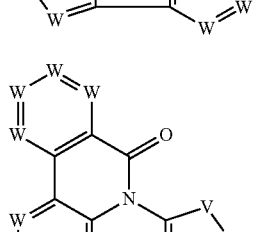

Formula (M67)

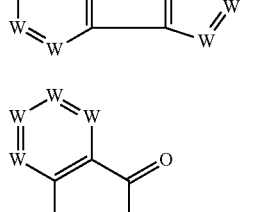

Formula (M68)

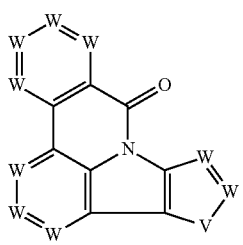

Formula (M69)

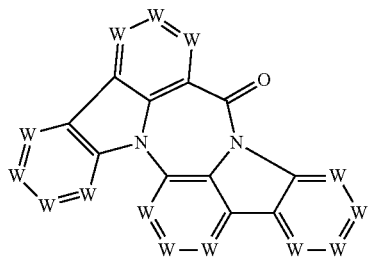

where the symbols used have the definitions given above.

It is further preferable when W is CR or N and is not a group of the formula (M51) or (M52). In a preferred embodiment of the compounds of formula (M60) to (M69), not more than one W symbol in total per cycle is N, and the remaining W symbols are CR. In a particularly preferred embodiment of the invention, all W symbols are CR. Particular preference is therefore given to the compounds of the following formulae (M60a) to (M69a):

Formula (M60a)

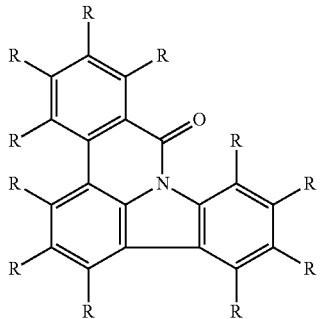

Formula (M61a)

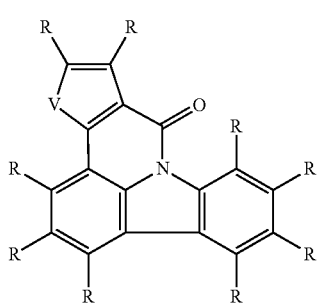

Formula (M62a)

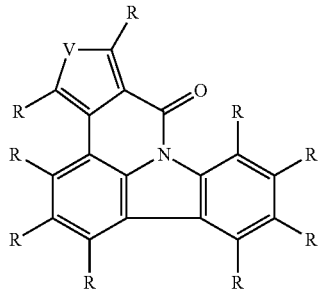

Formula (M63a)

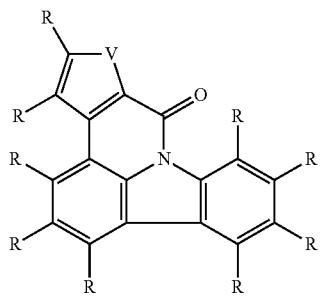

Formula (M64a)

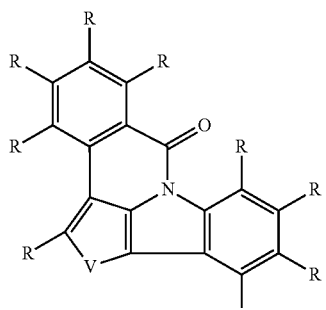

Formula (M65a)

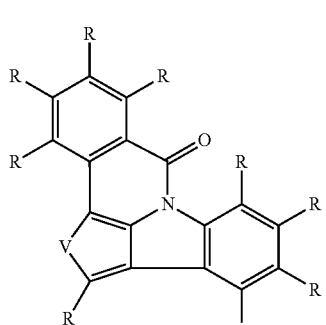

Formula (M66a)

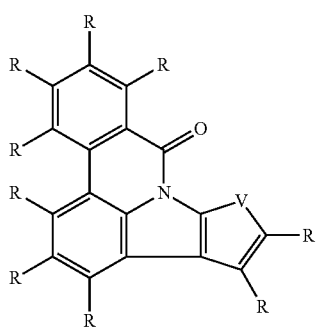

Formula (M67a)
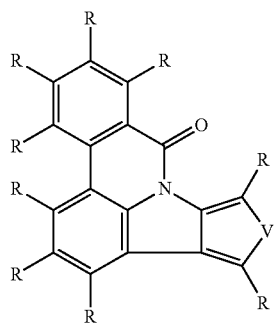
Formula (M68a)
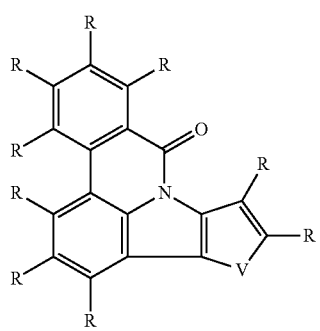
Formula (M69a)
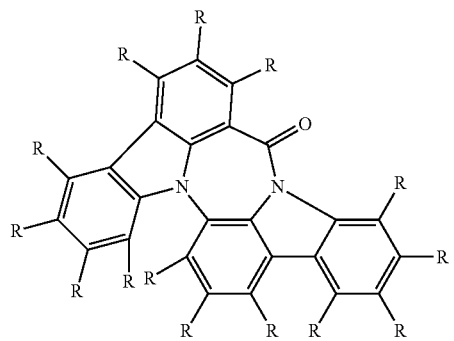
where the symbols used have the definitions given above.
Very particular preference is given to the structures of the formulae (M60b) to (M69b):
Formula (M60b)
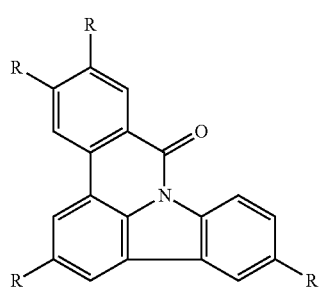
Formula (M61b)
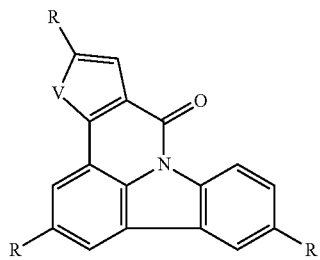
Formula (M62b)
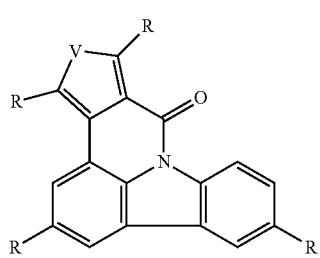
Formula (M63b)
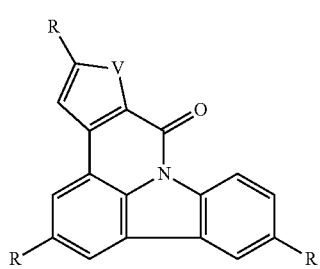
Formula (M64b)
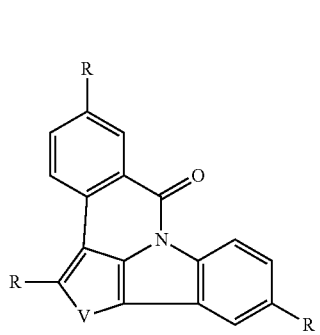
Formula (M65b)
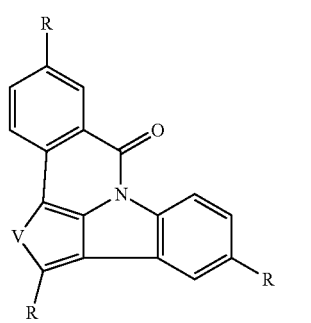

143
-continued

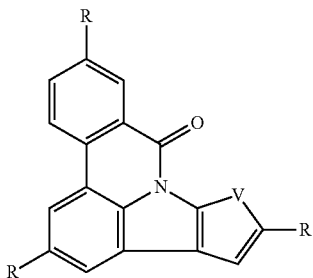

Formula (M66b)

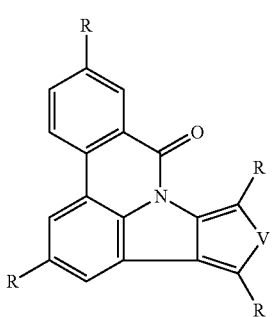

Formula (M67b)

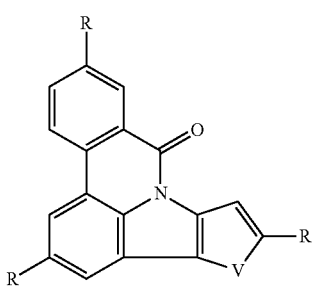

Formula (M68b)

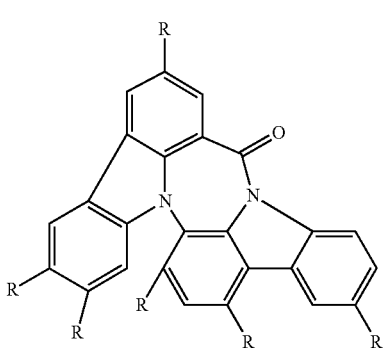

Formula (M69b)

where the symbols used have the definitions given above.

Very particular preference is given to the compounds of the formula (M60) or (M60a) or (M60b).

The bridging L group in the compounds of the formulae (M46a) is preferably selected from a single bond or an aromatic or heteroaromatic ring system which has 5 to 30 aromatic ring atoms and may be substituted by one or more R radicals. At the same time, the aromatic or heteroaromatic ring systems preferably do not contain any fused aryl or heteroaryl groups in which more than two aromatic six-membered rings are fused directly to one another. More preferably, they do not contain any aryl or heteroaryl groups in which aromatic six-membered rings are fused directly to one another at all.

In a further preferred embodiment of the invention, the index m in compounds of the formula (M46)=2 or 3, especially 2.

In a preferred embodiment of the invention, R in the formulae (M45) and (M46) and the preferred embodiments is the same or different at each instance and is selected from the group consisting of H, D, F, Cl, Br, CN, $N(Ar)_2$, $C(=O)Ar$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^1$ radicals, where one or more nonadjacent $CH_2$ groups may be replaced by O and where one or more hydrogen atoms may be replaced by D or F, an aromatic or heteroaromatic ring system which has 5 to 30 aromatic ring atoms and may be substituted in each case by one or more $R^1$ radicals, an aryloxy or heteroaryloxy group which has 5 to 30 aromatic ring atoms and may be substituted by one or more $R^1$ radicals, or a combination of these systems.

In a particularly preferred embodiment of the invention, R in the abovementioned formulae is the same or different at each instance and is selected from the group consisting of H, D, F, Cl, Br, CN, a straight-chain alkyl group having 1 to 10 carbon atoms or a branched or cyclic alkyl group having 3 to 10 carbon atoms, each of which may be substituted by one or more $R^1$ radicals, where one or more hydrogen atoms may be replaced by D or F, an aromatic or heteroaromatic ring system which has 5 to 18 aromatic ring atoms and may be substituted in each case by one or more $R^1$ radicals, or a combination of these systems.

At the same time, the R radicals, when they contain aromatic or heteroaromatic ring systems, preferably do not contain any fused aryl or heteroaryl groups in which more than two aromatic six-membered rings are fused directly to one another. More preferably, they do not contain any aryl or heteroaryl groups in which aromatic six-membered rings are fused directly to one another at all. Especially preferred here are phenyl, biphenyl, terphenyl, quaterphenyl, carbazole, dibenzothiophene, dibenzofuran, indenocarbazole, indolocarbazole, triazine or pyrimidine, each of which may also be substituted by one or more $R^1$ radicals.

At the same time, for compounds which are processed by vacuum evaporation, the alkyl groups preferably have not more than five carbon atoms, more preferably not more than 4 carbon atoms, most preferably not more than 1 carbon atom.

The compounds of the formulae (M45) and (M46) are known in principle. These compounds can be synthesized by the methods described in WO 2011/116865 and WO 2011/137951.

Examples of preferred compounds according to the embodiments detailed above are the compounds detailed in the following table:

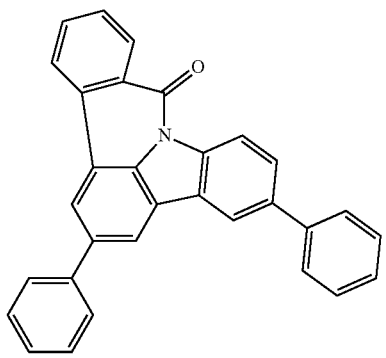 [SMILES: O=c1c2ccccc2c2cc(-c3ccccc3)cc3c4cc(-c5ccccc5)ccc4n1c23]
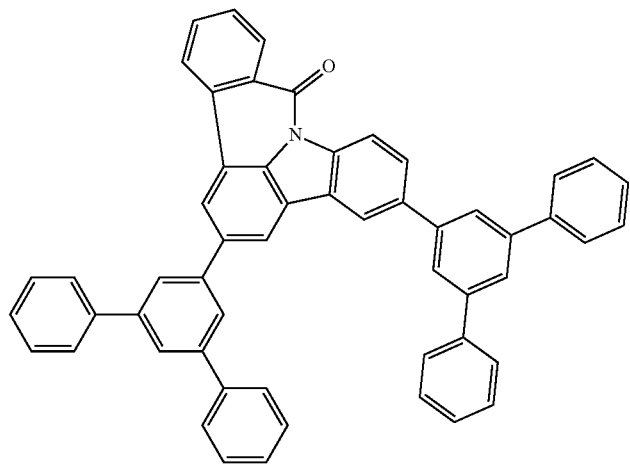
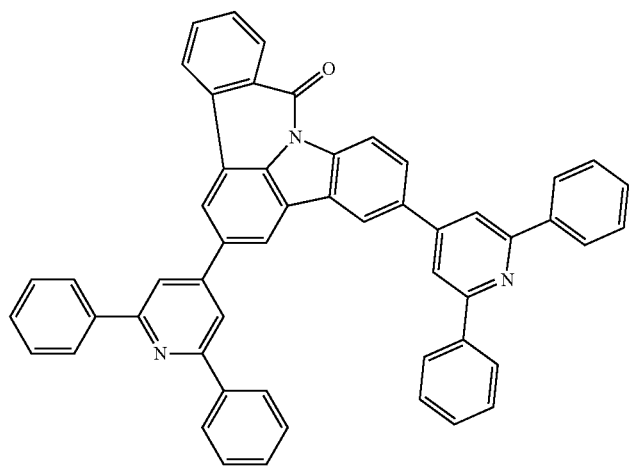 [SMILES: O=c1c2ccccc2c2cc(-c3cc(-c4ccccc4)nc(-c4ccccc4)c3)cc3c4cc(-c5cc(-c6ccccc6)nc(-c6ccccc6)c5)ccc4n1c23]
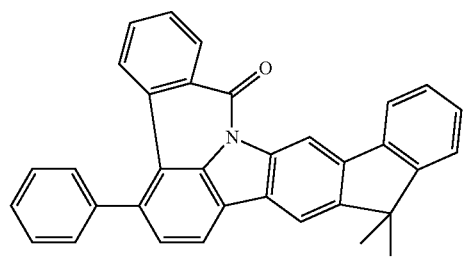 [SMILES: CC1(C)c2ccccc2-c2cc3c(cc21)c1ccc(-c2ccccc2)c2c4ccccc4c(=O)n3c12]

-continued
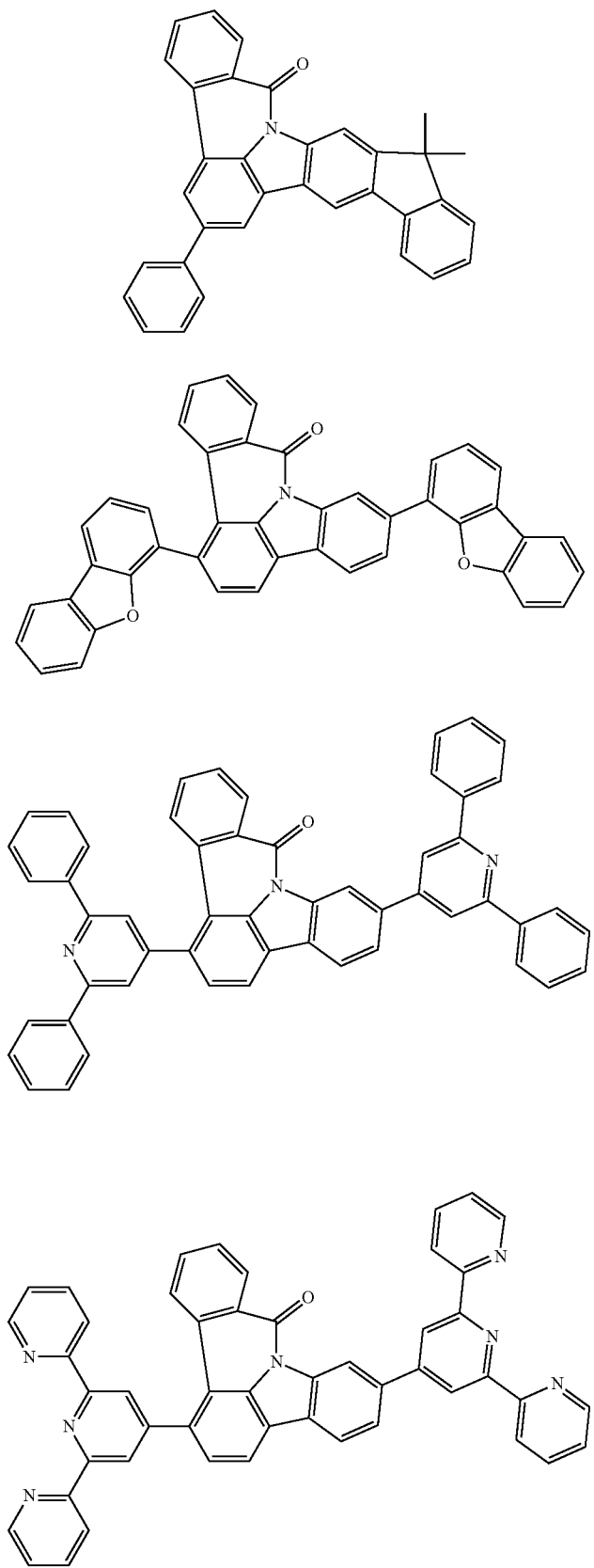

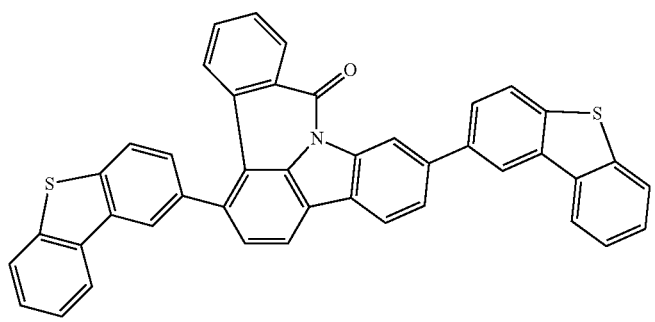 [SMILES: O=c1c2ccccc2c2c(-c3ccc4sc5ccccc5c4c3)ccc3c4ccc(-c5ccc6sc7ccccc7c6c5)cc4n1c32]
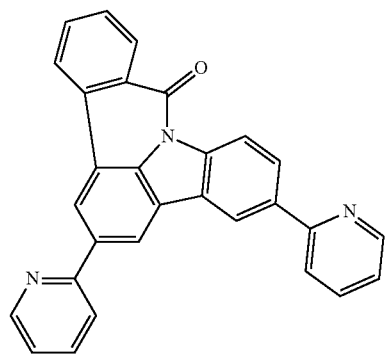 [SMILES: O=c1c2ccccc2c2cc(-c3ccccn3)cc3c4cc(-c5ccccn5)ccc4n1c23]
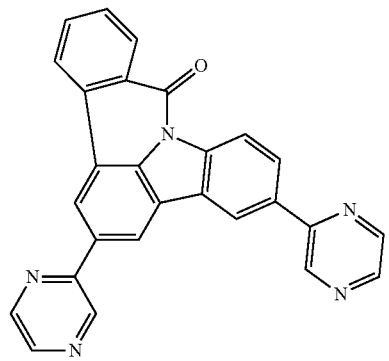 [SMILES: O=c1c2ccccc2c2cc(-c3cnccn3)cc3c4cc(-c5cnccn5)ccc4n1c23]
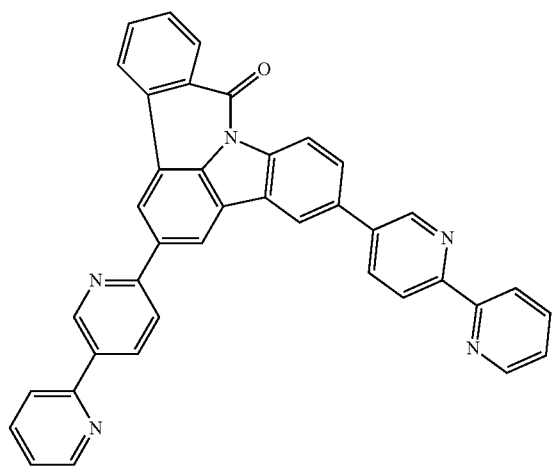 [SMILES: O=c1c2ccccc2c2cc(-c3ccc(-c4ccccn4)cn3)cc3c4cc(-c5ccc(-c6ccccn6)nc5)ccc4n1c23]

-continued
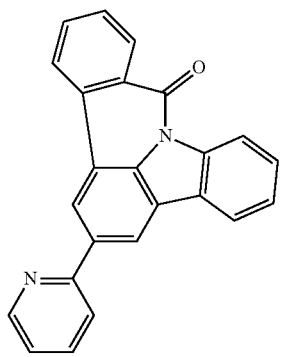 [SMILES: O=c1c2ccccc2c2cc(-c3ccccn3)cc3c4ccccc4n1c23]
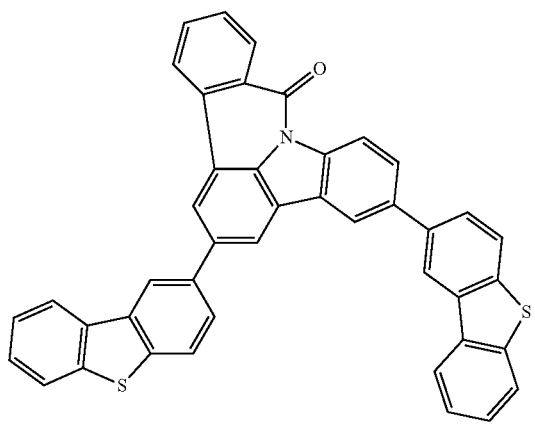 [SMILES: O=c1c2ccccc2c2cc(-c3ccc4sc5ccccc5c4c3)cc3c4cc(-c5ccc6sc7ccccc7c6c5)ccc4n1c23]
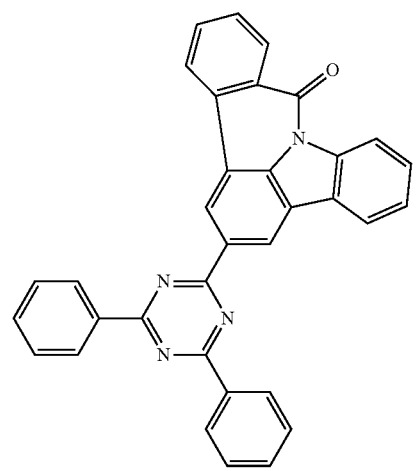 [SMILES: O=c1c2ccccc2c2cc(-c3nc(-c4ccccc4)nc(-c4ccccc4)n3)cc3c4ccccc4n1c23]

-continued
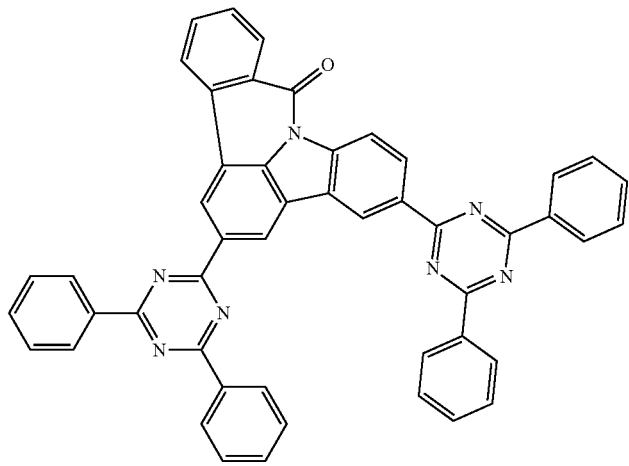 [SMILES: O=c1c2ccccc2c2cc(-c3nc(-c4ccccc4)nc(-c4ccccc4)n3)cc3c4cc(-c5nc(-c6ccccc6)nc(-c6ccccc6)n5)ccc4n1c23]
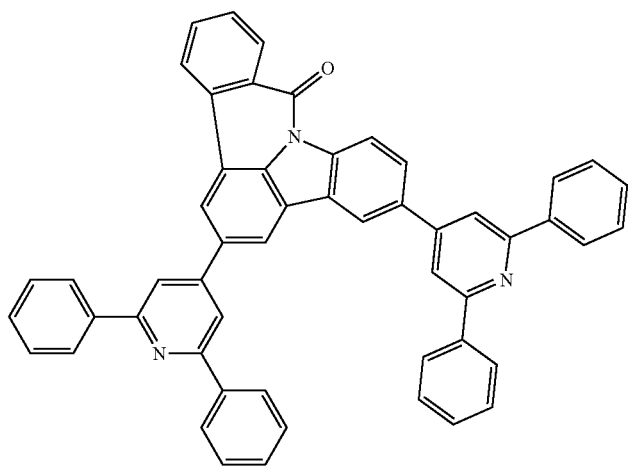 [SMILES: O=c1c2ccccc2c2cc(-c3cc(-c4ccccc4)nc(-c4ccccc4)c3)cc3c4cc(-c5cc(-c6ccccc6)nc(-c6ccccc6)c5)ccc4n1c23]
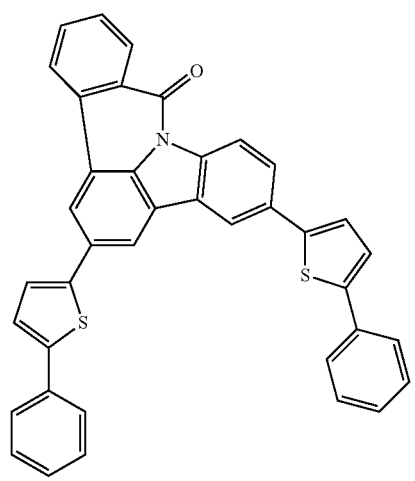 [SMILES: O=c1c2ccccc2c2cc(-c3ccc(-c4ccccc4)s3)cc3c4cc(-c5ccc(-c6ccccc6)s5)ccc4n1c23]

-continued
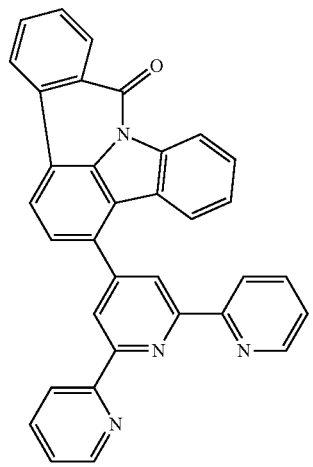 [SMILES: O=c1c2ccccc2c2ccc(-c3cc(-c4ccccn4)nc(-c4ccccn4)c3)c3c4ccccc4n1c23]
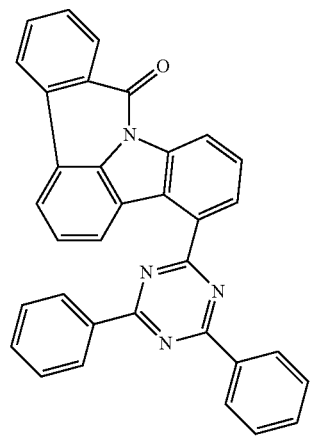 [SMILES: O=c1c2ccccc2c2cccc3c4c(-c5nc(-c6ccccc6)nc(-c6ccccc6)n5)cccc4n1c23]
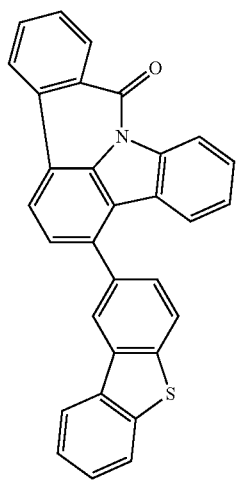 [SMILES: O=c1c2ccccc2c2ccc(-c3ccc4sc5ccccc5c4c3)c3c4ccccc4n1c23]

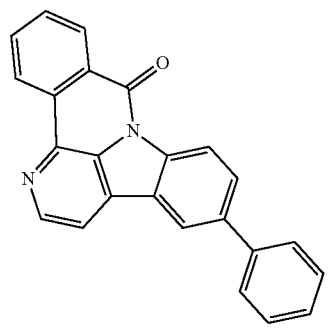 [SMILES: O=c1c2ccccc2c2nccc3c4cc(-c5ccccc5)ccc4n1c32]
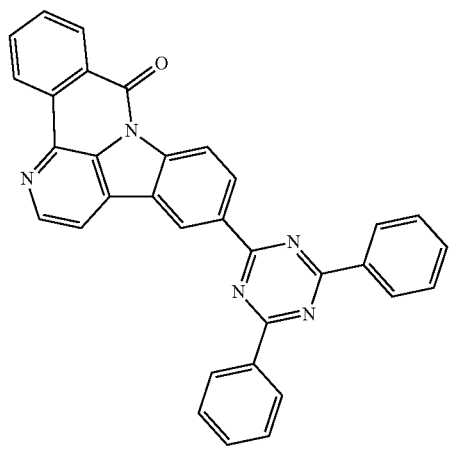 [SMILES: O=c1c2ccccc2c2nccc3c4cc(-c5nc(-c6ccccc6)nc(-c6ccccc6)n5)ccc4n1c32]
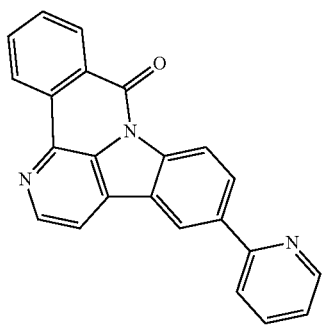 [SMILES: O=c1c2ccccc2c2nccc3c4cc(-c5ccccn5)ccc4n1c32]
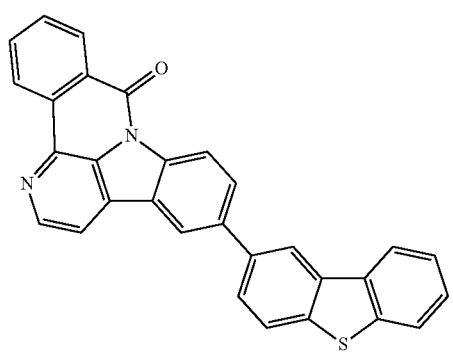 [SMILES: O=c1c2ccccc2c2nccc3c4cc(-c5ccc6sc7ccccc7c6c5)ccc4n1c32]

-continued
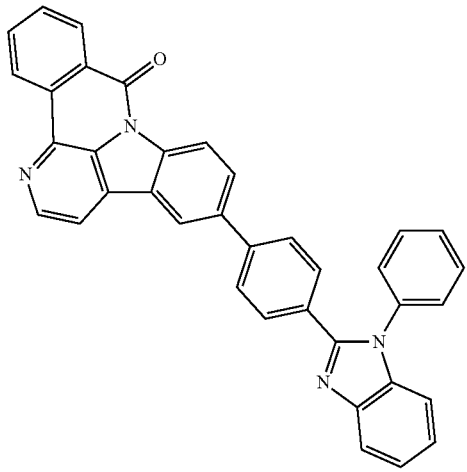 [SMILES: O=c1c2ccccc2c2nccc3c4cc(-c5ccc(-c6nc7ccccc7n6-c6ccccc6)cc5)ccc4n1c32]
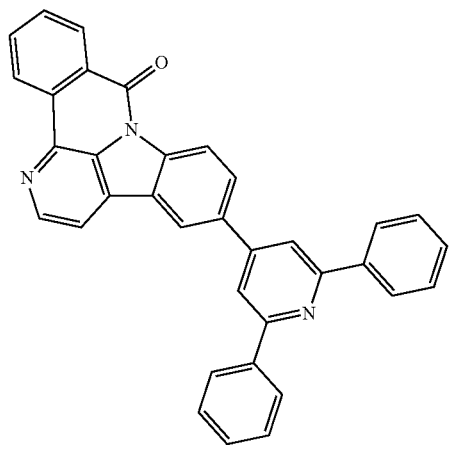 [SMILES: O=c1c2ccccc2c2nccc3c4cc(-c5cc(-c6ccccc6)nc(-c6ccccc6)c5)ccc4n1c32]
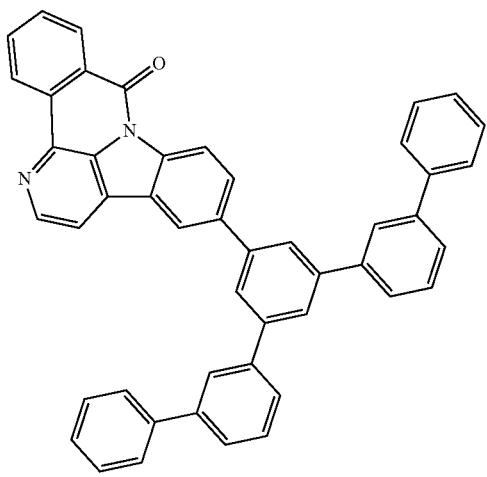 [SMILES: O=c1c2ccccc2c2nccc3c4cc(-c5cc(-c6cccc(-c7ccccc7)c6)cc(-c6cccc(-c7ccccc7)c6)c5)ccc4n1c32]

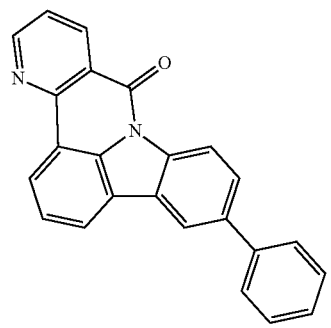
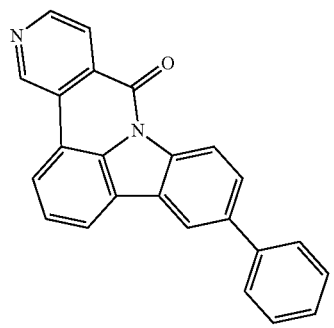 [SMILES: O=c1c2ccncc2c2cccc3c4cc(-c5ccccc5)ccc4n1c23]
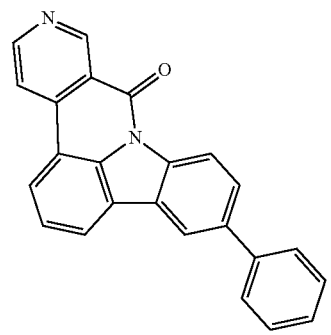 [SMILES: O=c1c2cnccc2c2cccc3c4cc(-c5ccccc5)ccc4n1c23]
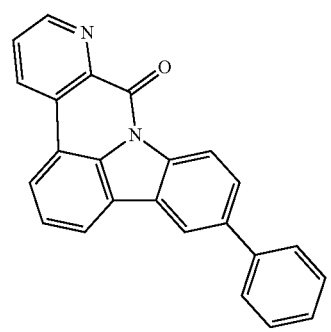 [SMILES: O=c1c2ncccc2c2cccc3c4cc(-c5ccccc5)ccc4n1c23]

-continued
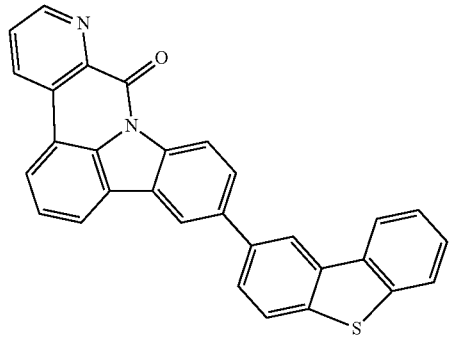 [SMILES: O=c1c2ncccc2c2cccc3c4cc(-c5ccc6sc7ccccc7c6c5)ccc4n1c23]
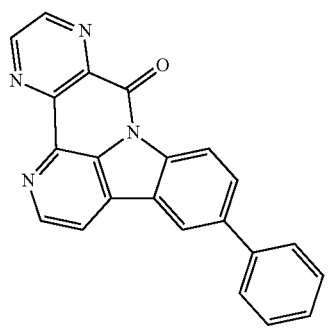
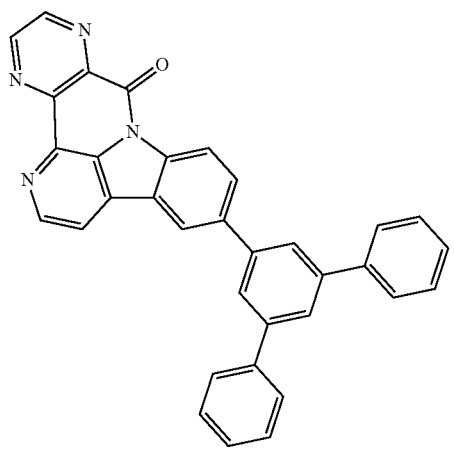 [SMILES: O=c1c2nccnc2c2nccc3c4cc(-c5cc(-c6ccccc6)cc(-c6ccccc6)c5)ccc4n1c32]
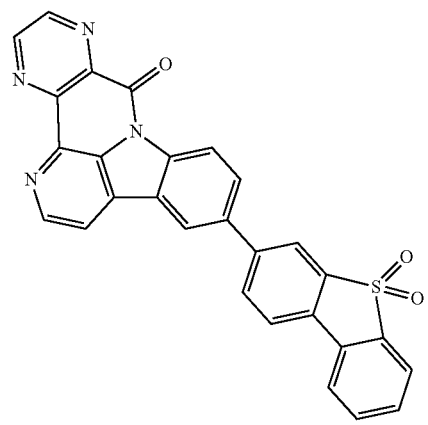 [SMILES: O=c1c2nccnc2c2nccc3c4cc(-c5ccc6c(c5)S(=O)(=O)c5ccccc5-6)ccc4n1c32]

-continued
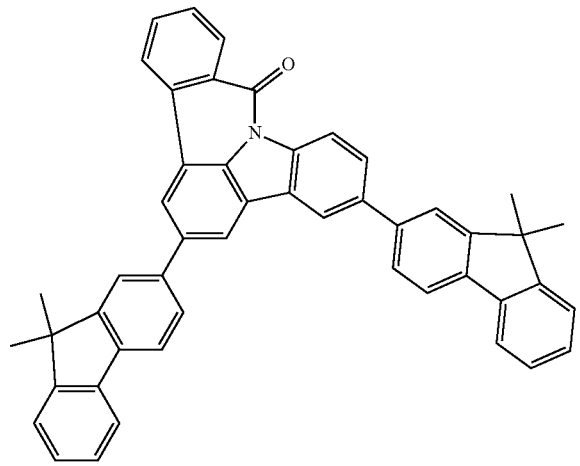 [SMILES: CC1(C)c2ccccc2-c2ccc(-c3ccc4c(c3)c3cc(-c5ccc6c(c5)C(C)(C)c5ccccc5-6)cc5c6ccccc6c(=O)n4c53)cc21]
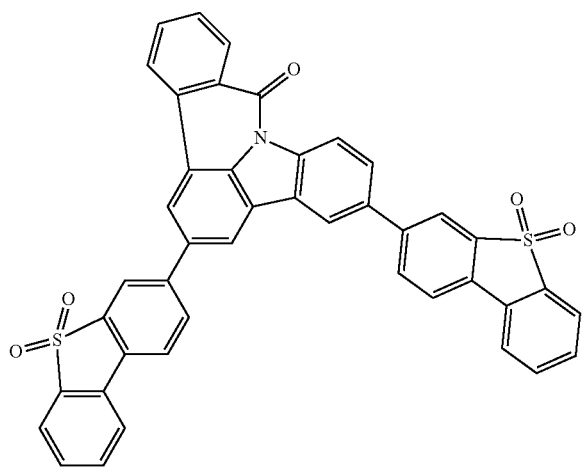 [SMILES: O=c1c2ccccc2c2cc(-c3ccc4c(c3)S(=O)(=O)c3ccccc3-4)cc3c4cc(-c5ccc6c(c5)S(=O)(=O)c5ccccc5-6)ccc4n1c23]
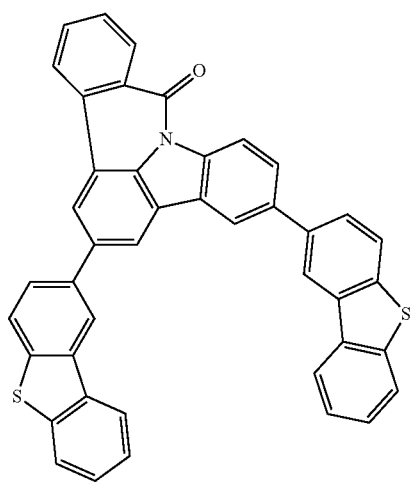 [SMILES: O=c1c2ccccc2c2cc(-c3ccc4sc5ccccc5c4c3)cc3c4cc(-c5ccc6sc7ccccc7c6c5)ccc4n1c23]

-continued
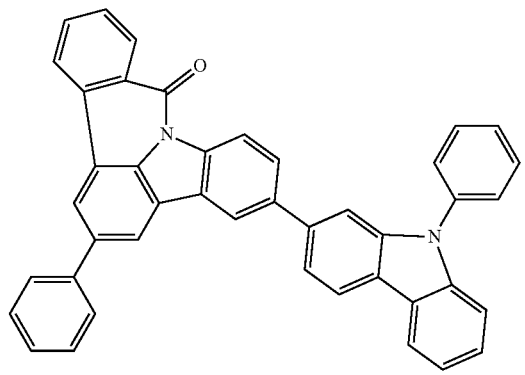 [SMILES: O=c1c2ccccc2c2cc(-c3ccccc3)cc3c4cc(-c5ccc6c7ccccc7n(-c7ccccc7)c6c5)ccc4n1c23]
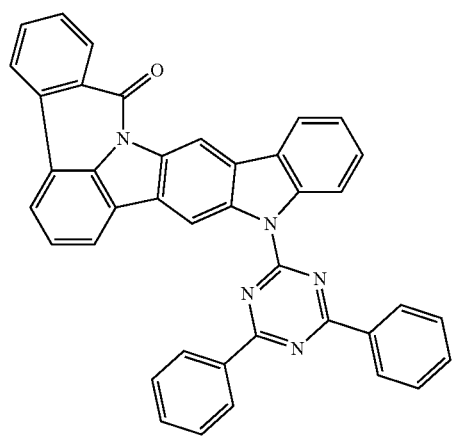 [SMILES: O=c1c2ccccc2c2cccc3c4cc5c(cc4n1c23)c1ccccc1n5-c1nc(-c2ccccc2)nc(-c2ccccc2)n1]
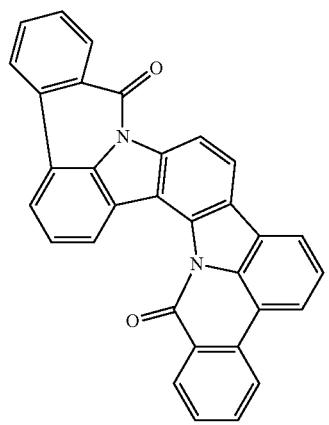 [SMILES: O=c1c2ccccc2c2cccc3c4c(ccc5c6cccc7c8ccccc8c(=O)n(c76)c54)n1c23]
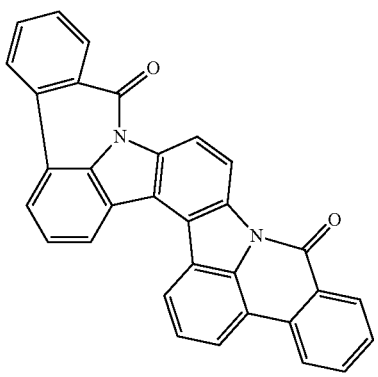 [SMILES: O=c1c2ccccc2c2cccc3c4c5c6cccc7c8ccccc8c(=O)n(c5ccc4n1c23)c76]

-continued
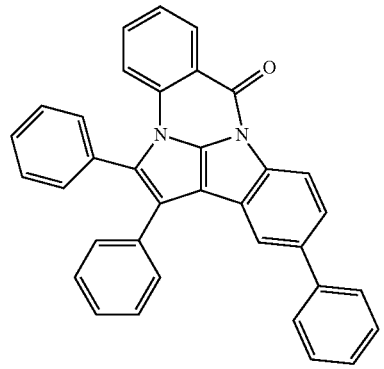 [SMILES: O=c1c2ccccc2n2c(-c3ccccc3)c(-c3ccccc3)c3c4cc(-c5ccccc5)ccc4n1c32]
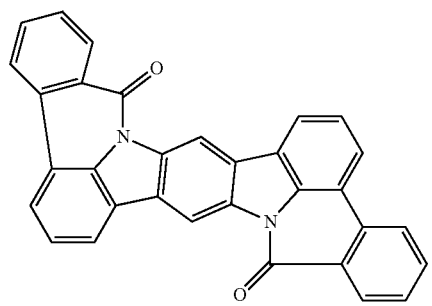 [SMILES: O=c1c2ccccc2c2cccc3c4cc5c(cc4n1c23)c1cccc2c3ccccc3c(=O)n5c21]
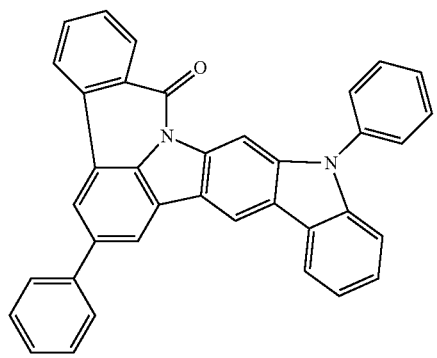 [SMILES: O=c1c2ccccc2c2cc(-c3ccccc3)cc3c4cc5c6ccccc6n(-c6ccccc6)c5cc4n1c23]
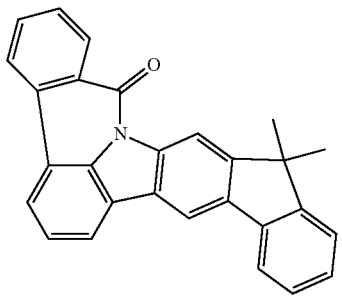 [SMILES: CC1(C)c2ccccc2-c2cc3c4cccc5c6ccccc6c(=O)n(c3cc21)c54]
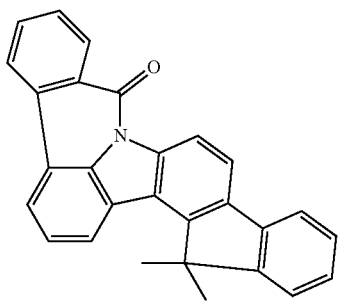 [SMILES: CC1(C)c2ccccc2-c2ccc3c(c21)c1cccc2c4ccccc4c(=O)n3c21]

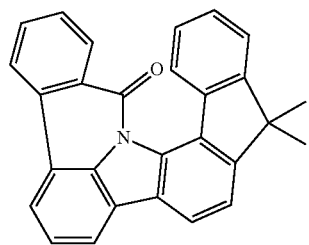 [SMILES: CC1(C)c2ccccc2-c2c1ccc1c3cccc4c5ccccc5c(=O)n(c21)c43]
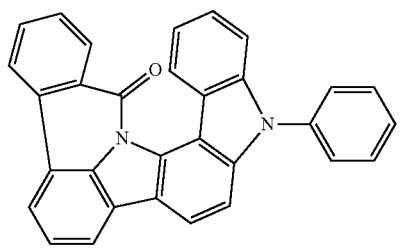 [SMILES: O=c1c2ccccc2c2cccc3c4ccc5c(c6ccccc6n5-c5ccccc5)c4n1c23]
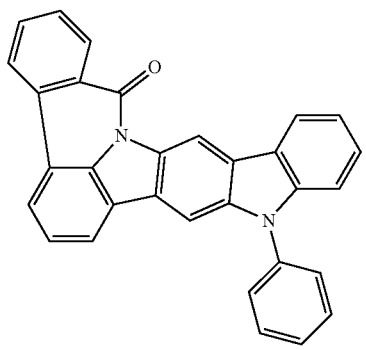 [SMILES: O=c1c2ccccc2c2cccc3c4cc5c(cc4n1c23)c1ccccc1n5-c1ccccc1]
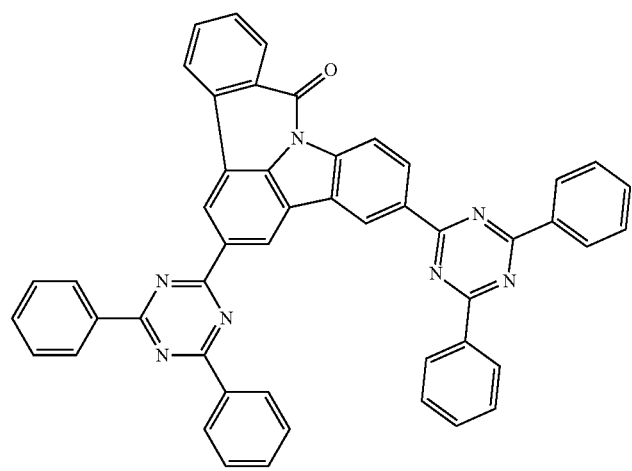

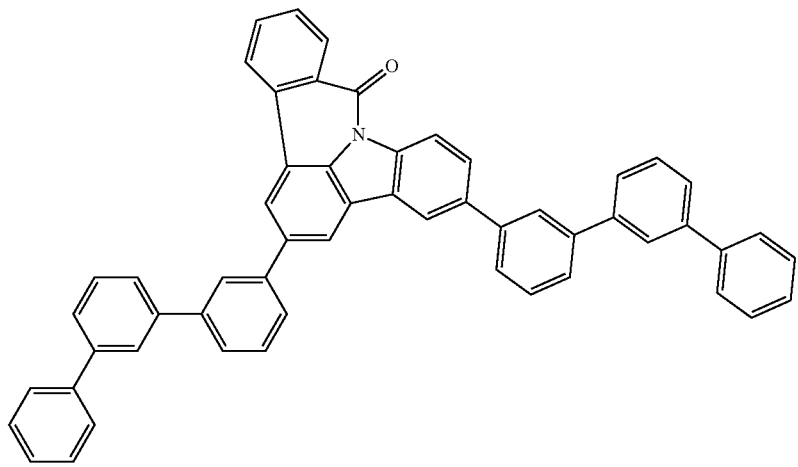 [SMILES: O=c1c2ccccc2c2cc(-c3cccc(-c4cccc(-c5ccccc5)c4)c3)cc3c4cc(-c5cccc(-c6cccc(-c7ccccc7)c6)c5)ccc4n1c23]
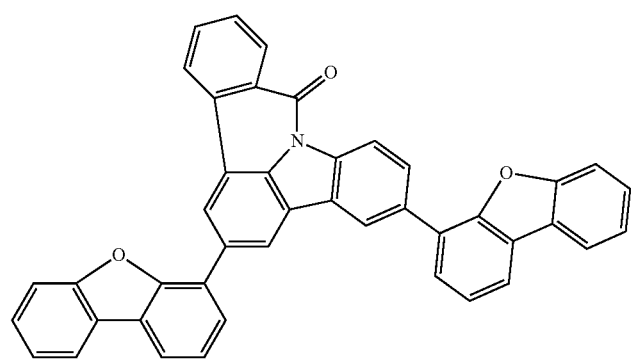 [SMILES: O=c1c2ccccc2c2cc(-c3cccc4c3oc3ccccc34)cc3c4cc(-c5cccc6c5oc5ccccc56)ccc4n1c23]
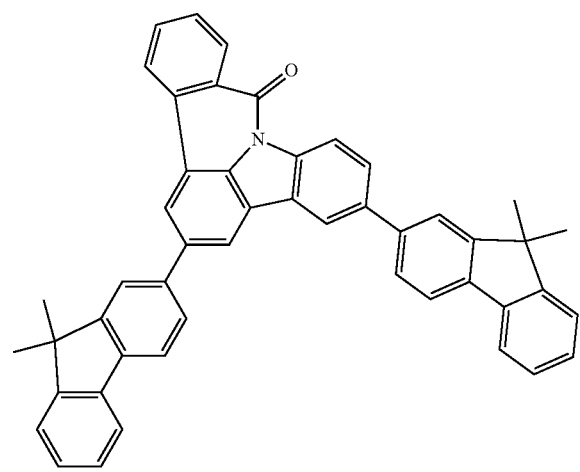 [SMILES: CC1(C)c2ccccc2-c2ccc(-c3ccc4c(c3)c3cc(-c5ccc6c(c5)C(C)(C)c5ccccc5-6)cc5c6ccccc6c(=O)n4c53)cc21]

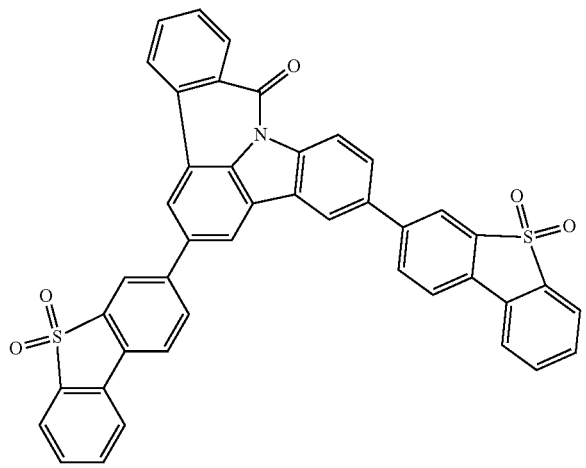 [SMILES: O=c1c2ccccc2c2cc(-c3ccc4c(c3)S(=O)(=O)c3ccccc3-4)cc3c4cc(-c5ccc6c(c5)S(=O)(=O)c5ccccc5-6)ccc4n1c23]
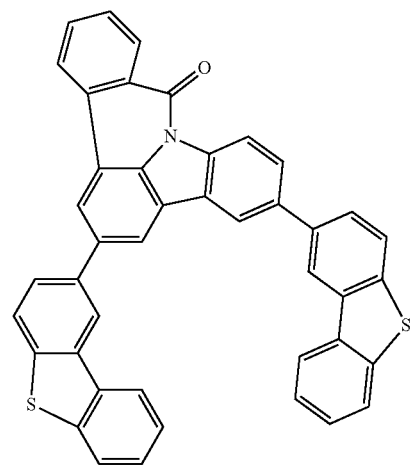 [SMILES: O=c1c2ccccc2c2cc(-c3ccc4sc5ccccc5c4c3)cc3c4cc(-c5ccc6sc7ccccc7c6c5)ccc4n1c23]
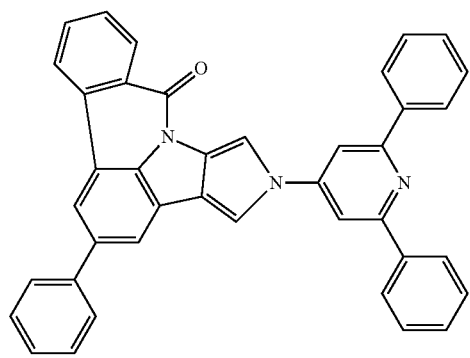 [SMILES: O=c1c2ccccc2c2cc(-c3ccccc3)cc3c4cn(-c5cc(-c6ccccc6)nc(-c6ccccc6)c5)cc4n1c23]

-continued
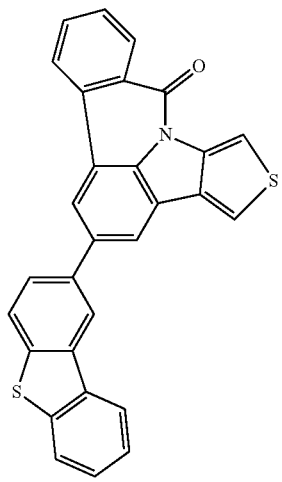 [SMILES: O=c1c2ccccc2c2cc(-c3ccc4sc5ccccc5c4c3)cc3c4cscc4n1c23]
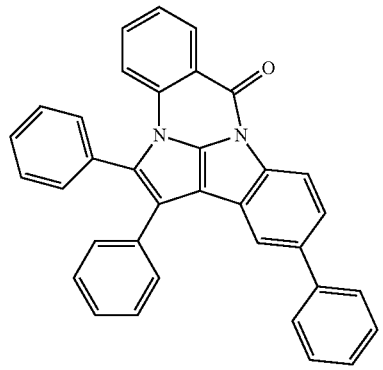 [SMILES: O=c1c2ccccc2n2c(-c3ccccc3)c(-c3ccccc3)c3c4cc(-c5ccccc5)ccc4n1c32]
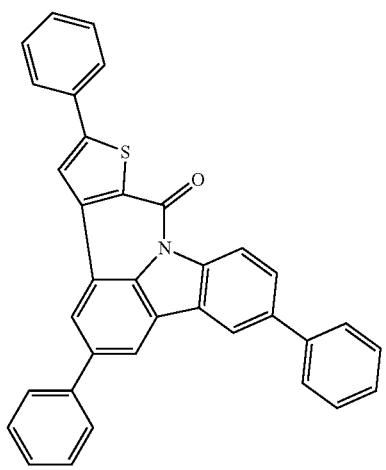 [SMILES: O=c1c2sc(-c3ccccc3)cc2c2cc(-c3ccccc3)cc3c4cc(-c5ccccc5)ccc4n1c23]

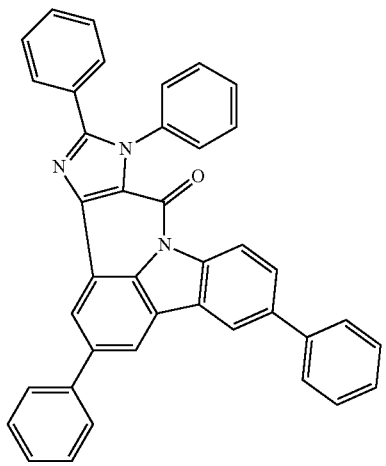 [SMILES: O=c1c2c(nc(-c3ccccc3)n2-c2ccccc2)c2cc(-c3ccccc3)cc3c4cc(-c5ccccc5)ccc4n1c32]
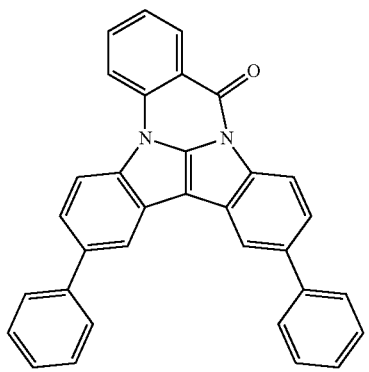 [SMILES: O=c1c2ccccc2n2c3ccc(-c4ccccc4)cc3c3c4cc(-c5ccccc5)ccc4n1c32]
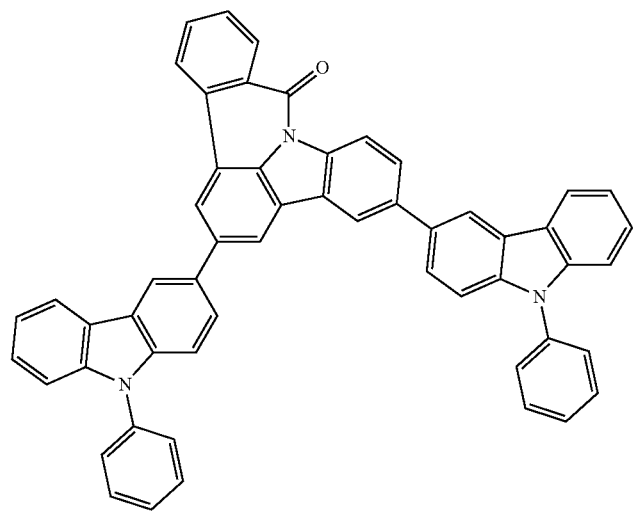 [SMILES: O=c1c2ccccc2c2cc(-c3ccc4c(c3)c3ccccc3n4-c3ccccc3)cc3c4cc(-c5ccc6c(c5)c5ccccc5n6-c5ccccc5)ccc4n1c23]

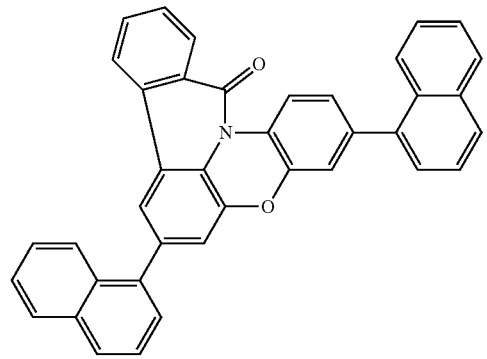 [SMILES: O=c1c2ccccc2c2cc(-c3cccc4ccccc34)cc3c2n1-c1ccc(-c2cccc4ccccc24)cc1O3]
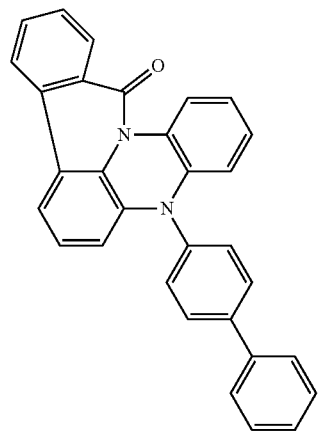 [SMILES: O=c1c2ccccc2c2cccc3c2n1-c1ccccc1N3c1ccc(-c2ccccc2)cc1]
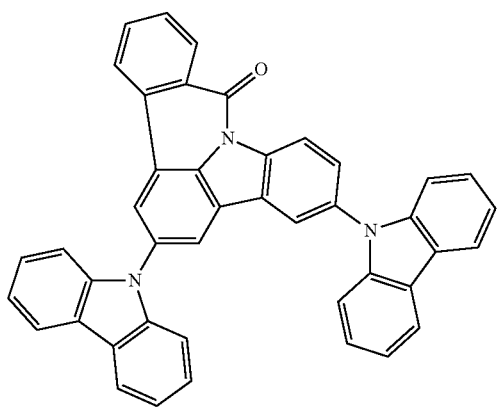 [SMILES: O=c1c2ccccc2c2cc(-n3c4ccccc4c4ccccc43)cc3c4cc(-n5c6ccccc6c6ccccc65)ccc4n1c23]

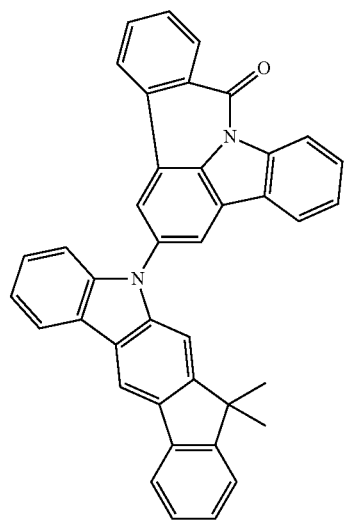 [SMILES: CC1(C)c2ccccc2-c2cc3c4ccccc4n(-c4cc5c6ccccc6c(=O)n6c7ccccc7c(c4)c56)c3cc21]
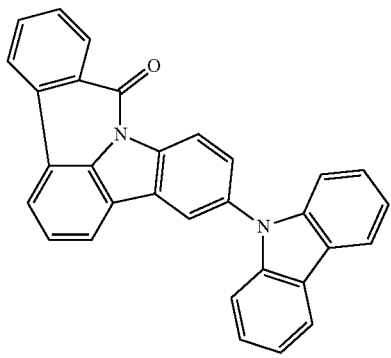 [SMILES: O=c1c2ccccc2c2cccc3c4cc(-n5c6ccccc6c6ccccc65)ccc4n1c23]
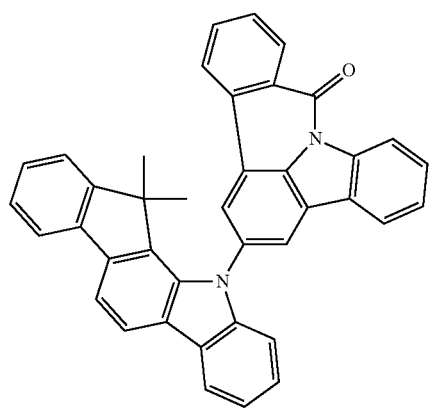 [SMILES: CC1(C)c2ccccc2-c2ccc3c4ccccc4n(-c4cc5c6ccccc6c(=O)n6c7ccccc7c(c4)c56)c3c21]

-continued
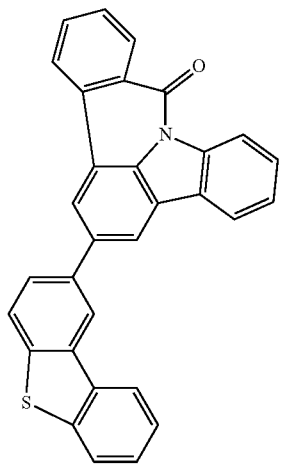 [SMILES: O=c1c2ccccc2c2cc(-c3ccc4sc5ccccc5c4c3)cc3c4ccccc4n1c23]
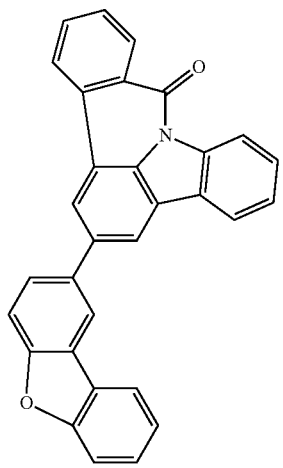 [SMILES: O=c1c2ccccc2c2cc(-c3ccc4oc5ccccc5c4c3)cc3c4ccccc4n1c23]
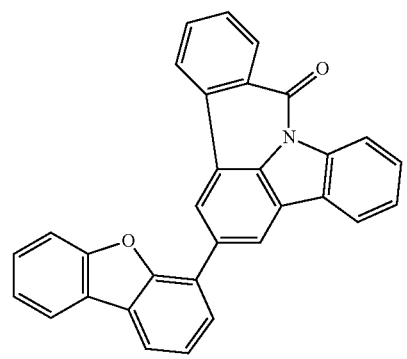 [SMILES: O=c1c2ccccc2c2cc(-c3cccc4c3oc3ccccc34)cc3c4ccccc4n1c23]

-continued
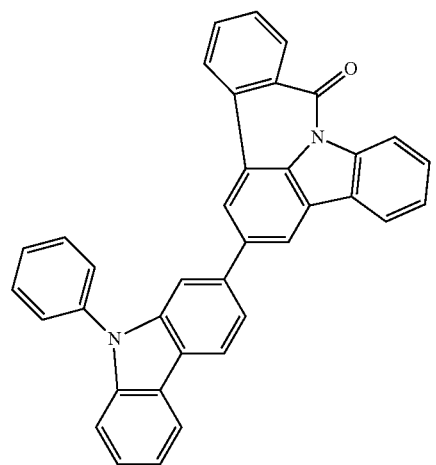 [SMILES: O=c1c2ccccc2c2cc(-c3ccc4c5ccccc5n(-c5ccccc5)c4c3)cc3c4ccccc4n1c23]
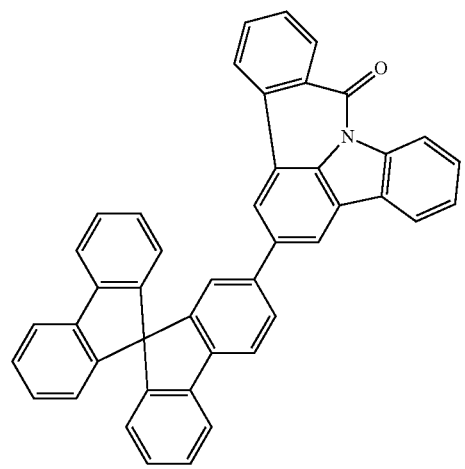 [SMILES: O=c1c2ccccc2c2cc(-c3ccc4c(c3)C3(c5ccccc5-c5ccccc53)c3ccccc3-4)cc3c4ccccc4n1c23]
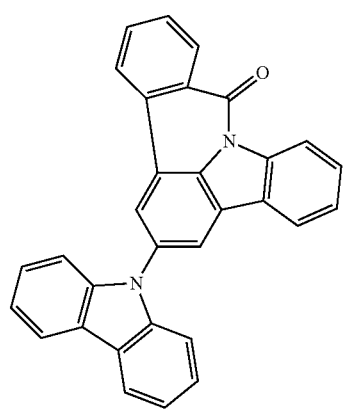 [SMILES: O=c1c2ccccc2c2cc(-n3c4ccccc4c4ccccc43)cc3c4ccccc4n1c23]

-continued
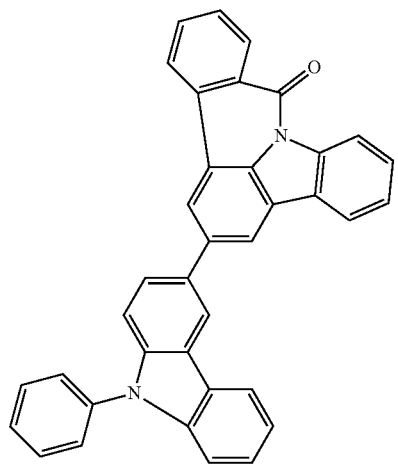 [SMILES: O=c1c2ccccc2c2cc(-c3ccc4c(c3)c3ccccc3n4-c3ccccc3)cc3c4ccccc4n1c23]
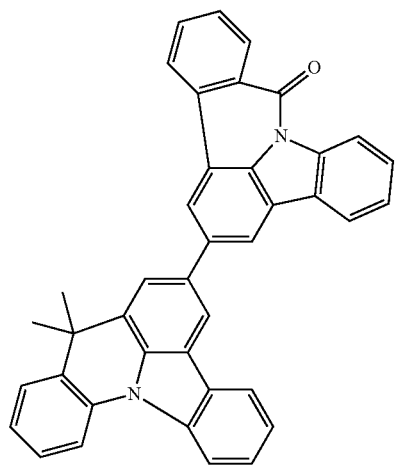 [SMILES: CC1(C)c2ccccc2-n2c3ccccc3c3cc(-c4cc5c6ccccc6c(=O)n6c7ccccc7c(c4)c56)cc1c32]
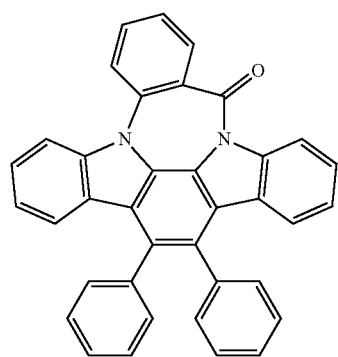 [SMILES: O=c1c2ccccc2n2c3ccccc3c3c(-c4ccccc4)c(-c4ccccc4)c4c5ccccc5n1c4c32]

-continued
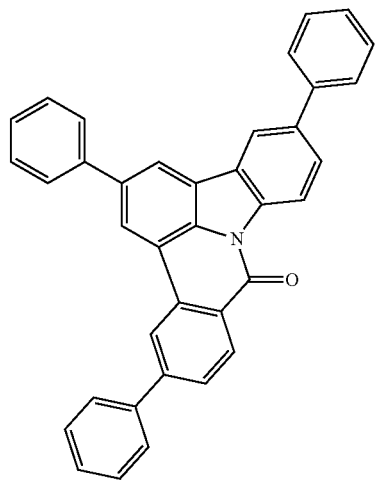 [SMILES: O=c1c2ccc(-c3ccccc3)cc2c2cc(-c3ccccc3)cc3c4cc(-c5ccccc5)ccc4n1c23]
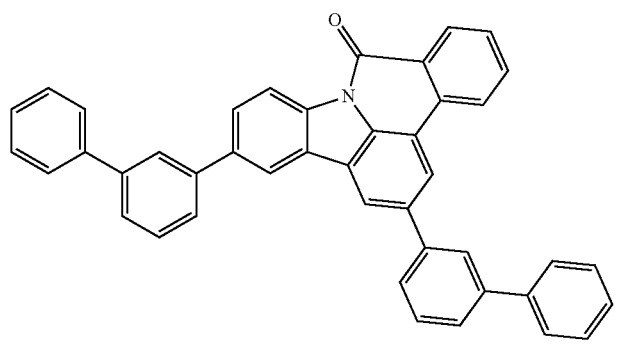 [SMILES: O=c1c2ccccc2c2cc(-c3cccc(-c4ccccc4)c3)cc3c4cc(-c5cccc(-c6ccccc6)c5)ccc4n1c23]
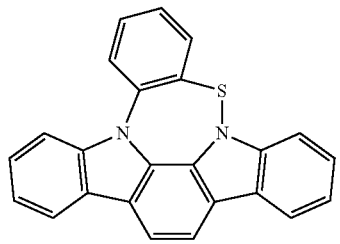 [SMILES: c1ccc2c(c1)sn1c3ccccc3c3ccc4c5ccccc5n2c4c31]
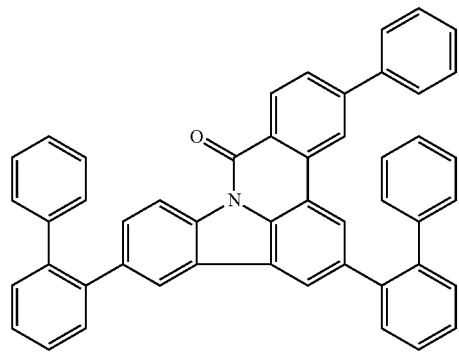 [SMILES: O=c1c2ccc(-c3ccccc3)cc2c2cc(-c3ccccc3-c3ccccc3)cc3c4cc(-c5ccccc5-c5ccccc5)ccc4n1c23]

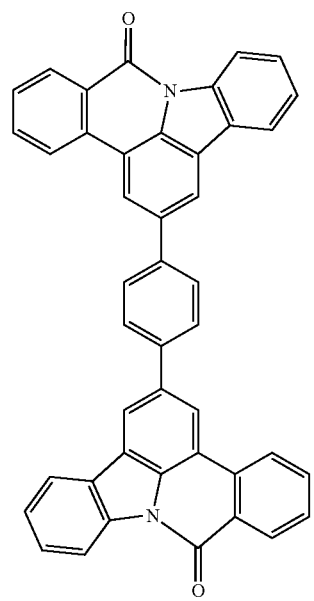 [SMILES: O=c1c2ccccc2c2cc(-c3ccc(-c4cc5c6ccccc6c(=O)n6c7ccccc7c(c4)c56)cc3)cc3c4ccccc4n1c23]
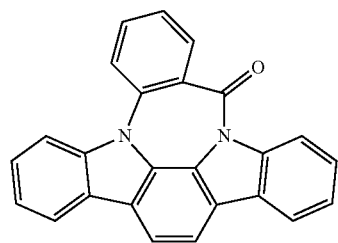 [SMILES: O=c1c2ccccc2n2c3ccccc3c3ccc4c5ccccc5n1c4c32]
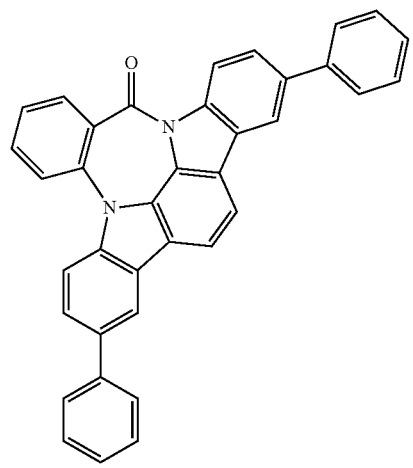 [SMILES: O=c1c2ccccc2n2c3ccc(-c4ccccc4)cc3c3ccc4c5cc(-c6ccccc6)ccc5n1c4c32]
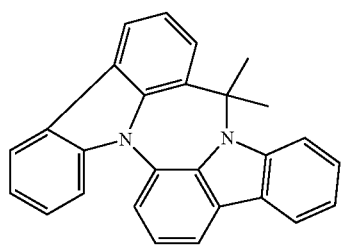 [SMILES: CC1(C)c2cccc3c4ccccc4n(c23)-c2cccc3c4ccccc4n1c23]

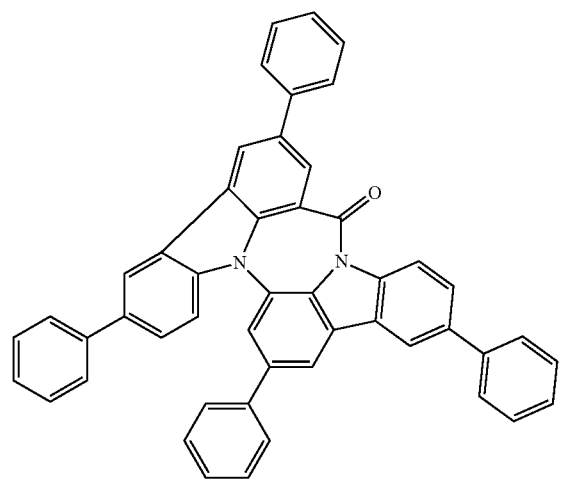 [SMILES: O=c1c2cc(-c3ccccc3)cc3c4cc(-c5ccccc5)ccc4n(c4cc(-c5ccccc5)cc5c6cc(-c7ccccc7)ccc6n1c54)c23]
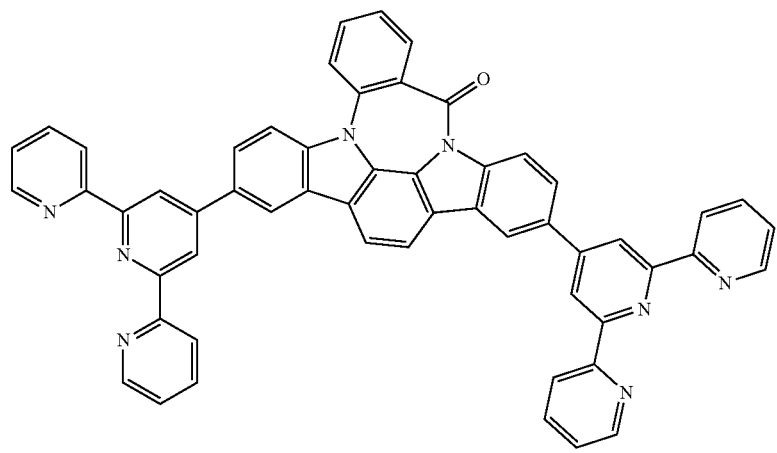 [SMILES: O=c1c2ccccc2n2c3ccc(-c4cc(-c5ccccn5)nc(-c5ccccn5)c4)cc3c3ccc4c5cc(-c6cc(-c7ccccn7)nc(-c7ccccn7)c6)ccc5n1c4c32]
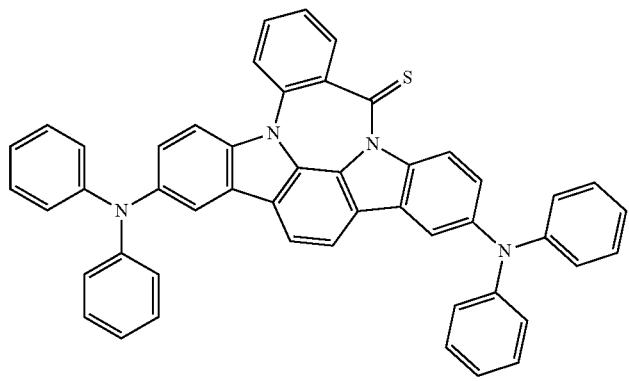 [SMILES: S=c1c2ccccc2n2c3ccc(N(c4ccccc4)c4ccccc4)cc3c3ccc4c5cc(N(c6ccccc6)c6ccccc6)ccc5n1c4c32]

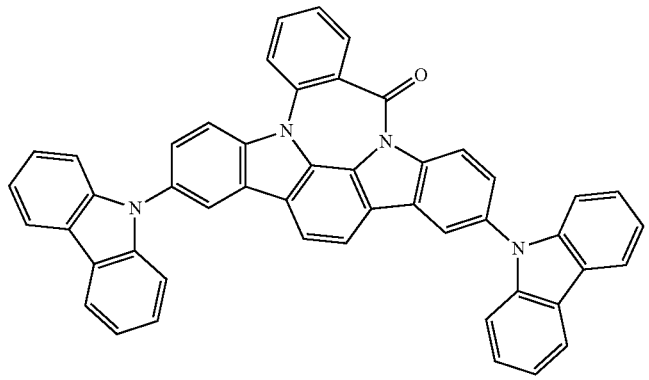 [SMILES: O=c1c2ccccc2n2c3ccc(-n4c5ccccc5c5ccccc54)cc3c3ccc4c5cc(-n6c7ccccc7c7ccccc76)ccc5n1c4c32]
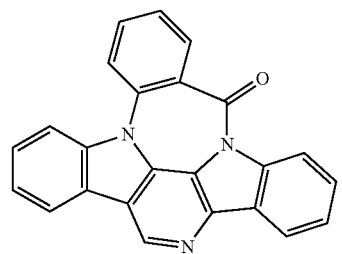 [SMILES: O=c1c2ccccc2n2c3ccccc3c3cnc4c5ccccc5n1c4c32]
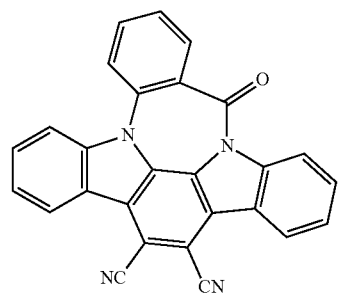 [SMILES: N#Cc1c(C#N)c2c3ccccc3n3c4ccccc4c(=O)n4c5ccccc5c1c4c23]
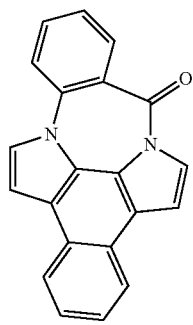 [SMILES: O=c1c2ccccc2n2ccc3c4ccccc4c4ccn1c4c32]
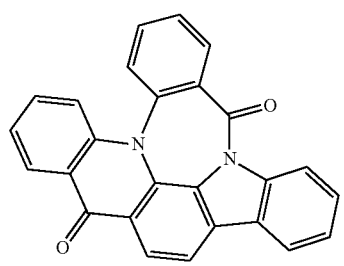 [SMILES: O=c1c2ccccc2n2c3ccccc3c(=O)n3c4ccccc4c4ccc1c2c43]

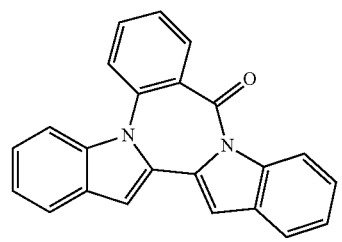 [SMILES: O=c1c2ccccc2n2c3ccccc3cc2c2cc3ccccc3n12]
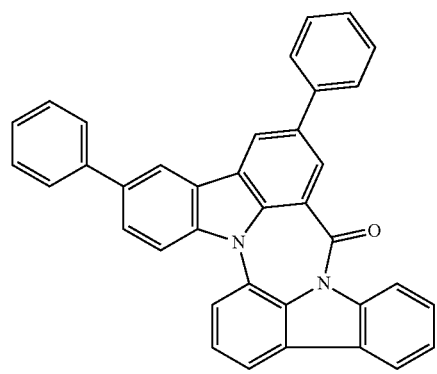 [SMILES: O=c1c2cc(-c3ccccc3)cc3c4cc(-c5ccccc5)ccc4n(c4cccc5c6ccccc6n1c54)c23]
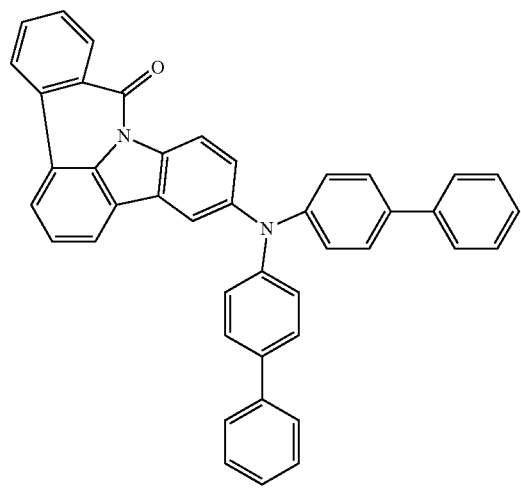 [SMILES: O=c1c2ccccc2c2cccc3c4cc(N(c5ccc(-c6ccccc6)cc5)c5ccc(-c6ccccc6)cc5)ccc4n1c23]
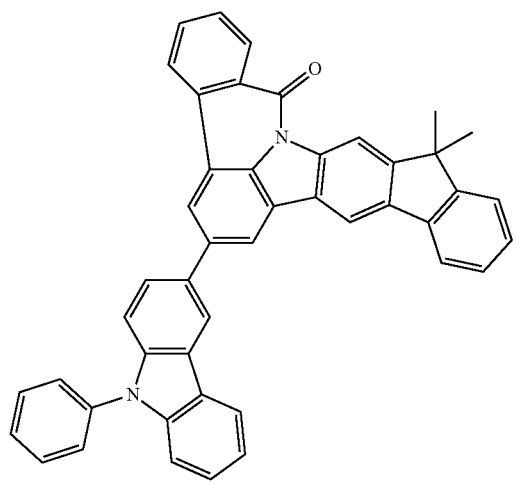 [SMILES: CC1(C)c2ccccc2-c2cc3c4cc(-c5ccc6c(c5)c5ccccc5n6-c5ccccc5)cc5c6ccccc6c(=O)n(c3cc21)c54]

-continued
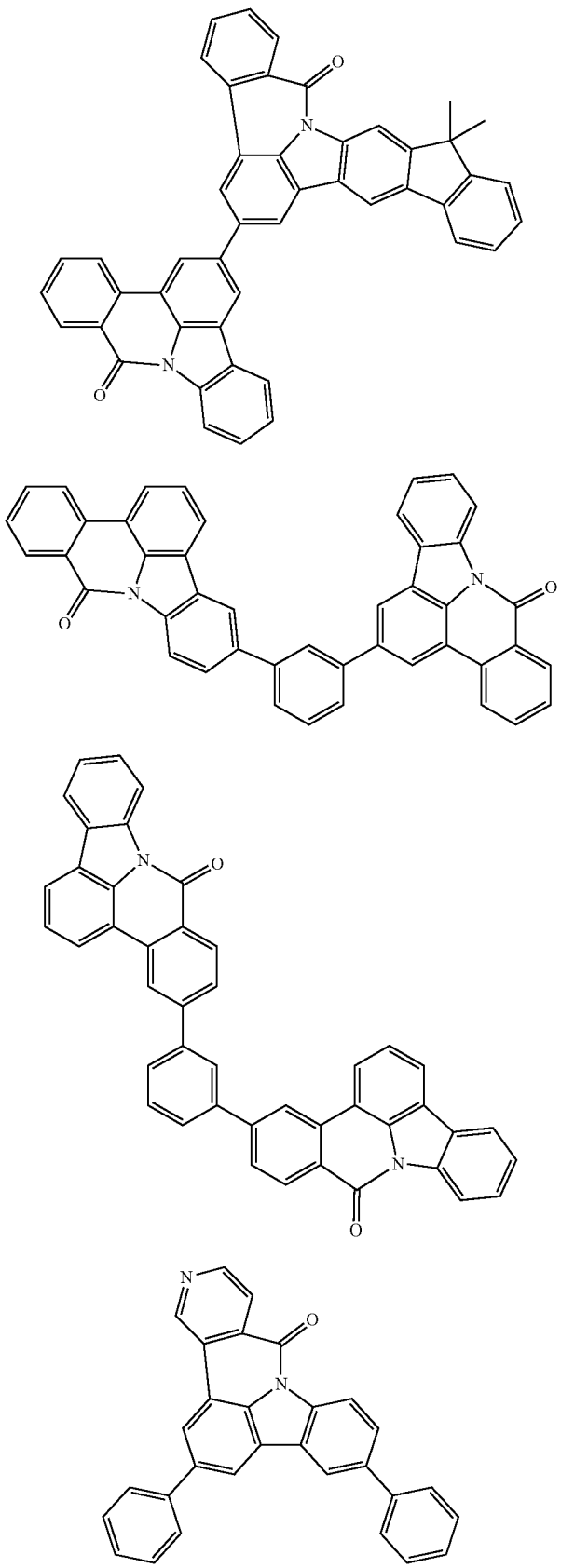

Aromatic ketones or aromatic phosphine oxides are additionally suitable as electron-conducting compound. An aromatic ketone in the context of this application is understood to mean a carbonyl group to which two aromatic or heteroaromatic groups or aromatic or heteroaromatic ring systems are bonded directly. An aromatic phosphine oxide in the context of this application is understood to mean a P=O group to which three aromatic or heteroaromatic groups or aromatic or heteroaromatic ring systems are bonded directly.

When the electron-conducting compound is an aromatic ketone or an aromatic phosphine oxide, this compound is preferably selected from the compounds of the following formulae (M70) or (M71):

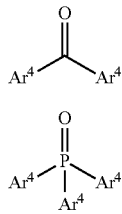

Formula (M70)

Formula (M71)

where R, $R^1$, $R^2$ and Ar have the definitions listed above and the further symbols used are as follows:

$Ar^4$ is the same or different at each instance and is an aromatic or heteroaromatic ring system which has 5 to 80 aromatic ring atoms, preferably up to 60 aromatic ring atoms, each of which may be substituted by one or more R groups.

Suitable compounds according to (M70) and (M71) are especially the ketones disclosed in WO 2004/093207 and WO 2010/006680 and the phosphine oxides disclosed in WO 2005/003253. These are incorporated into the present invention by reference.

It is apparent from the definition of the compound of formula (M70) and (M70) that these must not just contain one carbonyl group or phosphine oxide group, but may also contain two or more of these groups.

Preferably, the $Ar^4$ group in compounds of formula (M70) or (M71) is an aromatic ring system having 6 to 40 aromatic ring atoms, meaning that it does not contain any heteroaryl groups. As defined above, the aromatic ring system need not necessarily have only aromatic groups; instead, it is also possible for two aryl groups to be interrupted by a nonaromatic group, for example by a further carbonyl group or phosphine oxide group.

In a further preferred embodiment of the invention, the $Ar^4$ group has not more than two fused rings. It is thus preferably formed from phenyl and/or naphthyl groups only, more preferably from phenyl groups only, but does not contain any larger fused aromatics, for example anthracene.

Preferred $Ar^4$ groups bonded to the carbonyl group are the same or different at each instance and are phenyl, 2-, 3- or 4-tolyl, 3- or 4-o-xylyl, 2- or 4-m-xylyl, 2-p-xylyl, o-, m- or p-tert-butylphenyl, o-, m- or p-fluorophenyl, benzophenone, 1-, 2- or 3-phenylmethanone, 2-, 3- or 4-biphenyl, 2-, 3- or 4-o-terphenyl, 2-, 3- or 4-m-terphenyl, 2-, 3- or 4-p-terphenyl, 2'-p-terphenyl, 2'-, 4'- or 5'-m-terphenyl, 3'- or 4'-o-terphenyl, p-, m,p-, o,p-, m,m-, o,m- or o,o-quaterphenyl, quinquephenyl, sexiphenyl, 1-, 2-, 3- or 4-fluorenyl, 2-, 3- or 4-spiro-9,9'-bifluorenyl, 1-, 2-, 3- or 4-(9,10-dihydro) phenanthrenyl, 1- or 2-naphthyl, 2-, 3-, 4-, 5-, 6-, 7- or 8-quinolinyl, 1-, 3-, 4-, 5-, 6-, 7- or 8-isoquinolinyl, 1- or 2-(4-methylnaphthyl), 1- or 2-(4-phenylnaphthyl), 1- or 2-(4-naphthylnaphthyl), 1-, 2- or 3-(4-naphthylphenyl), 2-, 3- or 4-pyridyl, 2-, 4- or 5-pyrimidinyl, 2- or 3-pyrazinyl, 3- or 4-pyridanzinyl, 2-(1,3,5-triazin)yl, 2-, 3- or 4-(phenylpyridyl), 3-, 4-, 5- or 6-(2,2''-bipyridyl), 2-, 4-, 5- or 6-(3,3'-bipyridyl), 2- or 3-(4,4'-bipyridyl) and combinations of one or more of these radicals.

The $Ar^4$ groups may be substituted by one or more R radicals. These R radicals are preferably the same or different at each instance and are selected from the group consisting of H, D, F, C(=O)Ar, P(=O)(Ar)$_2$, S(=O)Ar, S(=O)$_2$Ar, a straight-chain alkyl group having 1 to 4 carbon atoms or a branched or cyclic alkyl group having 3 to 5 carbon atoms, each of which may be substituted by one or more $R^1$ radicals, where one or more hydrogen atoms may be replaced by F, or an aromatic ring system which has 6 to 24 aromatic ring atoms and may be substituted by one or more $R^1$ radicals, or a combination of these systems; at the same time, it is also possible for two or more adjacent R substituents together to form a mono- or polycyclic, aliphatic or aromatic ring system. When the organic electroluminescent device is applied from solution, straight-chain, branched or cyclic alkyl groups having up to 10 carbon atoms are also preferred as R substituents. The R radicals are more preferably the same or different at each instance and are selected from the group consisting of H, C(=O)Ar or an aromatic ring system which has 6 to 24 aromatic ring atoms and may be substituted by one or more $R^1$ radicals, but is preferably unsubstituted.

In another preferred embodiment of the invention, the Ar group is the same or different at each instance and is an aromatic ring system which has 6 to 24 aromatic ring atoms and may be substituted by one or more $R^1$ radicals. More preferably, Ar is the same or different at each instance and is an aromatic ring system having 6 to 12 aromatic ring atoms.

Preference is further given to benzophenone derivatives each substituted at the 3,5,3',5' positions by an aromatic or heteroaromatic ring system having 5 to 30 aromatic ring atoms, which may in turn be substituted by one or more R radicals according to the definition above. Additionally preferred are ketones substituted by at least one spirobifluorene group.

Preferred aromatic ketones and phosphine oxides are therefore the compounds of the following formulae (M72) to (M75):

Formula (M72)

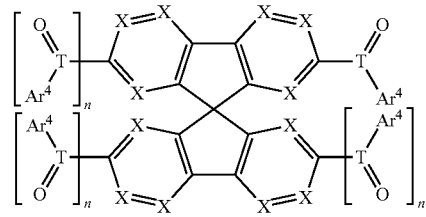

-continued

Formula (M73)

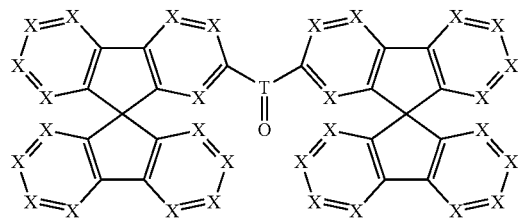

Formula (M74)

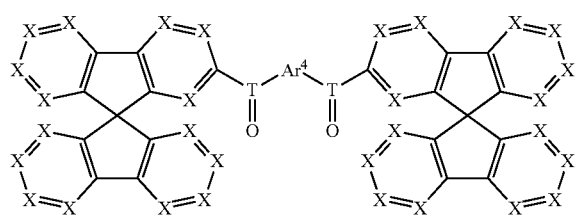

Formula (M75)

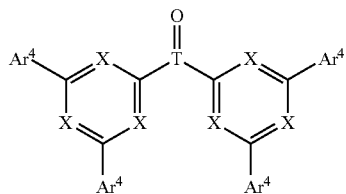

where X, Ar$^4$, R, R$^1$ and R$^2$ have the same definition as described above and in addition:

T is the same or different at each instance and is C or P(Ar$^4$);

n is the same or different at each instance and is 0 or 1.

Preferably, Ar$^4$ in the abovementioned formulae (M72) and (M75) is an aromatic or heteroaromatic ring system which has 5 to 30 aromatic ring atoms and may be substituted by one or more R$^1$ radicals. Particular preference is given to the abovementioned Ar$^4$ groups.

Examples of suitable compounds of formula (M70) and (M71) are the compounds depicted below:

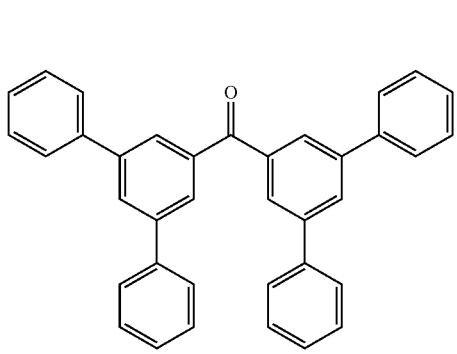

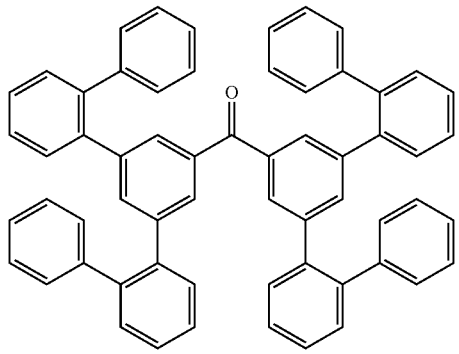

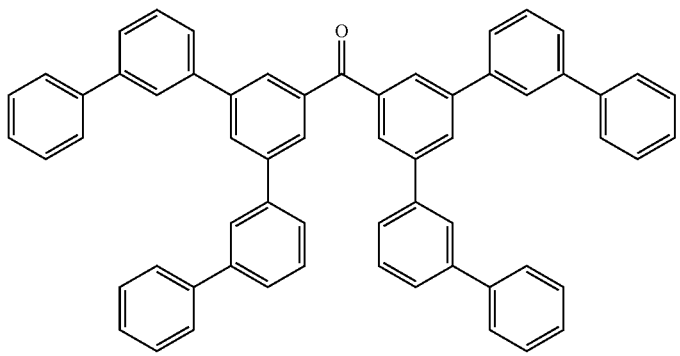

-continued
207
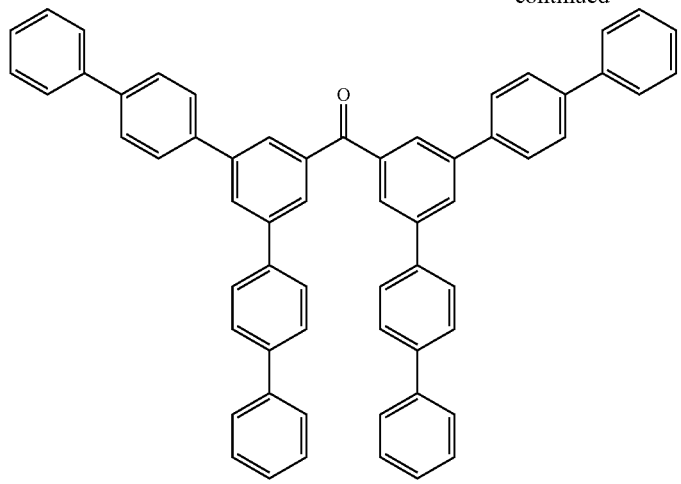
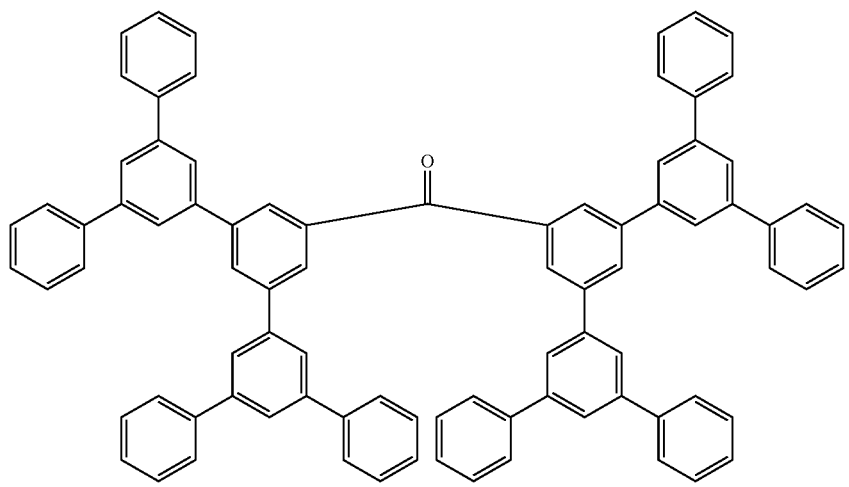
208
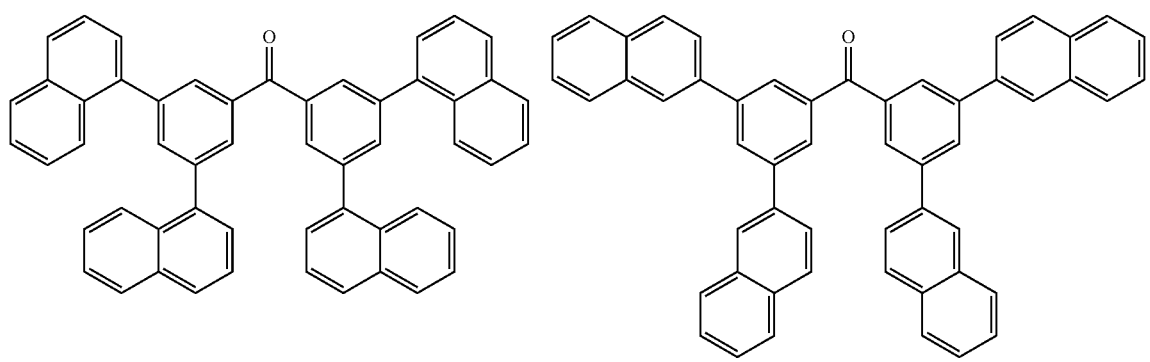
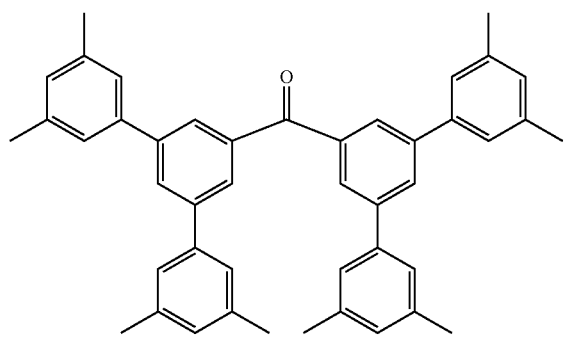

209
210
-continued
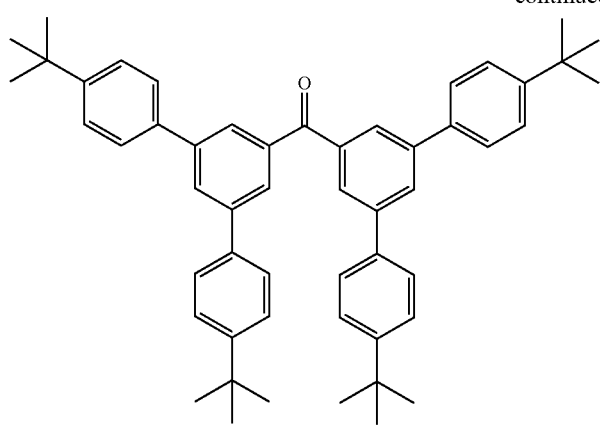
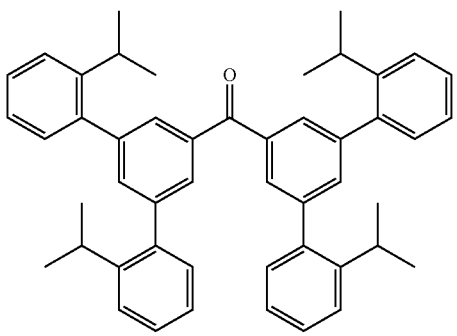
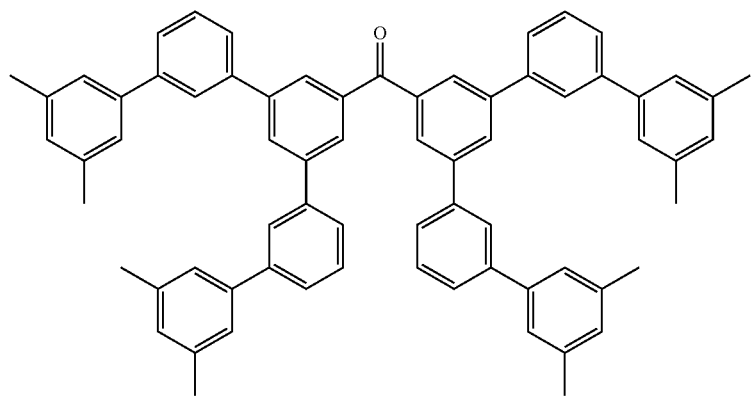
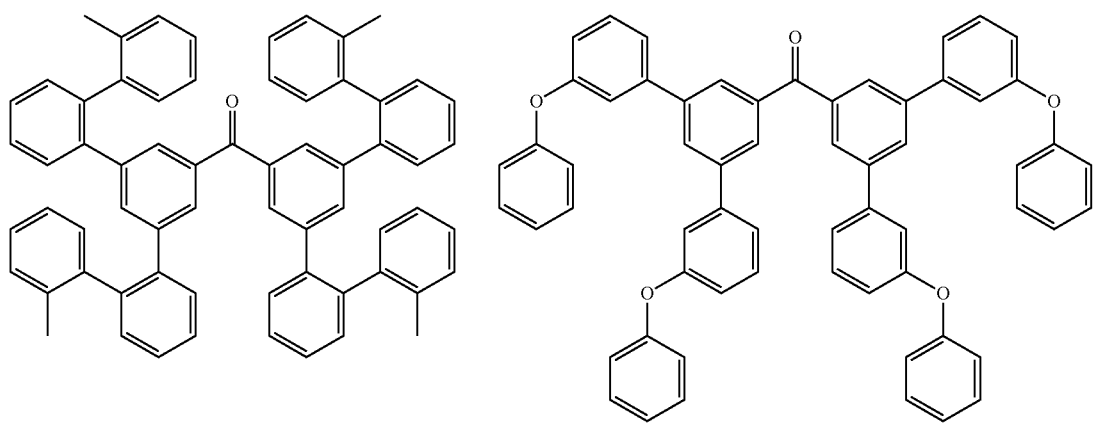

-continued
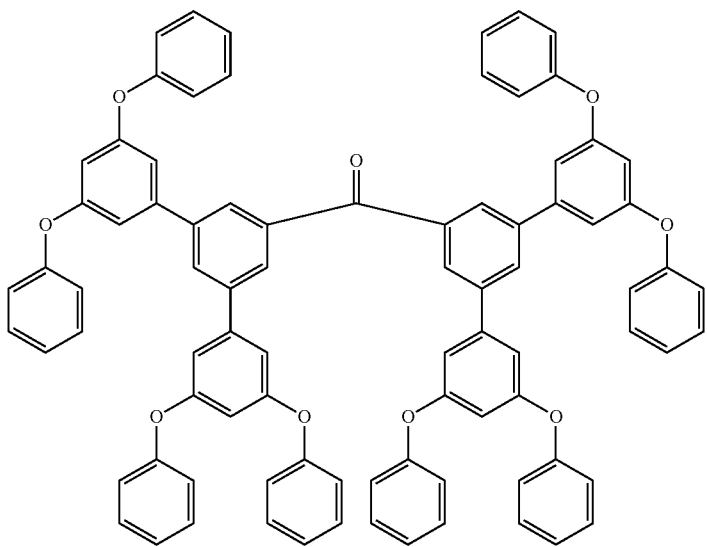
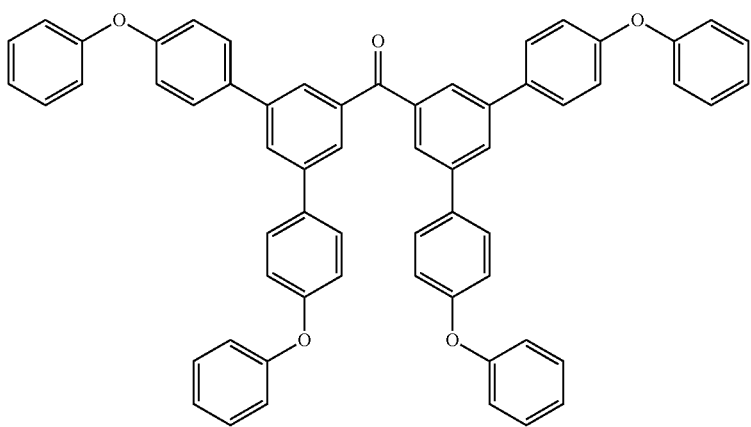
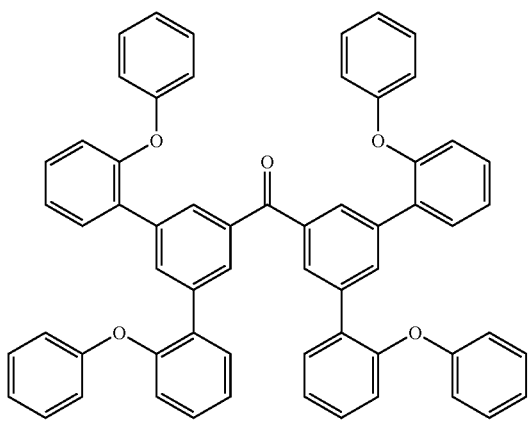

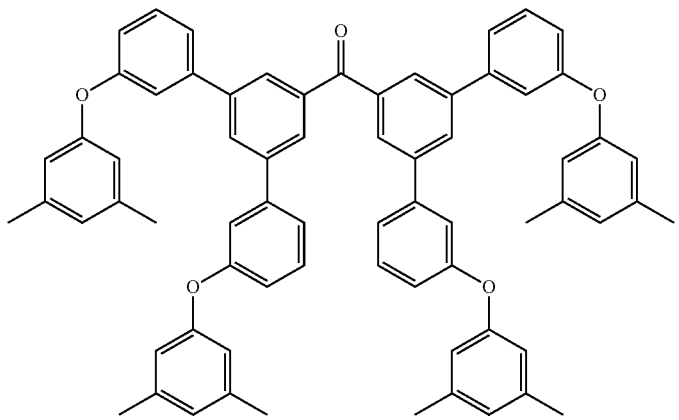
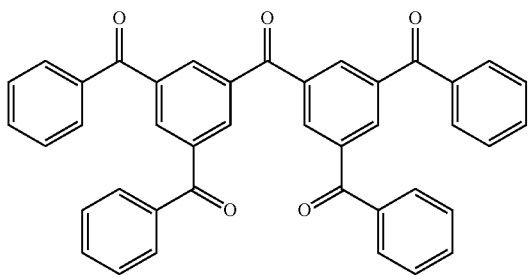
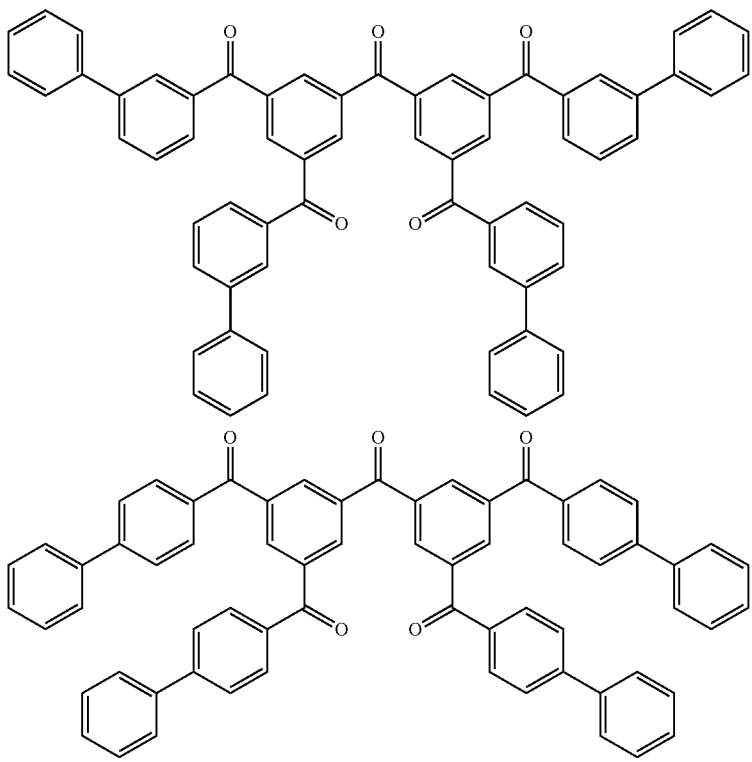

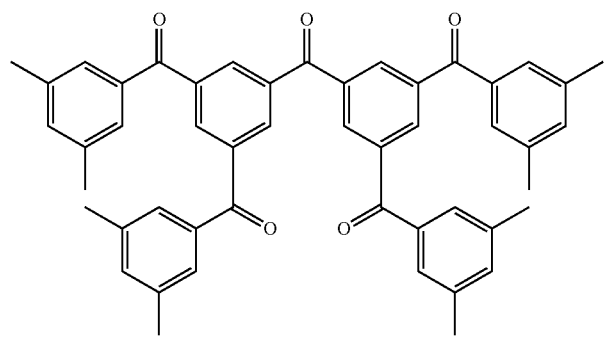
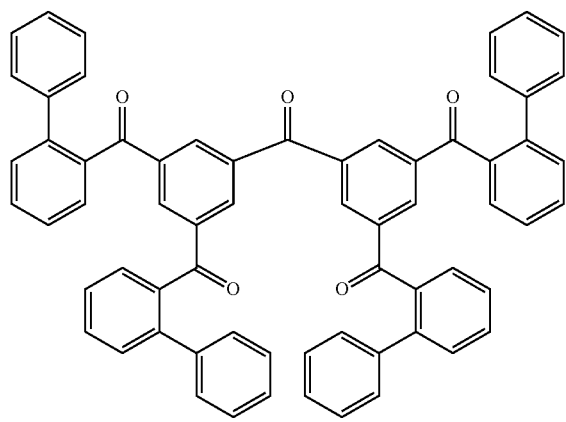
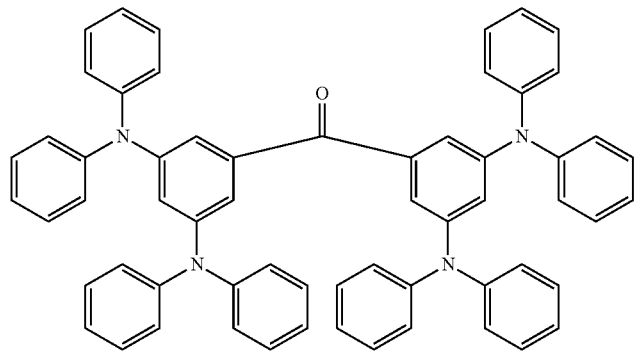
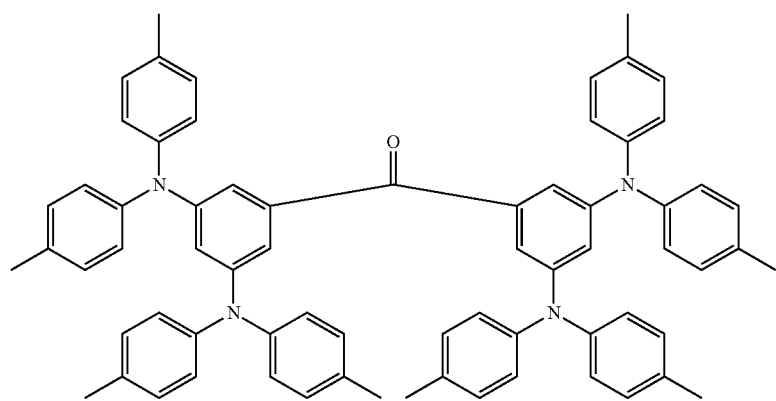

217
-continued
218
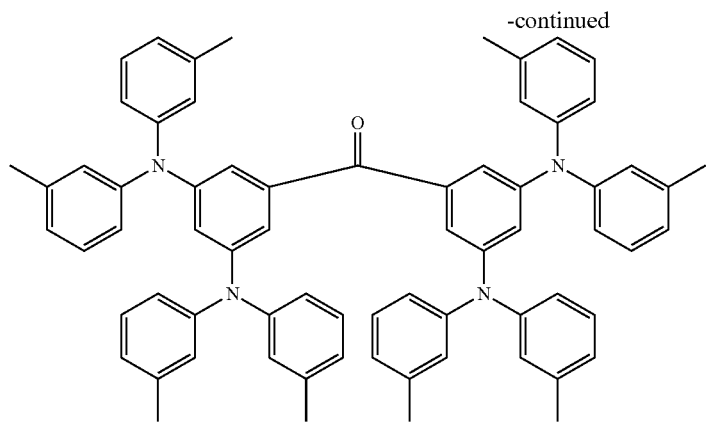
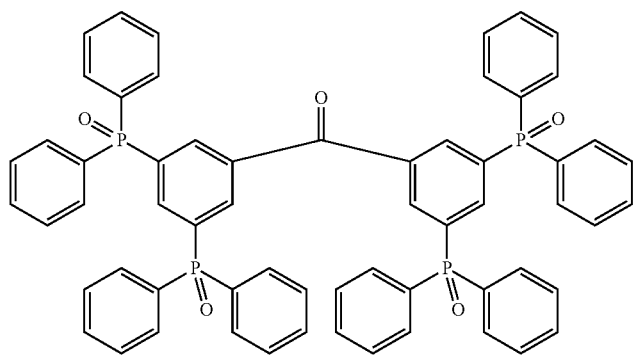
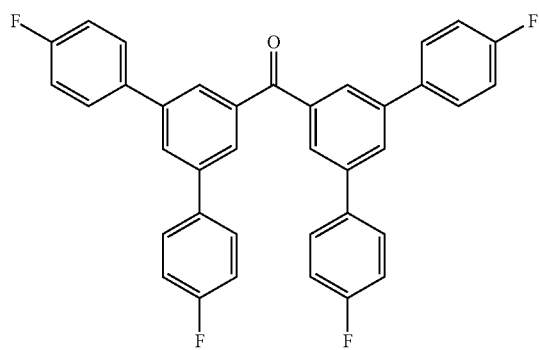
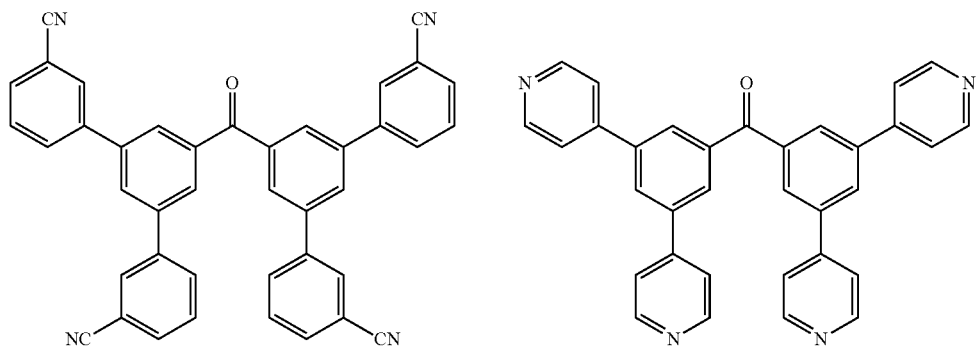

219
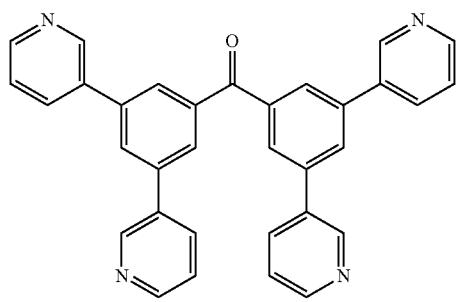
220
-continued
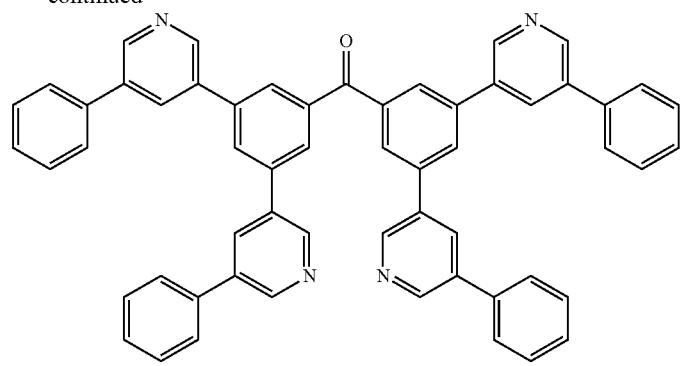
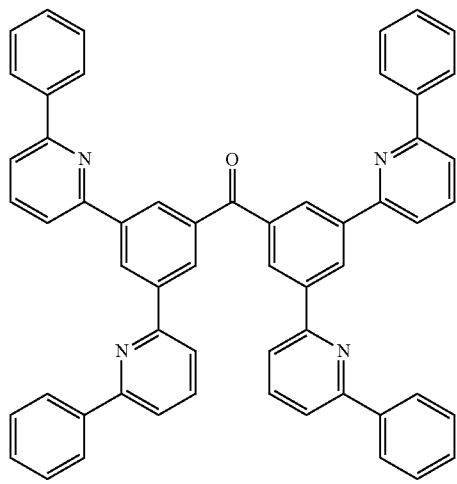
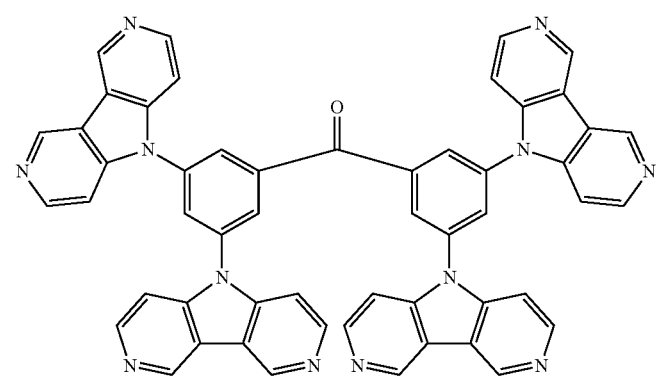
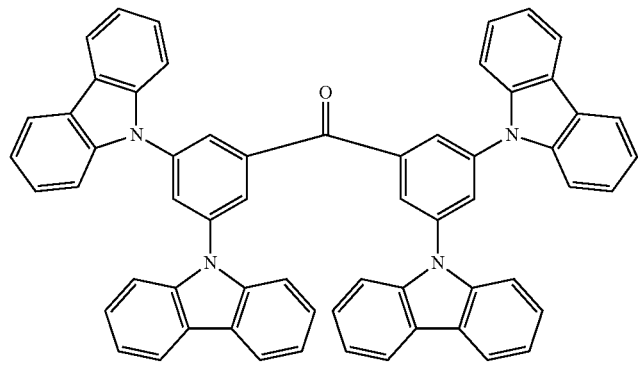
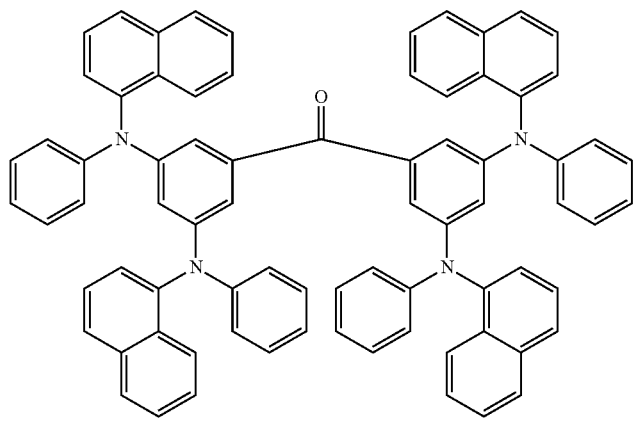
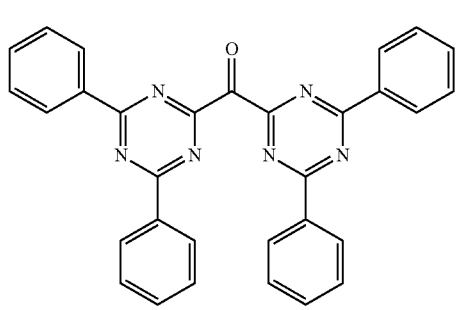

-continued
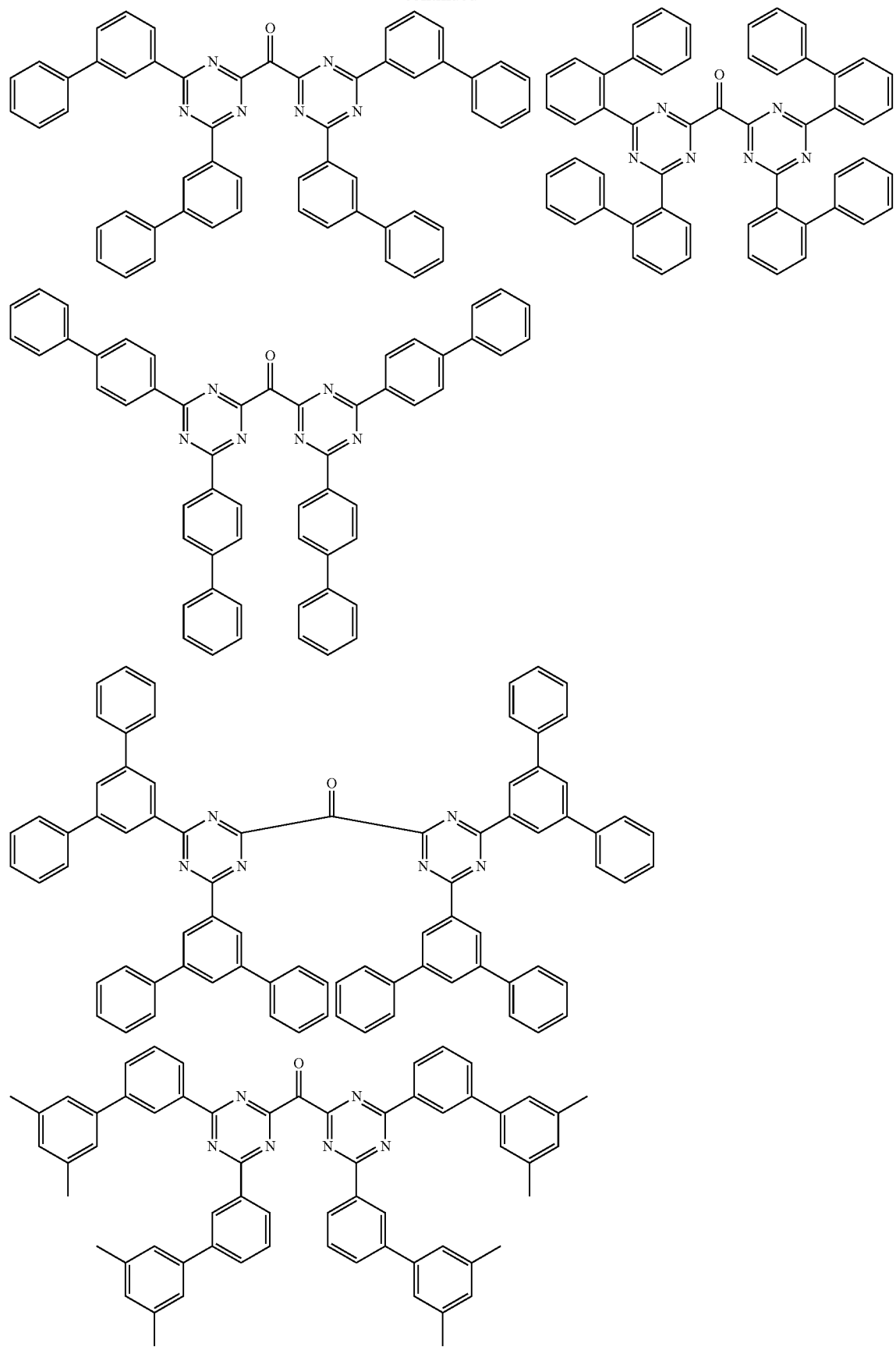

-continued
| 223 | 224 |
|---|---|
| 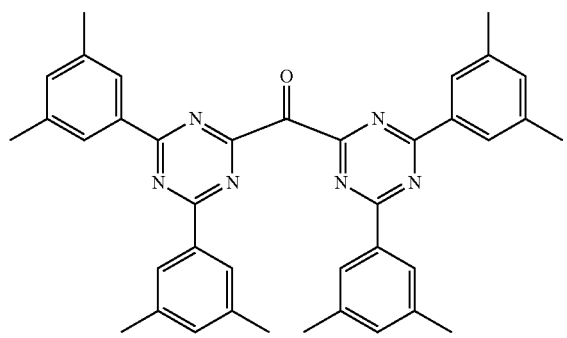 | 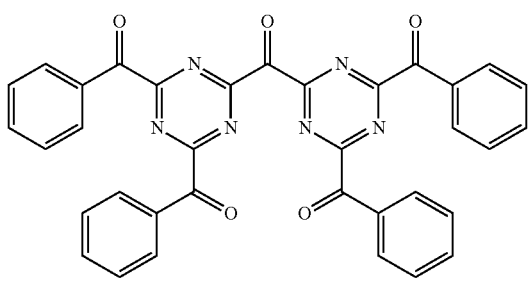 |
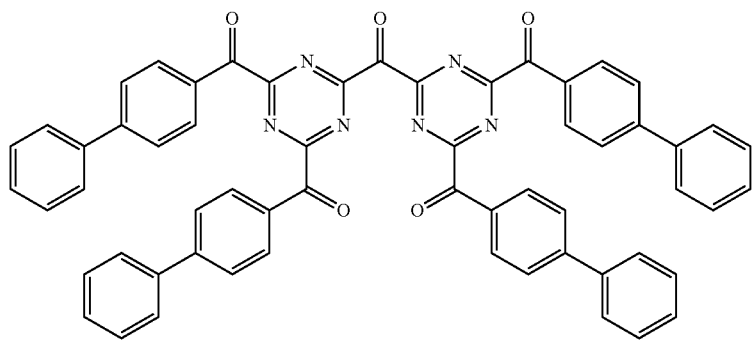
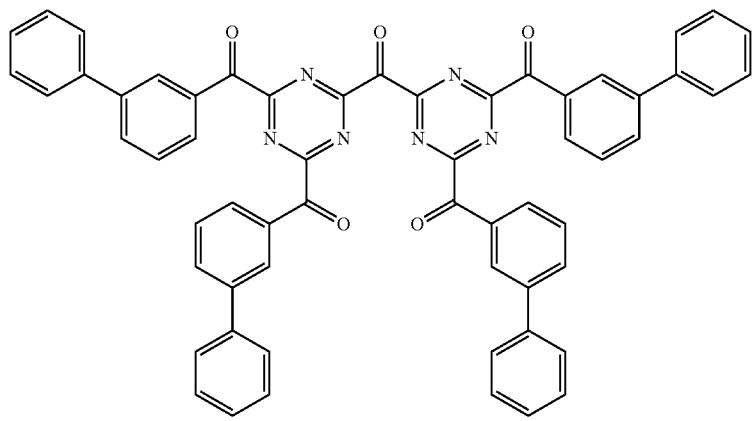
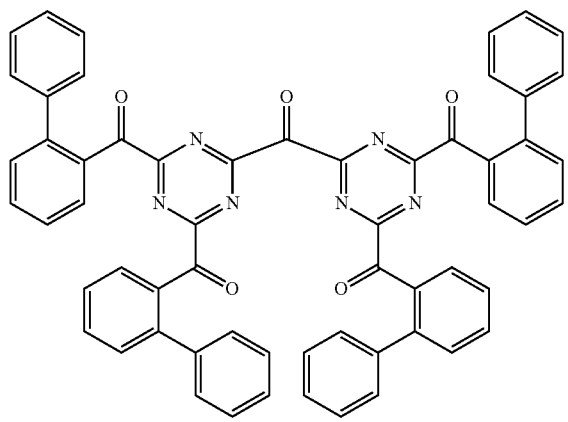
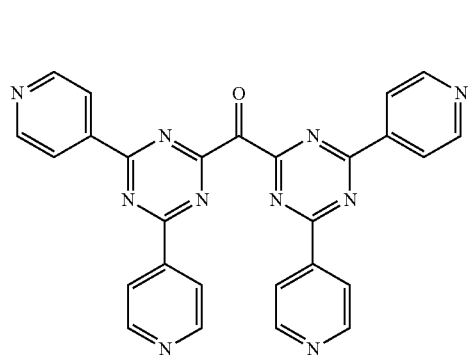

225
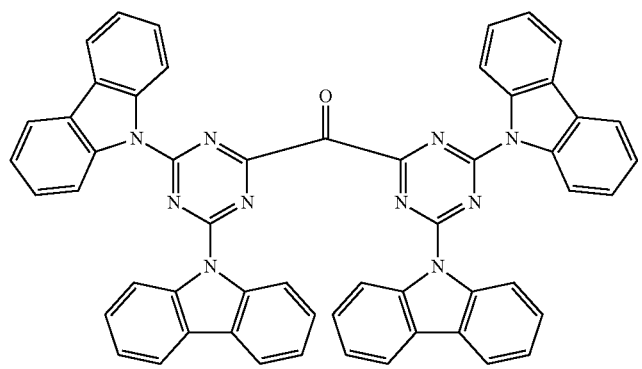
-continued
226
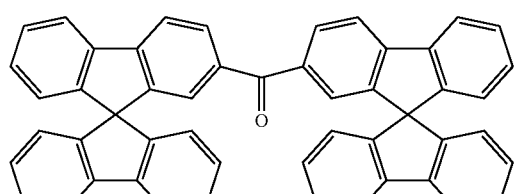
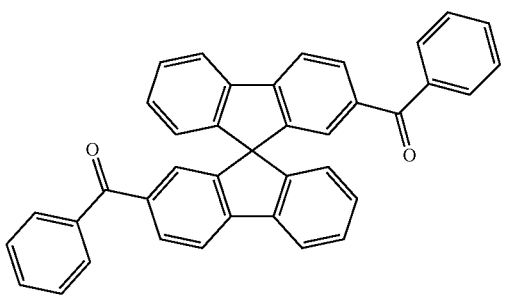
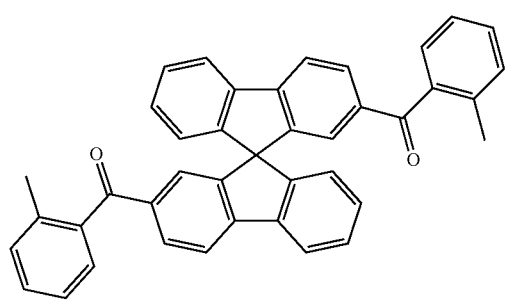
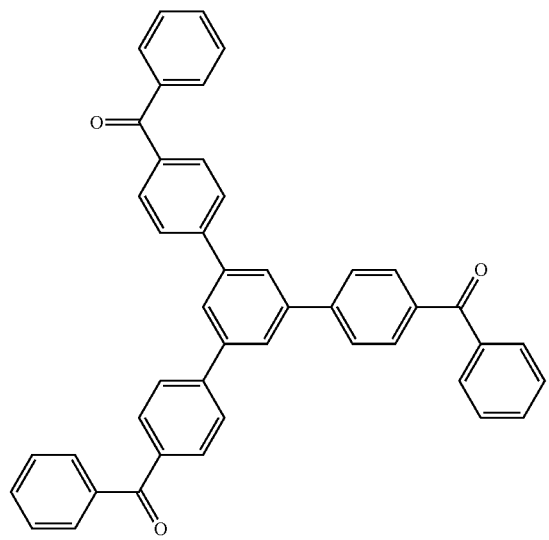
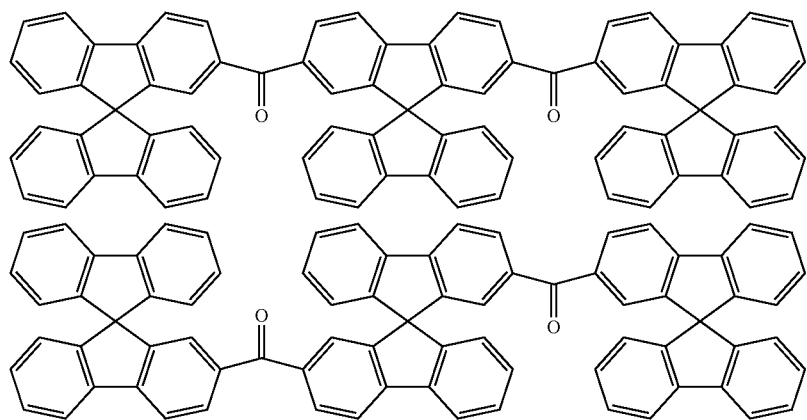

227
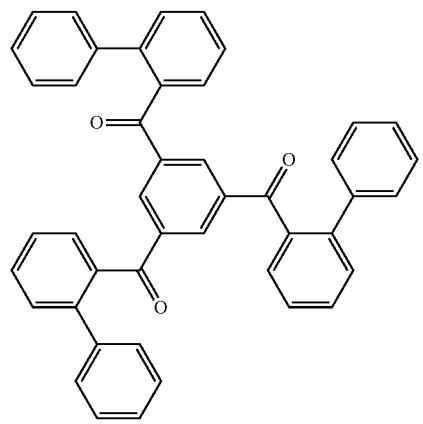
228
-continued
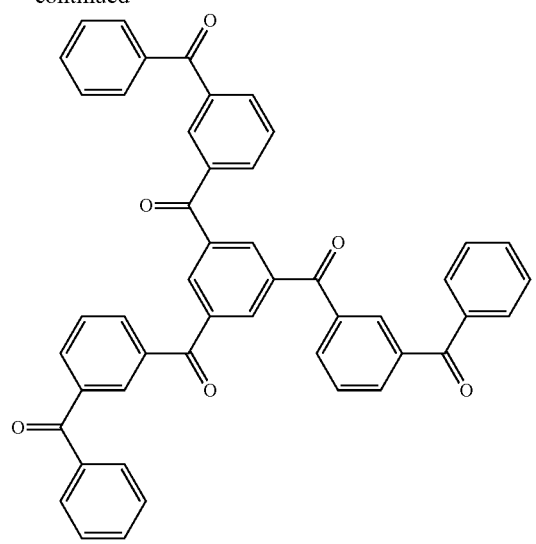
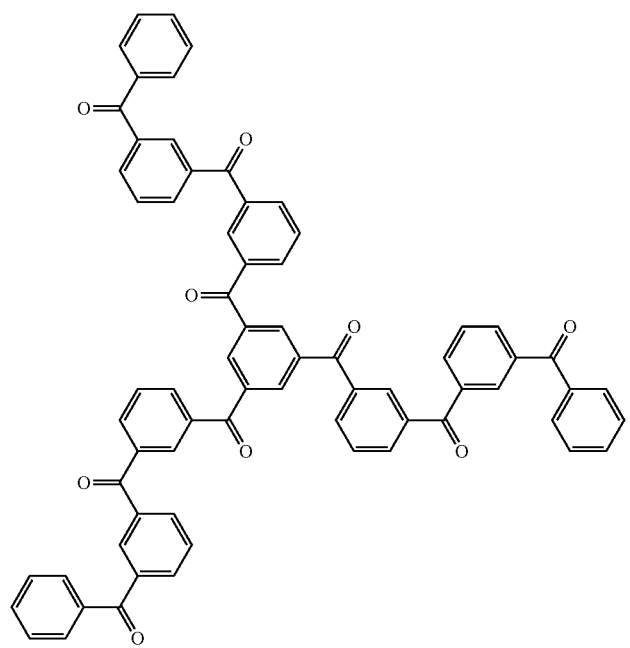

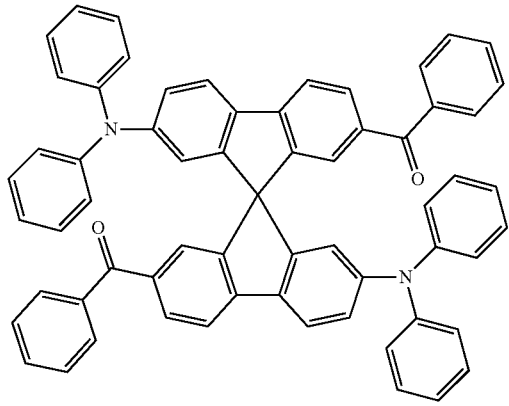
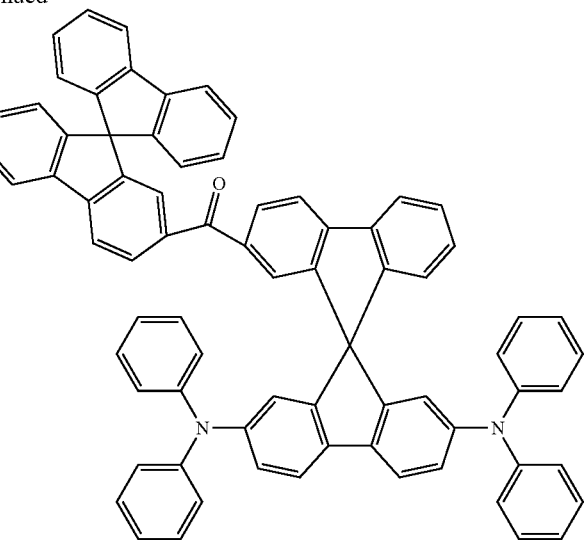
Examples of suitable aromatic phosphine oxide derivatives are the compounds depicted below:
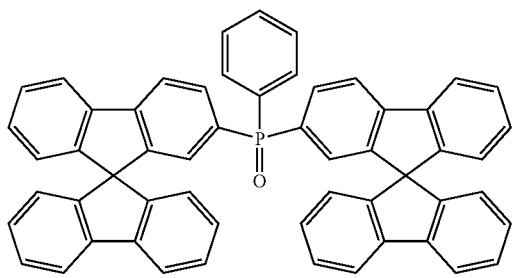
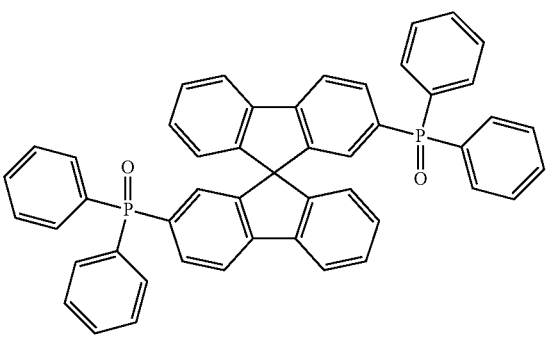
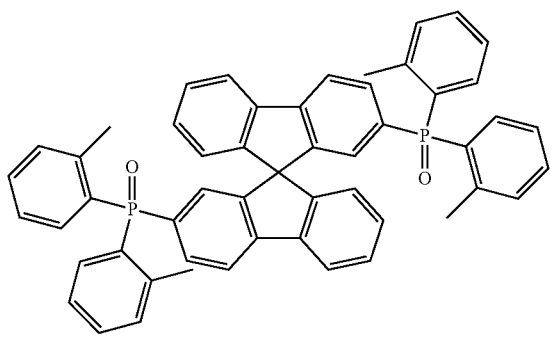
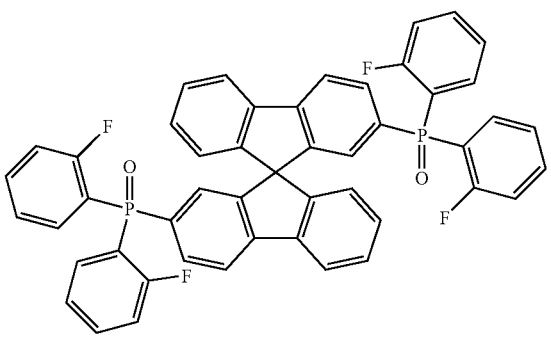
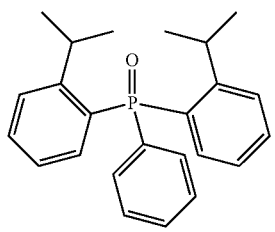
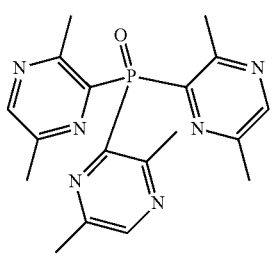
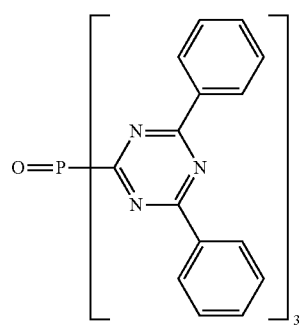

231 232
-continued
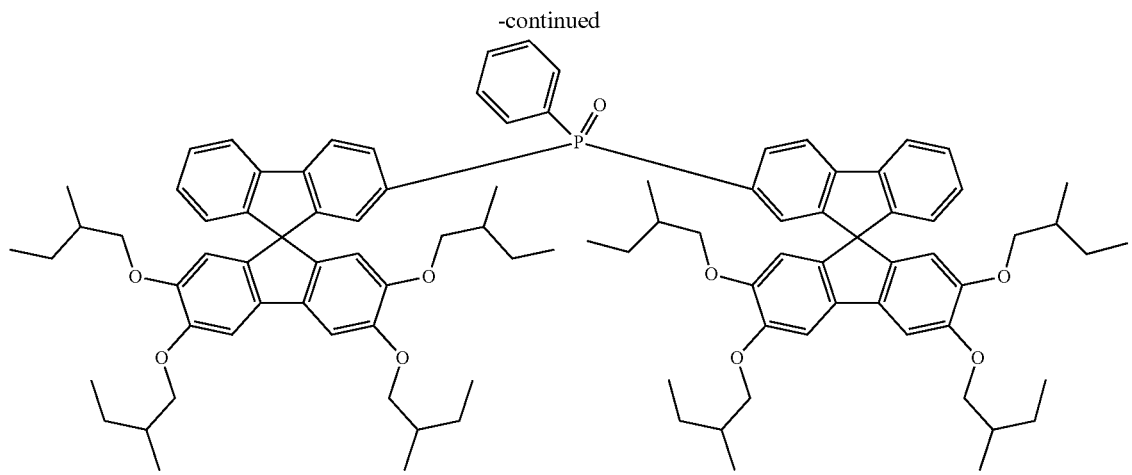
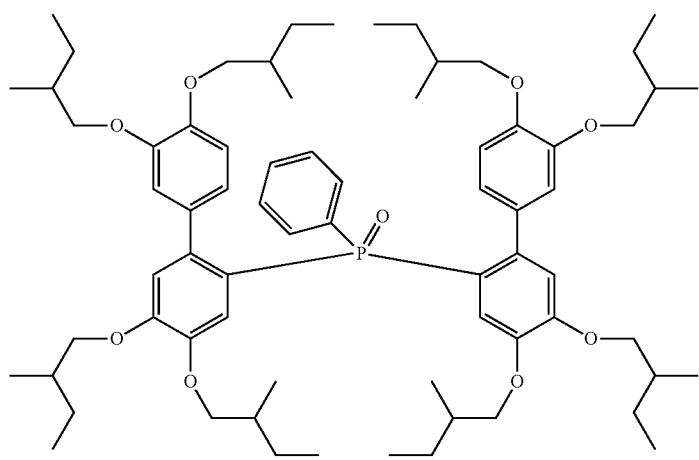
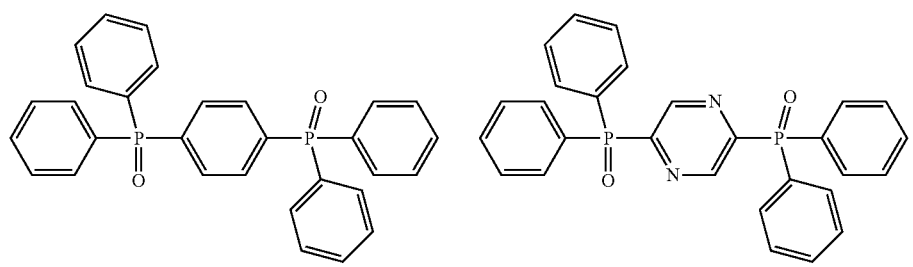
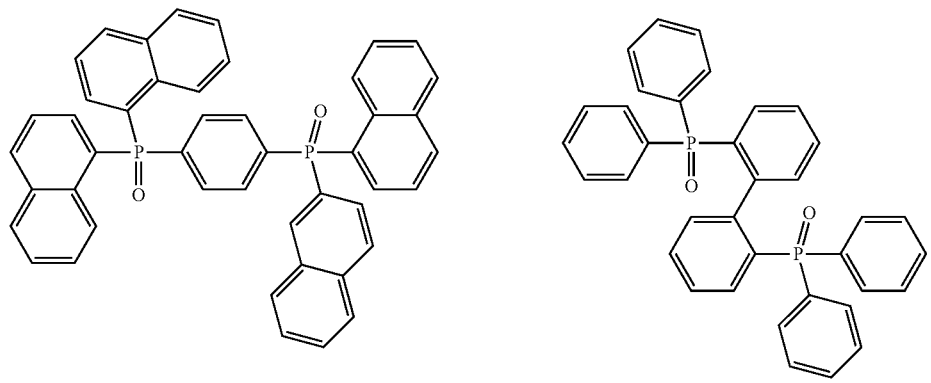

233
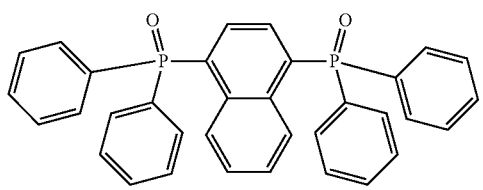
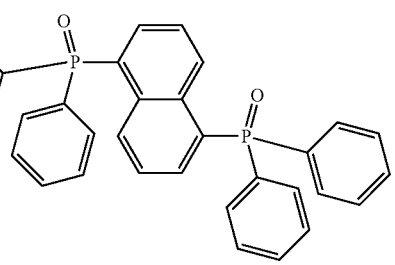
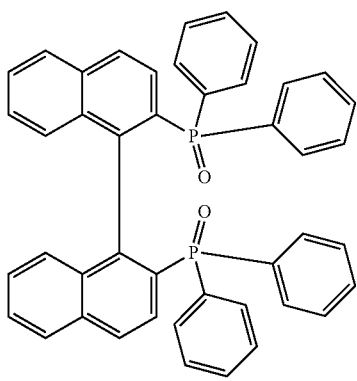
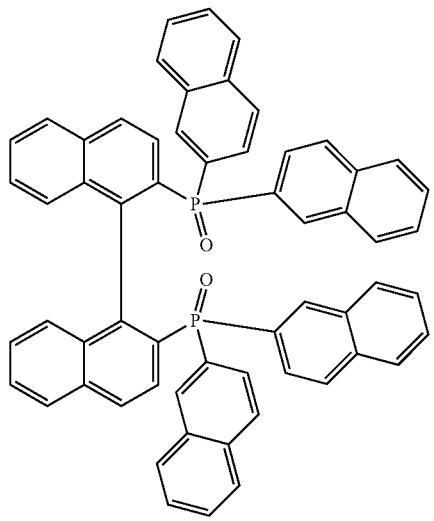
Suitable metal complexes which can be used as matrix material in the organic electroluminescent device according to the invention are Be complexes, Zn complexes and Al complexes. Suitable examples are the Zn complexes disclosed in WO 2009/062578.
Examples of suitable metal complexes are the complexes listed in the following table:
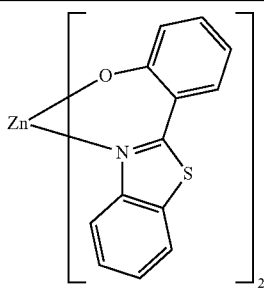
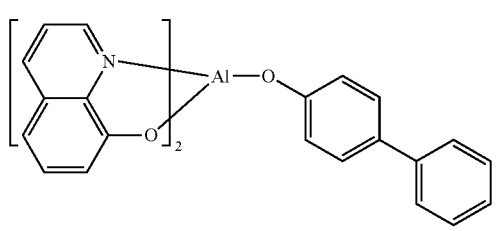
234
-continued
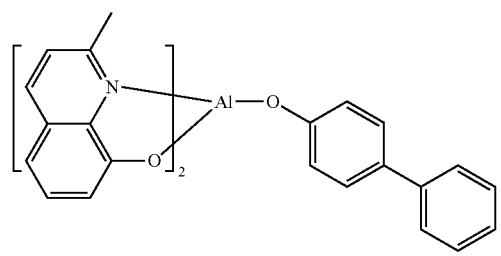
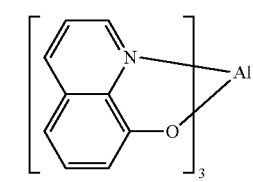
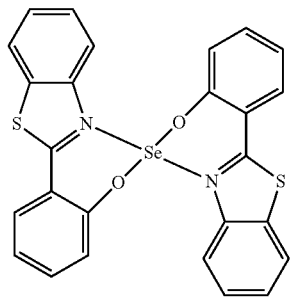

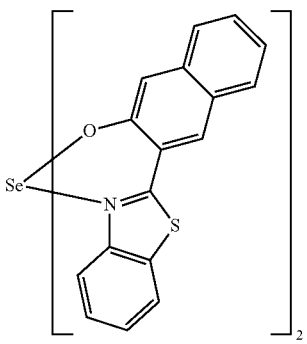

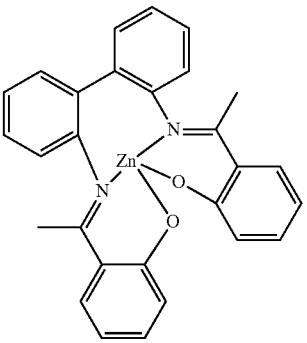

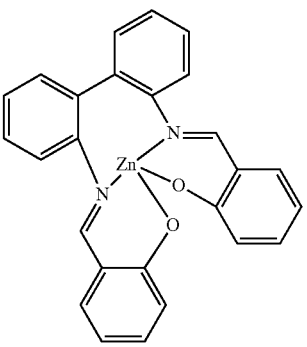

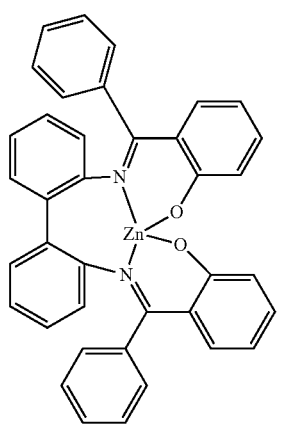

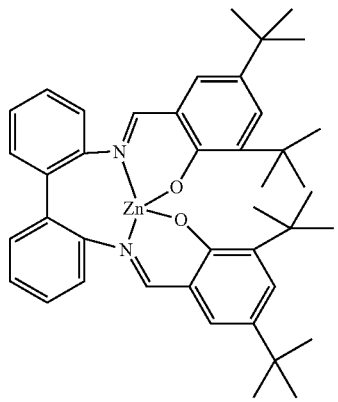

Suitable azaphospholes which can be used as matrix material in the organic electroluminescent device of the invention are those compounds as disclosed in WO 2010/054730. This application is incorporated into the present invention by reference.

Suitable azaboroles which can be used as matrix material in the organic electroluminescent device of the invention are especially azaborole derivatives substituted by at least one electron-conducting substituent. Such compounds are disclosed in the as yet unpublished application EP 11010103.7. This application is incorporated into the present invention by reference.

Suitable matrix compounds are additionally the compounds of the following formula (M76):

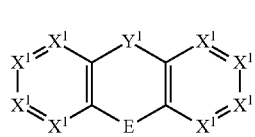

Formula (M76)

where R, Z and E are as defined above and the further symbols used are as follows:

$X^1$ is the same or different at each instance and is CR or N or one $X^1$-$X^1$ group is a group of the following formula (M77), with the proviso that, in the compound of the formula (M76), at least one $X^1$-$X^1$ group is a group of the formula (M77) and that not more than one $X^1$-$X^1$ group per cycle is a group of the formula (M77),

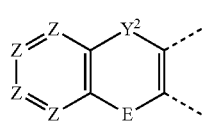

Formula (M77)

where the carbon atoms with the dotted bonds indicate the binding of the group;

$Y^1$, $Y^2$ are the same or different at each instance and are selected from the group consisting of $CR_2$, NR, O, S, $SiR_2$, BR, PR and P(=O)R.

These compounds may, according to the exact structure and substitution, be hole-transporting, electron-transporting, bipolar, or neither hole- nor electron-transporting.

The $X^1$-$X^1$ group here is indicated by a single bond. Since the $X^1$-$X^1$ group in the compound of the formula (M77), however, is incorporated within an aromatic group, it is obvious that what is meant thereby is an aromatic bond, meaning that the bonding level of the bond between the two $X^1$ atoms is between 1 and 2. The group of the formula (M77) is bonded in any desired positions, and the $Y^1$ and $Y^2$ groups may be either in cis or trans configuration relative to one another. The $X^1$ groups which are not a group of the formula (M77) are the same or different at each instance and are CR or N.

In a preferred embodiment of the invention, E is the same or different at each instance and is selected from the group consisting of a single bond, $CR_2$, NR, O and S. More preferably, E is a single bond.

Preferred compounds of the formula (M76) are the compounds of the following formulae (M78) to (M84):

Formula (M78)
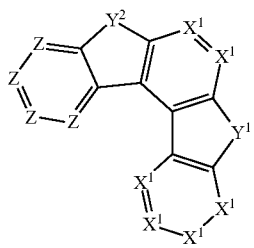

Formula (M79)
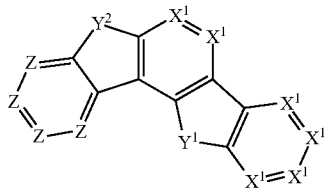

Formula (M80)
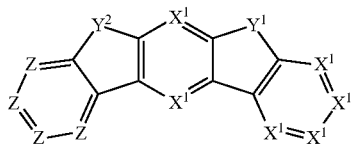

Formula (M81)
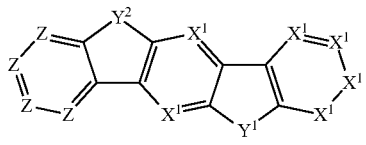

Formula (M82)
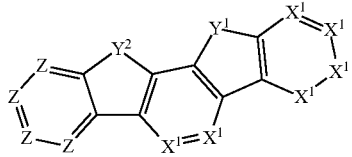

Formula (M83)
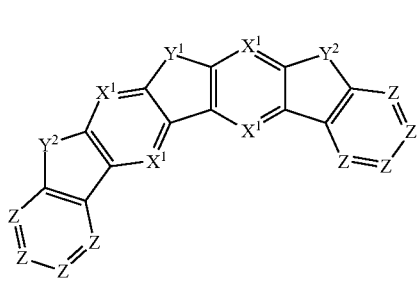

Formula (M84)
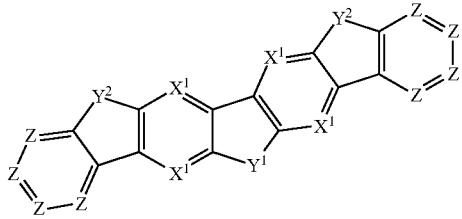

where Z, $Y^1$, $Y^2$, R, $R^1$ and $R^2$ have the definitions given above and in addition:

$X^1$ is the same or different at each instance and is CR or N.

In preferred groups of the abovementioned formulae (M76) and (M78) to (M84), not more than two $X^1$ symbols per cycle are N; more preferably, not more than one $X^1$ symbol per cycle is N. Most preferably, the $X^1$ symbol is the same or different at each instance and is CR.

In preferred groups of the abovementioned formulae (M77) to (M84), not more than two Z symbols per cycle are N; more preferably, not more than one Z symbol per cycle is N. Most preferably, the Z symbol is the same or different at each instance and is CR.

Especially preferably, in the formulae (M78) to (M84), all $X^1$ symbols and all Z symbols are the same or different and are CR.

Preferred embodiments of the formulae (M78) to (M84) are the compounds of the following formulae (M78a) to (M84a):

Formula (M78a)
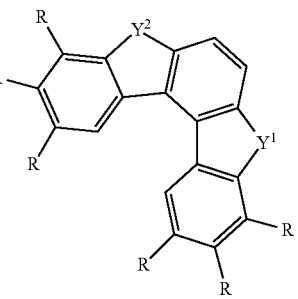

Formula (M79a)
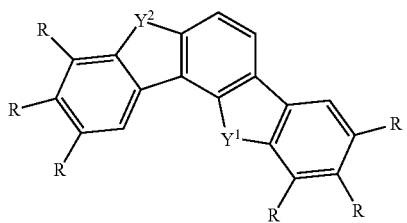

Formula (M80a)
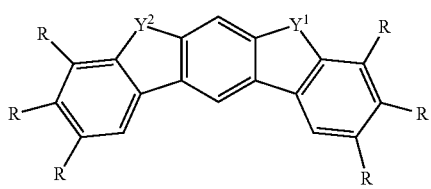

-continued

Formula (M81a)
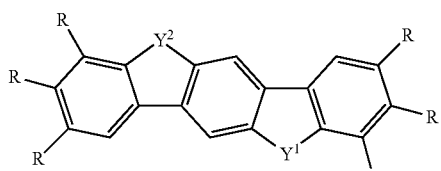

Formula (M82a)
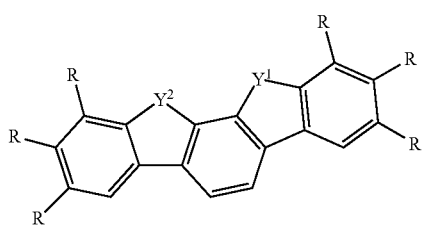

Formula (M83a)
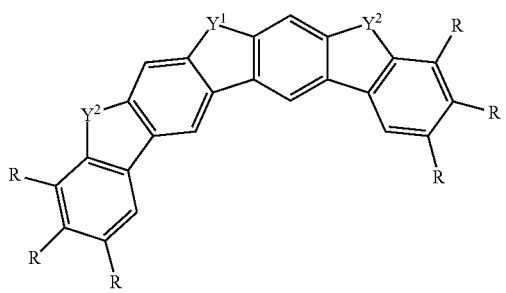

Formula (M84a)
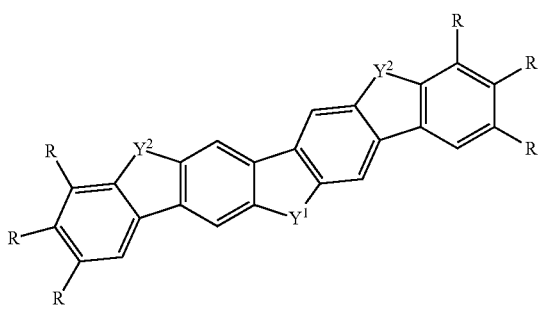

where the symbols used have the definitions given above.

In a further preferred embodiment of the invention, $Y^1$ and $Y^2$ are the same or different at each instance and are selected from the group consisting of $CR_2$, NR, O and S.

In the groups of the formula (M76) or (M78) to (M84) or (M78a) to (M84a), all combinations are possible for the $Y^1$ and $Y^2$ groups. Preferably, at least one $Y^1$ and/or $Y^2$ group is a heteroatom, i.e. preferably at least one of the $Y^1$ and/or $Y^2$ groups is different from $CR_2$.

Suitable combinations of $Y^1$ and $Y^2$ are the combinations listed in the following table:

| $Y^1$ | $Y^2$ |
|---|---|
| $CR_2$ | $CR_2$ |
| $CR_2$ | NR |
| $CR_2$ | O |
| $CR_2$ | S |
| NR | $CR_2$ |
| NR | NR |
| NR | O |
| NR | S |
| O | $CR_2$ |
| O | NR |
| O | O |
| O | S |
| S | $CR_2$ |
| S | NR |
| S | O |
| S | S |

Preference is given to compounds of the formula (M76) or (M78) to (M84) or (M78a) to (M84a) in which one of the $Y^1$ and $Y^2$ groups is $CR_2$ and the other of the $Y^1$ and $Y^2$ groups is NR, or in which both $Y^1$ and $Y^2$ groups are NR or in which both $Y^1$ and $Y^2$ groups are O.

When $Y^1$ or $Y^2$ is NR, the R substituent bonded to this nitrogen atom is preferably an aromatic or heteroaromatic ring system which has 5 to 24 aromatic ring atoms and may also be substituted by one or more $R^1$ radicals. At the same time, the aromatic or heteroaromatic ring systems preferably do not contain any fused aryl or heteroaryl groups in which more than two aromatic six-membered rings are fused directly to one another. In a particularly preferred embodiment, this R substituent is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^1$ radicals. Thus, it is preferable when R does not, for example, have any naphthyl groups or higher fused aryl groups and likewise does not have any quinoline groups, acridine groups, etc. In contrast, it is possible that R includes, for example, carbazole groups, dibenzofuran groups, fluorene groups, etc., since there are no 6-membered aromatic or heteroaromatic rings fused directly to one another in these structures. Preferred R substituents are selected from the group consisting of benzene, ortho-, meta- or para-biphenyl, ortho-terphenyl, meta-terphenyl, para-terphenyl or branched terphenyl, ortho-quaterphenyl, meta-quaterphenyl, para-quaterphenyl or branched quaterphenyl, 1-, 2-, 3- or 4-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, 2-, 3- or 4-pyridine, 2-, 4- or 5-pyrimidine, pyrazine, pyridazine, triazine, phenanthrene or combinations of two or three of these groups, each of which may be substituted by one or more $R^1$ radicals.

Preferred biphenyl, terphenyl and quaterphenyl groups are the structures of the above-depicted formulae (Bi-1) to (Bi-3), (Ter-1) to (Ter-3) and (Quater-1) to (Quater-4).

When $Y^1$ or $Y^2$ is $CR_2$, R is preferably the same or different at each instance and is a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^1$ radicals. At the same time, the R radicals may also form a ring system with one another and hence form a spiro system. Most preferably, R is a methyl group or a phenyl group.

In a preferred embodiment of the invention, at least one of the $Y^1$ and $Y^2$ groups is NR, and the corresponding R group is an aromatic or heteroaromatic ring system as described above. In this case, it may also be preferable when all R substituents bonded to the base skeleton of the compound of formula (M76) or the preferred embodiments are H.

In a further preferred embodiment of the compound of formula (M76) or the preferred embodiments outlined above, at least one R substituent bonded to the base skeleton of the compound of formula (M76) is a radical other than H and D. More particularly, at least one of the R radicals explicitly shown in the formulae (M78a) to (M84a) is not H or D.

This R substituent other than H and D is preferably an aromatic or heteroaromatic ring system which has 5 to 24 aromatic ring atoms and may also be substituted by one or more $R^1$ radicals. At the same time, the aromatic or heteroaromatic ring systems preferably do not contain any fused aryl or heteroaryl groups in which more than two aromatic six-membered rings are fused directly to one another. In a particularly preferred embodiment, this R substituent is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^1$ radicals. Thus, it is preferable when R does not, for example, have any naphthyl groups or higher fused aryl groups and likewise does not have any quinoline groups, acridine groups, etc. In contrast, it is possible that R includes, for example, carbazole groups, dibenzofuran groups, fluorene groups, etc., since there are no 6-membered aromatic or heteroaromatic rings fused directly to one another in these structures. Preferred R substituents are selected from the group consisting of benzene, ortho-, meta- or para-biphenyl, ortho-terphenyl, meta-terphenyl, para-terphenyl or branched terphenyl, ortho-quaterphenyl, meta-quaterphenyl, para-quaterphenyl or branched quaterphenyl, 1-, 2-, 3- or 4-fluorenyl, 1-, 2-, 3- or 4-spirobifluorenyl, 1- or 2-naphthyl, pyrrole, furan, thiophene, indole, benzofuran, benzothiophene, 1-, 2- or 3-carbazole, 1-, 2- or 3-dibenzofuran, 1-, 2- or 3-dibenzothiophene, indenocarbazole, indolocarbazole, 2-, 3- or 4-pyridine, 2-, 4- or 5-pyrimidine, pyrazine, pyridazine, triazine, phenanthrene or combinations of two or three of these groups, each of which may be substituted by one or more $R^1$ radicals. Preferred biphenyl, terphenyl and quaterphenyl groups are the structures of the above-depicted formulae (Bi-1) to (Bi-3), (Ter-1) to (Ter-3) and (Quater-1) to (Quater-4).

In a preferred embodiment of the invention, the above-mentioned preferences occur simultaneously. Preference is thus given to the compounds of the formulae (M78a) to (M84a) in which $Y^1$ and $Y^2$ are the same or different at each instance and are selected from $CR_2$, NR, O and S, especially in the combinations mentioned above, and in which the preferences mentioned above apply to R.

Examples of preferred compounds of formula (M76) are the compounds detailed in the table which follows. Further suitable compounds are the structures listed above for the compounds of the formulae (M1) and (M2), which simultaneously also contain structures of the formula (M76).

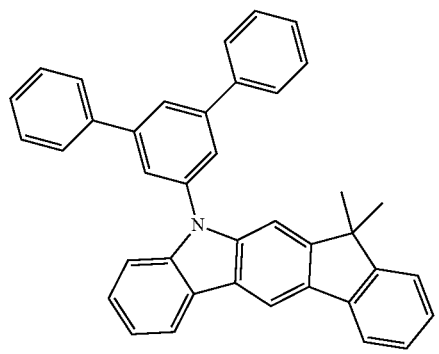 [SMILES: CC1(C)c2ccccc2-c2cc3c4ccccc4n(-c4cc(-c5ccccc5)cc(-c5ccccc5)c4)c3cc21]

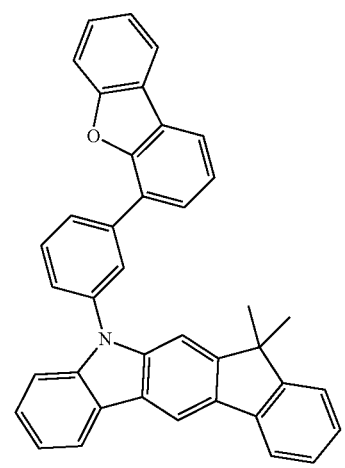 [SMILES: CC1(C)c2ccccc2-c2cc3c4ccccc4n(-c4cccc(-c5cccc6c5oc5ccccc56)c4)c3cc21]

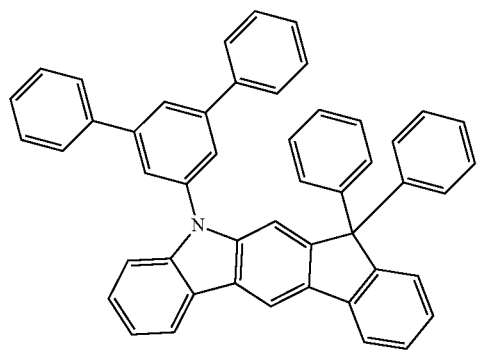 [SMILES: c1ccc(-c2cc(-c3ccccc3)cc(-n3c4ccccc4c4cc5c(cc43)C(c3ccccc3)(c3ccccc3)c3ccccc3-5)c2)cc1]

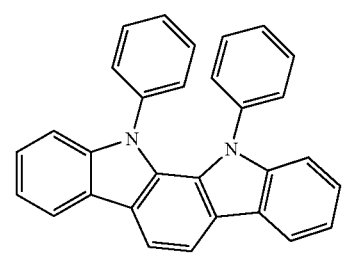 [SMILES: c1ccc(-n2c3ccccc3c3ccc4c5ccccc5n(-c5ccccc5)c4c32)cc1]

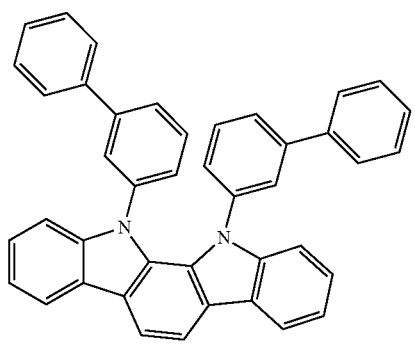 [SMILES: c1ccc(-c2cccc(-n3c4ccccc4c4ccc5c6ccccc6n(-c6cccc(-c7ccccc7)c6)c5c43)c2)cc1]
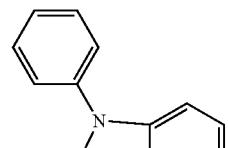
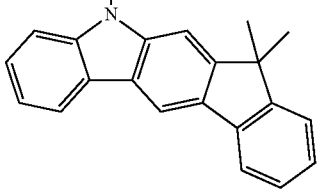
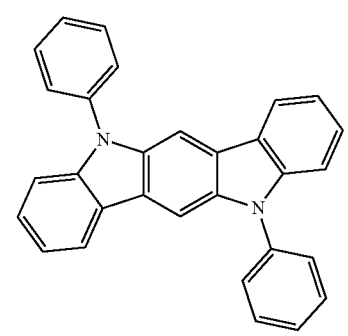 [SMILES: c1ccc(-n2c3ccccc3c3cc4c(cc32)c2ccccc2n4-c2ccccc2)cc1]
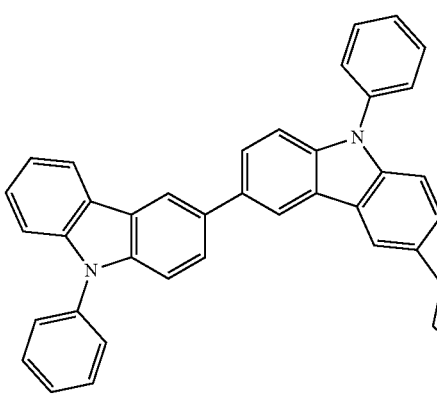
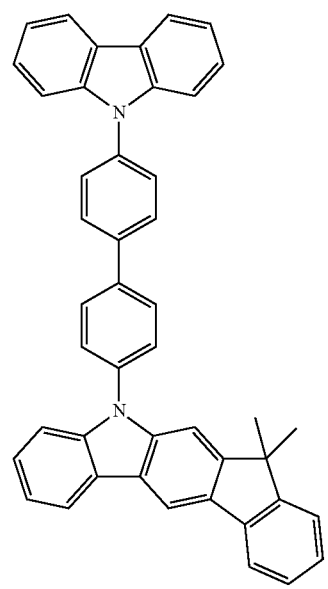 [SMILES: CC1(C)c2ccccc2-c2cc3c4ccccc4n(-c4ccc(-c5ccc(-n6c7ccccc7c7ccccc76)cc5)cc4)c3cc21]
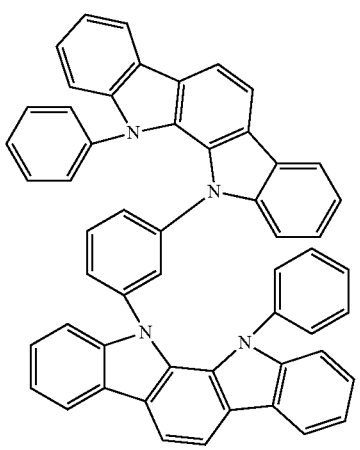 [SMILES: c1ccc(-n2c3ccccc3c3ccc4c5ccccc5n(-c5cccc(-n6c7ccccc7c7ccc8c9ccccc9n(-c9ccccc9)c8c76)c5)c4c32)cc1]

245
-continued
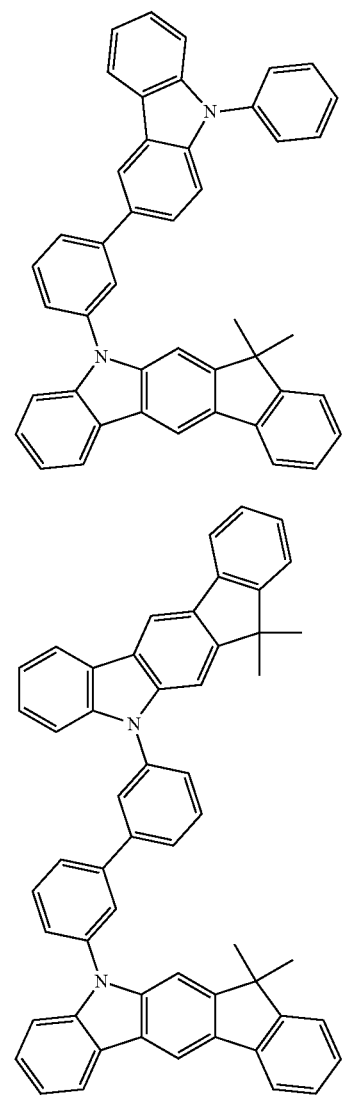
246
-continued
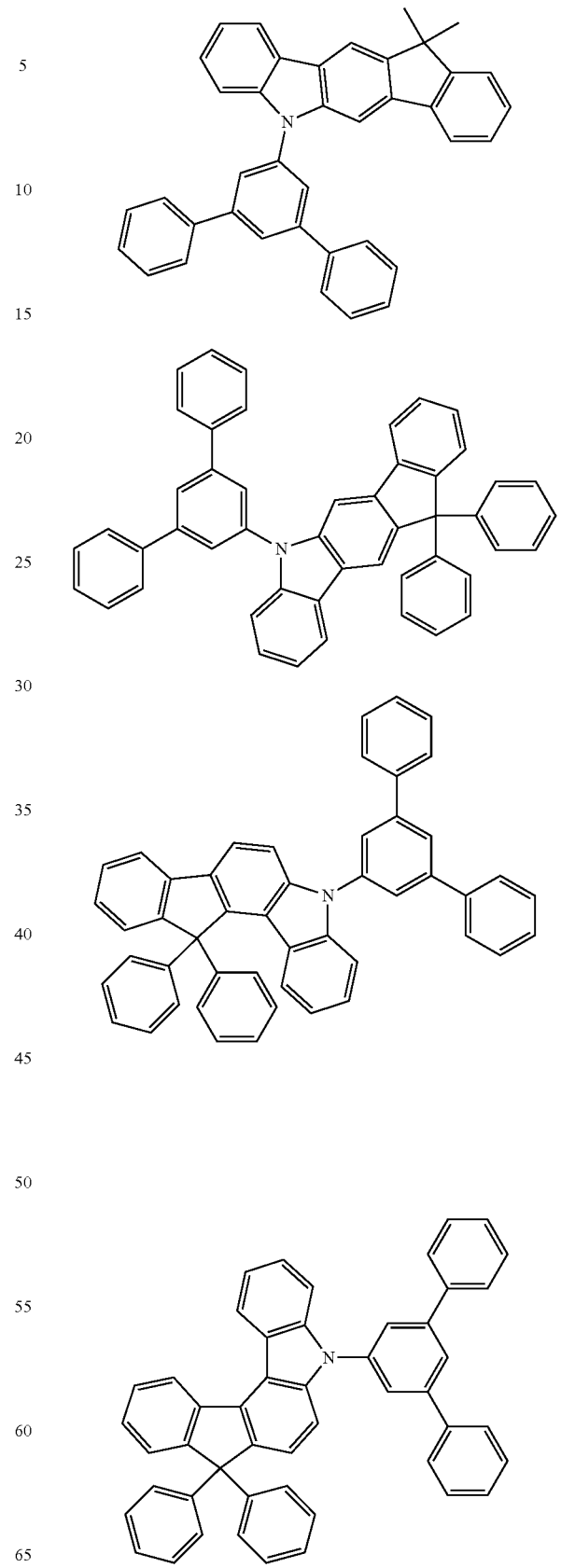

247
-continued
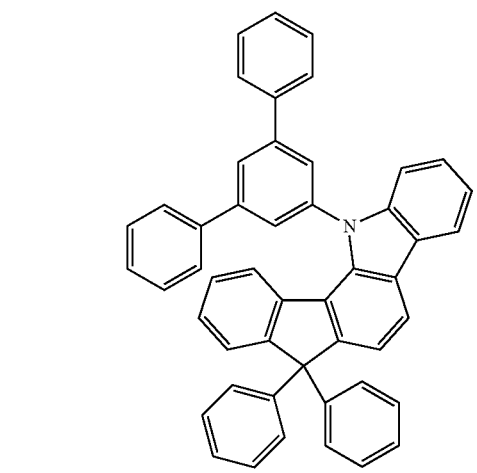 [SMILES: c1ccc(-c2cc(-c3ccccc3)cc(-n3c4ccccc4c4ccc5c(c43)-c3ccccc3C5(c3ccccc3)c3ccccc3)c2)cc1]
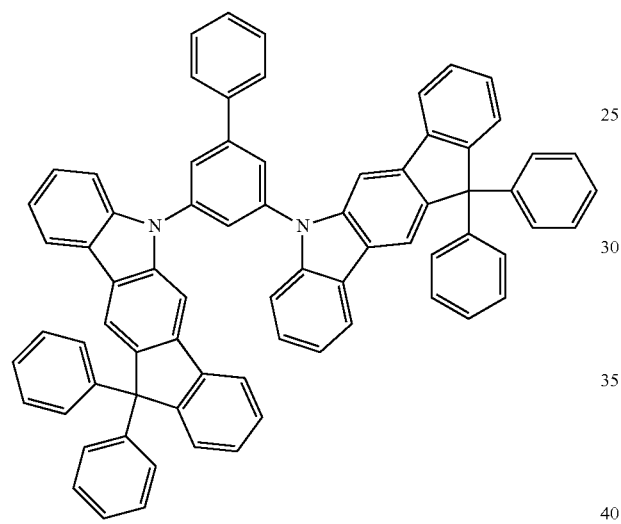
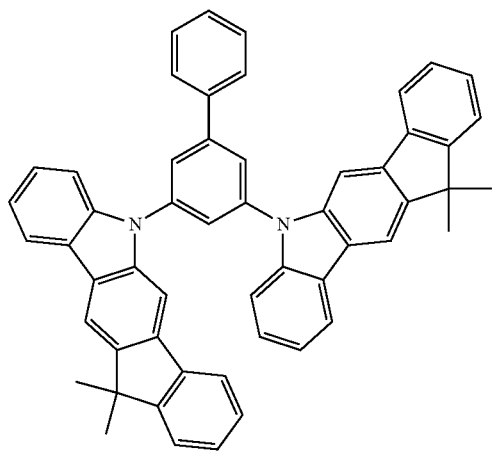 [SMILES: CC1(C)c2ccccc2-c2cc3c(cc21)c1ccccc1n3-c1cc(-c2ccccc2)cc(-n2c3ccccc3c3cc4c(cc32)-c2ccccc2C4(C)C)c1]
248
-continued
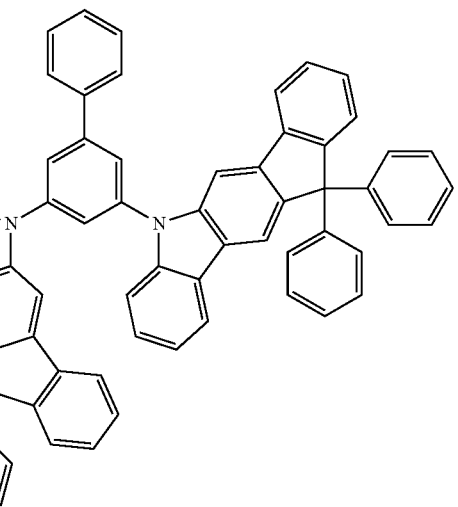
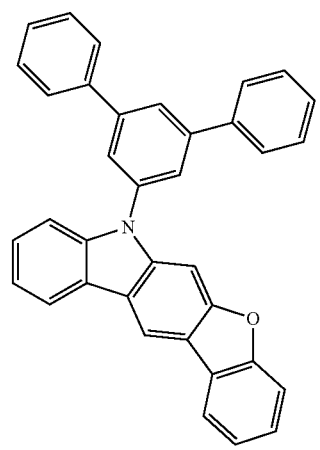 [SMILES: c1ccc(-c2cc(-c3ccccc3)cc(-n3c4ccccc4c4cc5c(cc43)oc3ccccc35)c2)cc1]
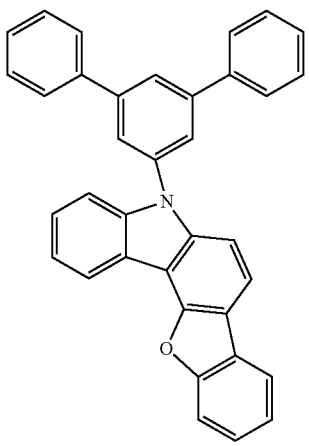 [SMILES: c1ccc(-c2cc(-c3ccccc3)cc(-n3c4ccccc4c4c5oc6ccccc6c5ccc43)c2)cc1]

| 249 -continued | 250 -continued |
|---|---|
| 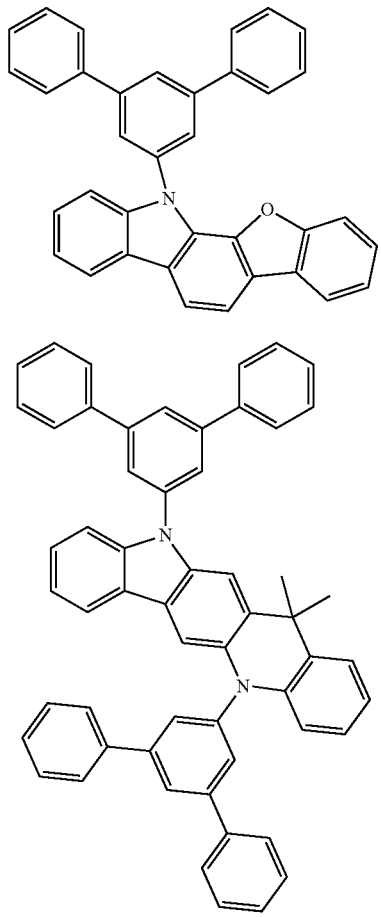 | 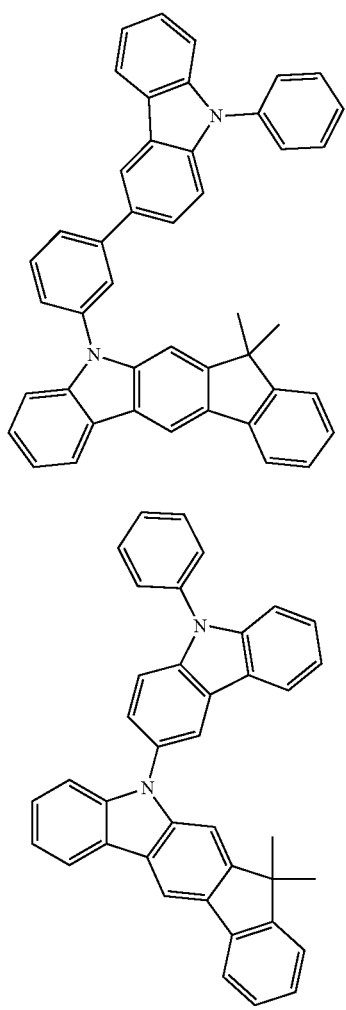 |
| 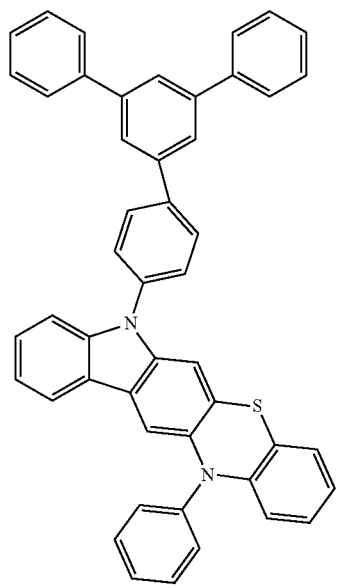 [SMILES: c1ccc(-c2cc(-c3ccccc3)cc(-c3ccc(-n4c5ccccc5c5cc6c(cc54)Sc4ccccc4N6c4ccccc4)cc3)c2)cc1] | 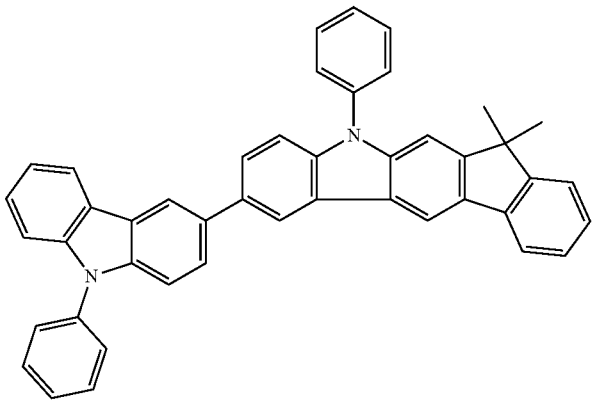 [SMILES: CC1(C)c2ccccc2-c2cc3c4cc(-c5ccc6c(c5)c5ccccc5n6-c5ccccc5)ccc4n(-c4ccccc4)c3cc21] |

Further preference once again is given to the matrix compounds of the following formulae (M85) to (M91):

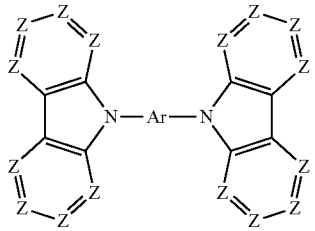
Formula (M85)

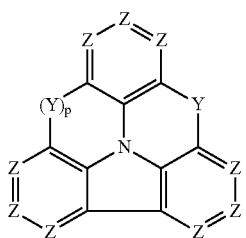
Formula (M86)

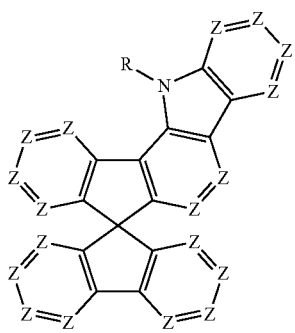
Formula (M87)

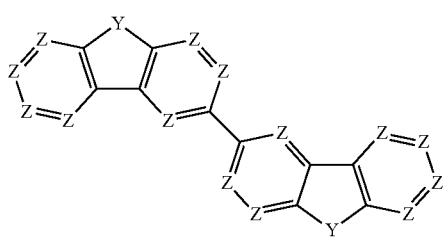
Formula (M88)

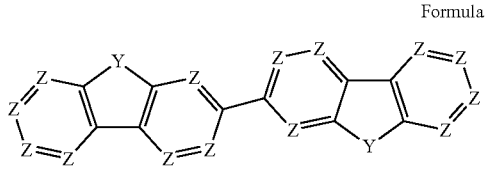
Formula (M89)

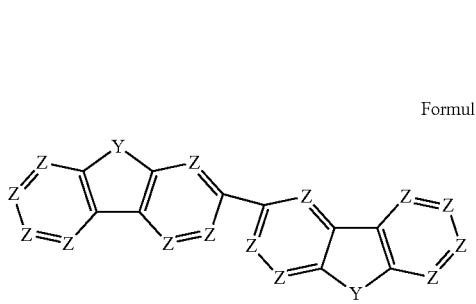
Formula (M90)

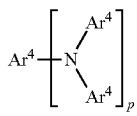
Formula (M91)

where the symbols and indices used have the same definitions as described above, and p is 1, 2, 3, 4, 5 or 6, especially 1, 2 or 3. In addition, in the structure of the formula (M91), two $Ar^4$ groups which bind to the same nitrogen atom may be bridged to one another by a group selected from NR, O, $CR_2$ and S.

Particularly the compounds of the formula (M91) are hole-transporting compounds.

In addition, preferred embodiments of the compounds of the formulae (M85) to (M91) are those compounds in which the symbols and indices used have the preferred embodiments detailed above.

Preferred embodiments of the compounds of the formula (M85) are the structures listed in the following table:

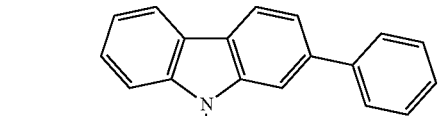

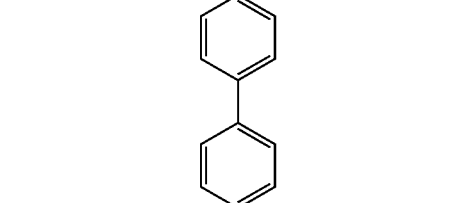

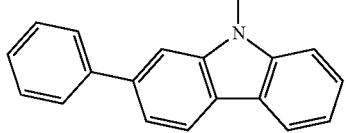

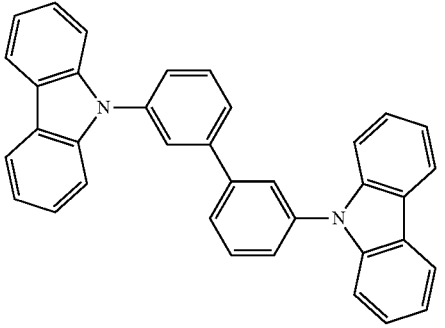 [SMILES: c1cc(-c2cccc(-n3c4ccccc4c4ccccc43)c2)cc(-n2c3ccccc3c3ccccc32)c1]

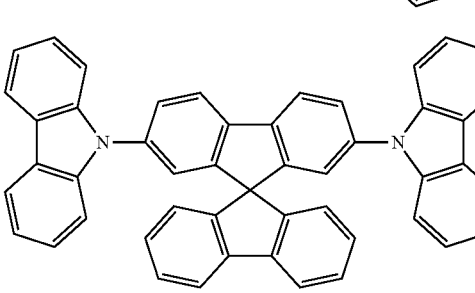

253
-continued
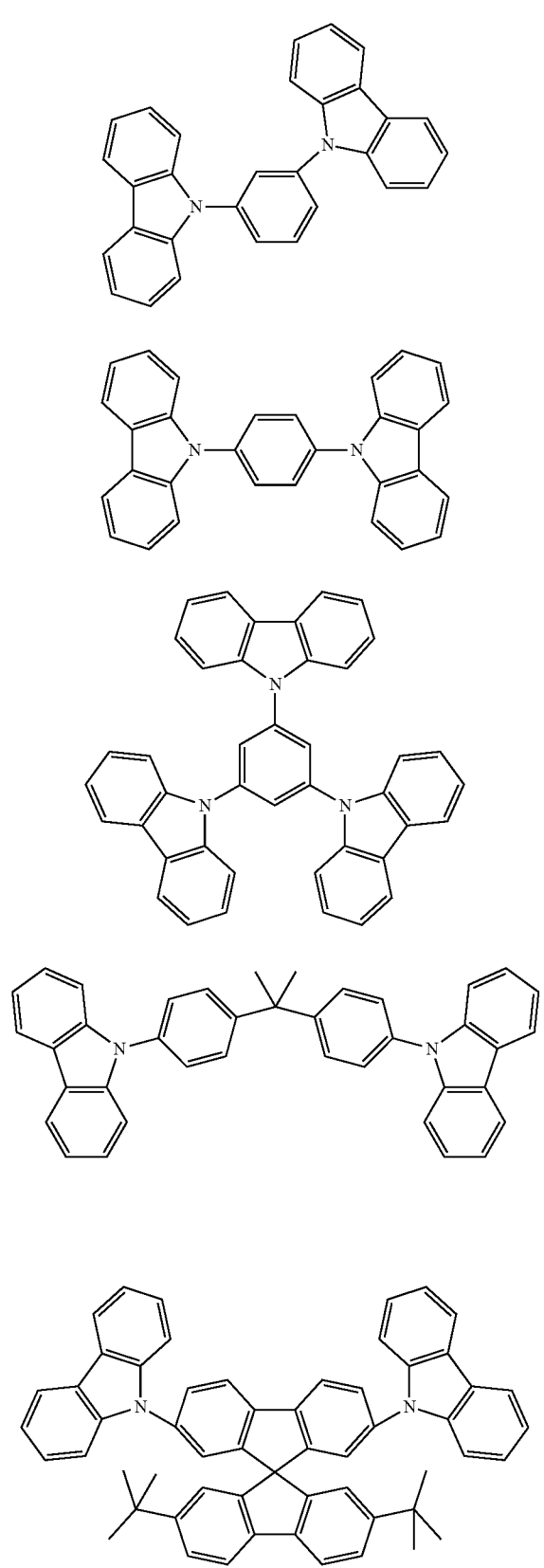
254
-continued
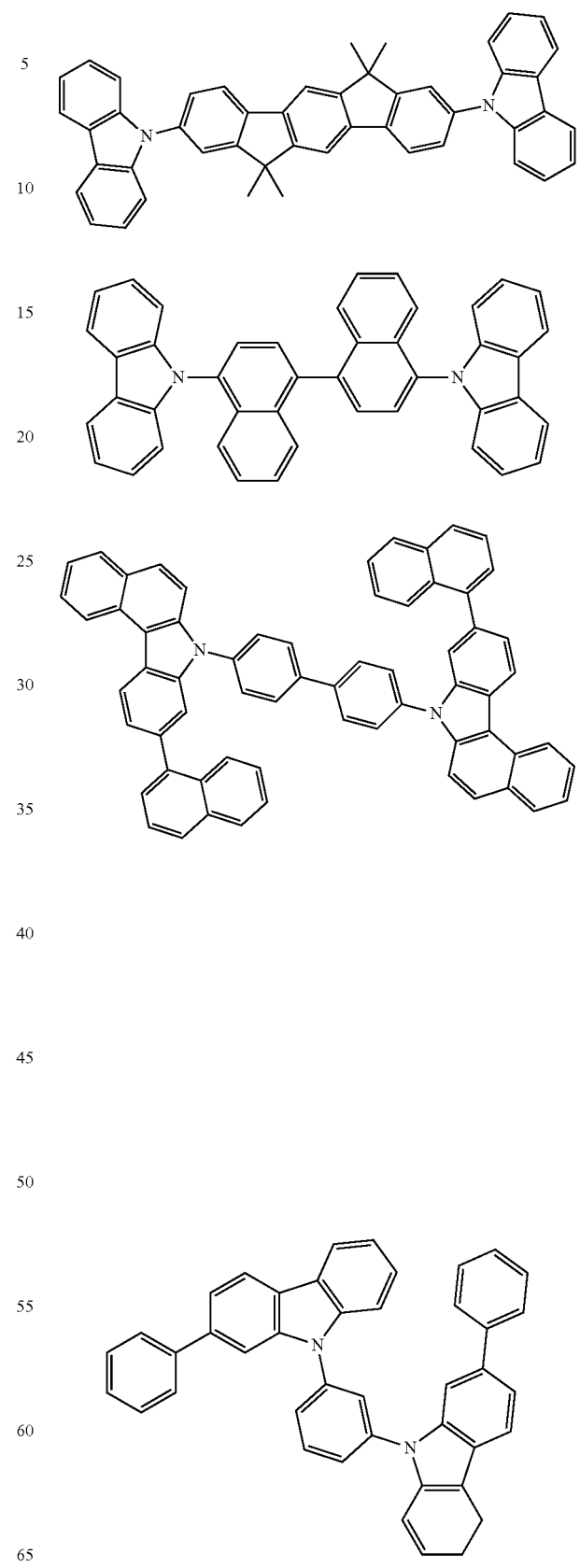

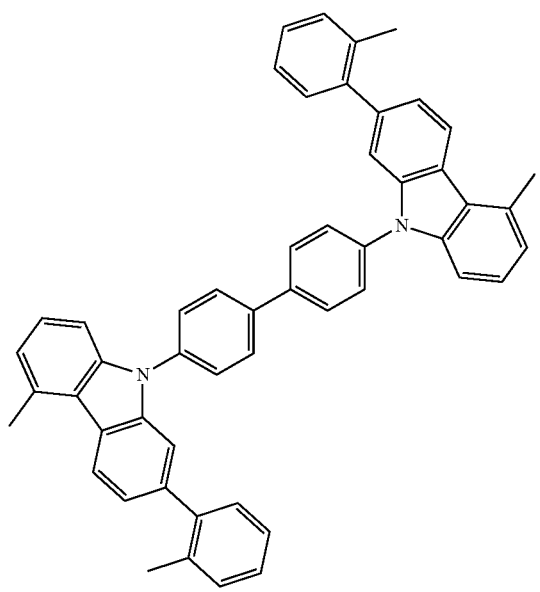
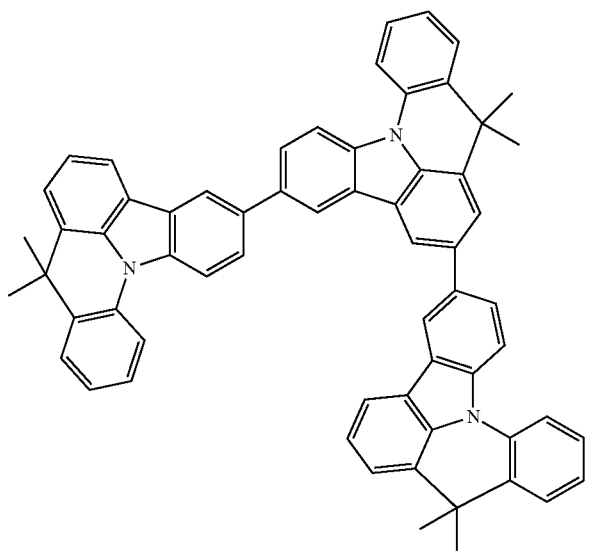 [SMILES: CC1(C)c2ccccc2-n2c3ccc(-c4ccc5c(c4)c4cc(-c6ccc7c(c6)c6cccc8c6n7-c6ccccc6C8(C)C)cc6c4n5-c4ccccc4C6(C)C)cc3c3cccc1c32]
Preferred embodiments of the compounds of the formula (M86) are the structures listed in the following table:
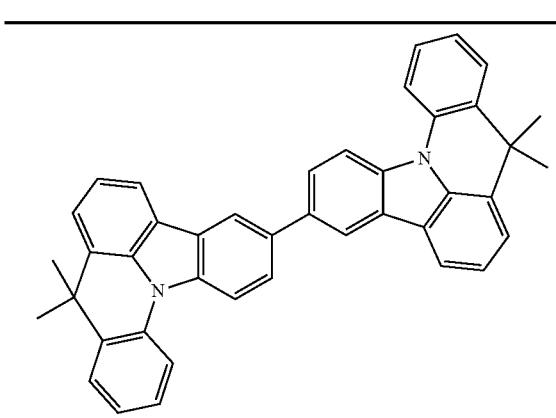
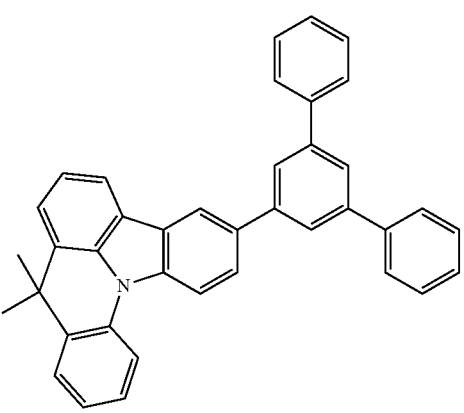 [SMILES: CC1(C)c2ccccc2-n2c3ccc(-c4cc(-c5ccccc5)cc(-c5ccccc5)c4)cc3c3cccc1c32]
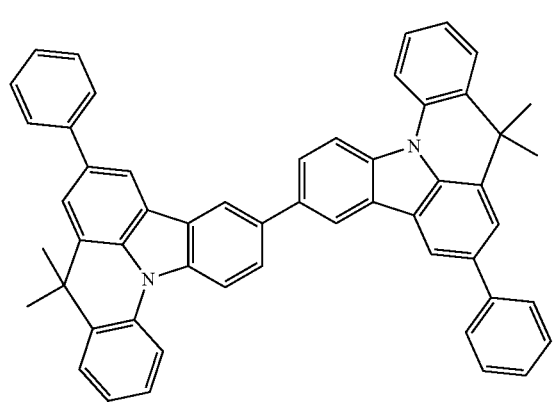
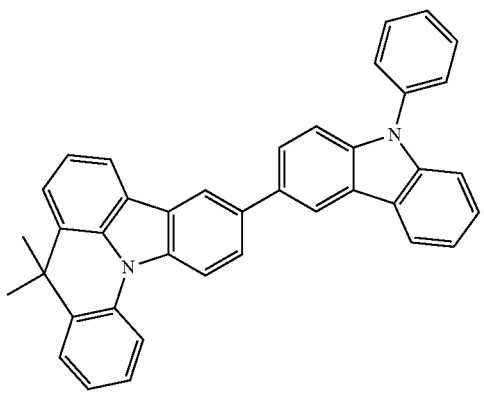 [SMILES: CC1(C)c2ccccc2-n2c3ccc(-c4ccc5c(c4)c4ccccc4n5-c4ccccc4)cc3c3cccc1c32]

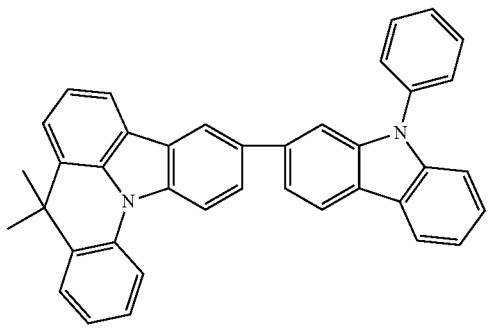 [SMILES: CC1(C)c2ccccc2-n2c3ccc(-c4ccc5c6ccccc6n(-c6ccccc6)c5c4)cc3c3cccc1c32]
Preferred embodiments of the compounds of the formula (M87) are the structures listed in the following table:
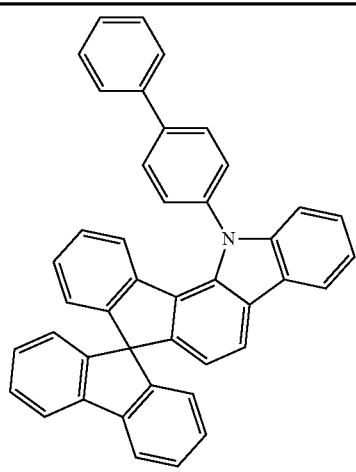
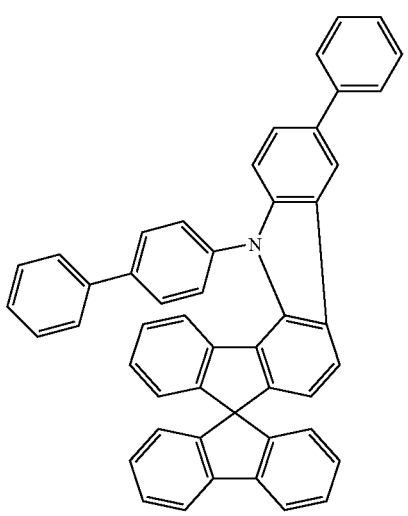 [SMILES: c1ccc(-c2ccc(-n3c4ccc(-c5ccccc5)cc4c4ccc5c(c43)-c3ccccc3C53c4ccccc4-c4ccccc43)cc2)cc1]
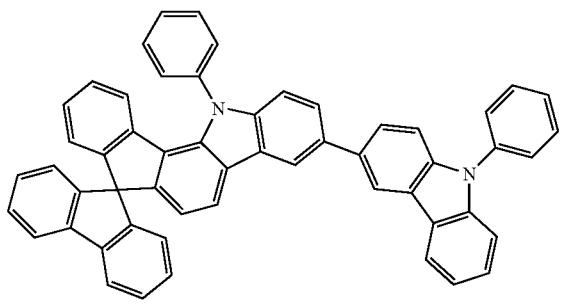 [SMILES: c1ccc(-n2c3ccccc3c3cc(-c4ccc5c(c4)c4ccc6c(c4n5-c4ccccc4)-c4ccccc4C64c5ccccc5-c5ccccc54)ccc32)cc1]
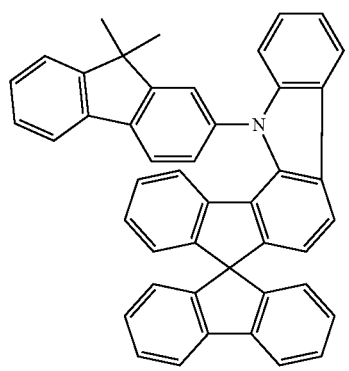
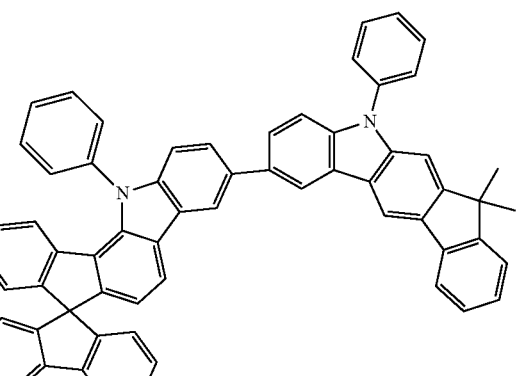
Preferred embodiments of the compounds of the formula (M88) to (M90) are the structures listed in the following table:

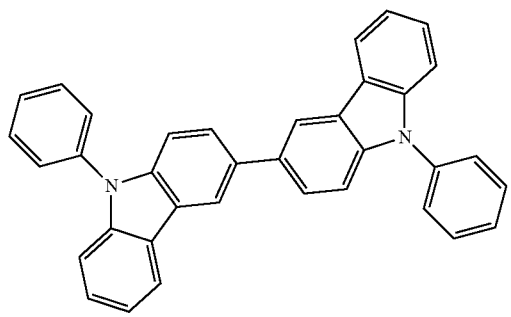 [SMILES: c1ccc(-n2c3ccccc3c3cc(-c4ccc5c(c4)c4ccccc4n5-c4ccccc4)ccc32)cc1]
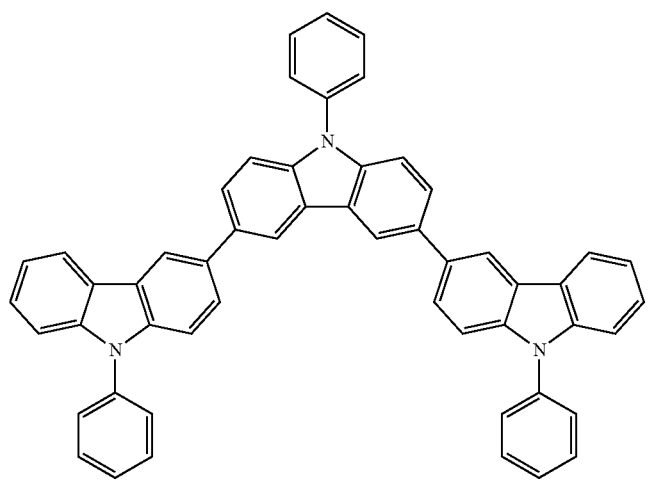 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]
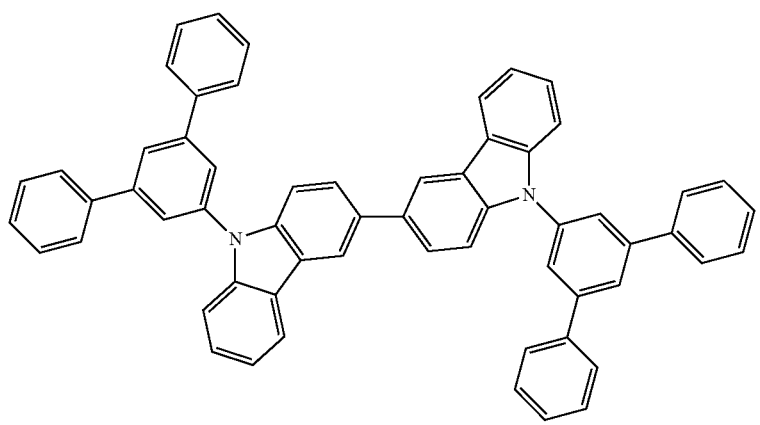 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1]
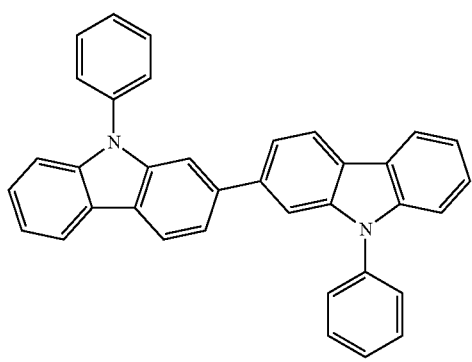 [SMILES: c1ccc(-n2c3ccccc3c3ccc(-c4ccc5c6ccccc6n(-c6ccccc6)c5c4)cc32)cc1]

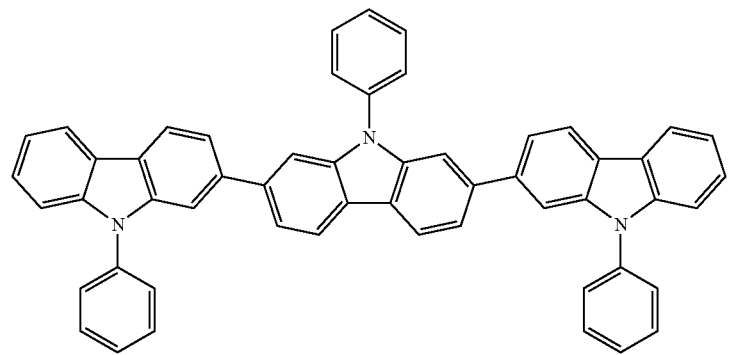 [SMILES: c1ccc(-n2c3ccccc3c3ccc(-c4ccc5c6ccc(-c7ccc8c9ccccc9n(-c9ccccc9)c8c7)cc6n(-c6ccccc6)c5c4)cc32)cc1]
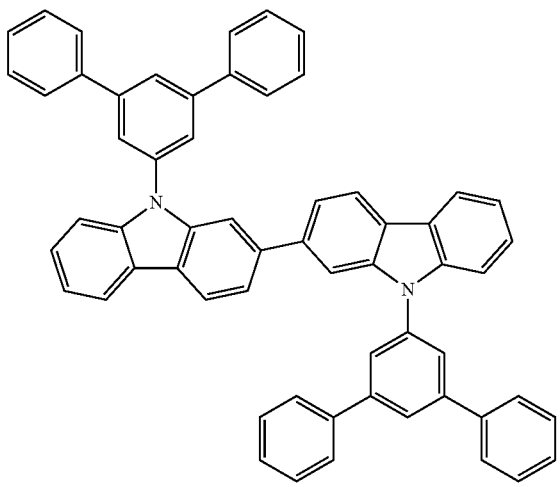 [SMILES: c1ccc(-c2cc(-c3ccccc3)cc(-n3c4ccccc4c4ccc(-c5ccc6c7ccccc7n(-c7cc(-c8ccccc8)cc(-c8ccccc8)c7)c6c5)cc43)c2)cc1]
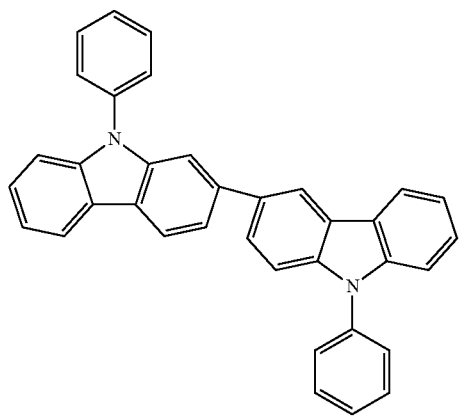 [SMILES: c1ccc(-n2c3ccccc3c3cc(-c4ccc5c6ccccc6n(-c6ccccc6)c5c4)ccc32)cc1]

-continued

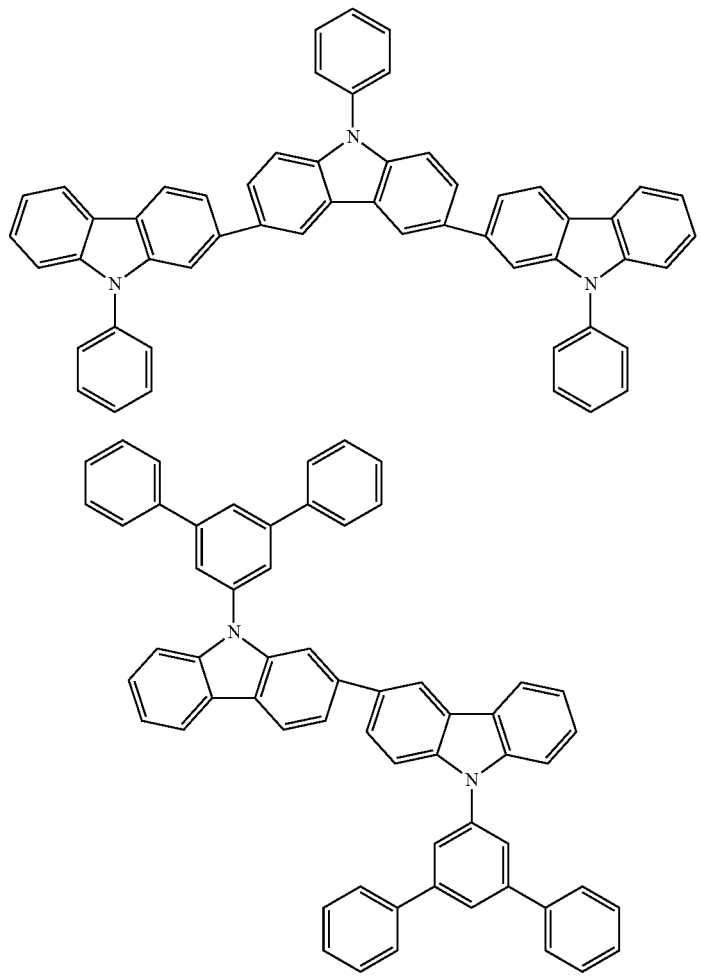

There follows a detailed description of the organic electroluminescent device.

The organic electroluminescent device comprises cathode, anode and emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. However, it should be pointed out that not necessarily every one of these layers need be present.

In the further layers of the inventive organic electroluminescent device, especially in the hole injection and transport layers and in the electron injection and transport layers, it is possible to use any materials as typically used according to the prior art. The hole transport layers may also be p-doped or the electron transport layers may also be n-doped. A p-doped layer is understood to mean a layer in which free holes are generated and which has increased conductivity as a result. A comprehensive discussion of doped transport layers in OLEDs can be found in Chem. Rev. 2007, 107, 1233. More preferably, the p-dopant is capable of oxidizing the hole transport material in the hole transport layer, i.e. has a sufficiently high redox potential, especially a higher redox potential than the hole transport material. Suitable dopants are in principle any compounds which are electron acceptor compounds and which can increase the conductivity of the organic layer by oxidizing the host. The person skilled in the art, in the context of his common knowledge in the art, is able to identify suitable compounds without any great effort. Especially suitable dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709 and US 2010/0096600.

The person skilled in the art will therefore be able, without exercising inventive skill, to use all the materials known for organic electroluminescent devices in combination with the emitting layer of the invention.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. On the other hand, metal/metal oxide electrons (e.g. $Al/Ni/NiO_x$, $Al/PtO_x$) may also be preferred. In this case, at least one of the electrodes has to be transparent or semitransparent in order to enable the emission of light. A preferred structure uses a transparent anode. Preferred anode materials here are conductive mixed metal oxides. Particular preference is given to indium tin oxide (ITO) or indium zinc oxide (IZO). Preference is further given to conductive doped organic materials, especially conductive doped polymers.

The device is correspondingly (according to the application) structured, contact-connected and finally hermetically sealed, since the lifetime of such devices is severely shortened in the presence of water and/or air.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution. Since the fluorescent compound having high steric shielding typically has good solubility in a multitude of standard organic solvents by virtue of the shielding groups, the production of the emitting layer from solution is preferred.

These methods are known in general terms to those skilled in the art and can be applied by those skilled in the art without exercising inventive skill to organic electroluminescent devices comprising the compounds of the invention.

The present invention therefore further provides a process for producing an inventive organic electroluminescent device, characterized in that at least one layer is applied by a sublimation method and/or in that at least one layer is applied by an OVPD (organic vapor phase deposition) method or with the aid of a carrier gas sublimation and/or in that at least one layer is applied from solution, by spin-coating or by a printing method.

The organic electroluminescent devices of the invention are notable for one or more of the following surprising advantages over the prior art:
1. The organic electroluminescent devices of the invention have an improved lifetime over devices according to the prior art which contain a TADF compound as emitting compound but do not contain a sterically shielded fluorescent compound.
2. The organic electroluminescent devices of the invention frequently have a narrower emission spectrum compared to devices according to the prior art which contain a TADF compound as emitting compound but do not contain a sterically shielded fluorescent compound, which leads to greater color purity of the emission.
3. The organic electroluminescent devices of the invention have significantly higher efficiency compared to devices according to the prior art where the fluorescent compound does not have high steric shielding.

The invention is illustrated in detail by the examples which follow, without any intention of restricting it thereby. The person skilled in the art will be able to use the information given to execute the invention over the entire scope disclosed and produce further inventive organic electroluminescent devices without exercising inventive skill.

EXAMPLES

Synthesis Examples

Synthesis of a Sterically Shielded Fluorescent Compound

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Synthesis Example 1 a) Synthesis of Compound 1

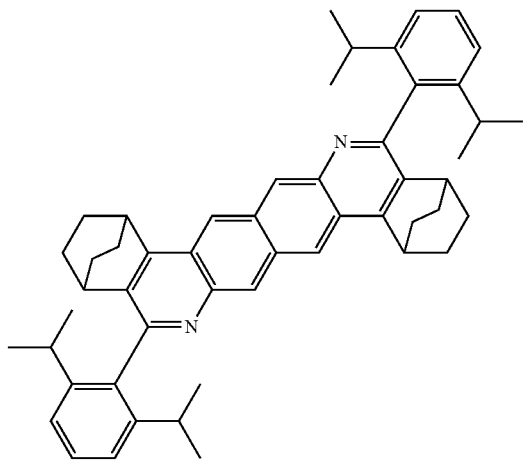 [SMILES: CC(C)c1cccc(C(C)C)c1-c1nc2cc3cc4c5c(c(-c6c(C(C)C)cccc6C(C)C)nc4cc3cc2c2c1C1CCC2CC1)C1CCC5CC1]

To a well-stirred mixture of 15.8 g (100 mmol) of 2,6-diaminonaphthalene [2243-67-6], 47.6 g (250 mmol) of 2,6-bis(1-methylethyl)benzaldehyde [179554-06-4], 27.1 g (250 mol) of bicyclo[2.2.2]oct-2-ene [931-64-6] and 300 mL of dichloromethane are added dropwise 2.8 g (20 mmol) of boron trifluoride etherate [60-29-7], and then the mixture is heated under reflux for 80 h. After cooling, the reaction mixture is washed twice with 200 mL each time of water, the organic phase is dried over magnesium sulfate and then the dichloromethane is removed under reduced pressure. The residue is taken up in 300 mL of o-dichlorobenzene, 87 g (1 mol) of manganese dioxide are added and the mixture is heated under reflux on a water separator for 16 h. After cooling, 500 mL of ethyl acetate are added, the manganese dioxide is filtered off with suction through a Celite layer, the manganese dioxide is washed with 200 mL of ethyl acetate and the combined filtrates are freed of the solvents under reduced pressure. The residue is chromatographed on silica gel with n-heptane/ethyl acetate (2:1). Yield: 6.4 g (9 mmol) 9%; purity about 97% by $^1$H NMR.

b) Synthesis of Compound 2

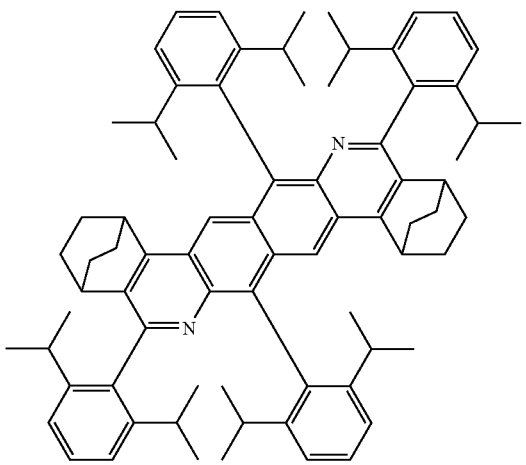 [SMILES: CC(C)c1cccc(C(C)C)c1-c1nc2c(-c3c(C(C)C)cccc3C(C)C)c3cc4c5c(c(-c6c(C(C)C)cccc6C(C)C)nc4c(-c4c(C(C)C)cccc4C(C)C)c3cc2c2c1C1CCC2CC1)C1CCC5CC1]

A mixture of 6.4 g (9 mmol) of compound 1, 4.3 g (22 mmol) of 2-chloro-1,3-bis(1-methylethyl)benzene [54845-36-2], 2.5 g (25 mmol) of sodium tert-butoxide, 44 mg (0.1 mmol) of dirhodium tetraacetate [85503-41-3], 52 mg (0.2 mmol) of 1,3-diphenyl-1H-imidazolium chloride [26956-10-5], 50 g of glass beads (diameter 3 mm) and 200 ml of o-xylene is heated under reflux for 48 h. After cooling, the salts are filtered off through Celite, the solvent is removed under reduced pressure and the residue is chromatographed on silica gel (n-heptane/ethyl acetate (9:1)) until a purity of >99.8% by HPLC has been attained. Yield: 1.1 g (1.1 mmol), 12%.

General Description of the Determination of the Relevant Parameters

1) Determination of the Energy Levels of the Molecular Orbitals and Singlet and Triplet Levels The energy levels of the molecular orbitals and the energy of the lowest triplet state $T_1$ and of the lowest excited singlet state $S_1$ of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "#AM1 opt") with charge 0 and multiplicity 1. Subsequently, on the basis of the optimized geometry, a single-point energy calculation is effected for the electronic ground state and the triplet level. This is done using the TDDFT (time dependent density functional theory) method B3PW91 with the 6-31G(d) basis set (Gaussian input line "#B3PW91/6-31G(d) td=(50-50, nstates=4)") (charge 0, multiplicity 1). For organometallic compounds (referred to as the "M-org." method), the geometry is optimized by the Hartree-Fock method and the LanL2 MB basis set (Gaussian input line "#HF/LanL2 MB opt") (charge 0, multiplicity 1). The energy calculation is effected, as described above, analogously to that for the organic substances, except that the "LanL2DZ" basis set is used for the metal atom and the "6-31G(d)" basis set for the ligands (Gaussian input line "#B3PW91/gen pseudo=lanl2 td=(50-50,nstates=4)"). From the energy calculation, the HOMO, for example, is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. The energies in Hartree units are obtained in an analogous manner for the other energy levels such as HOMO-1, HOMO-2, . . . LUMO+1, LUMO+2 etc.

In the context of this application, the ((HEh*27.212)–0.9899)/1.1206 values in eV, calibrated using CV measurements, are considered to be the energy levels of the populated orbitals.

In the context of this application, the ((LEh*27.212)–2.0041)/1.385 values in eV, calibrated using CV measurements, are considered to be the energy levels of the unpopulated orbitals.

The lowest triplet state $T_1$ of a material is defined as the relative excitation energy (in eV) of the triplet state having the lowest energy which is found by the quantum-chemical energy calculation.

The lowest excited singlet state $S_1$ is defined as the relative excitation energy (in eV) of the singlet state having the second-lowest energy which is found by the quantum-chemical energy calculation.

The method described herein is independent of the software package used and always gives the same results. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01".

Table 2 states the HOMO and LUMO energy levels and $S_1$ and $T_1$ of the various materials.

2) Determination of the Photoluminescence Quantum Efficiency (PLQE) Of the TADF Compound A 50 nm-thick film of the layer comprising a TADF material is applied to a quartz substrate. This film comprises the same materials in the same concentration ratios as the corresponding layer in the OLED except for the fluorescent compound. If the layer in the OLED contains, for example, the material IC1 to an extent of 85%, the material D1 to an extent of 10% and the material SE1 (fluorescent compound) to an extent of 5%, the film for the determination of the PLQE contains the materials IC1 and D1 in a volume ratio of 85:10. To produce the film, the same production conditions are used as for production of the emission layer for the OLEDs.

An absorption spectrum of this film is measured in the wavelength range of 350-500 nm. For this purpose, the reflection spectrum R(λ) and the transmission spectrum T00 of the sample are determined at an angle of incidence of 6° (i.e. incidence virtually at right angles). The absorption spectrum in the context of this application is defined as A(λ)=1−R(λ)−T(λ).

If A(λ)≤0.3 in the range of 350-500 nm, the wavelength corresponding to the maximum of the absorption spectrum in the range of 350-500 nm is defined as $\lambda_{exc}$. If, for any wavelength, A(λ)>0.3, $\lambda_{exc}$ is defined as being the greatest wavelength at which A(λ) changes from a value of less than 0.3 to a value of greater than 0.3 or from a value of greater than 0.3 to a value of less than 0.3.

The PLQE is determined using a Hamamatsu C9920-02 measurement system. The principle is based on the excitation of the sample with light of a defined wavelength and the measurement of the radiation absorbed and emitted. During the measurement, the sample is within an Ulbricht sphere ("integrating sphere"). The spectrum of the excitation light is approximately Gaussian with a half-height width of <10 nm and a peak wavelength $\lambda_{exc}$ as defined above.

The PLQE is determined by the evaluation method customary for said measurement system. The measurement is effected at room temperature. It should be strictly ensured that the sample does not come into contact with oxygen at any time, since the PLQE of materials having a small energy gap between $S_1$ and $T_1$ is very greatly reduced by oxygen (H. Uoyama et al., Nature 2012, Vol. 492, 234).

The PLQE is reported in the respective examples together with the excitation wavelength used.

3) Determination of Peak Emission Wavelength $\lambda_{max}$

To determine the peak emission wavelength of the TADF compounds and the fluorescent compound, the particular material is dissolved in toluene. In this case, a concentration of 0.5 mg/100 mL is used. The solution is excited with a wavelength of 350 nm in a Hitachi F-4500 fluorescence spectrometer. The measurement is effected at room temperature. The peak emission wavelength $\lambda_{max}$ is the wavelength at which the emission spectrum obtained reaches its maximum value.

4) Determination of the PLQE of the Fluorescent Compound

To determine the PLQE of the fluorescent compound, the material is dissolved in toluene. In this case, a concentration of 1 mg/100 mL is used. To determine the PLQE, the solution is analyzed in a Hamamatsu 09920-02 measurement system (for description see above). The measurement is effected at room temperature. The excitation wavelength used is the wavelength 0.27*$\lambda_{max}$+300 nm, where $\lambda_{max}$ represents the peak emission wavelength of the fluorescent compound as defined above.

5) Determination of Decay Time

The decay time is determined using a sample which is produced as described above under "Determination of the PL quantum efficiency (PLQE)". The sample is excited at room temperature by a laser pulse (wavelength 266 nm, pulse duration 1.5 ns, pulse energy 200 μJ, beam diameter 4 mm). At this time, the sample is under reduced pressure (<$10^{-5}$ mbar). After excitation (defined as t=0), the profile of the intensity of the photoluminescence emitted against time is measured. The photoluminescence exhibits a steep drop at the start, which is attributable to the prompt fluorescence of the TADF compound. Later on, a slower drop is observed, delayed fluorescence (see, for example, H. Uoyama et al., Nature, vol. 492, no. 7428, 234-238, 2012 and K. Masui et al., Organic Electronics, vol. 14, no. 11, pp. 2721-2726, 2013). The decay time to in the context of this application is the decay time of the delayed fluorescence and is determined as follows: A time $t_d$ at which the prompt fluorescence has abated to well below the intensity of the delayed fluorescence is chosen, such that the determination of the decay time that follows is not affected by the prompt fluorescence. This choice can be executed by a person skilled in the art and forms part of his common art knowledge. For the measurement data from the time $t_d$, the decay time $t_a=t_e-t_d$ is determined. In this formula, $t_e$ is that time after t=$t_d$ sat which the intensity has for the first time dropped to 1/e of its value at t=$t_d$.

6) Determination of the Shielding Parameter S of the Fluorescent Compound a) Determination of the active atoms of a molecular orbital First of all, for each individual molecular orbital, a determination of which atoms are active is conducted. In other words, a generally different set of active atoms is found for each molecular orbital. There follows an illustrative description of how the active atoms of the HOMO molecular orbital are determined. For all other molecular orbitals (e.g. HOMO-1, LUMO, LUMO+1, etc.), the active atoms are determined analogously.

For the fluorescent compounds, a quantum-chemical calculation as described above is conducted. This calculation gives the different molecular orbitals from which, with the aid of SCPA Population Analysis, the participation of all atoms in the molecule in the different molecular orbitals is determined. SCPA Population Analysis, also called C-squared Population Analysis, is described in Ros, P.; Schuit, G. C. A. Theoret. Chim. Acta (Berl.) 1966, 4, 1-12 and is implemented, for example, in the AOMix software package.

Hereinafter, N denotes the number of atoms in the molecule, and $P'_{HOMO}(a)$ the participation of the atom numbered a (a=1 . . . N) in the HOMO molecular orbital (analogously for all other molecular orbitals). The participation levels are defined such that $$\sum_{a=1}^{N} P'_{HOMO}(a) = 1$$

i.e. the sum total of all participation levels is one. The atomic participation levels normalized to one are designated $P_{HOMO}(a)$, i.e.

$P_{HOMO}(a)=P'_{HOMO}(a)/\text{MAX}(P'_{HOMO}(a), a=1 \ldots N)$

If $P_{HOMO}(a) \geq 0.2$, the atom a is considered to be active with respect to the HOMO molecular orbital. An analogous definition applies to all other molecular orbitals.

b) Charge-Exchanging Molecular Orbitals of the Fluorescent Compound

Charge-exchanging molecular orbitals are considered to be the HOMO and LUMO, and all molecular orbitals that are separated in energy by 75 meV or less from the HOMO or LUMO.

In addition, active populated molecular orbitals are considered to be all of those whose energy E satisfies the following condition: E(LUMO)−E≤gap(TADF). In addition, active unpopulated molecular orbitals are considered to be all of those whose energy E satisfies the following condition: E−E(HOMO)≤gap(TADF). E(LUMO) here is the LUMO energy level and E(HOMO) the HOMO energy level of the fluorescent compound. In addition, gap(TADF)=E(LUMO, TADF)−E(HOMO,TADF). E(LUMO,TADF) here is the LUMO energy level of the TADF compound and E(HOMO, TADF) the HOMO energy level of the TADF compound. If the OLED contains two or more TADF compounds, gap (TADF) is the greatest of the values for the TADF compounds present.

c) Determination of the Active Atoms in the Fluorescent Compound

If one atom in at least one charge-exchanging molecular orbital is active, it is considered to be active in respect of the fluorescent compound. Only atoms that are inactive (non-active) in all charge-exchanging molecular orbitals are inactive in respect of the fluorescent compound.

Example

Active and Inactive Atoms of Rubrene

The material rubrene is shown below with the numbers a of the carbon atoms present. The numbers of the hydrogen atoms are not stated, since these are inactive without exception.

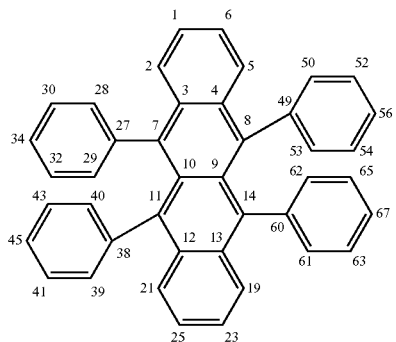 [SMILES: c1ccc(-c2c3ccccc3c(-c3ccccc3)c3c(-c4ccccc4)c4ccccc4c(-c4ccccc4)c23)cc1]

The table which follows shows the participations P and the normalized participations P of the carbon atoms in the HOMO and LUMO molecular orbitals, calculated by the method described above. The participations of the hydrogen atoms are not shown. In addition, the last column shows whether the atoms are active ("A") or inactive ("I"), assuming that only HOMO and LUMO are charge-exchanging.

| a | P′$_{HOMO}$(a) | P′$_{LUMO}$(a) | P$_{HOMO}$(a) | P$_{LUMO}$(a) | Active/inactive |
|---|---|---|---|---|---|
| 1 | 0.035 | 0.034 | 0.31 | 0.29 | A |
| 2 | 0.042 | 0.040 | 0.38 | 0.33 | A |
| 3 | 0.020 | 0.025 | 0.18 | 0.20 | A |
| 4 | 0.020 | 0.025 | 0.18 | 0.20 | A |
| 5 | 0.042 | 0.040 | 0.38 | 0.33 | A |
| 6 | 0.035 | 0.034 | 0.31 | 0.29 | A |
| 7 | 0.112 | 0.120 | 1.00 | 1.00 | A |
| 8 | 0.112 | 0.120 | 1.00 | 1.00 | A |
| 9 | 0.004 | 0.002 | 0.04 | 0.01 | I |
| 10 | 0.004 | 0.002 | 0.04 | 0.01 | I |
| 11 | 0.112 | 0.120 | 1.00 | 1.00 | A |
| 12 | 0.020 | 0.025 | 0.18 | 0.20 | A |
| 13 | 0.020 | 0.025 | 0.18 | 0.20 | A |
| 14 | 0.112 | 0.120 | 1.00 | 1.00 | A |
| 19 | 0.042 | 0.040 | 0.38 | 0.33 | A |
| 21 | 0.042 | 0.040 | 0.38 | 0.33 | A |
| 23 | 0.035 | 0.034 | 0.31 | 0.29 | A |
| 25 | 0.035 | 0.034 | 0.31 | 0.29 | A |
| 27 | 0.003 | 0.003 | 0.03 | 0.02 | I |
| 28 | 0.012 | 0.007 | 0.10 | 0.06 | I |
| 29 | 0.012 | 0.009 | 0.10 | 0.07 | I |
| 30 | 0.004 | 0.002 | 0.03 | 0.01 | I |
| 32 | 0.002 | 0.004 | 0.02 | 0.03 | I |
| 34 | 0.004 | 0.006 | 0.04 | 0.05 | I |
| 38 | 0.003 | 0.003 | 0.03 | 0.02 | I |
| 39 | 0.012 | 0.007 | 0.10 | 0.06 | I |
| 40 | 0.012 | 0.009 | 0.10 | 0.07 | I |
| 41 | 0.004 | 0.002 | 0.03 | 0.01 | I |
| 43 | 0.002 | 0.004 | 0.02 | 0.03 | I |
| 45 | 0.004 | 0.006 | 0.04 | 0.05 | I |
| 49 | 0.003 | 0.003 | 0.03 | 0.02 | I |
| 50 | 0.012 | 0.007 | 0.10 | 0.06 | I |
| 51 | 0.012 | 0.009 | 0.10 | 0.07 | I |
| 52 | 0.004 | 0.002 | 0.03 | 0.01 | I |
| 54 | 0.002 | 0.004 | 0.02 | 0.03 | I |
| 56 | 0.004 | 0.006 | 0.04 | 0.05 | I |
| 60 | 0.003 | 0.003 | 0.03 | 0.02 | I |
| 61 | 0.012 | 0.007 | 0.10 | 0.06 | I |
| 62 | 0.012 | 0.009 | 0.10 | 0.07 | I |
| 63 | 0.004 | 0.002 | 0.03 | 0.01 | I |
| 65 | 0.002 | 0.004 | 0.02 | 0.03 | I |
| 67 | 0.004 | 0.006 | 0.04 | 0.05 | I | d) Determination of V(D$_{cut}$)

The active surface refers to the van der Waals surface of the active atoms of the fluorescent compound. This is the surface of the van der Waals volume of the active atoms. If a sphere having the van der Waals radius corresponding to the particular type of atom is placed around each active atom, with the atom forming the center of the sphere, the union of all these spheres is the van der Waals volume of the active atoms. The van der Waals radii Now of the different elements are reported in angstroms in the following table:

| Element | | | | | | | | | | | | |
|---|---|---|---|---|---|---|---|---|---|---|---|---|
| | H | He | Li | Be | B | C | N | O | F | Ne | Na | Mg | Al |
| r$_{VDW}$ (Å) | 1.2 | 1.22 | 1.52 | 1.7 | 2.08 | 1.85 | 1.54 | 1.4 | 1.35 | 1.6 | 2.31 | 1.73 | 2.05 |

| Element | | | | | | | | | | | | |
|---|---|---|---|---|---|---|---|---|---|---|---|---|
| | Si | P | S | Cl | Ar | K | Ca | Sc | Ti | C | Cr | Mn | Fe |
| r$_{VDW}$ (Å) | 2 | 1.9 | 1.85 | 1.81 | 1.91 | 2.31 | 1.97 | 1.7 | 1.7 | 1.7 | 1.7 | 1.7 | 1.7 |

| Element | | | | | | | | | | | | |
|---|---|---|---|---|---|---|---|---|---|---|---|---|
| | Co | Ni | Cu | Zn | Ga | Ge | As | Se | Br | Kr | Rb | Sr | Y |
| r$_{VDW}$ (Å) | 1.7 | 1.7 | 1.7 | 1.7 | 1.7 | 1.7 | 2 | 2 | 2.1 | 2.1 | 1.7 | 1.7 | 1.7 |

-continued

| Element | | | | | | | | | | | | |
|---|---|---|---|---|---|---|---|---|---|---|---|---|
| | Zr | Nb | Mo | Tc | Ru | Rh | Pd | Ag | Cd | In | Sn | Sb | Te |
| $r_{VDW}$ (Å) | 1.7 | 1.7 | 1.7 | 1.7 | 1.7 | 1.7 | 1.7 | 1.7 | 1.7 | 1.7 | 1.7 | 2.2 | 2.2 |

| Element | | | | | | | | | | | | |
|---|---|---|---|---|---|---|---|---|---|---|---|---|
| | I | Xe | Cs | Ba | La | Ce | Pr | Nd | Pm | Sm | Eu | Gd | Tb |
| $r_{VDW}$ (Å) | 2.15 | 2.16 | 1.7 | 1.7 | 1.7 | 1.7 | 1.7 | 1.7 | 1.7 | 1.7 | 1.7 | 1.7 | 1.7 |

| Element | | | | | | | | | | | | |
|---|---|---|---|---|---|---|---|---|---|---|---|---|
| | Dy | Ho | Er | Tm | Yb | Lu | Hf | Ta | W | Re | Os | Ir | Pt |
| $r_{VDW}$ (Å) | 1.7 | 1.7 | 1.7 | 1.7 | 1.7 | 1.7 | 1.7 | 1.7 | 1.7 | 1.7 | 1.7 | 1.7 | 1.72 |

| Element | | | | | | | | | | | | |
|---|---|---|---|---|---|---|---|---|---|---|---|---|
| | Au | Hg | Tl | Pb | Bi | Po | At | Rn | Fr | Ra | Ac | Th | Pa |
| $r_{VDW}$ (Å) | 1.66 | 1.55 | 1.7 | 1.7 | 1.7 | 1.7 | 1.7 | 1.7 | 1.7 | 1.7 | 1.7 | 1.7 | 1.7 |

| Element | | | | | | | |
|---|---|---|---|---|---|---|---|
| | U | Np | Pu | Am | Cm | Bk | Cf |
| $r_{VDW}$ (Å) | 1.7 | 1.7 | 1.7 | 1.7 | 1.7 | 1.7 | 1.7 |

The Connolly surface (also referred to as solvent-excluded surface) of the fluorescent compound as a whole refers to the surface of the solvent-excluded volume (Michael L. Connolly, "Computation of Molecular Volume", J. Am. Chem. Soc., 1985, Vol. 107, p. 1118-1124). If the van der Waals volume of the fluorescent compound as a whole (defined analogously to the above-described van der Waals volume of the active atoms) is considered to be hard, i.e. to be a volume which cannot be penetrated, the solvent-excluded volume in the context of the present invention is the portion of the space that cannot be occupied by a hard sphere with radius 0.4 nm. The area of the Connolly surface of the fluorescent compound as a whole is referred to as $A_{con}$.

The area of that proportion of the Connolly surface having a distance of not more than $d_{cut}$ from the active surface is referred to as $A_{cut}$. For a given value of $d_{cut}$, the parameter $V(d_{cut})$ is defined as $A_{cut}/A_{con}$.

e) Determination of the Shielding Parameter S for the Fluorescent Compound

The parameter S which describes the steric shielding of the fluorescent compounds of this invention is defined as $S = (V(0.2 \text{ nm})/2 + V(0.3 \text{ nm})/3 + V(0.4 \text{ nm})/4 + V(0.5 \text{ nm})/5 + V(0.6 \text{ nm})/6) \cdot (20/29)$ The parameter S depends on the structure of the fluorescent compound and of the TADF compound used (see "Charge-exchanging molecular orbitals of the fluorescent compound" further up).

A fluorescent compound is considered to be sterically shielded in the context of the present application when the above-defined shielding parameter $S \leq 0.6$.

Examples of Organic Electroluminescent Devices

Production of the OLEDs

Glass plaques coated with structured ITO (indium tin oxide) of thickness 50 nm are subjected to wet cleaning (dishwasher, Merck Extran detergent), then baked in a nitrogen atmosphere at 250° C. for 15 min and, prior to coating, treated with an oxygen plasma for 130 s. These plasma-treated glass plaques form the substrates to which the OLEDs are applied. The substrates remain under reduced pressure prior to coating. The coating begins no later than 10 min after the plasma treatment. After the production, the OLEDs are encapsulated for protection against oxygen and water vapor. The exact layer structure of the OLEDs can be found in the examples. The materials required for production of the OLEDs are shown in table 1.

All materials are applied by thermal vapor deposition in a vacuum chamber. The emission layer(s) always consist(s) of at least one matrix material (host material) to the emitting material. The latter is added to the matrix material(s) in a particular proportion by volume by coevaporation. Details given in such a form as IC1:D1:SE1 (92%:5%:3%) mean here that the material IC1 is present in the layer in a proportion by volume of 92%, D1 in a proportion of 5% and SE1 in a proportion of 3%. Analogously, the electron transport layer may also consist of a mixture of two materials.

The OLEDs are characterized in a standard manner. For this purpose, the electroluminescence spectra at 1000 cd/m² and current-voltage-luminance (UIL) characteristics are measured, from which it is possible to determine the external quantum efficiency (EQE, measured in %) assuming Lambertian emission characteristics. The parameter U1000 refers to the voltage which is required for a luminance of 1000 cd/m². EQE1000 refers to the external quantum efficiency at an operating luminance of 1000 cd/m².

The lifetime LT is defined as the time after which the luminance drops from the starting luminance to a certain proportion L1 in the course of operation with constant current. Figures of j0=10 mA/cm², L1=80% mean that the luminance in the course of operation at 10 mA/cm² falls to 80% of its starting value after the time LD.

The TADF material used is the compound D1. This has an energy gap between $S_1$ and $T_1$ of 0.09 eV.

For the two materials rubrene and SE1, in conjunction with material D1, the HOMO and LUMO molecular orbitals are charge-exchanging. The shielding parameter is S=0.755 for rubrene and 0.518 for SE1.

For the emission maximum of compound D1, $\lambda_{max}$=511 nm, for rubrene $\lambda_{max}$=555 nm, and for SE1 $\Delta_{max}$=572 nm.

Example 1

Fluorescent Compounds Having Different Shielding Parameters S in the Emission Layer Comprising a TADF Compound The OLEDs consist of the following layer sequence which is applied to the substrate after the plasma treatment: 85 nm SpMA1, 15 nm IC1:D1:emitter (92%:5%:3%), 10 nm IC1, 45 nm ST2:LiQ (50%:50%), aluminum (100 nm).

The PLQE of the layer containing the TADF compound is 94% ($\lambda_{exc}$=350 nm), the decay time 5.4 µs ($t_d$=7 µs).

If rubrene is used as emitter (S=0.755), this gives EQE1000=4.6%, U1000=4.6 V and LD=220 h for j0=10 mA/cm², L1=85%. With the emitter SE1 (S=0.518), much better values of EQE1000=8.2%, U1000=4.4 V and LD=440 h are obtained for j0=10 mA/cm², L1=85%. In both cases, orange emission is obtained.

For an OLED of otherwise identical construction which does not contain any fluorescent compound in the emission layer, i.e. IC1 and D1 in a volume ratio of 92:5 only, a lifetime LD=37 h for j0=10 mA/cm², L1=85%, is obtained.

The PLQE of rubrene is 94%, excitation wavelength 450 nm. The PLQE of SE1 is 97%, excitation wavelength 454 nm.

Example 1a

Higher Concentration of the Fluorescent Compound

The OLEDs are produced as in example 1, except using an IC1:D1:SE1 (89%:5%:6%) layer for the 15 nm-thick IC1:D1:emitter (92%:5%:3%) layer. There is a distinct increase in the lifetime compared to example 1; LD 1120 h is obtained for j0=10 mA/cm², L1=85%. In addition, there is an improvement in color purity. While the residual emission of the TADF compound at 500 nm is 9% of the peak emission (at 567 nm) in example 1, this is reduced to only 3% of the peak emission (at 571 nm) for 6% SE1.

Example 1b

Higher Concentration of the TADF Compound

The OLEDs are produced as in example 1, except using an IC1:D1:SE1 (87%:10%:3%) layer for the 15 nm-thick IC1:D1:emitter (92%:5%:3%) layer. There is a distinct increase in the lifetime compared to example 1; LD=655 h is obtained for j0=10 mA/cm², L1=85%.

The PLQE of the layer containing the TADF compound is 87% ($\lambda_{exc}$=350 nm) for this example, the decay time 4.9 µs ($t_d$=7 µs).

Example 1c

Higher Concentration of the Fluorescent and TADF Compounds

The OLEDs are produced as in example 1, except using an IC1:D1:SE1 (84%:10%:6%) layer for the 15 nm-thick IC1:D1 (92%:5%:3%) layer. There is a distinct increase in the lifetime compared to example 1; LD=1605 h is obtained for j0=10 mA/cm², L1=85%. There is an improvement in the color purity over example 1 to the same degree as described in example 1a.

Example 1d

Use of a Different Electron Transport Layer

The OLEDs are produced as in example 1, with the difference that the 45 nm-thick ST2:LiQ (50%:50%) layer is replaced by the sequence of 45 nm ST2, 3 nm LiQ.

If rubrene is used as emitter (S=0.755), this gives EQE1000=4.8%, U1000=4.6 V and LD=115 h for j0=10 mA/cm², L1=85%. With the emitter SE1 (S=0.518), much better values of EQE1000=8.4%, U1000=3.6 V and LD=150 h are obtained for j0=10 mA/cm², L1=85%. In both cases, orange emission is obtained.

Example 2

Comparison with an OLED Comprising an Anthracene Matrix

The OLEDs are produced with the fluorescent compound SE1 as in example 1, with the difference that the 15 nm-thick IC1:D1:SE1 (92%:5%:3%) layer is replaced by a 30 nm-thick AM1:SE1 (97%:3%) layer. The layer thickness of the emission layer is optimized for the AM1 matrix material used and is better than in the case of use of a 15 nm-thick emission layer. Anthracene-containing materials such as AM1 are matrix materials that are very frequently used in the prior art for fluorescent compounds, for example the material SE1. Nevertheless, with U1000=4.9 V, EQE1000=4.8%, much poorer values are obtained than in example 1.

Example 3

Fluorescent Compounds Having Different Shielding Parameters S in a Layer Adjoining the Layer Containing the TADF Material The OLEDs are produced as in example 1, with the difference that the 15 nm-thick IC1:D1:emitter (92%:5%:3%) layer is replaced by the sequence of 7.5 nm IC1:D1 (95%:5%), 7.5 nm IC1:emitter (97%:3%), i.e. two adjoining layers.

The PLQE of the layer containing the TADF compound is 92% ($\lambda_{exc}$=350 nm), the decay time 5.4 µs ($t_d$=7 µs).

If rubrene is used as emitter (S=0.755), this gives EQE1000=8.8%, U1000=3.8 V and LD=130 h for j0=10 mA/cm², L1=80%. With the emitter SE1 (S=0.518), a much better efficiency is found; EQE1000=14.2%, U1000=3.7 V and LD=135 h are obtained for j0=10 mA/cm², L1=80%.

Example 4

The OLEDs are produced as in example 3, with the difference that the 85 nm SpMA1 is replaced by 75 nm SpMA1 and 10 nm SpMA2.

If rubrene is used as emitter (S=0155), this gives EQE1000® 8.0%, U1000=3.8 V and LD=150 h for j0=10 mA/cm², L1=80%. With the emitter SE1 (S=0.518), a much better efficiency is found; EQE1000=15.1%, U1000=3.8 V and LD=150 h are obtained for j0=10 mA/cm², L1=80%.

TABLE 1
Structural formulae of the materials for the OLEDs
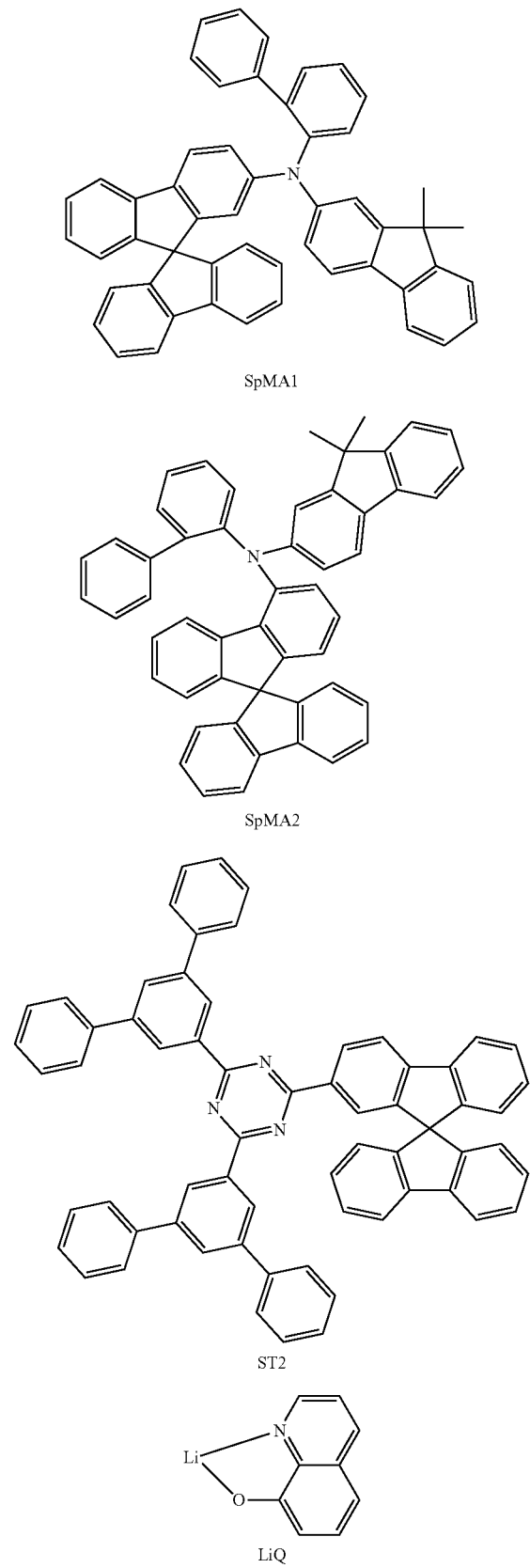
SpMA1
SpMA2
ST2
LiQ
TABLE 1-continued
Structural formulae of the materials for the OLEDs
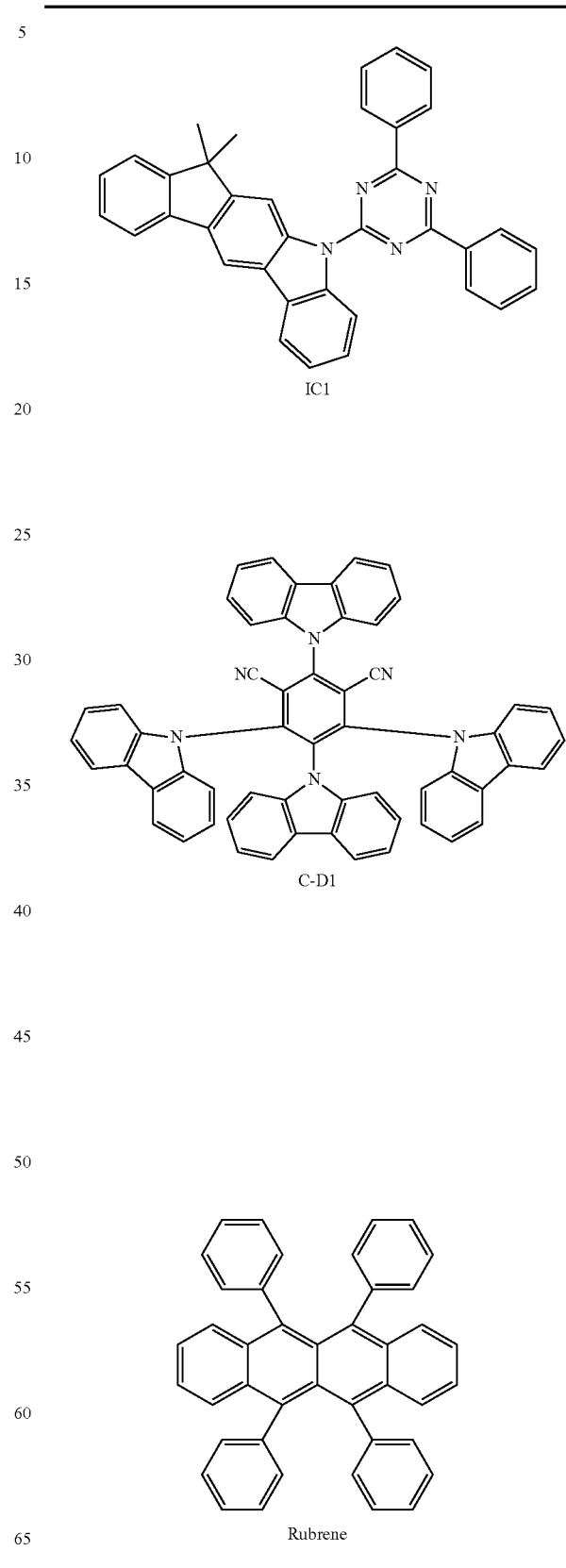
IC1
C-D1
Rubrene

TABLE 1-continued

Structural formulae of the materials for the OLEDs

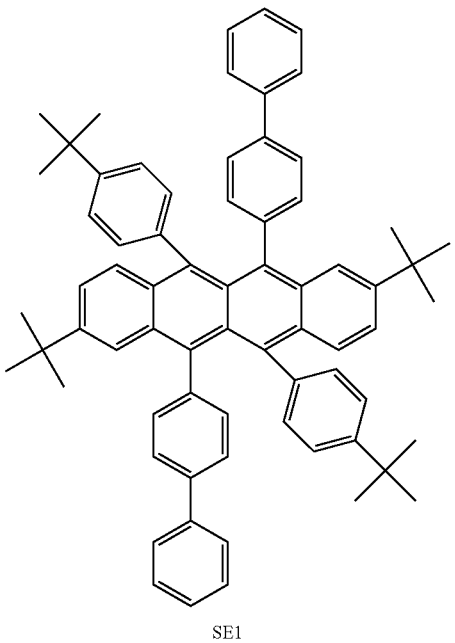 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

SE1

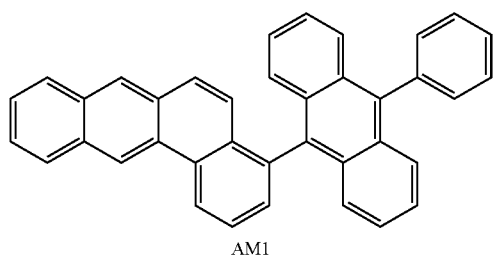

AM1

TABLE 2

HOMO, LUMO, $T_1$, $S_1$ of the relevant materials

| Material | Method | HOMO (eV) | LUMO (eV) | $S_1$ (eV) | $T_1$ (eV) |
|---|---|---|---|---|---|
| C-D1 | org. | −6.11 | −3.40 | 2.50 | 2.41 |
| IC1 | org. | −5.79 | −2.83 | 3.09 | 2.69 |
| SpMA1 | org. | −5.25 | −2.18 | 3.34 | 2.58 |
| SpMA2 | org. | −5.35 | −2.34 | 3.14 | 2.62 |
| ST2 | org. | −6.03 | −2.82 | 3.32 | 2.68 |
| LiQ | M-org. | −5.17 | −2.39 | 2.85 | 2.13 |

Comparative Example According to the Prior Art

US 2012/248968 describes OLEDs comprising a TADF compound and a fluorescent emitter material. The compound GH-4 used has an energy gap of 0.04 eV between $S_1$ and $T_1$. For the fluorescent emitter GD-1 with GH-4 as TADF compound, S=0.834. The external quantum efficiency shown for this combination is EQE=5.04% for 1 mA/cm² (corresponding to 174 cd/m²) and EQE=4.59% for 10 mA/cm² (1585 cd/m²). Since efficiency generally decreases toward higher luminances, the EQEs exhibited in the present invention for 1000 cd/m² are thus distinctly higher.

The compounds GH-4 and GD-1 used in the prior art are shown below:

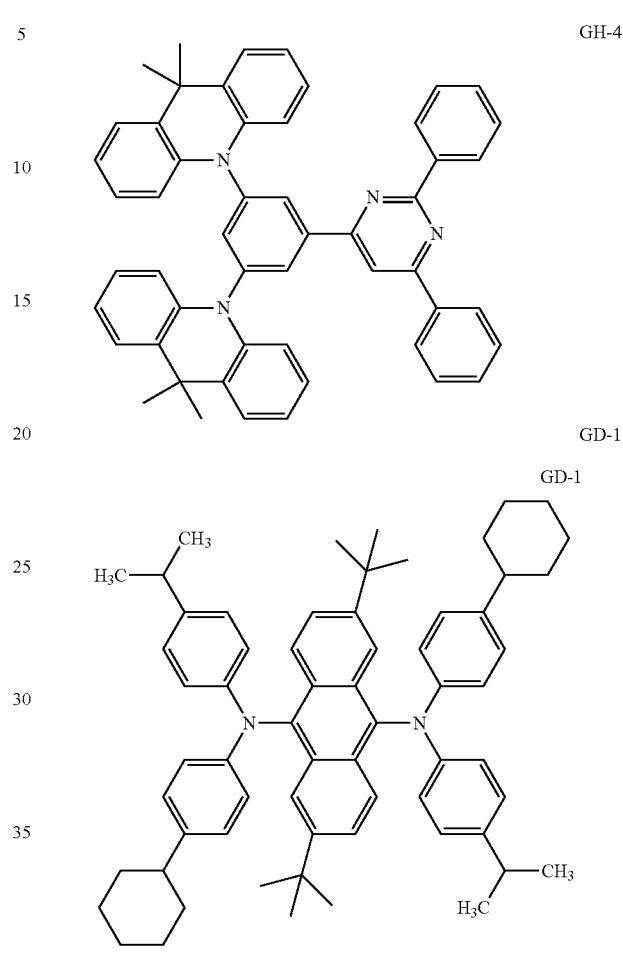

The invention claimed is:

1. An organic electroluminescent device comprising cathode, anode and at least one emitting layer comprising a sterically shielded fluorescent compound, wherein the emitting layer comprises a luminescent organic compound having a gap between the lowest triplet state $T_1$ and the first excited singlet state $S_1$ of <0.30 eV (TADF compound), where the peak emission wavelength of the sterically shielded fluorescent compound is greater than or equal to the peak emission wavelength of the TADF compound;
wherein the sterically shielded fluorescent compound comprises a fluorescent base skeleton comprising a rigid n system substituted by one or more sterically demanding substituents, where the sterically demanding substituents are one or more fused-on aliphatic groups of the formulae (Ring-1A) to (Ring-7A)

(Ring-1A)

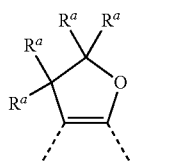 (Ring-1B)
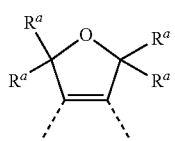 (Ring-1C)
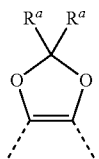 (Ring-1D)
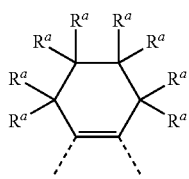 (Ring-2A)
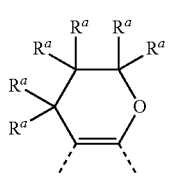 (Ring-2B)
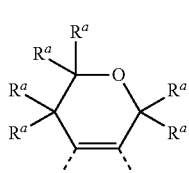 (Ring-2C)
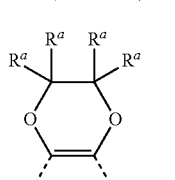 (Ring-2D)
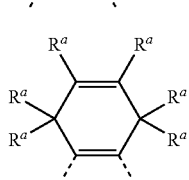 (Ring-2E)
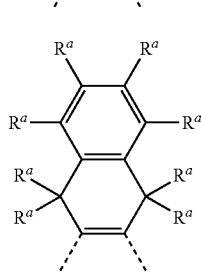 (Ring-2F)
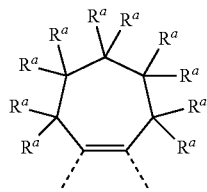 (Ring-3A)
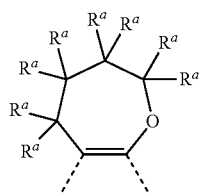 (Ring-3B)
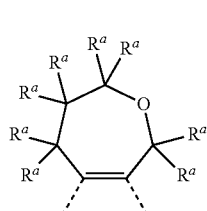 (Ring-3C)
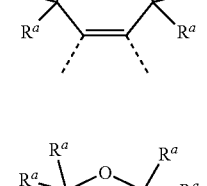 (Ring-3D)
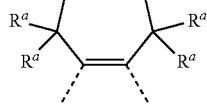 (Ring-3E)
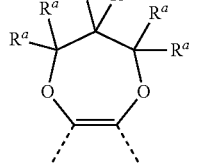 (Ring-4A)
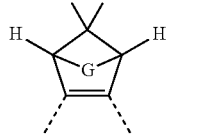 (Ring-4B)
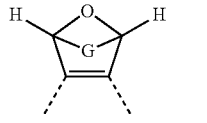 (Ring-5A)
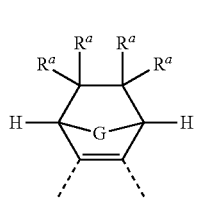

-continued (Ring-6A)
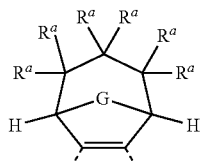

(Ring-7A)
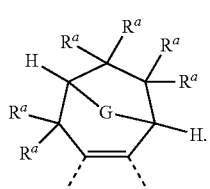

where the dotted bonds indicate the linkage of the two carbon atoms within the fluorescent base skeleton and in addition:

G is an alkylene group which has 1, 2 or 3 carbon atoms and optionally substituted by one or more $R^b$ radicals or an ortho-bonded arylene group which has 5 to 14 aromatic ring atoms and optionally substituted by one or more $R^b$ radicals;

$R^a$ is in each case independently selected from the group consisting of H, D, F, a straight-chain alkyl group having 1 to 40 carbon atoms and a branched or cyclic alkyl group having 3 to 40 carbon atoms, each of which is optionally substituted by one or more $R^b$ radicals, an aromatic ring system having 5 to 60 aromatic ring atoms, each of which is optionally substituted by one or more $R^b$ radicals, or an aralkyl group which has 5 to 60 aromatic ring atoms and is optionally substituted by one or more $R^a$ radicals, where it is optionally possible for two or more adjacent $R^a$ substituents to form a ring system which may be substituted by one or more $R^b$ radicals;

$R^b$ is selected from the group consisting of H, D, F, an aliphatic hydrocarbyl radical having 1 to 20 carbon atoms, and an aromatic ring system having 5 to 30 aromatic ring atoms, where two or more adjacent $R^b$ substituents together may form a ring system;

and wherein the emitting layer further comprises at least one matrix compound, which is one or more compounds selected from the group consisting of triarylamines, carbazoles, dibenzofurans, indolocarbazoles, indenocarbazoles, azacarbazoles, bipolar matrix materials, silanes, azaboroles, diazasiloles, diazaphopholes, triazines, pyrimidines, quinoxalines, and bridged carbazoles, with the proviso that the matrix is not a TADF compound;

and wherein $T_1$(matrix)−$T_1$(TADF)≥0.1 eV, where $T_1$(matrix) and $T_1$(TADF) are respectively the lowest triplet energy of the matrix compound and the lowest triplet energy of the TADF compound.

2. The organic electroluminescent device of claim 1, wherein the peak emission wavelength of the sterically shielded fluorescent compound is at least 10 nm greater than the TADF compound.

3. The organic electroluminescent device as of claim 1, wherein the TADF compound has a luminescence quantum efficiency of at least 40%.

4. The organic electroluminescent device of claim 1, wherein the TADF compound has a decay time of ≤50 μs.

5. The organic electroluminescent device of claim 1, wherein the gap between $S_1$ and $T_1$ of the TADF compound is ≤0.25 eV.

6. The organic electroluminescent device of claim 1, wherein the sterically shielded fluorescent compound has a luminescence quantum efficiency of at least 60%.

7. The organic electroluminescent device of claim 1, wherein the fluorescent base skeleton is selected from the group consisting of formulae (1) to (70):

Formula (1)
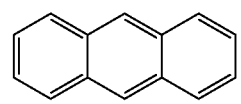

Formula (2)
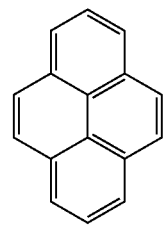

Formula (3)
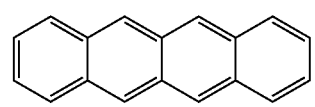

Formula (4)
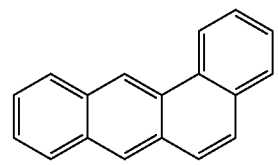

Formula (5)
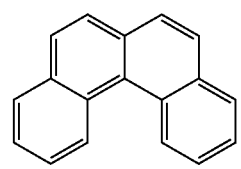

Formula (6)
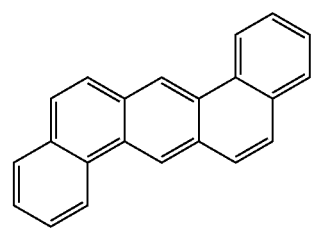

Formula (7)
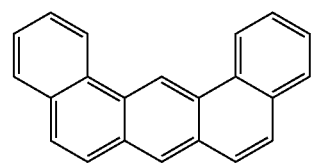

285
-continued
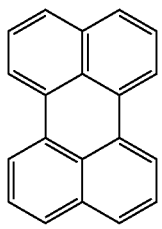
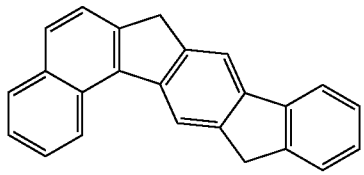
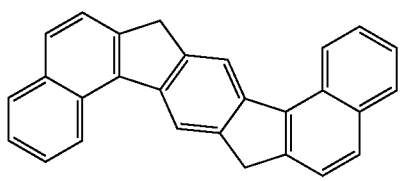
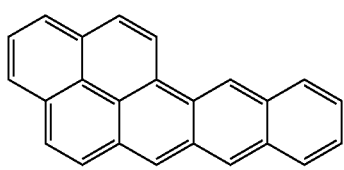
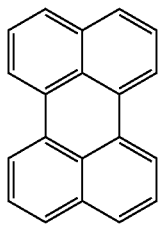
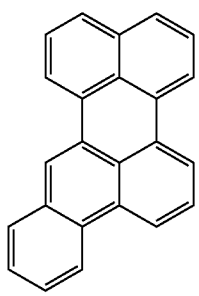
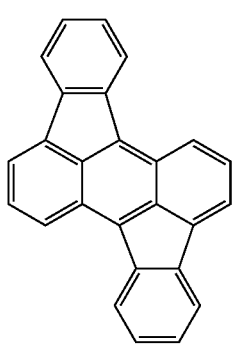
286
-continued
Formula (8)
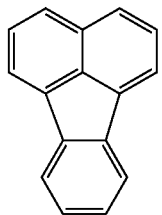
Formula (9)
Formula (10)
Formula (11)
Formula (12)
Formula (13)
Formula (14)
Formula (15)
Formula (16)
Formula (17)
Formula (18)
Formula (19)
Formula (20)

287
-continued
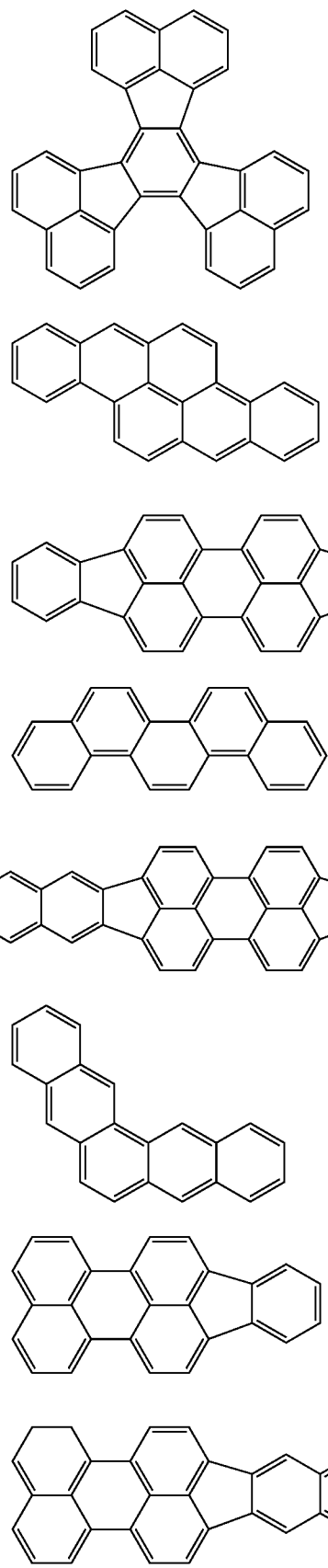
Formula (21)
Formula (22)
Formula (23)
Formula (24)
Formula (25)
Formula (26)
Formula (27)
Formula (28)
288
-continued
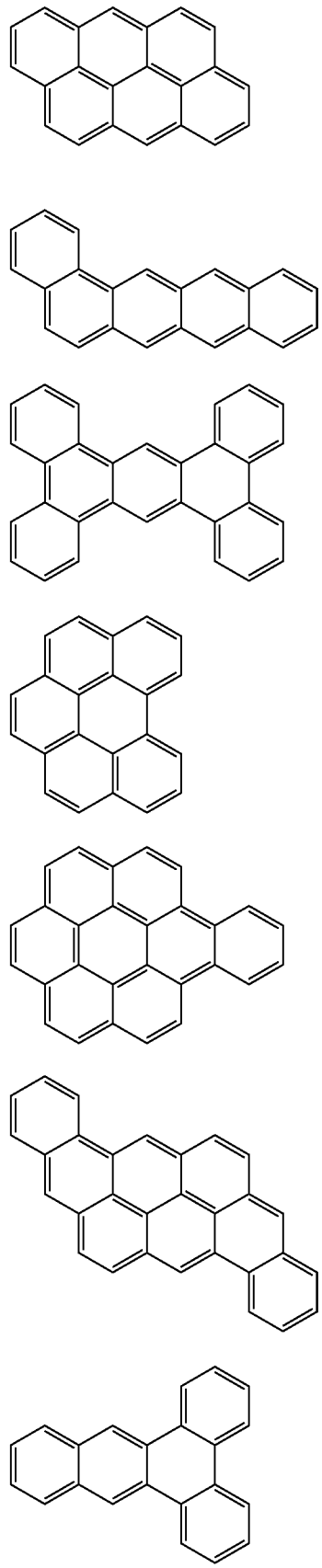
Formula (29)
Formula (30)
Formula (31)
Formula (32)
Formula (33)
Formula (34)
Formula (35)

Formula (36)
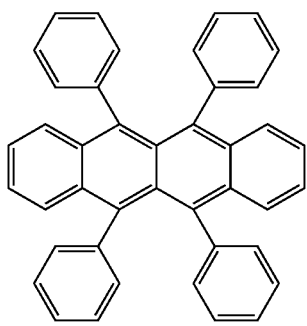
Formula (37)
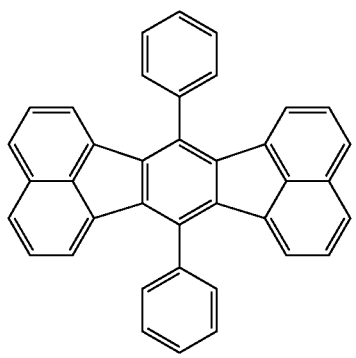
Formula (38)
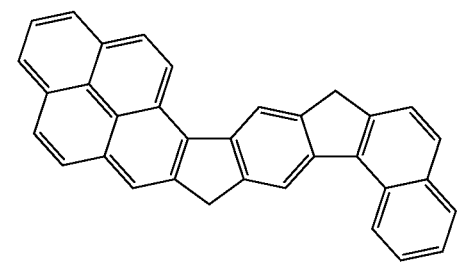
Formula (39)
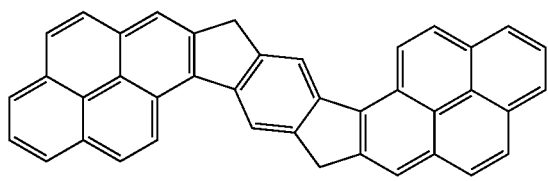
Formula (40)
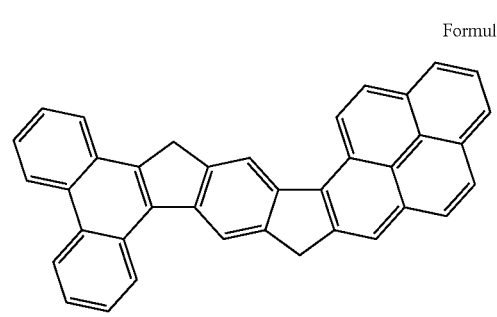
Formula (41)
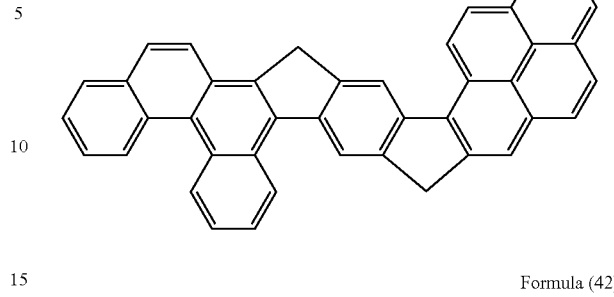
Formula (42)
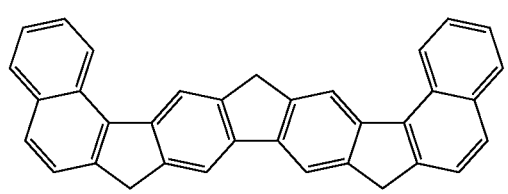
Formula (43)
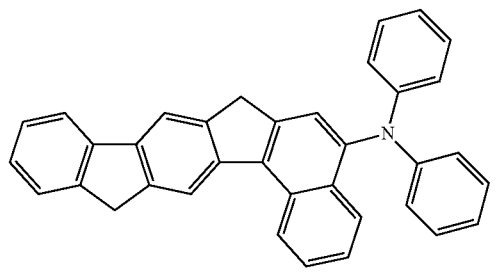
Formula (44)
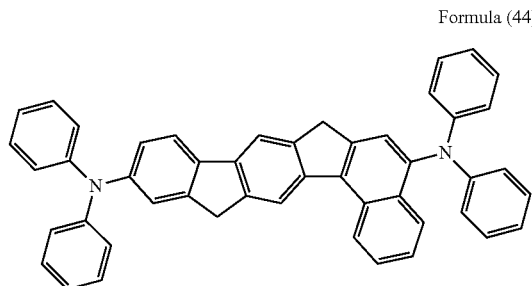
Formula (45)
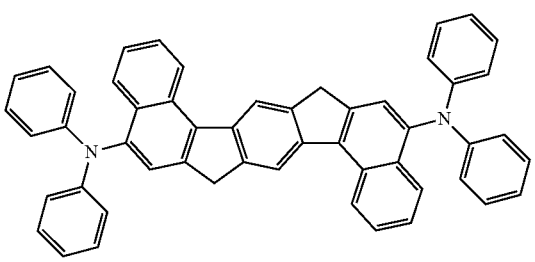

Formula (46)
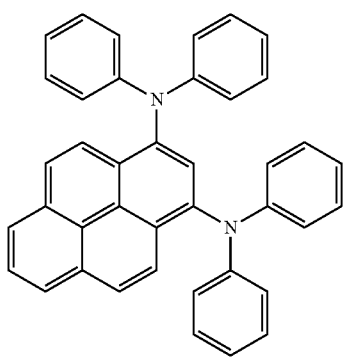
Formula (47)
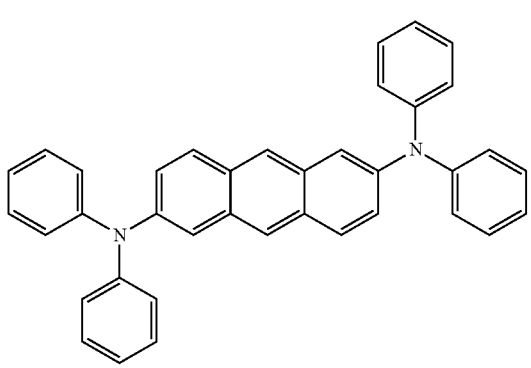
Formula (48)
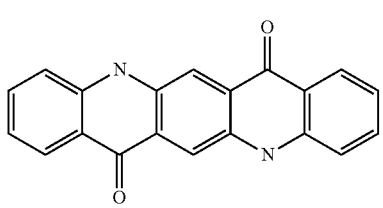
Formula (49)
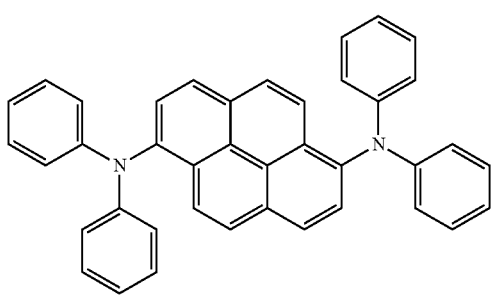
Formula (50)
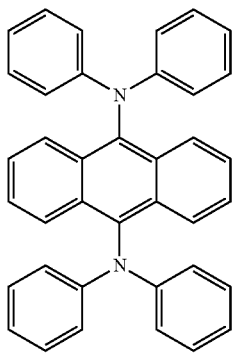
Formula (51)
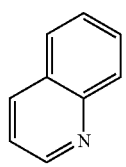
Formula (52)
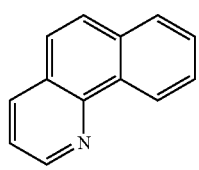
Formula (53)
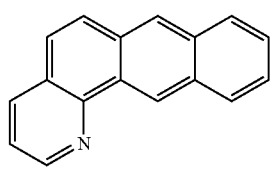
Formula (54)
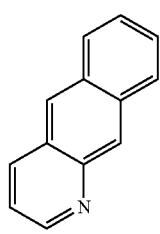
Formula (55)
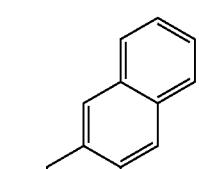
Formula (56)
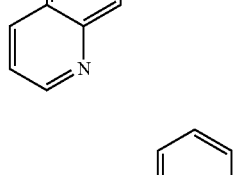
Formula (57)
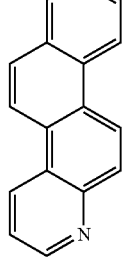

-continued
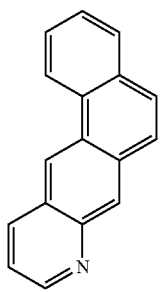
Formula (58)
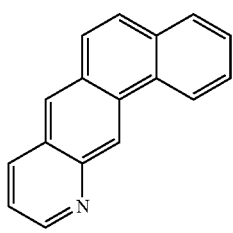
Formula (59)
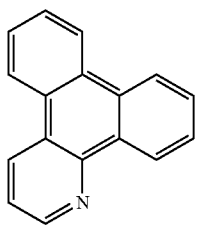
Formula (60)
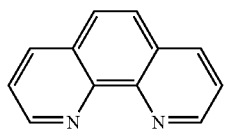
Formula (61)
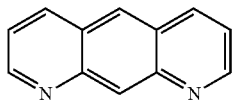
Formula (62)
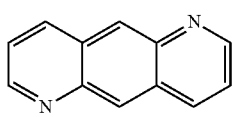
Formula (63)
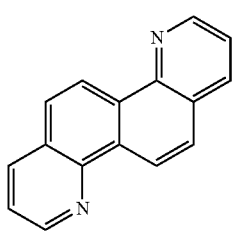
Formula (64)
-continued
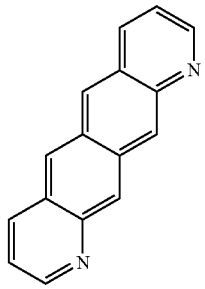
Formula (65)
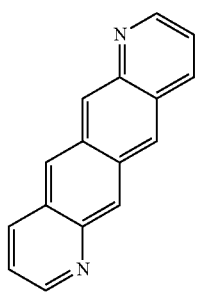
Formula (66)
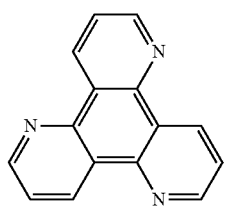
Formula (67)
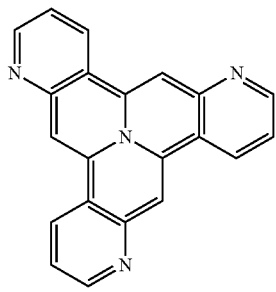
Formula (68)
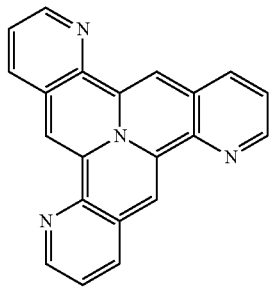
Formula (69)
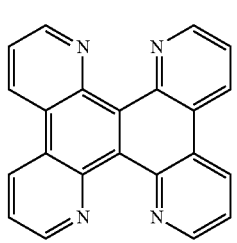
Formula (70)

where optionally one, two, three or four carbon atoms in the fused aromatic base skeleton in the groups of formulae (1) to (50) are replaced by nitrogen.

8. The organic electroluminescent device of claim 1, wherein the (Ring-1A) too (Ring-7A) groups do not have any acidic benzylic protons.

9. A process for producing the organic electroluminescent device of claim 1, comprising applying at least one layer by a sublimation method and/or applying at least one layer by an organic vapor phase deposition method or with the aid of a carrier gas sublimation and/or applying at least one layer from solution, by spin-coating or by a printing method.

10. The organic electroluminescent device of claim 1, wherein the gap between $S_1$ and $T_1$ of the TADF compound is ≤0.15 eV.

11. The organic electroluminescent device of claim 1, wherein the gap between $S_1$ and $T_1$ of the TADF compound is ≤0.10 eV.

12. The organic electroluminescent device of claim 1, wherein the sterically shielded fluorescent compound has a luminescence quantum efficiency of at least 80%.

13. The organic electroluminescent device of claim 1, wherein the sterically shielded fluorescent compound has a luminescence quantum efficiency of at least 90%.

14. The organic electroluminescent device of claim 1, wherein $R^a$ in the benzylic positions is not H or D.

* * * * *